US008143408B2

(12) United States Patent
Besidski et al.

(10) Patent No.: US 8,143,408 B2
(45) Date of Patent: Mar. 27, 2012

(54) N-(8-HETEROARYLTETRAHYDRO-NAPHTALENE-2YL) OR N-(5-HETEROARYLCHROMANE-3-YL) CARBOXAMIDE DERIVATIVES FOR THE TREATMENT OF PAIN

(75) Inventors: Yevgeni Besidski, Södertälje (SE); Inger Kers, Södertälje (SE); Martin Nylöf, Södertälje (SE); Lars Sandberg, Södertälje (SE); Karin Skogholm, Södertälje (SE)

(73) Assignee: AstraZeneca AB, Sodertalje (SE)

( * ) Notice: Subject to any disclaimer, the term of this patent is extended or adjusted under 35 U.S.C. 154(b) by 210 days.

(21) Appl. No.: 12/596,878

(22) PCT Filed: Apr. 22, 2008

(86) PCT No.: PCT/SE2008/050459
§ 371 (c)(1), (2), (4) Date: Dec. 22, 2009

(87) PCT Pub. No.: WO2008/130320
PCT Pub. Date: Oct. 30, 2008

(65) Prior Publication Data
US 2010/0137322 A1    Jun. 3, 2010

Related U.S. Application Data

(60) Provisional application No. 60/913,312, filed on Apr. 23, 2007.

(51) Int. Cl.
*C07D 401/00* (2006.01)
(52) U.S. Cl. ............... 546/268.1; 544/224; 544/242; 544/336; 544/180; 546/255; 546/282.7; 546/329; 514/247; 514/277; 514/336
(58) Field of Classification Search ............. 544/224, 544/242, 336, 180; 546/255, 268.1, 282.7, 546/329; 514/247, 277, 336
See application file for complete search history.

(56) References Cited

U.S. PATENT DOCUMENTS

| 2005/0137190 A1 | 6/2005 | Gonzalez, III et al. |
| 2006/0025415 A1 | 2/2006 | Gonzalez, III et al. |

FOREIGN PATENT DOCUMENTS

| WO | 9734883 A1 | 9/1997 |
| WO | WO 9734883 A1 * | 9/1997 |
| WO | WO 9901534 A1 * | 1/1999 |
| WO | 9905134 A1 | 2/1999 |
| WO | 9905135 A1 | 2/1999 |
| WO | 9914212 A1 | 3/1999 |
| WO | 9914213 A1 | 3/1999 |
| WO | WO 9914212 A1 * | 3/1999 |
| WO | 2005013914 A2 | 2/2005 |

OTHER PUBLICATIONS

Klugbauer et al., "Structure and functional expression of a new member of the tetrodotoxin-sensitive voltage-activated sodium channel family from human neuroendocrine cells," 1995, The EMBO Journal, vol. 14, No. 6, pp. 1084-1090.
Kretschmer et al., "Accumulation of PN1 and PN3 Sodium Channels in Painful Human Neuroma-Evidence from Immunocytochemistry," 2002, Acta Neurochir, vol. 144, pp. 803-810.
English abstract for WO 99/05135.

* cited by examiner

*Primary Examiner* — James O Wilson
*Assistant Examiner* — Alexander R Pagano
(74) *Attorney, Agent, or Firm* — Kenneth F. Mitchell

(57) ABSTRACT

The present invention relates to new compounds of formula (I) and to pharmaceutical composition containing said compounds and to the use of said compounds in therapy. The present invention further relates to processes for the preparation of said compounds and to new intermediates useful in the preparation thereof.

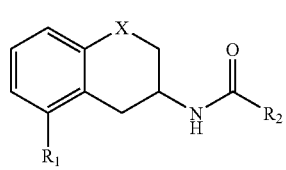

(I)

11 Claims, No Drawings

N-(8-HETEROARYLTETRAHYDRO-NAPHTALENE-2YL) OR N-(5-HETEROARYLCHROMANE-3-YL) CARBOXAMIDE DERIVATIVES FOR THE TREATMENT OF PAIN

This patent is a US National Stage under 35 U.S.C. §371 of International Application No. PCT/SE2008/050459 (filed 22 Apr. 2008; and published as WO2008/130320 on 30 Oct. 2008), which, in turn, claims priority to US Provisional Patent Application No. 60/913,312 (filed 23 Apr. 2007). The entire text of each of the above-referenced patent applications is incorporated by reference into this patent.

FIELD OF THE INVENTION

The present invention relates to new compounds, to pharmaceutical composition containing said compounds and to the use of said compounds in therapy. The present invention further relates to processes for the preparation of said compounds and to new intermediates useful in the preparation thereof.

BACKGROUND

Voltage-gated sodium channels are critical elements in the control of electrical excitability of various cell types, including muscle and neuronal cells. In muscle and neuronal cells voltage-gated sodium channels are mainly responsible for the rising phase of the action potential. Voltage-gated sodium channels are composed of a single alpha subunit and one or two beta subunits. There are 10 known alpha subunit proteins, of which nine are functional as an ion channel. The different alpha subunit proteins are herein referenced to as Nav1.x, with x being an integer between 1 and 9. This labelling is in accordance with the conventions of the International Pharmacological Association (REF). Alpha subunits are large proteins of an approximate weight of 260 kDA (~2000 amino acids), and are functional as voltage-gated sodium channels as monomeric structures. Four beta subunits are known at present. Beta subunits are smaller proteins of an approximate weight of 33-36 kDa. Beta subunits can modulate functional expression, as well as the characteristics of channel opening and closing (gating) of alpha subunits.

Five major lines of evidence support the notion that voltage-gated sodium channels are important therapeutic targets:
a) the biophysical characteristics of voltage-gated sodium channels,
b) the tissue expression pattern of voltage-gated sodium channels,
c) evidence from preclinical research,
d) the association between several congenital diseases and channelopathies of voltage-gated sodium channels, and
e) evidence from the usage of pharmacological agents active at voltage-gated sodium channels in the clinic.

A main biophysical characteristic of voltage-gated sodium channels is the fast opening and closing (activation and inactivation) of the channel upon an appropriate voltage stimulus. These features make voltage-gated sodium channels absolutely essential in the generation of the upstroke of the action potential in most neuronal and muscle cells, and thereby central to the functionality of such tissue. Thus, inhibitory pharmacological interference with the activity of NaV's is expected to have dampening effects on excitability of such tissue. Such agents may thus be useful in the treatment of diseases that involve hyperactivity of neuronal or muscle tissue.

As outlined above, there are nine functional alpha subunits of voltage-gated sodium channels. Each of these alpha subunits has a characteristic tissue expression pattern. Tissue-specific up- or down-regulation of the expression of several of the voltage-gated sodium channels in human diseases or preclinical disease models in animals strongly supports a central role for specific voltage-gated sodium channels in distinct diseases.

Nav1.7 is expressed in human neuromas, which are swollen and hypersensitive nerves and nerve endings that are often present in chronic pain states (Acta Neurochirurgica (2002) 144(8) 803-810). Nav1.7 is also expressed in dorsal root ganglion neurons and contributes to the small tetrodoxin (TTX) sensitive component seen in these cells. Nav1.7 may thus be a potential pain target in addition to its role in neuroendocrine excitability (EMBO Journal (1995) 14(6) 1084-1090).

The present invention relates to a novel group of compounds that exhibit Nav1.7 inhibiting activity, and are therefore expected to be useful in the prophylaxis and treatment of different acute and chronic pain conditions.

WO 97/34883, WO 99/14212, WO 99/05135 and WO 99/14213 describe compounds for use in treatment of pain. The compounds described in these prior art documents bind to serotonine receptors. The compounds of the present invention have little to none activity towards the serotonine receptor. The compounds of the present invention also are contemplated to have an improved pharmacokinetic profile compared to the compounds in the prior art, including a higher oral bioavailability, a decreased clearance and a decreased volume of distribution. Without being bound to any theory, the difference in pharmacokinetic profile is believed to be due to the fact that the right hand side of the molecule is aromatic in the compounds of the present invention while this is not the case for the known compounds.

DISCLOSURE OF THE INVENTION

According to the invention there is provided compounds of formula I,

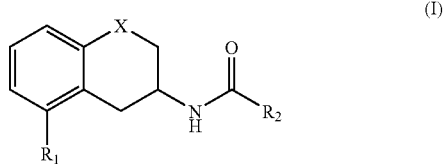

wherein:
X is O or $CH_2$;
$R_1$ is pyridinyl, pyrazolyl, isoxazolyl, pyrimidinyl, pyridazinyl, imidazopyridinyl or pyrazinyl, which may be independently mono-, di- or tri-substituted with $R_{11}$, $R_{12}$, and/or $R_{13}$;
wherein $R_{11}$, $R_{12}$ and $R_{13}$ are independently selected from halogen, $C_{1-6}$alkyl, $C_{1-6}$alkoxy, $C_{3-6}$ cycloalkyl, $C_{1-6}$hydroxyalkyl, $C_{3-6}$ cycloalkyloxy, $C_{3-6}$cycloalkyl$C_{1-6}$alkoxy, cyano, hydroxy, $C_{1-6}$haloalkyl, $C_{1-6}$haloalkoxy, $C_{1-6}$haloalkoxy$C_{1-6}$alkoxy, $C_{1-6}$haloalkoxy$C_{1-6}$alkyl, $C_{1-6}$alkylsulfonic acid-, $C_{1-6}$haloalkylsulfonic acid-, $C_{3-6}$cycloalkylsulfonic acid-, $C_{3-6}$halocycloalkylsulfonic acid-, $C_{3-6}$cycloalkyl$C_{1-6}$alkylsulfonic acid-, $C_{3-6}$halocycloalkyl$C_{1-6}$alkylsulfonic acid-, $C_{1-6}$alkylsulfonyl-, $C_{1-6}$haloalkylsulfonyl-, $C_{3-6}$cycloalkylsulfonyl-, $C_{3-6}$halocycloalkylsulfonyl-, $C_{3-6}$ cycloalkyl$C_{1-6}$alkylsulfonyl, $C_{3-6}$halocycloalkyl$C_{1-6}$alkyl-sulfonyl, phenyl, phenyl$C_{1-6}$alkyl-, phenoxy, $C_{1-6}$alkylphenyl-, $C_{1-6}$ alkoxyphenyl-, $C_{1-6}$alkylamine, $C_{1-6}$haloalkylamine, —C(O)NHC$_{1-6}$alkyl, —C(O)N(C$_{1-6}$alkyl)$_2$ and —C(O)NH$_2$;

$R_2$ is pyrazinyl, phenyl, pyridinyl, quinoxalinyl, triazolyl, pyridonyl, naphthyridinyl, pyrimidinyl or quinolinyl, which may be independently mono-, di-, or tri-substituted with $R_{14}$, $R_{15}$ and/or $R_{16}$;

wherein $R_{14}$, $R_{15}$ and $R_{16}$ are independently selected from halogen, $C_{1-6}$alkyl, $C_{2-6}$alkenyl, $C_{3-6}$alkynyl, $C_{1-6}$alkoxy, $C_{2-6}$alkenyloxy, $C_{3-6}$alkynyloxy, $C_{3-6}$cycloalkyl, $C_{3-6}$heterocycloalkyl, $C_{3-6}$cycloalkyloxy, $C_{3-6}$heterocycloalkyloxy, $C_{3-6}$cycloalkyl$C_{1-6}$alkoxy, $C_{1-6}$alkyl-$C_{3-6}$cycloalkyl$C_{1-6}$alkoxy, $C_{3-6}$heterocycloalkyl$C_{1-6}$alkoxy, $C_{1-6}$alkyl-$C_{3-6}$heterocycloalkyl$C_{1-6}$alkoxy, $C_{1-6}$alkoxy$C_{1-6}$alkoxy, $C_{1-6}$alkoxy$C_{1-6}$alkyl, $C_{1-6}$hydroxyalkyl, $C_{1-6}$haloalkyl, $C_{1-6}$haloalkoxy, $C_{1-6}$haloalkoxy$C_{1-6}$alkoxy, $C_{1-6}$haloalkoxy$C_{1-6}$alkyl, cyano, hydroxyl, NR$^4$R$^5$, $C_{1-6}$alkylsulfonic acid-, $C_{1-6}$haloalkylsulfonic acid-, $C_{3-6}$cycloalkylsulfonic acid-, $C_{3-6}$halocycloalkylsulfonic acid-, $C_{3-6}$cycloalkyl$C_{1-6}$alkylsulfonic acid-, $C_{3-6}$halocycloalkyl$C_{1-6}$alkylsulfonic acid-, $C_{1-6}$alkylsulfonyl-, $C_{1-6}$haloalkylsulfonyl-, $C_{3-6}$cycloalkylsulfonyl-, $C_{3-6}$halocycloalkylsulfonyl-, $C_{3-6}$cycloalkyl-$C_{1-6}$alkylsulfonyl-, $C_{3-6}$halocycloalkyl-$C_{1-6}$alkyl-sulfonyl, phenyl, phenyl$C_{1-6}$alkyl-, phenoxy, $C_{1-6}$alkylphenyl-, $C_{1-6}$alkoxyphenyl-, —C(O)NR$^4$R$^5$, —C(O)C$_{3-6}$cycloalkyl, —C(O)C$_{3-6}$heterocycloalkyl, —C(O)C$_{3-6}$cycloalkyl$C_{1-6}$alkoxy, —C(O)C$_{3-6}$heterocycloalkyl$C_{1-6}$alkoxy, —C(O)C$_{3-6}$cycloalkyl$C_{1-6}$alkyl and —C(O)C$_{3-6}$heterocycloalkyl$C_{1-6}$alkyl; and R$^4$ and R$^5$ are independently selected from hydrogen, $C_{1-6}$alkyl, $C_{1-6}$haloalkyl, $C_{1-6}$hydroxyalkyl, $C_{1-6}$alkoxy$C_{1-6}$alkyl, $C_{3-6}$cycloalkyl, $C_{3-6}$halocycloalkyl, $C_{3-6}$heterocycloalkyl and $C_{3-6}$heterocycloalkyl$C_{1-6}$alkyl, or pharmaceutically-acceptable salts thereof.

One embodiment relates to compounds of formula I, wherein:

X is O or CH$_2$;

$R_1$ is pyridinyl, pyrazolyl, isoxazolyl, pyrimidinyl, pyridazinyl, imidazopyridinyl or pyrazinyl, which may be independently mono- or di-substituted with $R_{11}$, $R_{12}$, and/or $R_{13}$;

wherein $R_{11}$, $R_{12}$ and $R_{13}$ are independently selected from halogen, $C_{1-6}$alkyl, $C_{1-6}$alkoxy, $C_{3-6}$cycloalkyl, $C_{1-6}$hydroxyalkyl, cyano, $C_{1-6}$alkylsulfonyl-, —C(O)NHC$_{1-6}$alkyl and —C(O)N(C$_{1-6}$alkyl)$_2$;

$R_2$ is pyrazinyl, phenyl, pyridinyl, quinoxalinyl, triazolyl, pyridonyl, naphthyridinyl, pyrimidinyl or quinolinyl, which may be independently mono- or di-substituted with $R_{14}$, $R_{15}$ and/or $R_{16}$;

wherein $R_{14}$, $R_{15}$ and $R_{16}$ are independently selected from halogen, $C_{1-6}$alkyl, $C_{1-6}$alkoxy, $C_{3-6}$alkynyloxy, $C_{3-6}$cycloalkyloxy, $C_{3-6}$heterocycloalkyloxy, $C_{3-6}$cycloalkyl$C_{1-6}$alkoxy, $C_{3-6}$heterocycloalkyl$C_{1-6}$alkoxy, $C_{1-6}$alkyl-$C_{3-6}$heterocycloalkyl$C_{1-6}$alkoxy, $C_{1-6}$alkoxy$C_{1-6}$alkoxy, $C_{1-6}$alkoxy$C_{1-6}$alkyl, $C_{1-6}$haloalkoxy, $C_{1-6}$haloalkoxy$C_{1-6}$alkoxy, NR$^4$R$^5$, $C_{1-6}$haloalkylsulfonic acid-, $C_{1-6}$alkylsulfonyl-, $C_{3-6}$cycloalkylsulfonyl-, phenyl, $C_{1-6}$alkoxyphenyl-, —C(O)NR$^4$R$^5$ and —C(O)C$_{3-6}$heterocycloalkyl; and R$^4$ and R$^5$ are independently selected from hydrogen, $C_{1-6}$alkyl, $C_{1-6}$haloalkyl, $C_{1-6}$alkoxy$C_{1-6}$alkyl, $C_{3-6}$halocycloalkyl and $C_{3-6}$heterocycloalkyl, or pharmaceutically-acceptable salts thereof.

In one embodiment $R_1$ is pyridine-4-yl, pyridine-3-yl, pyridine-2-yl, pyrazole-4-yl, isoxazole-4-yl, pyrimidine-5-yl, pyridazine-4-yl, imidazo[1,2-a]pyridine-6-yl or pyrazine-2-yl.

In another embodiment any one of $R_1$ as defined above is independently mono-, di- or tri-substituted with $R_{11}$, $R_{12}$, and/or $R_{13}$, wherein $R_{11}$, $R_{12}$, and $R_{13}$ are independently selected from cyano, fluoro, iodo, chloro, bromo, methyl, ethyl, n-propyl, i-propyl, n-butyl, i-butyl, s-butyl, t-butyl, and all isomeric forms of pentyl and hexyl, methoxy, ethoxy, hydroxymethyl, hydroxyethyl, hydroxypropyl, propoxy, i-propoxy, n-butoxy, t-butoxy, i-butoxy, methylsulfonyl, ethylsulfonyl, n-propylsulfonyl, i-propylsulfonyl, n-butylsulfonyl, i-butylsulfonyl, s-butylsulfonyl, t-butylsulfonyl, and all isomeric forms of pentyl- and hexyl-sulfonyl, methylamide, dimethylamide, N-ethyl-N-methylamide, ethylamide, diethylamide, cyclopropyl, cyclobutyl and cyclopentyl.

In another embodiment any one of $R_1$ as defined above is independently mono- or di-substituted with $R_{11}$, $R_{12}$, and/or $R_{13}$, wherein $R_{11}$, $R_{12}$, and $R_{13}$ are independently selected from cyano, fluoro, methyl, ethyl, methoxy, ethoxy, hydroxymethyl, methylsulfonyl, methylamide, dimethylamide and cyclopropyl.

In one embodiment $R_1$ is pyridine-4-yl, pyridine-3-yl or pyridine-2-yl, which is mono-substituted with cyano, fluoro, methyl, methoxy, hydroxymethyl or methylsulfonyl.

In another embodiment $R_1$ is pyridine-4-yl, pyridine-3-yl or pyridine-2-yl, which is di-substituted with methoxy and fluoro, or dimethylamide and methoxy or methylamide and methoxy or methyl and fluoro.

In a further embodiment $R_1$ is pyrimidine-5-yl, which is mono-substituted with methyl, ethyl, methoxy, ethoxy, dimethylamide or cyclopropyl.

In yet another embodiment $R_1$ is pyrazine-2-yl, which is mono- or di-substituted with methyl or mono-substituted with hydroxymethyl.

In yet a further embodiment $R_1$ is pyridazine-4-yl, which is di-substituted with methoxy.

In one embodiment $R_1$ is methyl-substituted pyrazole-4-yl.

In a further embodiment $R_1$ is isoxazole-4-yl, which is di-substituted with methyl.

In yet a further embodiment $R_1$ is imidazo[1,2-a]pyridine-6-yl.

In one embodiment $R_2$ is pyrazine-2-yl, phenyl, pyridine-4-yl, pyridine-3-yl, quinoxaline-2-yl, 1,2,3-triazole-4-yl, 2-pyridone-4-yl, 1,8-naphthyridine-2-yl, 1,5-naphthyridine-2-yl, 1,6-naphthyridine-3-yl, pyrimidine-5-yl or quinoline-2-yl.

In a further embodiment any one of $R_2$ as defined above is independently mono-, di- or tri-substituted with $R_{14}$, $R_{15}$, and/or $R_{16}$, wherein $R_{14}$ is NR$^4$R$^5$ and R$^4$ and R$^5$ are independently selected from hydrogen and $C_{1-6}$haloalkyl. In yet a further embodiment $R_{14}$ is NR$^4$R$^5$ and R$^4$ and R$^5$ are independently selected from hydrogen and trifluoropropylamine.

In one embodiment any one of $R_2$ as defined above is independently mono-, di- or tri-substituted with $R_{14}$, $R_{15}$, and/or $R_{16}$, wherein $R_{14}$ is —C(O)NR$^4$R$^5$ and R$^4$ and R$^5$ are independently selected from hydrogen, $C_{1-6}$alkyl, $C_{1-6}$haloalkyl, $C_{1-6}$alkoxy$C_{1-6}$alkyl, $C_{3-6}$halocycloalkyl and $C_{3-6}$heterocycloalkyl. In another embodiment $R_{14}$ is —C(O)NR$^4$R$^5$ and R$^4$ and R$^5$ are independently selected from pentylamide, dipropylamide, N-methyl-N-butylamide, N-propoxypropylamide, N-difluorocyclohexylamide, tetrahydropyranylamide, trifluoroethylamide, trifluoropropylamide, trifluorobutylamide, N-trifluoroethyl-N-methylamide and N-trifluoropropyl-N-methylamide.

In yet another embodiment any one of $R_2$ as defined above is independently mono-, di- or tri-substituted with $R_{14}$, $R_{15}$, and/or $R_{16}$, wherein $R_{14}$, $R_{15}$, and $R_{16}$ are independently selected from fluoro, iodo, chloro, bromo, methyl, ethyl, n-propyl, i-propyl, n-butyl, i-butyl, s-butyl, t-butyl, and all isomeric forms of pentyl and hexyl, methoxy, ethoxy, propoxy, i-propoxy, n-butoxy, t-butoxy, i-butoxy, propynyloxy, butynyloxy, pentynyloxy, methoxyethoxy, methoxypropoxy, ethoxymethoxy, ethoxyethoxy, ethoxypropoxy, propoxymethoxy, propoxyethoxy, propoxypropoxy, methoxymethyl, methoxyethyl, methoxypropyl, ethoxymethyl, ethoxyethyl, ethoxypropyl, propoxymethyl, propoxyethyl, propoxypropyl, fluoromethyl, difluoromethyl, trifluoromethyl, fluoroethyl, difluoroethyl, trifluoroethyl, fluoropropyl, difluoropropyl, trifluoropropyl, fluorobutyl, difluorobutyl, trifluorobutyl, bromopropyl, fluoromethoxy, difluoromethoxy, trifluoromethoxy, fluoroethoxy, difluoroethoxy, trifluoroethoxy, fluoropropoxy, difluoropropoxy, trifluoropropoxy, fluorobutoxy, difluorobutoxy, trifluorobutoxy, fluoropentoxy, difluoropentoxy, trifluoropentoxy, trifluoromethoxymethoxy, trifluoromethoxyethoxy, trifluoroethoxymethoxy, trifluoroethoxyethoxy, trifluoromethoxymethyl, trifluoromethoxyethyl, trifluoroethoxymethyl, trifluoroethoxyethyl, trifluoromethylamine, trifluoroethylamine, trifluoropropylamine, trifluoromenthanesulfonic acid, difluoromenthanesulfonic acid, fluoromenthanesulfonic acid, menthanesulfonyl, ethanesulfonyl, propanesulfonyl, butanesulfonyl, phenyl, cyclopropylsulfonyl, cyclobutylsulfonyl, cyclopentylsulfonyl, methylamide, ethylamide, propylamide, butylamide, pentylamide, dimethylamide, diethylamide, dipropylamide, N-methyl-N-ethylamide, N-methyl-N-propylamide, N-methyl-N-butylamide, N-methyl-N-pentylamide, N-ethyl-N-propylamide, N-ethyl-N-butylamide, N-ethyl-N-pentylamide, N-propyl-N-methylamide, N-propyl-N-ethylamide, N-propyl-N-butylamide, N-propyl-N-pentylamide, N-methoxymethylamide, N-methoxyethylamide, N-methoxypropylamide, N-methoxybutylamide, N-ethoxyethylamide, N-ethoxypropylamide, N-ethoxybutylamide, N-propoxymethylamide, N-propoxyethylamide, N-propoxypropylamide, N-propoxybutylamide, N-difluorocyclopropylamide, N-difluorocyclobutylamide, N-difluorocyclopenylamide, N-difluorocyclohexylamide, tetrahydropyranylamide, oxetanylamide, tetrahydropyranylamide, oxepanylamide, dioxanylamide, trifluoromethylamide, trifluoroethylamide, trifluoropropylamide, trifluorobutylamide, N-trifluoromethyl-N-methylamide, N-trifluoromethyl-N-ethylamide, N-trifluoromethyl-N-propylamide, N-trifluoroethyl-N-methylamide, N-trifluoroethyl-N-ethylamide, N-trifluoroethyl-N-propylamide, N-trifluoropropyl-N-methylamide, N-trifluoropropyl-N-ethylamide, N-trifluoropropyl-N-propylamide, oxetanyl, tetrahydrofuranyl, tetrahydropyranyl, oxepanyl, dioxanyl, oxetanyloxy, tetrahydrofuranyloxy, tetrahydropyranyloxy, oxepanyloxy, dioxanyloxy, oxetanylmethoxy, tetrahydrofuranylmethoxy, tetrahydropyranylmethoxy, oxepanylmethoxy, dioxanylmehoxy, cyclopropylmethoxy, cyclopylethoxy, cyclobutylmethoxy, cyclobutylethoxy, cyclopropyloxy, cyclopropyloxy, cyclobutyloxy, cyclopentyloxy, cyclohexyloxy, pyrrolidinyl, pyrrolidinyl-carbonyl, thiazolyl, thiazolylmethoxy, thiazolylethoxy, methyl-thiazolylmethoxy, methyl-thiazolylmethyl, isoxazolylmethoxy, isoxazolylethoxy, methyl-isoxazolylmethoxy, methyl-isoxazolylmethyl, imidazolyl, imidazolylmethoxy, imidazolylethoxy, methyl-imidazolylmethoxy, methyl-imidazolylmethyl, pyridinyl, pyridinylmethoxy, pyridinylethoxy, methyl-pyridinylmethoxy, methyl-pyridinylmethyl, pyrazinyl, pyrazinylmethoxy, pyrazinylethoxy, methylpyrazinylmethoxy and methylpyrazinylmethyl.

In another embodiment any one of $R_2$ as defined above is independently mono- or di-substituted with $R_{14}$, $R_{15}$, and/or $R_{16}$, wherein $R_{14}$, $R_{15}$, and $R_{16}$ are independently selected from chloro, methyl, n-butyl, i-butyl, methoxy, ethoxy, i-propoxy, n-butoxy, i-butoxy, butynyloxy, methoxyethoxy, methoxypropoxy, propoxyethoxy, methoxyethyl, trifluoromethoxy, difluoroethoxy, trifluoroethoxy, fluoropropoxy, difluoropropoxy, trifluoropropoxy, trifluoroethoxyethoxy, trifluoroethoxymethyl, trifluoropropylamine, trifluoromenthanesulfonic acid, butanesulfonyl, phenyl, cyclopentylsulfonyl, pentylamide, dipropylamide, N-methyl-N-butylamide, N-propoxypropylamide, N-difluorocyclohexylamide, tetrahydropyranylamide, trifluoroethylamide, trifluoropropylamide, trifluorobutylamide, N-trifluoroethyl-N-methylamide, N-trifluoropropyl-N-methylamide, tetrahydrofuranyloxy, tetrahydropyranyloxy, oxetanylmethoxy, tetrahydrofuranylmethoxy, tetrahydropyranylmethoxy, dioxanylmehoxy, cyclopropylmethoxy, cyclobutyloxy, cyclopentyloxy, pyrrolidinyl-carbonyl, thiazolylmethoxy, methyl-isoxazolylmethoxy, methyl-imidazolylmethoxy, pyridinylmethoxy and pyrazinylmethoxy.

In another embodiment of the invention both $R_1$ and $R_2$ are pyridinyl. In one embodiment of the invention both $R_1$ and $R_2$ are pyrimidinyl. In one embodiment $R_1$ is pyridinyl and $R_2$ is pyrimidinyl. In a further embodiment $R_1$ is pyrimidinyl and $R_2$ is pyridinyl. In yet a further embodiment $R_1$ is pyridinyl and $R_2$ is phenyl. In one embodiment $R_1$ is pyrazolyl and $R_2$ is phenyl.

In a further embodiment relates to compounds of formula I, wherein X is O.

In one embodiment relates to compounds of formula I, wherein X is $CH_2$.

For the avoidance of doubt the present invention relates to any one of compounds falling within the scope of formula I as defined above.

Another embodiment of the invention relates to compounds having formula (Ia)

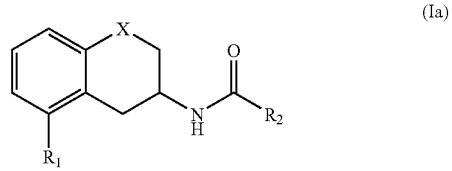

(Ia)

wherein

X is O or $CH_2$;

$R_1$ is an aromatic or non-aromatic heterocyclic ring other than piperazinyl or piperidinyl, which heterocyclic ring may be mono-, di- or tri-substituted with $R_{11}$, $R_{12}$, and/or $R_{13}$, wherein $R_{11}$, $R_{12}$, and/or $R_{13}$ is/are $C_{1-6}$ alkyl; $C_{3-6}$ cycloalkyl; $C_{3-6}$ cycloalkoxy; halogen; $(CH_2)_{0-6}CN$; OH; $C_{1-6}$ alkoxy; $NR_{20}R_{21}$; $O_{0-1}(CH_2)_{0-6}CF_3$; $O_{0-1}(CH_2)_{0-6}CHF_2$; $O_{0-1}(CH_2)_{0-6}CH_2F$; $O_{0-1}(CH_2)_{0-6}CH(CF_3)_2$; $O_{0-1}(CH_2)_{0-6}CH(CF_3)_2$; $O_{0-1}(CH_2)_{0-6}CH(CF_3)_2$; $SO_2(CH_2)_{0-6}CH_3$; $SO_3(CH_2)_{0-6}CH_3$; $SO_3CF_3$; $SO_2NR_{20}R_{21}$; phenyl; phenyl-$C_{1-6}$ alkyl; phenoxy; $C_{1-6}$ alkylphenyl; $C_{1-6}$ alkoxyphenyl; $C_{1-6}$ haloalkoxyphenyl; $C_{1-6}$ haloalkylphenyl;

$R_2$ is an aromatic or non-aromatic ring A, optionally containing one, two or three heteroatoms selected from N, O and S, which ring may be fused to one or two other aromatic or non-aromatic ring(s) B and/or C, said ring(s) B and/or C optionally containing one, two or three heteroatoms selected from N, O and S, which ring(s) A, B, and/or C may be mono-, di-, or tri-substituted with $R_{14}$, $R_{15}$, and/or $R_{16}$;

wherein $R_{14}$, $R_{15}$, and/or $R_{16}$ independently is/are $C_{1-6}$ alkyl; $C_{3-6}$ cycloalkyl; $C_{3-6}$ cycloalkoxy; $C_{3-6}$ cycloalkyl-$C_{1-6}$ alkoxy; halogen; $(CH_2)_{0-6}CN$; OH; $C_{1-6}$ alkoxy; $NR_{20}R_{21}$; $O_{0-1}(CH_2)_{0-6}CF_3$; $O_{0-1}(CH_2)_{0-6}CHF_2$; $O_{0-1}(CH_2)_{0-6}CH_2F$; $O_{0-1}(CH_2)_{0-6}CH(CF_3)_2$; $O_{0-1}(CH_2)_{0-6}CH(CF_3)_2$; $O_{0-1}(CH_2)_{0-6}CH(CF_3)_2$; $SO_2(CH_2)_{0-6}CH_3$; $SO_3(CH_2)_{0-6}CH_3$; $SO_3CF_3$; $SO_2NR_{20}R_{21}$; phenyl; phenyl-$C_{1-6}$ alkyl; phenoxy; $C_{1-6}$ alkylphenyl; $C_{1-6}$ alkoxyphenyl; $C_{1-6}$ haloalkoxyphenyl; $C_{1-6}$ haloalkylphenyl; an optionally substituted heterocyclic ring containing one or two heteroatoms selected from N, O, and S, wherein the substituent(s) is(are) selected from $C_{1-6}$ alkyl, $C_{3-6}$ cycloalkyl, phenyl-$C_{1-6}$ alkyl, $(CH_2)_mOR_{23}$, and $COR_{22}$; an optionally substituted heteroaromatic ring containing one or two heteroatoms selected from N, O and S wherein the substituent(s) is(are) selected from $C_{1-6}$ alkyl, $C_{3-6}$ cycloalkyl and phenyl-$C_{1-6}$ alkyl; or $COR_{22}$;

wherein $R_{20}$ is H, $C_{1-6}$ alkyl, or $C_{3-6}$ cycloalkyl;

$R_{21}$ is H, $C_{1-6}$ alkyl, or $C_{3-6}$ cycloalkyl; and $R_{22}$ is $C_{1-6}$ alkyl, $C_{3-6}$ cycloalkyl, $CF_3$, $NR_{20}R_{21}$, phenyl, a heteroaromatic ring containing one or two heteroatoms selected from N, O and S or a heterocyclic ring containing one or two heteroatoms selected from N, O, and S;

and $R_{23}$ is H, $C_{1-6}$ alkyl, $C_{3-6}$ cycloalkyl or phenyl-$C_{1-6}$ alkyl, and pharmaceutically-acceptable salts thereof.

For the avoidance of doubt it is to be understood that where in this specification a group is qualified by 'hereinbefore defined', 'defined hereinbefore' or 'defined above' the said group encompasses the first occurring and broadest definition as well as each and all of the other definitions for that group.

For the avoidance of doubt it is to be understood that in this specification '$C_{1-6}$' means a carbon group having 1, 2, 3, 4, 5 or 6 carbon atoms.

In this specification, unless stated otherwise, the term "alkyl" includes both straight and branched chain alkyl groups and may be, but are not limited to methyl, ethyl, n-propyl, i-propyl, n-butyl, i-butyl, s-butyl, t-butyl, n-pentyl, i-pentyl, neo-pentyl, n-hexyl or i-hexyl. The term $C_{1-4}$alkyl having 1 to 4 carbon atoms and may be but are not limited to methyl, ethyl, n-propyl, i-propyl or t-butyl. The term "$C_0$" in $C_{0-4}$ alkyl refers to a situation where no carbon atom is present.

In this specification, unless stated otherwise, the term "alkenyl" includes both straight and branched chain alkyl groups having at least one double bond between the carbons and may be, but are not limited to propenyl, butenyl or pentenyl.

In this specification, unless stated otherwise, the term "alkynyl" includes both straight and branched chain alkyl groups having at least one triple bond between the carbons and may be, but are not limited to propynyl, butynyl or pentynyl.

The term "$C_{3-6}$alkynyloxy" includes butynyloxy.

The term "alkoxy", unless stated otherwise, refers to radicals of the general formula —O—R, wherein R is selected from a hydrocarbon radical. The term "alkoxy" may include, but is not limited to methoxy, ethoxy, propoxy, isopropoxy, butoxy, t-butoxy och isobutoxy. The term "$C_{1-4}$alkoxyalkoxy" may include, but is not limited to methoxymethoxy, methoxyethoxy, methoxypropoxy, ethoxymethoxy, ethoxyethoxy, ethoxypropoxy, propoxymethoxy, propoxyethoxy and propoxypropoxy.

In this specification, unless stated otherwise, the term "cycloalkyl" refers to an monocyclic, bicyclic or bridged hydrocarbon ring system, which may be aromatic. The term "$C_{1-6}$cycloalkyl" may be, but is not limited to cyclopropyl, cyclobutyl, cyclopentyl, cyclohexyl, or when aromatic may be phenyl or naphthyl.

The term "$C_{1-6}$cycloalkyloxy" may be, but is not limited to cyclopropyloxy, cyclobutyloxy, cyclopentyloxy or cyclohexyloxy.

The term "$C_{3-6}$cycloalkyl$C_{1-6}$alkoxy-" may be, but is not limited to cyclopropylmethoxy, cyclopropylethoxy, cyclobutylmethoxy, cyclopentylpropoxy or cyclohexylbutoxy.

In this specification, unless stated otherwise, the term "heterocycloalkyl" refers to an monocyclic, bicyclic or bridged hydrocarbon ring system, which may be aromatic, having one or more heteroatoms independently selected from O, N or S. The term "$C_{1-6}$heterocycloalkyl" may be, but is not limited to pyrrolidinyl, piperidinyl oxetanyl, furanyl, tetrahydrofuranyl, pyranyl, tetrahydropyranyl, oxepanyl or dioxanyl or when aromatic may be oxazolyl, isoxazol, furyl, thiophenyl, pyrrolyl, pyrazolyl, imidazolyl, pyridinyl, pyrimidinyl, indolyl, indazolyl, pyridonyl or benzothienyl. Heteroaryl may also be quinolinyl, quinoxalinyl, naphthyridinyl, isoquinolinyl or thiazolyl.

The term "$C_{1-6}$alkyl-$C_{3-6}$heterocycloalkyl$C_{1-6}$alkoxy" may include, but is not limited to methyl-imidazolylmethoxy or ethyl-pyrrolidinylmethoxy.

The term "halo" or "halogen" refers to fluorine, chlorine, bromine and iodine radicals.

In this specification, unless stated otherwise, the term "haloalkyl" means an alkyl group as defined above, which is substituted with one or more halogen atoms as defined above. The term "$C_{1-6}$haloalkyl" may include, but is not limited to fluoromethyl, difluoromethyl, trifluoromethyl, chloromethyl, dichloromethyl, trichloromethyl or fluorochloromethyl. The term "$C_{1-3}$haloalkoxy" may include, but is not limited to fluoromethoxy, difluoromethoxy, trifluoromethoxy, fluoroethoxy, difluoroethoxy, difluoropropoxy or trifluoropropoxy.

For the avoidance of doubt, the propoxy in the halopropoxy substituent may be a n-propoxy or i-propoxy substituted with fluoro whereby the fluoro may be located anywhere on the propoxy carbon chain, such as for example n-propoxy substituted with trifluoro at the end as in example 19 or isopropoxy substituted with one fluoro on both ends of the propoxy substituent in example 27.

The term "hydroxyalkyl" means an alkyl group as defined above, which is substituted with one or more hydroxyl atoms, the term "$C_{3-6}$hydroxyalkyl" may include, but is not limited to hydroxymethyl, hydroxyethyl, hydroxypropyl, dihydroxypropyl, hydroxybutyl, dihydroxybutyl or hydroxypentyl.

The term "amine" or "amino" refers to radicals of the general formula —NRR', wherein R and R' are independently selected from hydrogen or a hydrocarbyl radical.

In this specification, unless stated otherwise, the term "alkylamine" means a substituents having one or two alkyl group as defined above, attached to a nitrogen atom. The term "$C_{1-3}$alkylamine" may include, but is not limited to methylamine, dimethylamine.

The term "$C_{1-3}$haloalkylamine" may include, but is not limited to trifluoropropylamine. For the avoidance of doubt, a group alkylamide includes an amide substituted with a carbon chain that may be straight or branched and includes all isomers of said alkyl group, such as isopentyl in example 111 or isobutyl in example 112, isopropoxy and n-propyl in example 186.

For the avoidance of doubt, a group R₂ substituted with a group C₁₋₆haloalkylsulfonic acid includes a trifluoromethylsulfonic acid group as in example 3.

It will be appreciated that throughout the specification, the number and nature of substituents on rings in the compounds of the invention will be selected so as to avoid sterically undesirable combinations.

Another embodiment of the invention relates to compounds selected from the group consisting of
N-[(3S)-5-Pyridin-4-yl-3,4-dihydro-2H-chromen-3-yl]-4-(trifluoromethoxy)benzamide,
4-Butoxy-N-[(3S)-5-pyridin-4-yl-3,4-dihydro-2H-chromen-3-yl]benzamide,
4-{[(2R)-8-Pyridin-4-yl-1,2,3,4-tetrahydronaphthalen-2-yl]carbamoyl}phenyl trifluoromethanesulfonate,
N-[(3S)-5-Pyridin-3-yl-3,4-dihydro-2H-chromen-3-yl]-4-(trifluoromethoxy)benzamide,
N-[(3S)-5-Pyridin-2-yl-3,4-dihydro-2H-chromen-3-yl]-4-(trifluoromethoxy)benzamide,
N-[(2R)-8-(1-Methyl-1H-pyrazol-4-yl)-1,2,3,4-tetrahydronaphthalen-2-yl]-4-(trifluoromethoxy)benzamide,
4-{[(2R)-8-(1-M ethyl-1H-pyrazol-4-yl)-1,2,3,4-tetrahydronaphthalen-2-yl]carbamoyl}phenyl trifluoromethanesulfonate,
5-Methyl-N-[(2R)-8-(1-methyl-1H-pyrazol-4-yl)-1,2,3,4-tetrahydronaphthalen-2-yl]-2-phenyl-2H-1,2,3-triazole-4-carboxamide,
N-[(2R)-8-(3,5-Dimethyl-1H-pyrazol-4-yl)-1,2,3,4-tetrahydronaphthalen-2-yl]-4-(trifluoromethoxy)benzamide,
N-[(2R)-8-(3,5-Dimethylisoxazol-4-yl)-1,2,3,4-tetrahydronaphthalen-2-yl]-4-(trifluoromethoxy)benzamide,
4-{[(2R)-8-(3,5-Dimethylisoxazol-4-yl)-1,2,3,4-tetrahydronaphthalen-2-yl]carbamoyl}phenyl trifluoromethanesulfonate,
N-[(2R)-8-pyridin-4-yl-1,2,3,4-tetrahydronaphthalen-2-yl]-6-(2,2,2-trifluoro ethoxy)nicotinamide,
N-[(2R)-8-pyridin-4-yl-1,2,3,4-tetrahydronaphthalen-2-yl]-6-(3,3,3-trifluoropropoxy)nicotinamide,
6-isopropoxy-N-[(2R)-8-pyridin-4-yl-1,2,3,4-tetrahydronaphthalen-2-yl]nicotinamide,
6-(cyclopentyloxy)-N-[(2R)-8-pyridin-4-yl-1,2,3,4-tetrahydronaphthalen-2-yl]nicotinamide,
2,4-dimethoxy-N-[(2R)-8-pyridin-4-yl-1,2,3,4-tetrahydronaphthalen-2-yl]benzamide,
5-methyl-2-phenyl-N-[(2R)-8-pyridin-4-yl-1,2,3,4-tetrahydronaphthalen-2-yl]-2H-1,2,3-triazole-4-carboxamide,
N-[(3S)-5-pyridin-4-yl-3,4-dihydro-2H-chromen-3-yl]-6-(2,2,2-trifluoroethoxy)nicotinamide,
N-[(3S)-5-pyridin-4-yl-3,4-dihydro-2H-chromen-3-yl]-6-(3,3,3-trifluoropropoxy)nicotinamide,
6-isopropoxy-N-[(3S)-5-pyridin-4-yl-3,4-dihydro-2H-chromen-3-yl]nicotinamide,
6-(cyclopentyloxy)-N-[(3S)-5-pyridin-4-yl-3,4-dihydro-2H-chromen-3-yl]nicotinamide,
2,4-dimethoxy-N-[(3S)-5-pyridin-4-yl-3,4-dihydro-2H-chromen-3-yl]benzamide,
5-methyl-2-phenyl-N-[(3S)-5-pyridin-4-yl-3,4-dihydro-2H-chromen-3-yl]-2H-1,2,3-triazole-4-carboxamide,
6-isobutoxy-N-[(3S)-5-pyridin-4-yl-3,4-dihydro-2H-chromen-3-yl]nicotinamide,
6-ethoxy-N-[(3S)-5-pyridin-4-yl-3,4-dihydro-2H-chromen-3-yl]nicotinamide,
6-(2,2-difluoroethoxy)-N-[(3S)-5-pyridin-4-yl-3,4-dihydro-2H-chromen-3-yl]nicotinamide,
6-[2-fluoro-1-(fluoromethyl)ethoxy]-N-[(3S)-5-pyridin-4-yl-3,4-dihydro-2H-chromen-3-yl]nicotinamide,
2-(cyclopentyloxy)-N-[(3S)-5-pyridin-4-yl-3,4-dihydro-2H-chromen-3-yl]pyrimidine-5-carboxamide,
6-(cyclobutyloxy)-N-[(3S)-5-pyridin-4-yl-3,4-dihydro-2H-chromen-3-yl]nicotinamide,
6-(cyclopropylmethoxy)-N-[(3S)-5-pyridin-4-yl-3,4-dihydro-2H-chromen-3-yl]nicotinamide,
N-[(2R)-8-(3,5-dimethylisoxazol-4-yl)-1,2,3,4-tetrahydronaphthalen-2-yl]-6-isopropoxynicotinamide,
6-(2,2-difluoroethoxy)-N-[(2R)-8-(3,5-dimethylisoxazol-4-yl)-1,2,3,4-tetrahydronaphthalen-2-yl]nicotinamide,
2-(cyclopentyloxy)-N-[(2R)-8-(3,5-dimethylisoxazol-4-yl)-1,2,3,4-tetrahydronaphthalen-2-yl]pyrimidine-5-carboxamide, and
6-(butylsulfonyl)-N-[(3S)-5-pyridin-4-yl-3,4-dihydro-2H-chromen-3-yl]nicotinamide,
6-chloro-N-[(3S)-5-pyridin-4-yl-3,4-dihydro-2H-chromen-3-yl]nicotinamide,
2-isopropoxy-N-[(3S)-5-pyridin-4-yl-3,4-dihydro-2H-chromen-3-yl]pyrimidine-5-carboxamide,
5-methoxy-N-[(3S)-5-pyridin-4-yl-3,4-dihydro-2H-chromen-3-yl]pyrazine-2-carboxamide,
5-isopropoxy-N-[(3S)-5-pyridin-4-yl-3,4-dihydro-2H-chromen-3-yl]pyrazine-2-carboxamide,
N-[(2R)-8-(3-fluoropyridin-4-yl)-1,2,3,4-tetrahydronaphthalen-2-yl]-6-isopropoxynicotinamide,
N-[(2R)-8-(3-fluoropyridin-4-yl)-1,2,3,4-tetrahydronaphthalen-2-yl]-6-(2,2,2-trifluoroethoxy)nicotinamide,
N-[(3S)-5-pyridin-4-yl-3,4-dihydro-2H-chromen-3-yl]quinoxaline-2-carboxamide,
5-isopropoxy-N-[(3S)-5-pyridin-3-yl-3,4-dihydro-2H-chromen-3-yl]pyrazine-2-carboxamide,
N-[(3S)-5-pyridin-3-yl-3,4-dihydro-2H-chromen-3-yl]-5-(3,3,3-trifluoropropoxy)pyrazine-2-carboxamide,
5-methoxy-N-[(3S)-5-pyridin-3-yl-3,4-dihydro-2H-chromen-3-yl]pyrazine-2-carboxamide,
N-[(3S)-5-pyridin-3-yl-3,4-dihydro-2H-chromen-3-yl]-1,8-naphthyridine-2-carboxamide,
N-[(3S)-5-pyridin-3-yl-3,4-dihydro-2H-chromen-3-yl]-1,5-naphthyridine-2-carboxamide,
2-methyl-N-[(3S)-5-pyridin-3-yl-3,4-dihydro-2H-chromen-3-yl]-1,6-naphthyridine-3-carboxamide,
N-[(3S)-5-(6-methoxypyridin-3-yl)-3,4-dihydro-2H-chromen-3-yl]-5-(3,3,3-trifluoropropoxy)pyrazine-2-carboxamide,
5-methoxy-N-[(3S)-5-(6-methoxypyridin-3-yl)-3,4-dihydro-2H-chromen-3-yl]Pyrazine-2-carboxamide,
6-isopropoxy-N-[(3S)-5-pyridin-3-yl-3,4-dihydro-2H-chromen-3-yl]nicotinamide,
N-[(3S)-5-pyridin-3-yl-3,4-dihydro-2H-chromen-3-yl]-6-(3,3,3-trifluoropropoxy)nicotinamide,
2-isobutyl-5-methyl-N-[(3S)-5-pyridin-3-yl-3,4-dihydro-2H-chromen-3-yl]-2H-1,2,3-triazole-4-carboxamide,
6-isopropoxy-N-[(3S)-5-pyrimidin-5-yl-3,4-dihydro-2H-chromen-3-yl]nicotinamide,
N-[(3S)-5-pyrimidin-5-yl-3,4-dihydro-2H-chromen-3-yl]-6-(3,3,3-trifluoropropoxy)nicotinamide,
6-isopropoxy-N-[(3S)-5-(2-methoxypyrimidin-5-yl)-3,4-dihydro-2H-chromen-3-yl]nicotinamide,
N-[(3S)-5-(2-methoxypyrimidin-5-yl)-3,4-dihydro-2H-chromen-3-yl]-6-(3,3,3-trifluoropropoxy)nicotinamide,
N-[(3S)-5-pyridin-3-yl-3,4-dihydro-2H-chromen-3-yl]-6-(2,2,2-trifluoroethoxy)nicotinamide,
6-isopropoxy-N-[(3S)-5-(2-methoxypyridin-4-yl)-3,4-dihydro-2H-chromen-3-yl]nicotinamide,
N-[(3S)-5-(2-methoxypyridin-4-yl)-3,4-dihydro-2H-chromen-3-yl]-6-(3,3,3-trifluoropropoxy)nicotinamide, 6-isopropoxy-N-[(3S)-5-(2-methylpyrimidin-5-yl)-3,4-dihydro-2H-chromen-3-yl]nicotinamide,
N-[(3S)-5-(2-methylpyrimidin-5-yl)-3,4-dihydro-2H-chromen-3-yl]-6-(3,3,3-trifluoropropoxy)nicotinamide,
N-[(3S)-5-(2-fluoropyridin-4-yl)-3,4-dihydro-2H-chromen-3-yl]-6-isopropoxynicotinamide,
N-[(3S)-5-(2-fluoropyridin-4-yl)-3,4-dihydro-2H-chromen-3-yl]-6-(3,3,3-trifluoropropoxy)nicotinamide,
N-[(3S)-5-pyridin-3-yl-3,4-dihydro-2H-chromen-3-yl]quinoxaline-2-carboxamide,
N-[(3S)-5-pyridin-3-yl-3,4-dihydro-2H-chromen-3-yl]quinoline-2-carboxamide,
6-isopropoxy-N-[(3S)-5-(3-methylpyridin-4-yl)-3,4-dihydro-2H-chromen-3-yl]nicotinamide,
N-[(3S)-5-(6-fluoropyridin-3-yl)-3,4-dihydro-2H-chromen-3-yl]-6-isopropoxynicotinamide,
N-[(3S)-5-(3-methylpyridin-4-yl)-3,4-dihydro-2H-chromen-3-yl]-6-(3,3,3-trifluoropropoxy)nicotinamide,
N-[(3S)-5-(6-fluoropyridin-3-yl)-3,4-dihydro-2H-chromen-3-yl]-6-(3,3,3-trifluoropropoxy)nicotinamide,
6-(2,4-dimethoxyphenyl)-N-[(3S)-5-pyridin-4-yl-3,4-dihydro-2H-chromen-3-yl]nicotinamide,
6-isopropoxy-N-[(3S)-5-(2-methoxypyridin-3-yl)-3,4-dihydro-2H-chromen-3-yl]nicotinamide,
N-[(3S)-5-(2-methoxypyridin-3-yl)-3,4-dihydro-2H-chromen-3-yl]-6-(3,3,3-trifluoropropoxy)nicotinamide,
6-isopropoxy-N-[(2S)-8-(2-methoxypyrimidin-5-yl)-1,2,3,4-tetrahydronaphthalen-2-yl]nicotinamide,
N-[(2R)-8-(2-fluoropyridin-3-yl)-1,2,3,4-tetrahydronaphthalen-2-yl]-6-isopropoxynicotinamide,
N-[(2R)-8-pyridazin-4-yl-1,2,3,4-tetrahydronaphthalen-2-yl]-6-(3,3,3-trifluoropropoxy)nicotinamide,
6-isopropoxy-N-[(3S)-5-(6-methoxypyridin-3-yl)-3,4-dihydro-2H-chromen-3-yl]nicotinamide,
N-[(3S)-5-(6-methoxypyridin-3-yl)-3,4-dihydro-2H-chromen-3-yl]-6-(3,3,3-trifluoropropoxy)nicotinamide,
6-isopropoxy-N-[(2R)-8-pyridazin-4-yl-1,2,3,4-tetrahydronaphthalen-2-yl]nicotinamide,
N-[(3S)-5-(5-fluoro-6-methoxypyridin-3-yl)-3,4-dihydro-2H-chromen-3-yl]-5-methoxypyrazine-2-carboxamide,
N-[(3S)-5-pyridazin-4-yl-3,4-dihydro-2H-chromen-3-yl]-6-(2,2,2-trifluoroethoxy)nicotinamide,
N-[(3S)-5-pyridazin-4-yl-3,4-dihydro-2H-chromen-3-yl]-6-(3,3,3-trifluoropropoxy)nicotinamide,
6-isopropoxy-N-[(2R)-8-(2-methoxypyrimidin-5-yl)-1,2,3,4-tetrahydronaphthalen-2-yl]nicotinamide,
5-methoxy-N-[(3S)-5-(2-methoxypyrimidin-5-yl)-3,4-dihydro-2H-chromen-3-yl]pyrazine-2-carboxamide,
N-[(2R)-8-(2-methoxypyrimidin-5-yl)-1,2,3,4-tetrahydronaphthalen-2-yl]-6-(3,3,3-trifluoropropoxy)nicotinamide,
N-[(2R)-8-(2-methoxypyrimidin-5-yl)-1,2,3,4-tetrahydronaphthalen-2-yl]-6-(2,2,2-trifluoroethoxy)nicotinamide,
N-[(3S)-5-(2-methoxypyrimidin-5-yl)-3,4-dihydro-2H-chromen-3-yl]-6-(2,2,2-trifluoroethoxy)nicotinamide,
N-[(2R)-8-(2-fluoropyridin-3-yl)-1,2,3,4-tetrahydronaphthalen-2-yl]-6-(2,2,2-trifluoroethoxy)nicotinamide,
N-[(3S)-5-(5-fluoro-6-methoxypyridin-3-yl)-3,4-dihydro-2H-chromen-3-yl]-6-(2,2,2-trifluoroethoxy)nicotinamide,
N-[(3S)-5-(2-methoxypyrimidin-5-yl)-3,4-dihydro-2H-chromen-3-yl]-4-methyl-2-(2,2,2-trifluoroethoxy)pyrimidine-5-carboxamide,
N-[(2R)-8-(2-methoxypyrimidin-5-yl)-1,2,3,4-tetrahydronaphthalen-2-yl]-4-methyl-2-(2,2,2-trifluoroethoxy)pyrimidine-5-carboxamide,
N-[(3S)-5-imidazo[1,2-a]pyridin-6-yl-3,4-dihydro-2H-chromen-3-yl]-6-(2,2,2-trifluoroethoxy)nicotinamide,
2-isopropoxy-N-[(3S)-5-(2-methoxypyrimidin-5-yl)-3,4-dihydro-2H-chromen-3-yl]-4-methylpyrimidine-5-carboxamide,
N-[(3S)-5-(2-ethoxypyrimidin-5-yl)-3,4-dihydro-2H-chromen-3-yl]-6-(2,2,2-trifluoroethoxy)nicotinamide,
6-(cyclobutyloxy)-N-[(3S)-5-(5-fluoro-6-methoxypyridin-3-yl)-3,4-dihydro-2H-chromen-3-yl]nicotinamide,
N-[(3S)-5-(2-ethylpyrimidin-5-yl)-3,4-dihydro-2H-chromen-3-yl]-6-(2,2,2-trifluoroethoxy)nicotinamide,
N-[(3S)-5-(2-cyclopropylpyrimidin-5-yl)-3,4-dihydro-2H-chromen-3-yl]-6-(3-fluoropropoxy)nicotinamide,
N-[(3S)-5-(5-fluoro-6-methoxypyridin-3-yl)-3,4-dihydro-2H-chromen-3-yl]-6-(3,3,3-trifluoropropoxy)nicotinamide,
N-[(3S)-5-(3,6-dimethoxypyridazin-4-yl)-3,4-dihydro-2H-chromen-3-yl]-6-(2,2,2-trifluoroethoxy)nicotinamide,
N-[(3S)-5-(6-methylpyrazin-2-yl)-3,4-dihydro-2H-chromen-3-yl]-6-(2,2,2-trifluoroethoxy)nicotinamide,
6-(3-fluoropropoxy)-N-[(3S)-5-(2-methoxypyrimidin-5-yl)-3,4-dihydro-2H-chromen-3-yl]nicotinamide,
6-(3-fluoropropoxy)-N-[(3S)-5-(2-methylpyrimidin-5-yl)-3,4-dihydro-2H-chromen-3-yl]nicotinamide,
N-[(3S)-5-(2-methylpyrimidin-5-yl)-3,4-dihydro-2H-chromen-3-yl]-6-(2,2,2-trifluoroethoxy)nicotinamide,
2-isopropoxy-N-[(2R)-8-(2-methoxypyrimidin-5-yl)-1,2,3,4-tetrahydronaphthalen-2-yl]isonicotinamide,
2-isopropoxy-N-[(3S)-5-(2-methylpyrimidin-5-yl)-3,4-dihydro-2H-chromen-3-yl]isonicotinamide,
6-(cyclobutyloxy)-N-[(3S)-5-(2-methylpyrimidin-5-yl)-3,4-dihydro-2H-chromen-3-yl]nicotinamide,
6-(cyclobutyloxy)-N-[(3S)-5-(2-methoxypyrimidin-5-yl)-3,4-dihydro-2H-chromen-3-yl]nicotinamide,
2-isopropoxy-N-[(3S)-5-(2-methoxypyrimidin-5-yl)-3,4-dihydro-2H-chromen-3-yl]isonicotinamide,
N-[(3S)-5-(3,5-dimethylpyrazin-2-yl)-3,4-dihydro-2H-chromen-3-yl]-6-(3-fluoropropoxy)nicotinamide,
N-[(3S)-5-(2-cyclopropylpyrimidin-5-yl)-3,4-dihydro-2H-chromen-3-yl]-6-(2,2,2-trifluoroethoxy)nicotinamide,
$N^5$-[(3S)-5-(2-methoxypyrimidin-5-yl)-3,4-dihydro-2H-chromen-3-yl]-$N^2,N^2$-dipropylpyridine-2,5-dicarboxamide,
$N^5$-[(3S)-5-(2-methoxypyrimidin-5-yl)-3,4-dihydro-2H-chromen-3-yl]-$N^2$-(3-methylbutyl)pyridine-2,5-dicarboxamide,
$N^2$-isobutyl-$N^5$-[(3S)-5-(2-methoxypyrimidin-5-yl)-3,4-dihydro-2H-chromen-3-yl]-$N^2$-methylpyridine-2,5-dicarboxamide,
N-[(3S)-5-pyridin-4-yl-3,4-dihydro-2H-chromen-3-yl]-6-(pyrrolidin-1-ylcarbonyl)nicotinamide,
N-[(3S)-5-pyridin-4-yl-3,4-dihydro-2H-chromen-3-yl]-6-(1,3-thiazol-2-ylmethoxy)nicotinamide,
6-[(5-methylisoxazol-3-yl)methoxy]-N-[(3S)-5-pyridin-4-yl-3,4-dihydro-2H-chromen-3-yl]nicotinamide,
6-[(1-methyl-1H-imidazol-2-yl)methoxy]-N-[(3S)-5-pyridin-4-yl-3,4-dihydro-2H-chromen-3-yl]nicotinamide,
6-(cyclopentylsulfonyl)-N-[(3S)-5-pyridin-4-yl-3,4-dihydro-2H-chromen-3-yl]nicotinamide,
N-[(3S)-5-pyridin-4-yl-3,4-dihydro-2H-chromen-3-yl]-6-(pyridin-2-ylmethoxy)nicotinamide,
N-[(3S)-5-pyridin-4-yl-3,4-dihydro-2H-chromen-3-yl]-6-(pyridin-3-ylmethoxy)nicotinamide,
6-(pyrazin-2-ylmethoxy)-N-[(3S)-5-pyridin-4-yl-3,4-dihydro-2H-chromen-3-yl]nicotinamide, N-[(3S)-5-(2-methoxypyrimidin-5-yl)-3,4-dihydro-2H-chromen-3-yl]-6-(tetrahydrofuran-2-ylmethoxy)nicotinamide, N-[(3S)-5-(2-methoxypyrimidin-5-yl)-3,4-dihydro-2H-chromen-3-yl]-6-(tetrahydro-2H-pyran-2-ylmethoxy)nicotinamide, N-[(3S)-5-(2-methoxypyrimidin-5-yl)-3,4-dihydro-2H-chromen-3-yl]-6-(tetrahydro-2H-pyran-4-ylmethoxy)nicotinamide, 6-(but-2-yn-1-yloxy)-N-[(3S)-5-(2-methoxypyrimidin-5-yl)-3,4-dihydro-2H-chromen-3-yl]nicotinamide, $N^5$-[(3S)-5-(2-methoxypyrimidin-5-yl)-3,4-dihydro-2H-chromen-3-yl]-$N^2$-(3,3,3-trifluoropropyl)pyridine-2,5-dicarboxamide, 6-(2-methoxyethoxy)-N-[(3S)-5-pyridin-4-yl-3,4-dihydro-2H-chromen-3-yl]nicotinamide, 6-(oxetan-2-ylmethoxy)-N-[(3S)-5-pyridin-4-yl-3,4-dihydro-2H-chromen-3-yl]nicotinamide, 6-{[(2R)-2-methoxypropyl]oxy}-N-[(3S)-5-pyridin-4-yl,3,4-dihydro-2H-chromen-3-yl]nicotinamide, N-[(3S)-5-pyridin-4-yl-3,4-dihydro-2H-chromen-3-yl]-6-(tetrahydro-2H-pyran-4-yloxy)nicotinamide, $N^5$-[(3S)-5-pyridin-4-yl-3,4-dihydro-2H-chromen-3-yl]-$N^2$-(tetrahydro-2H-pyran-4-yl)pyridine-2,5-dicarboxamide, $N^5$-[(3S)-5-pyridin-4-yl-3,4-dihydro-2H-chromen-3-yl]-$N^2$-(2,2,2-trifluoroethyl)pyridine-2,5-dicarboxamide, $N^5$-[(3S)-5-pyridin-3-yl-3,4-dihydro-2H-chromen-3-yl]-$N^2$-(3,3,3-trifluoropropyl)pyridine-2,5-dicarboxamide, N-[(3S)-5-pyridin-3-yl-3,4-dihydro-2H-chromen-3-yl]-5-(tetrahydro-2H-pyran-4-yloxy)pyrazine-2-carboxamide, N-[(3S)-5-(6-methoxypyridin-3-yl)-3,4-dihydro-2H-chromen-3-yl]-6-(tetrahydro-2H-pyran-4-yloxy)nicotinamide, N-[(3S)-5-(6-methoxypyridin-3-yl)-3,4-dihydro-2H-chromen-3-yl]-6-(tetrahydro-2H-pyran-3-yloxy)nicotinamide, N-[(3S)-5-pyridin-4-yl-3,4-dihydro-2H-chromen-3-yl]-6-(tetrahydro-2H-pyran-3-yloxy)nicotinamide, 6-(2-methoxyethoxy)-N-[(3S)-5-pyridin-3-yl-3,4-dihydro-2H-chromen-3-yl]nicotinamide, 2-(2-methoxyethyl)-5-methyl-N-[(3S)-5-pyridin-3-yl-3,4-dihydro-2H-chromen-3-yl]-2H-1,2,3-triazole-4-carboxamide, 6-(oxetan-2-ylmethoxy)-N-[(3S)-5-pyridin-3-yl-3,4-dihydro-2H-chromen-3-yl]nicotinamide, 6-(2-methoxyethoxy)-N-[(3S)-5-(2-methoxypyridin-4-yl)-3,4-dihydro-2H-chromen-3-yl]nicotinamide, 6-(2-methoxyethoxy)-N-[(3S)-5-(2-methylpyrimidin-5-yl)-3,4-dihydro-2H-chromen-3-yl]nicotinamide, 6-(2-methoxyethoxy)-N-[(3S)-5-(3-methylpyridin-4-yl)-3,4-dihydro-2H-chromen-3-yl]nicotinamide, N-[(3S)-5-(6-fluoropyridin-3-yl)-3,4-dihydro-2H-chromen-3-yl]-6-(2-methoxyethoxy)nicotinamide, N-[(2R)-8-(2-fluoropyridin-3-yl)-1,2,3,4-tetrahydronaphthalen-2-yl]-6-(2-methoxyethoxy)nicotinamide, N-[(2R)-8-(2-fluoropyridin-3-yl)-1,2,3,4-tetrahydronaphthalen-2-yl]-6-(tetrahydro-2H-pyran-4-yloxy)nicotinamide, N-[(2R)-8-pyridazin-4-yl-1,2,3,4-tetrahydronaphthalen-2-yl]-6-(tetrahydro-2H-pyran-3-yloxy)nicotinamide, N-[(2R)-8-(6-methylpyridin-3-yl)-1,2,3,4-tetrahydronaphthalen-2-yl]-2-(tetrahydro-2H-pyran-3-yloxy)pyrimidine-5-carboxamide, 1-butyl-N-[(3S)-5-(5-fluoro-6-methoxypyridin-3-yl)-3,4-dihydro-2H-chromen-3-yl]-2-oxo-1,2-dihydropyridine-4-carboxamide, N-[(3S)-5-(5-fluoro-6-methoxypyridin-3-yl)-3,4-dihydro-2H-chromen-3-yl]-2-(tetrahydrofuran-3-yloxy)pyrimidine-5-carboxamide, 1-butyl-N-[(3S)-5-(2-methoxypyrimidin-5-yl)-3,4-dihydro-2H-chromen-3-yl]-2-oxo-1,2-dihydropyridine-4-carboxamide, N-[(3S)-5-(6-fluoro-5-methylpyridin-3-yl)-3,4-dihydro-2H-chromen-3-yl]-6-(tetrahydro-2H-pyran-3-yloxy)nicotinamide, 1-butyl-N-[(3S)-5-(6-fluoro-5-methylpyridin-3-yl)-3,4-dihydro-2H-chromen-3-yl]-2-oxo-1,2-dihydropyridine-4-carboxamide, N-[(3S)-5-(6-fluoro-5-methylpyridin-3-yl)-3,4-dihydro-2H-chromen-3-yl]-2-(tetrahydro-2H-pyran-3-yloxy)pyrimidine-5-carboxamide, N-[(2S)-8-(2-methoxypyrimidin-5-yl)-1,2,3,4-tetrahydronaphthalen-2-yl]-6-(tetrahydro-2H-pyran-4-yloxy)nicotinamide, N-[(3S)-5-(2-methylpyrimidin-5-yl)-3,4-dihydro-2H-chromen-3-yl]-6-(tetrahydro-2H-pyran-4-yloxy)nicotinamide, N-[(2R)-8-(2-methoxypyrimidin-5-yl)-1,2,3,4-tetrahydronaphthalen-2-yl]-6-(tetrahydro-2H-pyran-4-yloxy)nicotinamide, N-[(3S)-5-(2-methoxypyrimidin-5-yl)-3,4-dihydro-2H-chromen-3-yl]-6-(tetrahydro-2H-pyran-3-yloxy)nicotinamide, N-[(3S)-5-(2-methoxypyrimidin-5-yl)-3,4-dihydro-2H-chromen-3-yl]-6-(tetrahydrofuran-3-yloxy)nicotinamide, N-[(2R)-8-(2-methylpyrimidin-5-yl)-1,2,3,4-tetrahydronaphthalen-2-yl]-6-(tetrahydrofuran-3-yloxy)nicotinamide, N-[(2R)-8-(2-methylpyrimidin-5-yl)-1,2,3,4-tetrahydronaphthalen-2-yl]-6-(tetrahydro-2H-pyran-3-yloxy)nicotinamide, N-[(2R)-8-(2-methylpyrimidin-5-yl)-1,2,3,4-tetrahydronaphthalen-2-yl]-6-(tetrahydrofuran-2-ylmethoxy)nicotinamide, N-[(2R)-8-(2-methoxypyrimidin-5-yl)-1,2,3,4-tetrahydronaphthalen-2-yl]-6-[2-(2,2,2-trifluoroethoxy)ethoxy]nicotinamide, N-[(3S)-5-(2-methoxypyrimidin-5-yl)-3,4-dihydro-2H-chromen-3-yl]-6-[2-(2,2,2-trifluoroethoxy)ethoxy]nicotinamide, 6-(1,4-dioxan-2-ylmethoxy)-N-[(2R)-8-(2-fluoropyridin-3-yl)-1,2,3,4-tetrahydronaphthalen-2-yl]nicotinamide, 6-(1,4-dioxan-2-ylmethoxy)-N-[(3S)-5-(2-methoxypyridin-4-yl)-3,4-dihydro-2H-chromen-3-yl]nicotinamide, 6-(1,4-dioxan-2-ylmethoxy)-N-[(3S)-5-(5-fluoro-6-methoxypyridin-3-yl)-3,4-dihyrdo-2H-chromen-3-yl]nicotinamide, $N^5$-[(2R)-8-(2-methoxypyrimidin-5-yl)-1,2,3,4-tetrahydronaphthalen-2-yl]-$N^2$-(3,3,3-trifluoropropyl)pyridine-2,5-dicarboxamide, 6-(but-2-yn-1-yloxy)-N-[(2R)-8-(2-methoxypyrimidin-5-yl)-1,2,3,4-tetrahydronaphthalen-2-yl]nicotinamide, N-[(3S)-5-imidazo[1,2-a]pyridin-6-yl-3,4-dihydro-2H-chromen-3-yl]-6-(tetrahydro-2H-pyran-4-yloxy)nicotinamide, $N^2$-(4,4-difluorocyclohexyl)-$N^5$-[(3S)-5-(2-methoxypyrimidin-5-yl)-3,4-dihydro-2H-chromen-3-yl]pyridine-2,5-dicarboxamide, $N^5$-[(3S)-5-(2-methoxypyrimidin-5-yl)-3,4-dihydro-2H-chromen-3-yl]-$N^2$-(4,4,4-trifluorobutyl)pyridine-2,5-dicarboxamide, N-[(3S)-5-(2-methoxypyrimidin-5-yl)-3,4-dihydro-2H-chromen-3-yl]-2-[2-(2,2,2-trifluoroethoxy)ethoxy]isonicotinamide, $N^2$-methyl-$N^5$-[(3S)-5-(2-methylpyrimidin-5-yl)-3,4-dihydro-2H-chromen-3-yl]-$N^2$-(2,2,2-trifluoroethyl)pyridine-2,5-dicarboxamide, $N^5$-[(3S)-5-(2-ethylpyrimidin-5-yl)-3,4-dihydro-2H-chromen-3-yl]-$N^2$-(3,3,3-trifluoropropyl)pyridine-2,5-dicarboxamide, N-{(3S)-5-[6-(methylsulfonyl)pyridin-3-yl]-3,4-dihydro-2H-chromen-3-yl}-6-[2-(2,2,2-trifluoroethoxy)ethoxy]nicotinamide, N-[(3S)-5-(6-cyanopyridin-3-yl)-3,4-dihydro-2H-chromen-3-yl]-6-[2-(2,2,2-trifluoroethoxy)ethoxy]nicotinamide, N-[(3S)-5-(2-cyclopropylpyrimidin-5-yl)-3,4-dihydro-2H-chromen-3-yl]-6-[2-(2,2,2-trifluoroethoxy)ethoxy]nicotinamide, N-[(3S)-5-(2-ethylpyrimidin-5-yl)-3,4-dihydro-2H-chromen-3-yl]-6-[2-(2,2,2-trifluoroethoxy)ethoxy]nicotinamide, $N^5$-[(3S)-5-(5-fluoro-6-methoxypyridin-3-yl)-3,4-dihydro-2H-chromen-3-yl]-$N^2$-(3,3,3-trifluoropropyl)pyridine-2,5-dicarboxamide, N-[(3S)-5-(5-fluoro-6-methoxypyridin-3-yl)-3,4-dihydro-2H-chromen-3-yl]-6-[2-(2,2,2-trifluoroethoxy)ethoxy]nicotinamide, 6-(cyclopentylsulfonyl)-N-[(3S)-5-(2-methoxypyrimidin-5-yl)-3,4-dihydro-2H-chromen-3-yl]nicotinamide, N-[(3S)-5-(6-methylpyrazin-2-yl)-3,4-dihydro-2H-chromen-3-yl]-6-[2-(2,2,2-trifluoroethoxy)ethoxy]nicotinamide, $N^5$-[(3S)-5-(2-methylpyrimidin-5-yl)-3,4-dihydro-2H-chromen-3-yl]-$N^2$-(3,3,3-trifluoropropyl)pyridine-2,5-dicarboxamide, 6-(2-isopropoxyethoxy)-N-[(3S)-5-(2-methoxypyrimidin-5-yl)-3,4-dihydro-2H-chromen-3-yl]nicotinamide, 6-(2-isopropoxyethoxy)-N-[(3S)-5-(2-methylpyrimidin-5-yl)-3,4-dihydro-2H-chromen-3-yl]nicotinamide, $N^2$-(3-isopropoxypropyl)-$N^5$-[(3S)-5-(2-methylpyrimidin-5-yl)-3,4-dihydro-2H-chromen-3-yl]pyridine-2,5-dicarboxamide, $N^2$-(3-isopropoxypropyl)-$N^5$-[(3S)-5-(2-methoxypyrimidin-5-yl)-3,4-dihydro-2H-chromen-3-yl]pyridine-2,5-dicarboxamide, $N^5$-[(3S)-5-(2-methylpyrimidin-5-yl)-3,4-dihydro-2H-chromen-3-yl]-$N^2$-(4,4,4-trifluorobutyl)pyridine-2,5-dicarboxamide, N-[(3S)-5-(2-methylpyrimidin-5-yl)-3,4-dihydro-2H-chromen-3-yl]-6-[2-(2,2,2-trifluoroethoxy)ethoxy]nicotinamide, N-[(2R)-8-(2-methoxypyrimidin-5-yl)-1,2,3,4-tetrahydronaphthalen-2-yl]-2-[2-(2,2,2-trifluoroethoxy)ethoxy]isonicotinamide, $N^5$-[(3S)-5-(2-methoxypyrimidin-5-yl)-3,4-dihydro-2H-chromen-3-yl]-$N^2$-methyl-$N^2$-(2,2,2-trifluoroethyl)pyridine-2,5-dicarboxamide, $N^5$-[(3S)-5-(5-fluoro-6-methoxypyridin-3-yl)-3,4-dihydro-2H-chromen-3-yl]-$N^2$-methyl-$N^2$-(2,2,2-trifluoroethyl)pyridine-2,5-dicarboxamide, N-[(3S)-5-(5-fluoro-6-methoxypyridin-3-yl)-3,4-dihydro-2H-chromen-3-yl]-6-[(2,2,2-trifluoroethoxy)methyl]nicotinamide, N-[(3S)-5-(2-methoxypyrimidin-5-yl)-3,4-dihydro-2H-chromen-3-yl]-6-[(2,2,2-trifluoroethoxy)methyl]nicotinamide, N-[(3S)-5-(2-methoxypyrimidin-5-yl)-3,4-dihydro-2H-chromen-3-yl]-2-[(3,3,3-trifluoropropyl)amino]pyrimidine-5-carboxamide, $N^5$-[(3S)-5-(2-cyclopropylpyrimidin-5-yl)-3,4-dihydro-2H-chromen-3-yl]-$N^2$-methyl-$N^2$-(2,2,2-trifluoroethyl)pyridine-2,5-dicarboxamide, $N^5$-[(3S)-5-(2-cyclopropylpyrimidin-5-yl)-3,4-dihydro-2H-chromen-3-yl]-$N^2$-(3,3,3-trifluoropropyl)pyridine-2,5-dicarboxamide, $N^5$-[(3S)-5-(2-cyclopropylpyrimidin-5-yl)-3,4-dihydro-2H-chromen-3-yl]-$N^2$-methyl-$N^2$-(3,3,3-trifluoropropyl)pyridine-2,5-dicarboxamide, N-[(3S)-5-(2-cyclopropylpyrimidin-5-yl)-3,4-dihydro-2H-chromen-3-yl]-2-oxo-1-(3,3,3-trifluoropropyl)-1,2-dihydropyridine-4-carboxamide, N-[(3S)-5-(5-fluoro-6-methoxypyridin-3-yl)-3,4-dihydro-2H-chromen-3-yl]-2-[(3,3,3-trifluoropropyl)amino]pyrimidine-5-carboxamide, N-[(3S)-5-(2-methylpyrimidin-5-yl)-3,4-dihydro-2H-chromen-3-yl]-2-[(3,3,3-trifluoropropyl)amino]pyrimidine-5-carboxamide, N-[(3S)-5-(3,5-dimethylpyrazin-2-yl)-3,4-dihydro-2H-chromen-3-yl]-6-[2-(2,2,2-trifluoroethoxy)ethoxy]nicotinamide, N-[(3S)-5-(2-methylpyrimidin-5-yl)-3,4-dihydro-2H-chromen-3-yl]-6-[(2,2,2-trifluoroethoxy)methyl]nicotinamide, 2-methoxy-N,N-dimethyl-5-[(3S)-3-({[6-(tetrahydro-2H-pyran-4-yloxy)pyridin-3-yl]carbonyl}amino)-3,4-dihydro-2H-chromen-5-yl]nicotinamide, 5-[(3S)-3-{[(6-isopropoxypyridin-3-yl)carbonyl]amino}-3,4-dihydro-2H-chromen-5-yl]-2-methoxy-N-methylnicotinamide, 2-methoxy-N-methyl-5-[(3S)-3-({[6-(tetrahydro-2H-pyran-4-yloxy)pyridin-3-yl]carbonyl}amino)-3,4-dihydro-2H-chromen-5-yl]nicotinamide, 5-[(3S)-3-{[(6-isopropoxypyridin-3-yl)carbonyl]amino}-3,4-dihydro-2H-chromen-5-yl]-2-methoxy-N,N-dimethylnicotinamide, 2-methoxy-N,N-dimethyl-5-[(3S)-3-({[6-(2,2,2-trifluoroethoxy)pyridin-3-yl]carbonyl}amino)-3,4-dihydro-2H-chromen-5-yl]nicotinamide, N,N-dimethyl-5-{(3S)-3-[({6-[2-(2,2,2-trifluoroethoxy)ethoxy]pyridin-3-yl}carbonyl)amino]-3,4-dihydro-2H-chromen-5-yl}pyrimidine-2-carboxamide, N-{(3S)-5-[6-(hydroxymethyl)pyridin-3-yl]-3,4-dihydro-2H-chromen-3-yl}-6-[2-(2,2,2-trifluoroethoxy)ethoxy]nicotinamide, 6-(3-fluoropropoxy)-N-{(3S)-5-[6-(hydroxymethyl)pyridin-3-yl]-3,4-dihydro-2H-chromen-3-yl}nicotinamide, N-{(3S)-5-[6-(hydroxymethyl)pyridin-3-yl]-3,4-dihydro-2H-chromen-3-yl}-6-(2,2,2-trifluoroethoxy)nicotinamide, and N-{(3S)-5-[5-(hydroxymethyl)pyrazin-2-yl]-3,4-dihydro-2H-chromen-3-yl}-6-[2-(2,2,2-trifluoroethoxy)ethoxy]nicotinamide, or pharmaceutically-acceptable salts thereof.

For the avoidance of doubt the present invention relates to any one of the specific compounds mentioned above.

The present invention relates to the compounds of formula I or Ia as hereinbefore defined as is well as to pharmaceutical acceptable salts thereof. Salts for use in pharmaceutical compositions will be pharmaceutically acceptable salts, but other salts may be useful in the production of the compounds of formula I or Ia.

A suitable pharmaceutically acceptable salt of the compounds of the invention is, for example, an acid-addition salt, for example a salt with an inorganic or organic acid. In addition, a suitable pharmaceutically acceptable salt of the compounds of the invention is an alkali metal salt, an alkaline earth metal salt or a salt with an organic base. Other pharmaceutically acceptable salts and methods of preparing these salts may be found in, for example, Remington's Pharmaceutical Sciences (18th Edition, Mack Publishing Co.).

The compounds of the present invention may also exists as solvents, solvated hydrates or co crystals.

The compounds of the invention may exhibit tautomerism. All tautomeric forms and mixtures thereof are included within the scope of the invention.

The compounds of the invention may also contain one or more asymmetric carbon atoms and may therefore exhibit optical and/or diastereoisomerism. Diastereoisomers may be separated using conventional techniques, e.g. chromatography or fractional crystallisation. The various stereoisomers may be isolated by separation of a racemic or other mixture of the compounds using conventional, e.g. fractional crystallisation or HPLC, techniques. Alternatively the desired optical isomers may be made by reaction of the appropriate optically active starting materials under conditions which will not cause racemisation or epimerisation, or by derivatisation, for example with a homochiral acid followed by separation of the diastereomeric esters by conventional means (e.g. HPLC, chromatography over silica). All stereoisomers are included within the scope of the invention.

Compounds of the present invention have been named with the aid of computer software (ACDLabs 8.0 or 9.0/Name (IUPAC)).

Process

Another object of the invention relates to processes (a), (b), (c), (d) or (e) for the preparation of compounds of general formula I or Ia and salts thereof.

(a) Acylation of a compound of formula II, with an acylating reagent such as a compound of formula III, wherein halo is fluoro, chloro or bromo and $R_1$, $R_2$, and X are as defined in formula I or Ia.

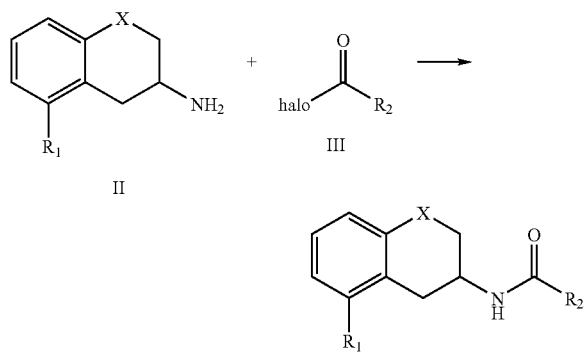

The reaction may be carried out using a suitable acylating reagent such as an acyl chloride, in a suitable solvent such as dichloromethane, chloroform, toluene or acetonitrile at a temperature between −20° C. and reflux. The reaction is advantageously effected by the presence of a base. A suitable base may be an organic amine base such as pyridine, 2,6-lutidine, collidine, triethylamine, morpholine, N-methylmorpholine, diazabicyclo[5.4.0]undec-7-ene or tetramethylguanidine or an alkali metal or an alkaline earth metal carbonate or hydroxide such as sodium carbonate, potassium carbonate, calcium carbonate, sodium hydroxide or potassium hydroxide. The reaction may be aided by the presence of 4-dimethylaminopyridine.

(b) Acylation of a compound of formula II, with a suitable carboxylic acid IV, wherein $R_1$, $R_2$, and X are as defined in formula I or Ia.

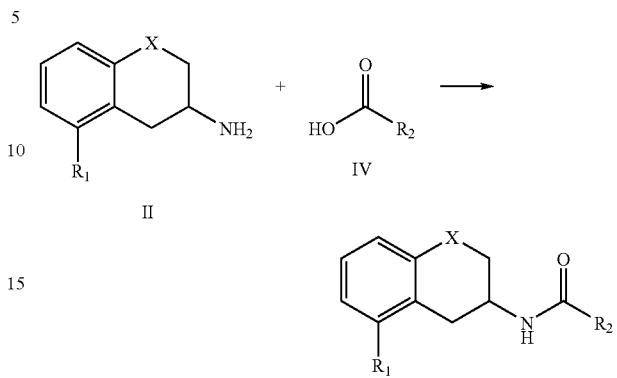

The transformation may be performed using a suitable activating reagent such as 2-(1H-benzotriazole-1-yl) -1,1,3,3-tetramethyluronium hexafluorophosphate or N,N'-carbonyldiimidazole with a suitable base such as triethylamine or diisopropylethylamine. The reaction may be performed in a suitable solvent such as dimethylformamide, acetonitrile or dichloromethane at a temperature between −20° C. and reflux.

(c) Acylation of a compound of formula II, with a suitable carboxylic acid ester V, wherein $R_1$, $R_2$, and X are as defined in formula I or Ia.

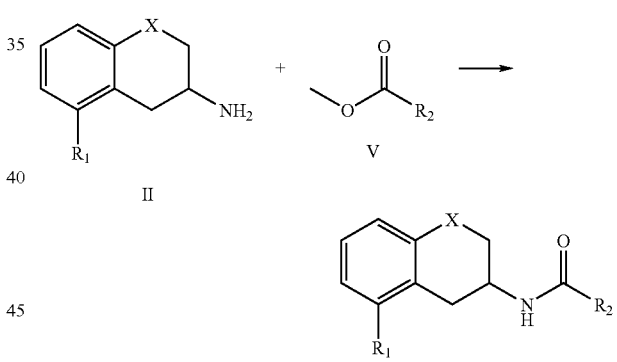

The transformation may be performed using a suitable activating reagent such as trimethylaluminium in a suitable solvent such as toluene, dichloromethane or dichloroethane at a temperature between 0 to 80° C.

(d) Alkoxylation of a chlorinated heterocycle of formula VI (where A is a pyrimidine or pyrazine ring) using a suitable alcohol VII in the presence of a strong base, wherein $R_1$, $R_2$, $R_{14}$, and X are as defined in formula I or Ia.

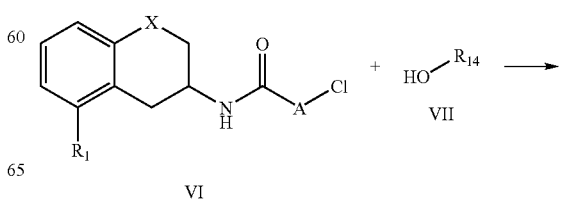

-continued

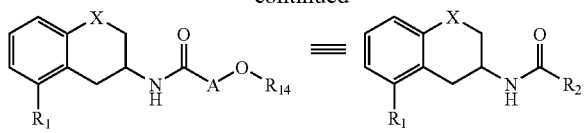

The transformation may be performed using a suitable strong base such as potassium tert-butoxide or sodium hydride in a suitable polar aprotic organic solvent such as tetrahydrofuran or N,N-dimethylformamide at a temperature between 0 to 65° C.

e) Arylation of a chromane- or tetralin borate VIII with a suitable halopyridine, halopyrimidine or halopyrazine IX, where halo is bromo or chloro (Suzuki cross coupling reaction), wherein $R_1$, $R_2$, and X are as defined in formula I or Ia.

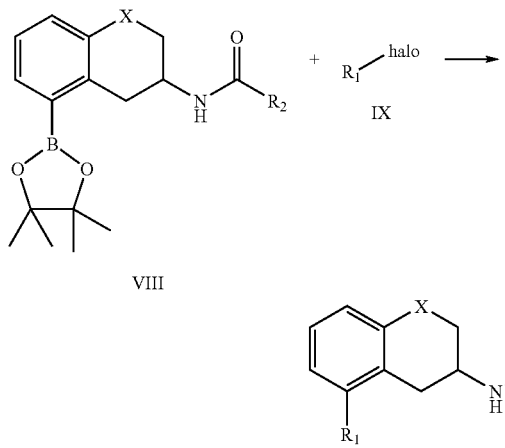

The transformation may be performed using a suitable palladium catalyst such as 1,1'-bis(diphenylphosphino)ferrocene-palladium(II)dichloride dichloromethane complex or dichloro[1,1'bis(di-tert-butylphosphino)ferrocene]palladium(II) and an inorganic base such as potassium carbonate or potassium phosphate. The reaction may be carried out in a suitable solvent such as isopropanol or dioxane, while the solvent may contain water, at a temperature between 80 to 150° C., optionally in a microwave synthesizer.

Protection and deprotection of functional groups may take place before or after any of the reaction steps described hereinbefore.

Protecting groups may be removed in accordance with techniques which are well known to those skilled in the art and as described hereinafter.

The use of protecting groups is fully described in "Protective Groups in Organic Chemistry", edited by J.W.F. McOmie, Plenum Press (1973), and "Protective Groups in Organic Synthesis", 3$^{rd}$ edition, T. W. Greene & P. G. M. Wutz, Wiley-Interscience (1999).

Persons skilled in the art will appreciate that, in order to obtain compounds of the invention in an alternative, and, on some occasions, more convenient, manner, the individual process steps mentioned herein may be performed in a different order, and/or the individual reactions may be performed at a different stage in the overall route (i.e. substituents may be added to and/or chemical transformations performed upon, different intermediates to those associated hereinbefore with a particular reaction). This will depend inter alia on factors such as the nature of other functional groups present in a particular substrate, the availability of key intermediates and the protecting group strategy (if any) to be adopted. Clearly, the type of chemistry involved will influence the choice of reagent that is used in the said synthetic steps, the need, and type, of protecting groups that are employed, and the sequence for accomplishing the synthesis.

It will also be appreciated by those skilled in the art that, although certain protected derivatives of compounds of formula I, which may be made prior to a final deprotection stage, may not possess pharmacological activity as such, they may be administered parenterally or orally and thereafter metabolised in the body to form compounds of the invention which are pharmacologically active. Such derivatives may therefore be described as "prodrugs". Moreover, certain compounds of formula I may act as prodrugs of other compounds of formula I.

All prodrugs of compounds of formula I are included within the scope of the invention.

Intermediates

A further embodiment of the invention relates to compounds selected from the group consisting of
(3S)-3-(Dibenzylamino)-3,4-dihydro-2H-chromen-5-yl trifluoromethanesulfonate,
(3S)—N,N-Dibenzyl-5-pyridin-4-ylchroman-3-amine,
(3S)-5-Pyridin-4-ylchroman-3-amine,
(2R)-8-Pyridin-4-yl-1,2,3,4-tetrahydronaphthalen-2-amine,
(3S)—N,N-dibenzyl-5-pyridin-3-ylchroman-3-amine,
(3S)-5-pyridin-3-ylchroman-3-amine,
(3S)—N,N-dibenzyl-5-pyridin-2-ylchroman-3-amine,
(3S)-5-pyridin-2-ylchroman-3-amine,
(2R)—N,N-Dibenzyl-8-(1-methyl-1H-pyrazol-4-yl)-1,2,3,4-tetrahydronaphthalen-2-amine,
(2R)-8-(1-Methyl-1H-pyrazol-4-yl)-1,2,3,4-tetrahydronaphthalen-2-amine,
(2R)—N,N-Dibenzyl-8-(3,5-dimethyl-1H-pyrazol-4-yl)-1,2,3,4-tetrahydronaphthalen-2-amine,
(2R)-8-(3,5-Dimethyl-1H-pyrazol-4-yl)-1,2,3,4-tetrahydronaphthalen-2-amine,
(2R)-8-(3,5-dimethylisoxazol-4-yl)-1,2,3,4-tetrahydronaphthalen-2-amine,
(3S)—N,N-dibenzyl-5-(4,4,5,5-tetramethyl-1,3,2-dioxaborolan-2-yl)chroman-3-amine,
(3S)-5-(4,4,5,5-tetramethyl-1,3,2-dioxaborolan-2-yl)chroman-3-amine,
[(7R)-7-(dibenzylamino)-5,6,7,8-tetrahydronaphthalen-1-yl]boronic acid,
(2R)—N,N-dibenzyl-8-(4,4,5,5-tetramethyl-1,3,2-dioxaborolan-2-yl)-1,2,3,4-tetrahydronaphthalen-2-amine,
(3S)—N,N-dibenzyl-5-(2-fluoropyridin-4-yl)chroman-3-amine,
(3S)-5-(2-fluoropyridin-4-yl)chroman-3-amine,
(3S)—N,N-dibenzyl-5-(2-methoxypyridin-4-yl)chroman-3-amine,
(3S)-5-(2-methoxypyridin-4-yl)chroman-3-amine,
(3S)—N,N-dibenzyl-5-(3-methylpyridin-4-yl)chroman-3-amine,
(3S)-5-(3-methylpyridin-4-yl)chroman-3-amine,
(3S)—N,N-dibenzyl-5-(6-methoxypyridin-3-yl)chroman-3-amine,
(3S)-5-(6-methoxypyridin-3-yl)chroman-3-amine,
(3S)—N,N-dibenzyl-5-(6-fluoropyridin-3-yl)chroman-3-amine,
(3S)-5-(6-fluoropyridin-3-yl)chroman-3-amine,
{5-[(3S)-3-(dibenzylamino)-3,4-dihydro-2H-chromen-5-yl]pyridin-2-yl}methanol, {5-[(3S)-3-amino-3,4-dihydro-2H-chromen-5-yl]pyridin-2-yl}methanol,
(3S)—N,N-dibenzyl-5-(2-methoxypyridin-3-yl)chroman-3-amine,
(3S)-5-(2-methoxypyridin-3-yl)chroman-3-amine,
(3S)—N,N-dibenzyl-5-(5-fluoro-6-methoxypyridin-3-yl)chroman-3-amine,
(3S)-5-(5-fluoro-6-methoxypyridin-3-yl)chroman-3-amine,
(3S)—N,N-dibenzyl-5-(6-fluoro-5-methylpyridin-3-yl)chroman-3-amine,
(3S)-5-(6-fluoro-5-methylpyridin-3-yl)chroman-3-amine,
5-bromo-2-methoxy-N,N-dimethylnicotinamide,
5-[(3S)-3-(dibenzylamino)-3,4-dihydro-2H-chromen-5-yl]-2-methoxy-N,N-dimethylnicotinamide,
5-[(3S)-3-amino-3,4-dihydro-2H-chromen-5-yl]-2-methoxy-N,N-dimethylnicotinamide,
5-bromo-2-methoxy-N-methylnicotinamide,
5-[(3S)-3-(dibenzylamino)-3,4-dihydro-2H-chromen-5-yl]-2-methoxy-N-methylnicotinamide,
5-[(3S)-3-amino-3,4-dihydro-2H-chromen-5-yl]-2-methoxy-N-methylnicotinamide,
(3S)—N,N-dibenzyl-5-pyrimidin-5-ylchroman-3-amine,
(3S)-5-pyrimidin-5-ylchroman-3-amine,
(3S)—N,N-dibenzyl-5-(2-methoxypyrimidin-5-yl)chroman-3-amine,
(3S)-5-(2-methoxypyrimidin-5-yl)chroman-3-amine,
(3S)—N,N-dibenzyl-5-(2-methylpyrimidin-5-yl)chroman-3-amine,
(3S)-5-(2-methylpyrimidin-5-yl)chroman-3-amine,
(3S)—N,N-dibenzyl-5-(2-ethylpyrimidin-5-yl)chroman-3-amine,
(3S)-5-(2-ethylpyrimidin-5-yl)chroman-3-amine,
(3S)—N,N-dibenzyl-5-(2-cyclopropylpyrimidin-5-yl)chroman-3-amine,
(3S)-5-(2-cyclopropylpyrimidin-5-yl)chroman-3-amine,
(3S)—N,N-dibenzyl-5-(2-ethoxypyrimidin-5-yl)chroman-3-amine,
(3S)-5-(2-ethoxypyrimidin-5-yl)chroman-3-amine,
5-[(3S)-3-(dibenzylamino)-3,4-dihydro-2H-chromen-5-yl]-N,N-dimethylpyrimidine-2-carboxamide,
5-[(3S)-3-amino-3,4-dihydro-2H-chromen-5-yl]-N,N-dimethylpyrimidine-2-carboxamide,
(3S)—N,N-dibenzyl-5-pyridazin-4-ylchroman-3-amine,
(3S)-5-pyridazin-4-ylchroman-3-amine,
(3S)—N,N-dibenzyl-5-(3,6-dimethoxypyridazin-4-yl)chroman-3-amine,
(3S)-5-(3,6-dimethoxypyridazin-4-yl)chroman-3-amine,
(3S)—N,N-dibenzyl-5-(6-methylpyrazin-2-yl)chroman-3-amine,
(3S)-5-(6-methylpyrazin-2-yl)chroman-3-amine,
(3S)—N,N-dibenzyl-5-(3,5-dimethylpyrazin-2-yl)chroman-3-amine,
(3S)-5-(3,5-dimethylpyrazin-2-yl)chroman-3-amine,
(3S)—N,N-dibenzyl-5-imidazo[1,2-c]pyridin-6-ylchroman-3-amine,
(3S)-5-imidazo[1,2-a]pyridin-6-ylchroman-3-amine,
(2R)-8-(3-fluoropyridin-4-yl)-1,2,3,4-tetrahydronaphthalen-2-amine,
(2R)—N,N-dibenzyl-8-(2-fluoropyridin-3-yl)-1,2,3,4-tetrahydronaphthalen-2-amine,
(2R)-8-(2-fluoropyridin-3-yl)-1,2,3,4-tetrahydronaphthalen-2-amine,
(2R)—N,N-dibenzyl-8-(6-methylpyridin-3-yl)-1,2,3,4-tetrahydronaphthalen-2-amine,
(2R)-8-(6-methylpyridin-3-yl)-1,2,3,4-tetrahydronaphthalen-2-amine,
(2R)—N,N-dibenzyl-8-pyridazin-4-yl-1,2,3,4-tetrahydronaphthalen-2-amine,
(2R)-8-pyridazin-4-yl-1,2,3,4-tetrahydronaphthalen-2-amine,
(2S)—N,N-dibenzyl-8-(2-methoxypyrimidin-5-yl)-1,2,3,4-tetrahydronaphthalen-2-amine,
(2S)-8-(2-methoxypyrimidin-5-yl)-1,2,3,4-tetrahydronaphthalen-2-amine,
(2R)—N,N-dibenzyl-8-(2-methoxypyrimidin-5-yl)-1,2,3,4-tetrahydronaphthalen-2-amine,
(2R)-8-(2-methoxypyrimidin-5-yl)-1,2,3,4-tetrahydronaphthalen-2-amine,
(2R)—N,N-dibenzyl-8-(2-methylpyrimidin-5-yl)-1,2,3,4-tetrahydronaphthalen-2-amine,
(2R)-8-(2-methylpyrimidin-5-yl)-1,2,3,4-tetrahydronaphthalen-2-amine,
(5-chloropyrazin-2-yl)methanol,
6-(3,3,3-trifluoropropoxy)nicotinic acid,
6-(Butylthio)nicotinic acid,
Methyl 6-(butylsulfonyl)nicotinate,
6-isobutoxynicotinic acid,
6-(2,2-difluoroethoxy)nicotinic acid,
6-[2-fluoro-1-(fluoromethyl)ethoxy]nicotinic acid,
2-(cyclopentyloxy)pyrimidine-5-carboxylic acid,
6-(cyclobutyloxy)nicotinic acid,
6-(cyclopropylmethoxy)nicotinic acid,
2-isopropoxypyrimidine-5-carboxylic acid,
6-(3-fluoropropoxy)nicotinic acid,
5-(3,3,3-trifluoropropoxy)pyrazine-2-carboxylic acid,
6-(dipropylcarbamoyl)nicotinic acid,
6-[(3-methylbutyl)carbamoyl]nicotinic acid,
6-[isobutyl(methyl)carbamoyl]nicotinic acid,
methyl 6-[(3,3,3-trifluoropropyl)carbamoyl]nicotinate,
6-[(3,3,3-trifluoropropyl)carbamoyl]nicotinic acid,
6-[methyl(3,3,3-trifluoropropyl)carbamoyl]nicotinic acid,
methyl 6-[(2,2,2-trifluoroethyl)carbamoyl]nicotinate,
methyl 6-[methyl(2,2,2-trifluoroethyl)carbamoyl]nicotinate,
6-[methyl(2,2,2-trifluoroethyl)carbamoyl]nicotinic acid,
6-[(4,4-difluorocyclohexyl)carbamoyl]nicotinic acid,
6-[(4,4,4-trifluorobutyl)carbamoyl]nicotinic acid,
6-(1,3-thiazol-2-ylmethoxy)nicotinic acid,
6-[(5-methylisoxazol-3-yl)methoxy]nicotinic acid,
6-[(1-methyl-1H-imidazol-2-yl)methoxy]nicotinic acid,
6-(pyridin-2-ylmethoxy)nicotinic acid,
6-(pyridin-3-ylmethoxy)nicotinic acid,
6-(pyrazin-2-ylmethoxy)nicotinic acid,
6-(cyclopentylsulfonyl)nicotinic acid,
6-(tetrahydro-2H-pyran-2-ylmethoxy)nicotinic acid,
6-(tetrahydrofuran-2-ylmethoxy)nicotinic acid,
6-(oxetan-2-ylmethoxy)nicotinic acid,
6-(tetrahydro-2H-pyran-3-yloxy)nicotinic acid,
6-(tetrahydrofuran-3-yloxy)nicotinic acid,
6-(1,4-dioxan-2-ylmethoxy)nicotinic acid,
6-(tetrahydro-2H-pyran-4-ylmethoxy)nicotinic acid,
6-{[(2S)-2-methoxypropyl]oxy}nicotinic acid,
6-[2-(2,2,2-trifluoroethoxy)ethoxy]nicotinic acid,
6-(2-isopropoxyethoxy)nicotinic acid,
5-bromo-N-(3,3,3-trifluoropropyl)pyrimidin-2-amine,
2-[(3,3,3-trifluoropropyl)amino]pyrimidine-5-carboxylic acid,
6-[(2,2,2-trifluoroethoxy)methyl]nicotinic acid,
2-[2-(2,2,2-trifluoroethoxy)ethoxy]isonicotinic acid,
1-butyl-2-oxo-1,2-dihydropyridine-4-carboxylic acid,
2-oxo-1-(3,3,3-trifluoropropyl)-1,2-dihydropyridine-4-carboxylic acid,
ethyl 2-isobutyl-5-methyl-2H-1,2,3-triazole-4-carboxylate ethyl 2-(2-methoxyethyl)-5-methyl-2H-1,2,3-triazole-4-carboxylate and methyl 6-(tetrahydro-2H-pyran-4-ylcarbamoyl)nicotinate.

Another embodiment relates to the use of these compounds as intermediates in the preparation of the compounds of the invention.

Medical Use

The compounds of the invention exhibit voltage-gated sodium channel inhibiting activity, especially Nav1.7 blocking activity, for example as demonstrated in the test described below. The present invention relates to the compounds of formula I or Ia, which inhibit any sodium channel Modulation of voltage-gated sodium channels by pharmacological or genetical tools points to a central role for distinct voltage-gated sodium channels in several disease models.

A mouse line has been generated which through advanced molecular biology technologies eliminates the functional expression of Nav1.7 in DRG neurons that express Nav1.8 (Proceedings of the National Academy of Sciences USA (2004) 101(34) 12706-12711). This mouse line shows greatly reduced pain responses in several pain behaviour models. Likewise, Herpes-vector mediated knockdown of Nav1.7 in primary afferents of wildtype mice results in a decrease in inflammatory hyperalgesia (Human Gene Therapy (2005) 16(2) 271-277).

Antagonists of NaV channels have been shown to be useful for treating a variety of conditions, including acute and chronic nociceptive, visceral, inflammatory, central and peripheral neuropathic pain. More specifically, modulators of NaV activity are currently used or being tested in the clinic as anaesthetics, including local anaesthetics (Pain (2000) 87(1) 7-17), neuropathic pain relievers (European Journal of Pain (2002) 6(Supplement 1) 61-68), acute pain relievers (The Cochrane Database of Systematic Reviews (2005) 3), chronic pain relievers (Pharmacotherapy (2001) 21(9) 1070-1081), inflammatory pain relievers (Proceedings of the National Academy of Sciences USA (1999) 96(14) 7645-7649), headache relievers (Headache (2001) 41(Supplement 1) S25-S32).

The compounds of the invention are thus expected to be useful in both the prophylaxis and the treatment of a condition which is effected or facilitated by inhibition of voltage-gated sodium channels, in particular pain, such as acute and chronic pain disorders including but not limited to widespread pain, localized pain, nociceptive pain, inflammatory pain, central pain, central and peripheral neuropathic pain, central and peripheral neurogenic pain, central and peripheral neuralgia, low back pain, postoperative pain, visceral pain, pelvic pain, allodynia, anesthesia dolorosa, causalgia, dysesthesia, fibromyalgia, hyperalgesia, hyperesthesia, hyperpathia, ischemic pain, sciatic pain, pain associated with cystitis, including but not limited to interstitial cystitis, pain associated with multiple sclerosis, pain associated with arthritis, pain associated with osteoarthritis, pain associated with rheumatoid arthritis and pain associated with cancer.

Other indications that may be treated with the compounds of the inventions are, but not limited to, migraine, pruritus, fibromyalgia, tinnitus and epilepsy.

The compounds of the present invention may be administered alone or in combination with other compounds, especially therapeutically active compounds.

The compounds of the present invention may for example be combined with one or more of the following therapeutically active compounds:
proton pump inhibitors such as omeprazole, lansoprazole, rabeprazole, tentorpazole, pantoprazole, esomeprazole, revaprazan or sorprazan.

Thus one embodiment of the invention relates to a combination wherein a compound of formula (I) or (Ia) or a pharmaceutically acceptable salt, solvate or in vivo hydrolysable ester, solvates, hydrated solvates, hydrates or co crystals thereof, or a pharmaceutical composition or formulation comprising a compound of formula (I) or (Ia) is administered concurrently, simultaneously, sequentially or separately with another pharmaceutically active compound or compounds selected from the following:

(i) antidepressants such as agomelatine, amitriptyline, amoxapine, bupropion, citalopram, clomipramine, desipramine, doxepin duloxetine, elzasonan, escitalopram, fluvoxamine, fluoxetine, gepirone, imipramine, ipsapirone, maprotiline, nortriptyline, nefazodone, paroxetine, phenelzine, protriptyline, ramelteon, reboxetine, robalzotan, sertraline, sibutramine, thionisoxetine, tranylcypromaine, trazodone, trimipramine, venlafaxine and equivalents and pharmaceutically active isomer(s) and metabolite(s) thereof.

(ii) atypical antipsychotics including for example quetiapine and pharmaceutically active isomer(s) and metabolite(s) thereof.

(iii) antipsychotics including for example amisulpride, aripiprazole, asenapine, benzisoxidil, bifeprunox, carbamazepine, clozapine, chlorpromazine, debenzapine, divalproex, duloxetine, eszopiclone, haloperidol, iloperidone, lamotrigine, loxapine, mesoridazine, olanzapine, paliperidone, perlapine, perphenazine, phenothiazine, phenylbutylpiperidine, pimozide, prochlorperazine, risperidone, sertindole, sulpiride, suproclone, suriclone, thioridazine, trifluoperazine, trimetozine, valproate, valproic acid, zopiclone, zotepine, ziprasidone and equivalents and pharmaceutically active isomer(s) and metabolite(s) thereof.

(iv) anxiolytics including for example alnespirone, azapirones, benzodiazepines, barbiturates such as adinazolam, alprazolam, balezepam, bentazepam, bromazepam, brotizolam, buspirone, clonazepam, clorazepate, chlordiazepoxide, cyprazepam, diazepam, diphenhydramine, estazolam, fenobam, flunitrazepam, flurazepam, fosazepam, lorazepam, lormetazepam, meprobamate, midazolam, nitrazepam, oxazepam, prazepam, quazepam, reclazepam, tracazolate, trepipam, temazepam, triazolam, uldazepam, zolazepam and equivalents and pharmaceutically active isomer(s) and metabolite(s) thereof.

(v) anticonvulsants including for example carbamazepine, valproate, lamotrogine, gabapentin and equivalents and pharmaceutically active isomer(s) and metabolite(s) thereof.

(vi) Alzheimer's therapies including for example donepezil, memantine, tacrine and equivalents and pharmaceutically active isomer(s) and metabolite(s) thereof.

(vii) Parkinson's therapies including for example deprenyl, L-dopa, Requip, Mirapex, MAOB inhibitors such as selegine and rasagiline, comP inhibitors such as Tasmar, A-2 inhibitors, dopamine reuptake inhibitors, NMDA antagonists, Nicotine agonists, Dopamine agonists and inhibitors of neuronal nitric oxide synthase and equivalents and pharmaceutically active isomer(s) and metabolite(s) thereof.

(viii) migraine therapies including for example almotriptan, amantadine, bromocriptine, butalbital, cabergoline, dichloralphenazone, eletriptan, frovatriptan, lisuride, naratriptan, pergolide, pramipexole, rizatriptan, ropinirole, sumatriptan, zolmitriptan, zomitriptan, and equivalents and pharmaceutically active isomer(s) and metabolite(s) thereof.

(ix) stroke therapies including for example abciximab, activase, NXY-059, citicoline, crobenetine, desmoteplase, repinotan, traxoprodil and equivalents and pharmaceutically active isomer(s) and metabolite(s) thereof.
(x) urinary incontinence therapies including for example darafenacin, falvoxate, oxybutynin, propiverine, robalzotan, solifenacin, tolterodine and equivalents and pharmaceutically active isomer(s) and metabolite(s) thereof.
(xi) neuropathic pain therapies including for example gabapentin, lidoderm, pregablin and equivalents and pharmaceutically active isomer(s) and metabolite(s) thereof.
(xii) nociceptive pain therapies such as celecoxib, etoricoxib, lumiracoxib, rofecoxib, valdecoxib, diclofenac, loxoprofen, naproxen, paracetamol and equivalents and pharmaceutically active isomer(s) and metabolite(s) thereof.
(xiii) $GABA_b$ modulators such as baclofen, and equivalents and pharmaceutically active salts and metabolite(s) thereof.
(xiv) Glutamate receptor antagonists and equivalents and pharmaceutically active salts and metabolite(s) thereof.
(xv) insomnia therapies including for example agomelatine, allobarbital, alonimid, amobarbital, benzoctamine, butabarbital, capuride, chloral, cloperidone, clorethate, dexclamol, ethchlorvynol, etomidate, glutethimide, halazepam, hydroxyzine, mecloqualone, melatonin, mephobarbital, methaqualone, midaflur, nisobamate, pentobarbital, phenobarbital, propofol, ramelteon, roletamide, triclofos, secobarbital, zaleplon, zolpidem and equivalents and pharmaceutically active isomer(s) and metabolite(s) thereof.
(xvi) mood stabilizers including for example carbamazepine, divalproex, gabapentin, lamotrigine, lithium, olanzapine, quetiapine, valproate, valproic acid, verapamil, and equivalents and pharmaceutically active isomer(s) and metabolite(s) thereof.

Such combination products employ the compounds of this invention within the dosage range described herein and the other pharmaceutically active compound or compounds within therapeutically active dosage ranges and/or the dosage described in the publication reference.

One embodiment of the invention relates to compounds of formula I or Ia as defined above, or any of the specific compounds mentioned above, or pharmaceutically acceptable salts thereof, or any of the specific salts mentions for these compounds, for use in therapy.

Another embodiment relates to the use of compounds of formula I or Ia as defined above, or any of the specific compounds mentioned above, or pharmaceutically acceptable salts thereof, or any of the specific salts mentions for these compounds, in the manufacture of a medicament for treatment of pain.

A further embodiment relates to the use of compounds of formula I or Ia as defined above, or any of the specific compounds mentioned above, or pharmaceutically acceptable salts thereof, or any of the specific salts mentions for these compounds, in the manufacture of a medicament for treatment of acute or chronic nociceptive pain, visceral pain, inflammatory pain, and/or central or peripheral neuropathic pain.

One embodiment relates to a method of treatment of pain, or acute or chronic nociceptive pain, visceral pain, inflammatory pain, and/or central or peripheral neuropathic pain in a patient suffering from, or at risk of, said disease, which comprises administering to the patient a therapeutically effective amount of a compounds of formula I or Ia as defined above, or any of the specific compounds mentioned above, or pharmaceutically acceptable salts thereof, or any of the specific salts mentions for these compounds, or a pharmaceutical composition comprising said compounds.

An agent for the treatment of pain, or acute or chronic nociceptive pain, visceral pain, inflammatory pain, and/or central or peripheral neuropathic pain, which comprises as active ingredient a compounds of formula I or Ia as defined above, or any of the specific compounds mentioned above, or pharmaceutically acceptable salts thereof, or any of the specific salts mentions for these compounds, or a pharmaceutical composition comprising said compounds.

Pharmaceutical Compositions

The compounds of the invention will normally be administered orally, subcutaneously, intravenously, intraarterially, transdermally, intranasally, by inhalation, or by any other parenteral route, in the form of pharmaceutical preparations comprising the active ingredient either as a free base or a non-toxic organic or inorganic acid addition salt, in a pharmaceutically acceptable dosage form. Depending upon the disorder and patient to be treated, as well as the route of administration, the compositions may be administered at varying doses.

One embodiment relates to a pharmaceutical composition comprising as active ingredient a therapeutically effective amount of the compound of formula I or Ia as defined above, in association with one or more pharmaceutically acceptable diluents, excipients and/or inert carriers.

Another embodiment relates to said pharmaceutical composition according, for use in the treatment of pain or acute or chronic nociceptive pain, visceral pain, inflammatory pain, and/or central or peripheral neuropathic pain.

Suitable daily doses of the compounds of the invention in therapeutic treatment of humans are about 0.005 to 25.0 mg/kg body weight at oral administration and about 0.005 to 10.0 mg/kg body weight at parenteral administration. Example of ranges of daily doses of the compounds of the invention in therapeutic treatment of humans are about 0.005 to 10.0 mg/kg body weight at oral administration and about 0.005 to 5.0 mg/kg body weight at parenteral administration.

Compounds of the invention may also have the advantage that they may be more efficacious than, be less toxic than, have a broader range of activity than, be more potent than, be longer acting than, produce fewer side effects than, be more easily absorbed than, or that they may have other useful pharmacological properties over, compounds known in the prior art.

The invention is illustrated by way of the following examples.

EXAMPLES

General Methods

Starting materials used were available from commercial sources, or prepared according to literature procedures.

Mass spectra were recorded on one of the following instruments:

A) A LC-MS system consisting of a Waters Alliance 2795 HPLC, a Waters PDA 2996 diode array detector, a Sedex 85 ELS detector and a ZQ single quadrupole mass spectrometer. The mass spectrometer was equipped with an electrospray ion source (ES) operated in positive or negative ion mode. The capillary voltage was set to 3.2 kV and the cone voltage to 30 V, respectively. The mass spectrometer scanned between m/z 100-700 with a scan time of 0.3 s. The diode array detector scanned from 200-400 nm. The temperature of the ELS detector was adjusted to 40° C. and the pressure was set to 1.9 bars. Separation was performed on an X-Terra MS C8, 3.0 mm×50 mm, 3.5 μm (Waters) run at a flow rate of 1 ml/min. A linear gradient was applied starting at 100% A (A: 10 mM ammonium acetate in 5% acetonitrile, or 8 mM formic acid in 5% acetonitrile) ending at 100% B (B: acetonitrile). The column oven temperature was set to 40° C.

B) A LC-MS system consisting of a Waters sample manager 2777C, a Waters 1525μ binary pump, a Waters 1500 column oven, a Waters ZQ single quadrupole mass spectrometer, a Waters PDA 2996 diode array detector and a Sedex 85 ELS detector. The mass spectrometer was configured with an atmospheric pressure chemical ionisation (APCI) ion source which was further equipped with atmospheric pressure photo ionisation (APPI) device. The mass spectrometer scanned in the positive mode, switching between APCI and APPI mode. The mass range was set to m/z 120-800 using a scan time of 0.3 s. The APPI repeller and the APCI corona were set to 0.86 kV and 0.80 μA, respectively. In addition, the desolvation temperature (300° C.), desolvation gas (400 L/Hr) and cone gas (5 L/Hr) were constant for both APCI and APPI mode. Separation was performed using a Gemini column C18, 3.0 mm×50 mm, 3 μm, (Phenomenex) and run at a flow rate of 1 ml/min. A linear gradient was used starting at 100% A (A: 10 mM ammonium acetated in 5% methanol) and ending at 100% B (methanol). The column oven temperature was set to 40° C.

C) A LC-MS system consisting of a Waters Alliance 2795 HPLC and a Waters Micromass ZQ detector operating at 120° C. The mass spectrometer was equipped with an electrospray ion source (ESI) operated in a positive or negative ion mode. The mass spectrometer was scanned between m/z 100-1000 with a scan time of 0.3 s. The LC system used was 75% acetonitrile and 25% of a 0.1% formic acid solution in water.

D) An Agilent HP1100 system consisting of a G1322A Micro Vacuum Degasser, a G1312A Binary Pump, a G1367 A Well-Plate Autosampler, a G1316A Thermostatted Column Compartment, a G1315C Diode Array Detector and a 6120, G1978B mass spectrometer. The mass spectrometer was configured with an atmospheric pressure chemical ionisation (APCI) ion source operated in positive and negative ion mode. The APCI corona was set to 5.0 μA. The capillary voltage was set to 2.0 kV. In addition, the desolvation temperature (350° C.), desolvation gas (5 L/min). The mass spectrometer was scanned between m/z 100-1000. The column used was a Gemini C18 3.0×50, 3 μm (Phenomenex) run at a flow rate of 1.0 ml/min. The column oven temperature was set to 40° C. The diode array detector scanned from 200-400 nm. The purity method consisted of two or three parts: firstly a 3 minute column wash was applied (this part is optional), secondly a blank run was performed and finally the sample was analysed. A linear gradient was used for both the blank and the sample, starting at 100% A (A: 10 mM ammonium acetate in 5% acetonitrile) and ending at 95% B (B: acetonitrile) after 3.0 min, then 95% B during 1 min stop at 4.0 min. Integration was on at 0 to 4.0 min. The blank run was subtracted from the sample run at the wavelengths 220 nm, 254 nm, 290 nm and from the chromatograms of the mass spectrometer in positive and negative mode.

Preparative HPLC was run on one of the following systems:

A) Waters FractionLynx system with a Autosampler combined Automated Fraction Collector (Waters 2767), Gradient Pump (Waters 2525), Column Switch (Waters CFO) and PDA (Waters 2996). Column; XTerra® Prep MS C8 10 μm OBD™ 19×300 mm or XTerra® Prep MS C8 10 μm OBD™ 30×150 mm both with the guard column XTerra® Prep MS C8 10 μm 19×10 mm Cartridge. A gradient from 100% A (95% 0.1 M ammonium acetate in MilliQ water and 5% acetonitrile) to 100% B (100% acetonitrile) was applied for LC-separation at flow rate 20 ml/min. The PDA was scanned from 210-350 nm. UV triggering determined the fraction collection.

B) A semi preparative Shimadzu LC-8A HPLC with a Shimadzu SPD-10A UV-vis.-detector equipped with a Waters Symmetry® column (C18, 5 μm, 100 mm×19 mm). Gradient with acetonitrile/0.1% trifluoroacetic acid in MilliQ Water, typically run from 35% to 60% acetonitrile in 20 min. Flow rate: 10 mL/min. Alternatively, another column was used; Atlantis C18 19×100 mm, 5 μm column. Gradient with acetonitrile/0.1 M ammonium acetate in 5% acetonitrile in MilliQ Water, run from 0% to 35-50% acetonitrile, in 15 min. Flow rate: 15 mL/min.

NMR spectra were recorded on a Varian Mercury Plus 400 NMR Spectrometer, operating at 400 MHz and equipped with a Varian 400 ATB PFG probe; or on a Varian Unity+ 400 NMR Spectrometer, operating at 400 MHz for proton and 100 MHz for carbon-13, and equipped with a 5 mm BBO probe with Z-gradients; or on a Bruker av400 NMR spectrometer operating at 400 MHz for proton and 100 MHz for carbon-13, and equipped with a 3 mm flow injection SEI $^1$H/D-$^{13}$C probe head with Z-gradients, using a BEST 215 liquid handler for sample injection; or on a Bruker DPX400 NMR spectrometer, operating at 400 MHz for proton and 100 MHz for carbon-13, and equipped with a 4-nucleus probe with Z-gradients. The following reference signals were used: TMS δ 0.00, or the residual solvent signal of DMSO-d$_6$ δ 2.49, CD$_3$OD δ 3.31 or CDCl$_3$ δ 7.25 (unless otherwise indicated). Resonance multiplicities are denoted s, d, t, q, m and br for singlet, doublet, triplet, quartet, multiplet and broad, respectively.

Microwave irradiation was performed in a Creator™, Initiator™ or Smith Synthesizer™ Single-mode microwave cavity producing continuous irradiation at 2450 MHz. Column chromatography was performed using Merck Silica gel 60 (0.040-0.063 mm), or employing a Combi Flash® Companion™ system using RediSep™ normal-phase flash columns.

Compounds have been named using ACD/Name, version 8.0 or 9.0, software from Advanced Chemistry Development, Inc. (ACD/Labs), Toronto ON, Canada, www.acdlabs.com, 2004.

Rotamers may or may not be denoted in spectra depending upon ease of interpretation of spectra. Unless otherwise stated, chemical shifts are given in ppm with the solvent as internal standard.

Reactants

Following reactants, either new (see synthetic procedures described below), commercially available or described in the literature, were used for the preparation of the target compounds (examples 1-213).

Amines:
Amine 1: (3S)-5-pyridin-4-ylchroman-3-amine
Amine 2: (2R)-8-pyridin-4-yl-1,2,3,4-tetrahydronaphthalen-2-amine
Amine 3: (3S)-5-pyridin-3-ylchroman-3-amine
Amine 4: (3S)-5-pyridin-2-ylchroman-3-amine
Amine 5: (2R)-8-(1-methyl-1H-pyrazol-4-yl)-1,2,3,4-tetrahydronaphthalen-2-amine
Amine 6: (2R)-8-(3,5-dimethyl-1H-pyrazol-4-yl)-1,2,3,4-tetrahydronaphthalen-2-amine
Amine 7: (2R)-8-(3,5-dimethylisoxazol-4-yl)-1,2,3,4-tetrahydronaphthalen-2-amine
Amine 8: (3S)-5-(2-fluoropyridin-4-yl)chroman-3-amine
Amine 9: (3S)-5-(2-methoxypyridin-4-yl)chroman-3-amine Amine 10: (3S)-5-(3-methylpyridin-4-yl)chroman-3-amine
Amine 11: (3S)-5-(6-methoxypyridin-3-yl)chroman-3-amine
Amine 12: (3S)-5-(6-fluoropyridin-3-yl)chroman-3-amine
Amine 13: {5-[(3S)-3-amino-3,4-dihydro-2H-chromen-5-yl]pyridin-2-yl}methanol
Amine 14: (3S)-5-(2-methoxypyridin-3-yl)chroman-3-amine
Amine 15: (3S)-5-(5-fluoro-6-methoxypyridin-3-yl)chroman-3-amine
Amine 16: (3S)-5-(6-fluoro-5-methylpyridin-3-yl)chroman-3-amine
Amine 17: 5-[(3S)-3-amino-3,4-dihydro-2H-chromen-5-yl]-2-methoxy-N,N-dimethylnicotinamide
Amine 18: 5-[(3S)-3-amino-3,4-dihydro-2H-chromen-5-yl]-2-methoxy-N-methylnicotinamide
Amine 19: (3S)-5-pyrimidin-5-ylchroman-3-amine
Amine 20: (3S)-5-(2-methoxypyrimidin-5-yl)chroman-3-amine
Amine 21: (3S)-5-(2-methylpyrimidin-5-yl)chroman-3-amine
Amine 22: (3S)-5-(2-ethylpyrimidin-5-yl)chroman-3-amine
Amine 23: (3S)-5-(2-cyclopropylpyrimidin-5-yl)chroman-3-amine
Amine 24: (3S)-5-(2-ethoxypyrimidin-5-yl)chroman-3-amine
Amine 25: 5-[(3S)-3-amino-3,4-dihydro-2H-chromen-5-yl]-N,N-dimethylpyrimidine-2-carboxamide
Amine 26: (3S)-5-pyridazin-4-ylchroman-3-amine
Amine 27: (3S)-5-(3,6-dimethoxypyridazin-4-yl)chroman-3-amine
Amine 28: (3S)-5-(6-methylpyrazin-2-yl)chroman-3-amine
Amine 29: (3S)-5-(3,5-dimethylpyrazin-2-yl)chroman-3-amine
Amine 30: (3S)-5-imidazo[1,2-a]pyridin-6-ylchroman-3-amine
Amine 31: (2R)-8-(3-fluoropyridin-4-yl)-1,2,3,4-tetrahydronaphthalen-2-amine
Amine 32: (2R)-8-(2-fluoropyridin-3-yl)-1,2,3,4-tetrahydronaphthalen-2-amine
Amine 33: (2R)-8-(6-methylpyridin-3-yl)-1,2,3,4-tetrahydronaphthalen-2-amine
Amine 34: (2R)-8-pyridazin-4-yl-1,2,3,4-tetrahydronaphthalen-2-amine
Amine 35: (2S)-8-(2-methoxypyrimidin-5-yl)-1,2,3,4-tetrahydronaphthalen-2-amine
Amine 36: (2R)-8-(2-methoxypyrimidin-5-yl)-1,2,3,4-tetrahydronaphthalen-2-amine
Amine 37: (2R)-8-(2-methylpyrimidin-5-yl)-1,2,3,4-tetrahydronaphthalen-2-amine
Carboxylic Acids:
Acid 1: 5-methyl-2-phenyl-2H-1,2,3-triazole-4-carboxylic acid
Acid 2: 4-butoxybenzoic acid
Acid 3: 4-{[(trifluoromethyl)sulfonyl]oxy}benzoic acid
Acid 4: 6-(2,2,2-trifluoroethoxy)nicotinic acid
Acid 5: 6-(3,3,3-trifluoropropoxy)nicotinic acid
Acid 6: 6-isopropoxynicotinic acid
Acid 7: 6-(cyclopentyloxy)nicotinic acid
Acid 8: 2,4-dimethoxybenzoic acid
Acid 9: 6-isobutoxynicotinic acid
Acid 10: 6-ethoxynicotinic acid
Acid 11: 6-(2,2-difluoroethoxy)nicotinic acid
Acid 12: 6-[2-fluoro-1-(fluoromethyl)ethoxy]nicotinic acid
Acid 13: 2-(cyclopentyloxy)pyrimidine-5-carboxylic acid
Acid 14: 6-(cyclobutyloxy)nicotinic acid
Acid 15: 6-(cyclopropylmethoxy)nicotinic acid
Acid 16: 6-chloronicotinic acid
Acid 17: 2-isopropoxypyrimidine-5-carboxylic acid
Acid 18: 5-methoxypyrazine-2-carboxylic acid
Acid 19: 6-(3-fluoropropoxy)nicotinic acid
Acid 20: 5-(3,3,3-trifluoropropoxy)pyrazine-2-carboxylic acid
Acid 21: 1,8-naphthyridine-2-carboxylic acid
Acid 22: 1,5-naphthyridine-2-carboxylic acid
Acid 23: 2-methyl-1,6-naphthyridine-3-carboxylic acid
Acid 24: quinoline-2-carboxylic acid
Acid 25: 4-methyl-2-(2,2,2-trifluoroethoxy)pyrimidine-5-carboxylic acid
Acid 26: 2-isopropoxyisonicotinic acid
Acid 27: 6-(dipropylcarbamoyl)nicotinic acid
Acid 28: 6-[(3-methylbutyl)carbamoyl]nicotinic acid
Acid 29: 6-[isobutyl(methyl)carbamoyl]nicotinic acid
Acid 30: 6-[(3,3,3-trifluoropropyl)carbamoyl]nicotinic acid
Acid 31: 6-[methyl(3,3,3-trifluoropropyl)carbamoyl]nicotinic acid
Acid 32: 6-[methyl(2,2,2-trifluoroethyl)carbamoyl]nicotinic acid
Acid 33: 6-[(4,4-difluorocyclohexyl)carbamoyl]nicotinic acid
Acid 34: 6-[(4,4,4-trifluorobutyl)carbamoyl]nicotinic acid
Acid 35: 6-[(3-isopropoxypropyl)carbamoyl]nicotinic acid
Acid 36: 6-(1,3-thiazol-2-ylmethoxy)nicotinic acid
Acid 37: 6-[(5-methylisoxazol-3-yl)methoxy]nicotinic acid
Acid 38: 6-[(1-methyl-1H-imidazol-2-yl)methoxy]nicotinic acid
Acid 39: 6-(pyridin-2-ylmethoxy)nicotinic acid
Acid 40: 6-(pyridin-3-ylmethoxy)nicotinic acid
Acid 41: 6-(pyrazin-2-ylmethoxy)nicotinic acid
Acid 42: 6-(cyclopentylsulfonyl)nicotinic acid
Acid 43: 6-(tetrahydro-2H-pyran-2-ylmethoxy)nicotinic acid
Acid 44: 6-(tetrahydrofuran-2-ylmethoxy)nicotinic acid
Acid 45: 6-(oxetan-2-ylmethoxy)nicotinic acid
Acid 46: 6-(tetrahydro-2H-pyran-3-yloxy)nicotinic acid
Acid 47: 6-(tetrahydrofuran-3-yloxy)nicotinic acid
Acid 48: 6-(1,4-dioxan-2-ylmethoxy)nicotinic acid
Acid 49: 6-(tetrahydro-2H-pyran-4-ylmethoxy)nicotinic acid
Acid 50: 6-(2-methoxyethoxy)nicotinic acid
Acid 51: 6-{[(2S)-2-methoxypropyl]oxy}nicotinic acid
Acid 52: 6-(but-2-yn-1-yloxy)nicotinic acid
Acid 53: 6-(tetrahydro-2H-pyran-4-yloxy)nicotinic acid
Acid 54: 6-[2-(2,2,2-trifluoroethoxy)ethoxy]nicotinic acid
Acid 55: 6-(2-isopropoxyethoxy)nicotinic acid
Acid 56: 2-[(3,3,3-trifluoropropyl)amino]pyrimidine-5-carboxylic acid
Acid 57: 6-[(2,2,2-trifluoroethoxy)methyl]nicotinic acid
Acid 58: 2-[2-(2,2,2-trifluoroethoxy)ethoxy]isonicotinic acid
Acid 59: 1-butyl-2-oxo-1,2-dihydropyridine-4-carboxylic acid
Acid 60: 2-oxo-1-(3,3,3-trifluoropropyl)-1,2-dihydropyridine-4-carboxylic acid
Acid 61: 2-chloropyrimidine-5-carboxylic acid
Acid 62: 6-(2,4-dimethoxyphenyl)pyridine-3-carboxylic acid
Acyl Chlorides:
4-(trifluoromethoxy)benzoyl chloride
quinoxaline-2-carbonyl chloride
Carboxylic Acid Esters:
methyl 6-(butylsulfonyl)nicotinate
ethyl 2-isobutyl-5-methyl-2H-1,2,3-triazole-4-carboxylate ethyl 2-(2-methoxyethyl)-5-methyl-2H-1,2,3-triazole-4-carboxylate
methyl 5-chloropyrazine-2-carboxylate
methyl 2-chloropyrimidine-5-carboxylate
methyl 2-isopropoxy-4-methylpyrimidine-5-carboxylate
methyl 6-(pyrrolidin-1-ylcarbonyl)nicotinate
methyl 6-(tetrahydro-2H-pyran-4-ylcarbamoyl)nicotinate
methyl 6-[(3,3,3-trifluoropropyl)carbamoyl]nicotinate
methyl 6-[(2,2,2-trifluoroethyl)carbamoyl]nicotinate
General Methods of Synthesis.
Method A:

To a solution of the amine (1 mole equiv.) and triethylamine (1.2 mole equiv.) in dry dichloromethane the acid chloride (1.2 mole equiv.) was added. The reaction mixture was stirred at ambient temperature for 5-30 min and then concentrated in vacuo. The crude product was purified using preparative HPLC technic on reversed stationary phase to yield the target product.

Method B1:

Triethylamine (3 mole equiv.) and 2-(1H-benzotriazole-1-yl)-1,1,3,3-tetramethyluronium hexafluorophosphate (1.5 mole equiv.) were added to a solution of the carboxylic acid (1 mole equiv.) in anhydrous acetonitrile and the reaction mixture was stirred for 10 min. A solution of the amine (1 mole equiv.) in anhydrous acetonitrile was added and the reaction mixture was stirred at ambient temperature for 1-20 h. The volatiles were removed in vacuo and the crude residue was purified by preparative HPLC.

Method B2:

A mixture of the carboxylic acid (1 mole equiv.) and N,N'-carbonyldiimidazole (1 mole equiv.) in N,N-dimethylformamide was heated to 50° C. for 30 min. A solution of the amine (1 mole equiv.) in N,N-dimethylformamide was added and the reaction mixture was stirred at 50° C. for 4 h, then at ambient temperature over night. The crude was purified by preparative HPLC.

Method C:

A 2M solution of trimethylaluminum in hexane (3 mole equiv.) was slowly added to a solution of the amine (1 mole equiv.) in dry dichloromethane or toluene under an atmosphere of nitrogen. The reaction mixture was stirred at ambient temperature for 30 min then the carboxylic ester (1 mole equiv.) was added. The reaction mixture was heated to 40-80° C. for 3-20 h. Water or 1M hydrochloric acid was added carefully until gas evolution stopped. 1M sodium hydroxide was added until a basic pH was reached. The reaction mixture was extracted with dichloromethane and the organic layer was dried over sodium sulfate and concentrated in vacuo. The crude was purified by preparative HPLC.

Method D:

A chlorinated heterocycle was synthesised according to methods A-C. Alcohol (1.1 mole equiv.) was added to a 1M solution of potassium tert-butoxide (1.1 mole equiv) in tetrahydrofuran at 0° C. The mixture was stirred at 0° C. for 5 min. The chlorinated heterocycle was added and the reaction mixture was refluxed over night. The mixture was quenched with brine and extracted with ethyl acetate. The organic layer was dried over magnesium sulfate and concentrated in vacuo. The crude was purified by preparative HPLC.

Method E:

A chromane- or tetralin borate was synthesised according to methods A-C. A mixture of the chromane- or tetralin borate (1 mole equiv.), 2M potassium carbonate (3 mole equiv.), a substituted halopyridine, halopyrimidine or halopyrazine (1.2-1.4 mole equiv.) and 1,1'-bis(diphenylphosphino)ferrocene-palladium(II)dichloride dichloromethane complex (0.1 mole equiv.) in isopropanol was irradiated in a microwave synthesizer at 140° C. for 20 min. The volatiles were removed in vacuo and the residue was dissolved in ethyl acetate. The solution was filtered through a pad of celite and concentrated in vacuo. The residue was purified by column chromatography using a gradient of ethyl acetate in heptane.

The compounds below were prepared according to Methods A, B, C, D or E:

Example 1

N-[(3S)-5-Pyridin-4-yl-3,4-dihydro-2H-chromen-3-yl]-4-(trifluoromethoxy)-benzamide The title compound was synthesized according to method A, starting from Amine 1 and 4-(trifluoromethoxy)benzoyl chloride; $^1$H NMR (400 MHz, CDCl$_3$) δ ppm 8.57-8.68 (m, 2 H), 7.69-7.79 (m, 2 H), 7.19-7.30 (m, 5 H), 6.99 (dd, 1 H), 6.88 (dd, 1 H), 6.36 (d, 1 H), 4.62-4.71 (m, 1 H), 4.23-4.32 (m, 2 H), 3.12 (dd, 1 H), 2.70 (dd, 1 H); MS (ESI) m/z 415[M+H$^+$].

Example 2

4-Butoxy-N-[(3S)-5-pyridin-4-yl-3,4-dihydro-2H-chromen-3-yl]benzamide

The title compound was synthesized according to method B1, starting from Amine 1 and Acid 2; $^1$H NMR (400 MHz, CDCl$_3$) δ ppm 8.65 (d, 2 H), 7.65 (d, 2 H), 7.16-7.26 (m, 3 H), 6.98 (dd, 1 H), 6.81-6.91 (m, 3 H), 6.27 (d, 1 H), 4.58-4.70 (m, 1 H), 4.23-4.31 (m, 2 H), 3.98 (t, 2 H), 3.09 (dd, 1 H), 2.70 (dd, 1 H), 1.69-1.83 (m, 2 H), 1.43-1.55 (m, 2 H), 0.98 (t, 3H); MS (ESI) m/z 403[M+H$^+$].

Example 3

4-{[(2R)-8-Pyridin-4-yl-1,2,3,4-tetrahydronaphthalen-2-yl]carbamoyl}phenyl trifluoromethanesulfonate The title compound was synthesized according to method B1, starting from Amine 2 and Acid 3; $^1$H NMR (400 MHz, CDCl$_3$) δ ppm 8.65 (d, 2 H), 7.82 (d, 2 H), 7.33 (d, 2 H), 7.21-7.30 (m, 4 H), 7.07 (dd, 1 H), 6.02 (d, 1 H), 4.41 (br. s., 1 H), 2.93-3.18 (m, 3 H), 2.51-2.65 (m, 1 H), 2.19-2.30 (m, 1 H), 1.78-1.97 (m, 1 H); MS (ESI) m/z 477[M+H$^+$].

Example 4

N-[(3S)-5-Pyridin-3-yl-3,4-dihydro-2H-chromen-3-yl]-4-(trifluoromethoxy)-benzamide The title compound was synthesized according to method A, starting from Amine 3 and 4-(trifluoromethoxy)benzoyl chloride; $^1$H NMR (400 MHz, CDCl$_3$) δ ppm 8.58 (d, 2H) 7.74 (m, 2 H) 7.62 (m, 1 H) 7.35 (m, 1 H) 7.25 (m, 3 H) 6.97 (m, 1 H) 6.88 (m, 1 H) 6.43 (d, 1 H) 4.66 (m, 1 H) 4.27 (m, 2 H) 3.10 (m, 1 H) 2.69 (m, 1 H); MS (ESI) m/z 415[M+H$^+$].

Example 5

N-[(3S)-5-Pyridin-2-yl-3,4-dihydro-2H-chromen-3-yl]-4-(trifluoromethoxy)-benzamide The title compound was synthesized according to method A, starting from Amine 4 and 4-(trifluoromethoxy)benzoyl chloride; $^1$H NMR (400 MHz, CD$_3$OD) δ ppm 8.59 (d, 1 H)

7.83-7.98 (m, 3 H) 7.51 (d, 1 H) 7.42 (m, 1 H) 7.33 (d, 2 H) 7.24 (t, 1 H) 6.94 (d, 2 H) 4.39 (m, 1 H) 4.29 (m, 1 H) 4.13 (m, 1 H) 2.92 (m, 2 H); MS (ESI) m/z 415[M+H$^+$].

Example 6

N-[(2R)-8-(1-Methyl-1H-pyrazol-4-yl)-1,2,3,4-tetrahydronaphthalen-2-yl]-4-(trifluoromethoxy)-benzamide The title compound was synthesized according to method A, starting from Amine 5 and 4-(trifluoromethoxy)benzoyl chloride; $^1$H NMR (400 MHz, DMSO-d$_6$) δ ppm 8.53 (d, 1 H) 7.99 (d, 2 H) 7.82 (s, 1 H) 7.56 (s, 1 H) 7.45 (d, 2 H) 7.14 (d, 2 H) 7.04 (t, 1 H) 4.03-4.16 (m, 1 H) 3.86 (s, 3 H) 3.04 (dd, 1 H) 2.87-2.97 (m, 2 H) 2.76 (dd, 1 H) 2.00-2.11 (m, 1 H) 1.70-1.85 (m, 1 H); MS (ESI) m/z 416[M+H$^+$].

Example 7

4-{[(2R)-8-(1-Methyl-1H-pyrazol-4-yl)-1,2,3,4-tetrahydronaphthalen-2-yl]carbamoyl}phenyl trifluoromethanesulfonate The title compound was synthesized according to method B1, starting from Amine 5 and Acid 3; $^1$H NMR (400 MHz, CD$_3$OD) δ ppm 7.94-8.03 (m, 2 H) 7.70 (s, 1 H) 7.57 (s, 1 H) 7.44-7.52 (m, 2 H) 7.15 (d, 2 H) 7.04-7.11 (m, 1 H) 4.16-4.30 (m, 1 H) 3.92 (s, 3 H) 3.16 (dd, 1 H) 2.98-3.07 (m, 2 H) 2.79 (dd, 1 H) 2.15-2.24 (m, 1 H) 1.78-1.93 (m, 1 H); MS (ESI) m/z 480[M+H$^+$].

Example 8

5-Methyl-N-[(2R)-8-(1-methyl-1H-pyrazol-4-yl)-1,2,3,4-tetrahydronaphthalen-2-yl]-2-phenyl-2H-1,2,3-triazole-4-carboxamide The title compound was synthesized according to method B1, starting from Amine 5 and Acid 1; $^1$H NMR (400 MHz, CD$_3$OD) δ ppm 8.00-8.13 (m, 2 H) 7.72 (s, 1 H) 7.58 (s, 1 H) 7.48-7.56 (m, 2 H) 7.37-7.45 (m, 1 H) 7.11-7.17 (m, 2 H) 7.04-7.11 (m, 1 H) 4.19-4.30 (m, 1 H) 3.92 (s, 3 H) 3.15 (dd, 1 H) 2.97-3.06 (m, 2 H) 2.87 (dd, 1 H) 2.57 (s, 3 H) 2.14-2.23 (m, 1 H) 1.85-1.97 (m, 1 H); MS (ESI) m/z 413[M+H$^+$].

Example 9

N-[(2R)-8-(3,5-Dimethyl-1H-pyrazol-4-yl)-1,2,3,4-tetrahydronaphthalen-2-yl]-4-(trifluoromethoxy)-benzamide The title compound was synthesized according to method A, starting from Amine 6 and 4-(trifluoromethoxy)benzoyl chloride; $^1$H NMR (400 MHz, CD$_3$OD) δ ppm 7.85-7.92 (m, 2 H) 7.34 (d, 2 H) 7.10-7.21 (m, 2 H) 6.92 (dd, 1 H) 4.13-4.27 (m, 1 H) 2.98-3.08 (m, 2 H) 2.78 (dd, 1 H) 2.47 (dd, 1 H) 2.12-2.24 (m, 1 H) 2.05 (s, 3 H) 2.02 (s, 3 H) 1.72-1.89 (m, 1 H); MS (ESI) m/z 430[M+H$^+$].

Example 10

N-[(2R)-8-(3,5-Dimethylisoxazol-4-yl)-1,2,3,4-tetrahydronaphthalen-2-yl]-4-(trifluoromethoxy)-benzamide The title compound was synthesized according to method A, starting from Amine 7 and 4-(trifluoromethoxy)benzoyl chloride; $^1$H NMR (400 MHz, CD$_3$OD) δ ppm 7.78 (dd, 2 H) 7.25-7.29 (m, 2 H) 7.18-7.25 (m, 2 H) 6.96 (dd, 1 H) 6.01 (d, 1 H) 4.35-4.47 (m, 1 H) 2.94-3.15 (m, 2 H) 2.87 (td, 1 H) 2.30-2.41 (m, 1 H) 2.26 (s, 2 H) 2.23-2.29 (m, 1 H) 2.21 (s, 1 H) 2.11 (s, 1 H) 2.07 (s, 2 H) 1.72-1.87 (m, 1 H); MS (ESI) m/z 431[M+H$^+$].

Example 11

4-{[(2R)-8-(3,5-Dimethylisoxazol-4-yl)-1,2,3,4-tetrahydronaphthalen-2-yl]carbamoyl}phenyl trifluoromethanesulfonate The title compound was synthesized according to method B1, starting from Amine 7 and Acid 3; $^1$H NMR (400 MHz, CD$_3$OD) δ ppm 7.96 (d, 2 H) 7.40-7.50 (m, 2 H) 7.17-7.28 (m, 2 H) 6.89-7.01 (m, 1 H) 4.16-4.29 (m, 1 H) 2.99-3.11 (m, 2 H) 2.68-2.89 (m, 1 H) 2.50 (dd, 1 H) 2.17-2.29 (m, 4 H) 2.07 (d, 3 H) 1.74-1.93 (m, 1 H); MS (ESI) m/z 495 [M+H$^+$].

Example 12

N-[(2R)-8-pyridin-4-yl-1,2,3,4-tetrahydronaphthalen-2-yl]-6-(2,2,2-trifluoroethoxy)nicotinamide The title compound was synthesized according to method B1, starting from Amine 2 and Acid 4; $^1$H NMR (400 MHz, CD$_3$OD) δ ppm 8.47-8.65 (m, 3 H) 8.12 (dd, 1 H) 7.40 (d, 2 H) 7.17-7.30 (m, 2 H) 7.05 (dd, 1 H) 6.94 (d, 1 H) 4.85-4.97 (m, 2 H) 4.09-4.26 (m, 1 H) 3.00-3.10 (m, 2 H) 2.91 (dd, 1 H) 2.67-2.79 (m, 1 H) 2.11-2.24 (m, 1 H) 1.76-1.93 (m, 1 H); MS (ESI) m/z 428[M+H$^+$].

Example 13

N-[(2R)-8-pyridin-4-yl-1,2,3,4-tetrahydronaphthalen-2-yl]-6-(3,3,3-trifluoropropoxy)nicotinamide The title compound was synthesized according to method B1, starting from Amine 2 and Acid 5; $^1$H NMR (400 MHz, CD$_3$OD) δ ppm 8.42-8.68 (m, 3 H) 8.05 (d, 1 H) 7.39 (d, 2 H) 7.17-7.30 (m, 2 H) 7.05 (d, 1 H) 6.82 (d, 1 H) 4.57 (t, 2 H) 4.10-4.25 (m, 1 H) 2.99-3.10 (m, 2 H) 2.90 (dd, 1 H) 2.60-2.79 (m, 3 H) 2.10-2.24 (m, 1 H) 1.74-1.98 (m, 1 H); MS (ESI) m/z 442[M+H$^+$].

Example 14

6-isopropoxy-N-[(2R)-8-pyridin-4-yl-1,2,3,4-tetrahydronaphthalen-2-yl]nicotin-amide The title compound was synthesized according to method B1, starting from Amine 2 and Acid 6; $^1$H NMR (400 MHz, CD$_3$OD) δ ppm 8.43-8.64 (m, 3 H) 8.01 (dd, 1 H) 7.40 (d, 2 H) 7.13-7.29 (m, 2 H) 7.05 (d, 1 H) 6.72 (d, 1 H) 5.22-5.41 (m, 1 H) 4.08-4.25 (m, 1 H) 2.98-3.10 (m, 2 H) 2.90 (dd, 1 H) 2.64-2.78 (m, 1 H) 2.08-2.24 (m, 1 H) 1.79-1.93 (m, 1 H) 1.33 (d, 6 H); MS (ESI) m/z 388[M+H$^+$].

Example 15

6-(cyclopentyloxy)-N-[(2R)-8-pyridin-4-yl-1,2,3,4-tetrahydronaphthalen-2-yl]nicotin-amide The title compound was synthesized according to method B1, starting from Amine 2 and Acid 7; $^1$H NMR (400 MHz, CD$_3$OD) δ ppm 8.48-8.61 (m, 3 H) 8.02 (dd, 1 H) 7.40 (d, 2

H) 7.15-7.30 (m, 2 H) 7.01-7.07 (m, 1 H) 6.74 (d, 1 H) 5.35-5.44 (m, 1 H) 4.12-4.24 (m, 1 H) 2.99-3.09 (m, 2 H) 2.84-2.95 (m, 1 H) 2.64-2.78 (m, 1 H) 2.12-2.22 (m, 1 H) 1.92-2.03 (m, 2 H) 1.82-1.93 (m, 1 H) 1.71-1.83 (m, 4 H) 1.56-1.71 (m, 2 H); MS (ESI) m/z 414[M+H$^+$].

Example 16

2,4-dimethoxy-N-[(2R)-8-pyridin-4-yl-1,2,3,4-tetrahydronaphthalen-2-yl]-benzamide The title compound was synthesized according to method B1, starting from Amine 2 and Acid 8; $^1$H NMR (400 MHz, CD$_3$OD) δ ppm 8.57 (br. s., 2 H) 8.21 (d, 1 H) 7.86 (d, 1 H) 7.40 (d, 2 H) 7.20-7.32 (m, 2 H) 7.09 (dd, 1 H) 6.55-6.67 (m, 2 H) 4.25-4.39 (m, 1 H) 3.83 (s, 3 H) 3.79 (s, 3 H) 3.05 (t, 2 H) 2.97 (dd, 1 H) 2.70 (dd, 1 H) 2.08-2.21 (m, 1 H) 1.88-2.05 (m, 1 H); MS (ESI) m/z 389[M+H$^+$].

Example 17

5-methyl-2-phenyl-N-[(2R)-8-pyridin-4-yl-1,2,3,4-tetrahydronaphthalen-2-yl]-2H-1,2,3-triazole-4-carboxamide The title compound was synthesized according to method B1, starting from Amine 2 and Acid 1; $^1$H NMR (400 MHz, CD$_3$OD) δ ppm 8.58 (br. s., 2 H) 8.06 (d, 2 H) 7.51 (t, 2 H) 7.33-7.47 (m, 3 H) 7.19-7.29 (m, 2 H) 7.06 (dd, 1 H) 4.15-4.28 (m, 1 H) 3.00-3.11 (m, 2 H) 2.73-2.93 (m, 2 H) 2.53 (s, 3 H) 2.13-2.24 (m, 1 H) 1.83-1.98 (m, 1 H); MS (ESI) m/z 410[M+H$^+$].

Example 18

N-[(3S)-5-pyridin-4-yl-3,4-dihydro-2H-chromen-3-yl]-6-(2,2,2-trifluoroethoxy)nicotinamide The title compound was synthesized according to method B1, starting from Amine 1 and Acid 4; $^1$H NMR (400 MHz, CD$_3$OD) δ ppm 8.50-8.61 (m, 3 H) 8.10 (dd, 1 H) 7.41-7.46 (m, 2 H) 7.24 (t, 1 H) 6.93 (d, 2 H) 6.86 (dd, 1 H) 4.91 (q, 2 H) 4.35-4.43 (m, 1 H) 4.28-4.35 (m, 1 H) 4.01-4.11 (m, 1 H) 2.91-3.01 (m, 1 H) 2.78-2.87 (m, 1 H); MS (ESI) m/z 430 [M+H$^+$].

Example 19

N-[(3S)-5-pyridin-4-yl-3,4-dihydro-2H-chromen-3-yl]-6-(3,3,3-trifluoropropoxy)nicotin-amide The title compound was synthesized according to method B1, starting from Amine 1 and Acid 5; $^1$H NMR (400 MHz, CD$_3$OD) δ ppm 8.54-8.60 (m, 3 H) 8.04 (dd, 1 H) 7.38-7.45 (m, 2 H) 7.23 (t, 1 H) 6.93 (d, 1 H) 6.85 (dd, 1 H) 6.81 (d, 1 H) 4.57 (t, 2 H) 4.35-4.42 (m, 1 H) 4.27-4.35 (m, 1 H) 4.00-4.10 (m, 1 H) 2.89-3.00 (m, 1 H) 2.77-2.88 (m, 1 H) 2.61-2.76 (m, 2 H); MS (ESI) m/z 444[M+H$^+$].

Example 20

6-isopropoxy-N-[(3S)-5-pyridin-4-yl-3,4-dihydro-2H-chromen-3-yl]nicotin-amide

The title compound was synthesized according to method B1, starting from Amine 1 and Acid 6; $^1$H NMR (400 MHz, CD$_3$OD) δ ppm 8.59 (br. s., 2 H) 8.54 (d, 1 H) 8.00 (dd, 1 H) 7.44 (d, 2 H) 7.24 (t, 1 H) 6.94 (d, 1 H) 6.86 (dd, 1 H) 6.72 (d, 1 H) 5.24-5.36 (m, 1 H) 4.35-4.43 (m, 1 H) 4.28-4.35 (m, 1 H) 4.01-4.09 (m, 1 H) 2.91-2.99 (m, 1 H) 2.76-2.88 (m, 1 H) 1.32 (d, 6 H); MS (ESI) m/z 390[M+H$^+$].

Example 21

6-(cyclopentyloxy)-N-[(3S)-5-pyridin-4-yl-3,4-dihydro-2H-chromen-3-yl]nicotin-amide The title compound was synthesized according to method B1, starting from Amine 1 and Acid 7; $^1$H NMR (400 MHz, CD$_3$OD) δ ppm 8.58 (d, 2 H) 8.54 (d, 1 H) 8.00 (dd, 1 H) 7.44 (d, 2 H) 7.24 (t, 1 H) 6.94 (d, 1 H) 6.86 (dd, 1 H) 6.74 (d, 1 H) 5.37-5.43 (m, 1 H) 4.35-4.43 (m, 1 H) 4.30-4.35 (m, 1 H) 4.01-4.08 (m, 1 H) 2.90-2.99 (m, 1 H) 2.78-2.87 (m, 1 H) 1.90-2.03 (m, 2 H) 1.71-1.84 (m, 4 H) 1.55-1.70 (m, 2 H); MS (ESI) m/z 416[M+H$^+$].

Example 22

2,4-dimethoxy-N-[(3S)-5-pyridin-4-yl-3,4-dihydro-2H-chromen-3-yl]benzamide

The title compound was synthesized according to method B1, starting from Amine 1 and Acid 8; $^1$H NMR (400 MHz, CD$_3$OD) δ ppm 8.57 (d, 2 H) 7.89 (d, 1 H) 7.41 (d, 2 H) 7.28 (t, 1 H) 6.99 (d, 1 H) 6.89 (d, 1 H) 6.57-6.64 (m, 1 H) 6.55 (s, 1 H) 4.43-4.54 (m, 1 H) 4.18-4.32 (m, 2 H) 3.82 (s, 3 H) 3.72 (s, 3 H) 3.11 (dd, 1 H) 2.69 (dd, 1 H); MS (ESI) m/z 391[M+H$^+$].

Example 23

5-methyl-2-phenyl-N-[(3S)-5-pyridin-4-yl-3,4-dihydro-2H-chromen-3-yl]-2H-1,2,3-triazole-4-carboxamide The title compound was synthesized according to method B1, starting from Amine 1 and Acid 1; $^1$H NMR (400 MHz, CD$_3$OD) δ ppm 8.60 (d, 2 H) 8.05 (d, 2 H) 7.52 (t, 2 H) 7.45-7.48 (m, 2 H) 7.38-7.45 (m, 1 H) 7.27 (t, 1 H) 6.98 (d, 1 H) 6.89 (d, 1 H) 4.42-4.50 (m, 1 H) 4.36 (dd, 1 H) 4.09-4.16 (m, 1 H) 2.88-3.01 (m, 2 H) 2.56 (s, 3 H); MS (ESI) m/z 412[M+H$^+$].

Example 24

6-isobutoxy-N-[(3S)-5-pyridin-4-yl-3,4-dihydro-2H-chromen-3-yl]nicotin-amide

The title compound was synthesized according to method B1, starting from Amine 1 and Acid 9; $^1$H NMR (400 MHz, CD$_3$OD) δ ppm 8.59 (br. s., 2 H) 8.55 (d, 1 H) 8.03 (dd, 1 H) 7.45 (d, 2 H) 7.24 (t, 1 H) 6.94 (d, 1 H) 6.86 (dd, 1 H) 6.80 (d, 1 H) 4.35-4.45 (m, 1 H) 4.25-4.35 (m, 1 H) 4.02-4.13 (m, 3 H) 2.90-3.02 (m, 1 H) 2.76-2.89 (m, 1 H) 2.02-2.14 (m, 1 H) 0.96-1.05 (m, 6 H); MS (ESI) m/z 404[M+H$^+$].

Example 25

6-ethoxy-N-[(3S)-5-pyridin-4-yl-3,4-dihydro-2H-chromen-3-yl]nicotin-amide

The title compound was synthesized according to method B1, starting from Amine 1 and Acid 10; $^1$H NMR (400 MHz, CD$_3$OD) δ ppm 8.58 (br. s., 2 H) 8.54 (d, 1 H) 8.02 (dd, 1 H)

7.44 (d, 2 H) 7.23 (t, 1 H) 6.93 (d, 1 H) 6.85 (dd, 1 H) 6.77 (d, 1 H) 4.28-4.42 (m, 4 H) 4.00-4.08 (m, 1 H) 2.90-2.99 (m, 1 H) 2.78-2.88 (m, 1 H) 1.37 (t, 3 H); MS (ESI) m/z 376[M+H⁺].

Example 26

6-(2,2-difluoroethoxy)-N-[(3S)-5-pyridin-4-yl-3,4-dihydro-2H-chromen-3-yl]nicotin-amide The title compound was synthesized according to method B1, starting from Amine 1 and Acid 11; $^1$H NMR (400 MHz, CD$_3$OD) δ ppm 8.54-8.62 (m, 3 H) 8.08 (dd, 1 H) 7.44 (d, 2 H) 7.24 (t, 1 H) 6.94 (d, 1 H) 6.83-6.91 (m, 2 H) 6.19 (tt, 1 H) 4.57 (td, 2 H) 4.36-4.43 (m, 1 H) 4.29-4.35 (m, 1 H) 4.03-4.13 (m, 1 H) 2.92-3.01 (m, 1 H) 2.78-2.88 (m, 1 H); MS (ESI) m/z 412[M+H⁺].

Example 27

6-[2-fluoro-1-(fluoromethyl)ethoxy]-N-[(3S)-5-pyridin-4-yl-3,4-dihydro-2H-chromen-3-yl]nicotin-amide The title compound was synthesized according to method B1, starting from Amine 1 and Acid 12; $^1$H NMR (400 MHz, CD$_3$OD) δ ppm 8.55-8.61 (m, 3 H) 8.07 (dd, 1 H) 7.44 (d, 2 H) 7.24 (t, 1 H) 6.94 (d, 1 H) 6.84-6.89 (m, 2 H) 5.54-5.72 (m, 1 H) 4.77 (dd, 2 H) 4.65 (dd, 2 H) 4.36-4.44 (m, 1 H) 4.31-4.35 (m, 1 H) 4.02-4.09 (m, 1 H) 2.91-3.00 (m, 1 H) 2.77-2.88 (m, 1 H); MS (ESI) m/z 426[M+H⁺].

Example 28

2-(cyclopentyloxy)-N-[(3S)-5-pyridin-4-yl-3,4-dihydro-2H-chromen-3-yl]Pyrimidine-5-carboxamide The title compound was synthesized according to method B1, starting from Amine 1 and Acid 13; $^1$H NMR (400 MHz, CD$_3$OD) δ ppm 8.88 (s, 2 H) 8.58 (d, 2 H) 7.38-7.48 (m, 2 H) 7.24 (t, 1 H) 6.94 (d, 1 H) 6.86 (dd, 1 H) 5.41-5.53 (m, 1 H) 4.36-4.46 (m, 1 H) 4.23-4.35 (m, 1 H) 4.02-4.09 (m, 1 H) 2.93-3.04 (m, 1 H) 2.81 (dd, 1 H) 1.91-2.04 (m, 2 H) 1.74-1.89 (m, 4 H) 1.60-1.73 (m, 2 H); MS (ESI) m/z 417[M+H⁺].

Example 29

6-(cyclobutyloxy)-N-[(3S)-5-pyridin-4-yl-3,4-dihydro-2H-chromen-3-yl]nicotin-amide The title compound was synthesized according to method B1, starting from Amine 1 and Acid 14; $^1$H NMR (400 MHz, CD$_3$OD) δ ppm 8.58 (d, 2 H) 8.53 (d, 1 H) 8.02 (dd, 1 H) 7.44 (d, 2 H) 7.24 (t, 1 H) 6.94 (d, 1 H) 6.86 (d, 1 H) 6.75 (d, 1 H) 5.12-5.23 (m, 1 H) 4.35-4.43 (m, 1 H) 4.26-4.35 (m, 1 H) 4.01-4.09 (m, 1 H) 2.89-2.99 (m, 1 H) 2.76-2.87 (m, 1 H) 2.39-2.51 (m, 2 H) 2.03-2.18 (m, 2 H) 1.78-1.90 (m, 1 H) 1.63-1.78 (m, 1 H); MS (ESI) m/z 402[M+H⁺].

Example 30

6-(cyclopropylmethoxy)-N-[(3S)-5-pyridin-4-yl-3,4-dihydro-2H-chromen-3-yl]nicotin-amide The title compound was synthesized according to method B1, starting from Amine 1 and Acid 15; $^1$H NMR (400 MHz, CD$_3$OD) δ ppm 8.58 (d, 2 H) 8.54 (d, 1 H) 8.02 (dd, 1 H) 7.39-7.46 (m, 2 H) 7.24 (t, 1 H) 6.94 (d, 1 H) 6.86 (d, 1 H) 6.79 (d, 1 H) 4.35-4.43 (m, 1 H) 4.28-4.35 (m, 1 H) 4.15 (d, 2 H) 4.00-4.10 (m, 1 H) 2.91-2.99 (m, 1 H) 2.77-2.87 (m, 1 H) 1.19-1.33 (m, 1 H) 0.55-0.63 (m, 2 H) 0.29-0.36 (m, 2 H); MS (ESI) m/z 402[M+H⁺].

Example 31

N-[(2R)-8-(3,5-dimethylisoxazol-4-yl)-1,2,3,4-tetrahydronaphthalen-2-yl]-6-isopropoxy-nicotinamide The title compound was synthesized according to method B1, starting from Amine 7 and Acid 6; $^1$H NMR (400 MHz, CD$_3$OD) δ ppm 8.58 (d, 1 H) 8.03 (dd, 1 H) 7.18-7.26 (m, 2 H) 6.92-6.99 (m, 1 H) 6.74 (d, 1 H) 5.25-5.37 (m, 1 H) 4.16-4.27 (m, 1 H) 2.96-3.09 (m, 2 H) 2.69-2.84 (m, 1 H) 2.42-2.54 (m, 1 H) 2.22 (d, 3 H) 2.13-2.20 (m, 1 H) 2.06 (d, 3 H) 1.74-1.87 (m, 1 H) 1.33 (d, 6 H); MS (ESI) m/z 406[M+H⁺].

Example 32

6-(2,2-difluoroethoxy)-N-[(2R)-8-(3,5-dimethylisoxazol-4-yl)-1,2,3,4-tetrahydronaphthalen-2-yl]nicotin-amide The title compound was synthesized according to method B1, starting from Amine 7 and Acid 11; $^1$H NMR (400 MHz, CD$_3$OD) δ ppm 8.61 (d, 1 H) 8.11 (dd, 1 H) 7.17-7.25 (m, 2 H) 6.94-7.00 (m, 1 H) 6.90 (d, 1 H) 6.19 (tt, 1 H) 4.57 (td, 2 H) 4.15-4.27 (m, 1 H) 2.98-3.08 (m, 2 H) 2.68-2.87 (m, 1 H) 2.42-2.53 (m, 1 H) 2.22 (d, 3 H) 2.14-2.23 (m, 1 H) 2.06 (d, 3 H) 1.70-1.89 (m, 1 H); MS (ESI) m/z 428[M+H⁺].

Example 33

2-(cyclopentyloxy)-N-[(2R)-8-(3,5-dimethylisoxazol-4-yl)-1,2,3,4-tetrahydronaphthalen-2-yl]pyrimidine-5-carboxamide The title compound was synthesized according to method B1, starting from Amine 7 and Acid 13; $^1$H NMR (400 MHz, CD$_3$OD) δ ppm 8.92 (s, 2 H) 7.16-7.25 (m, 2 H) 6.92-6.99 (m, 1 H) 5.39-5.55 (m, 1 H) 4.15-4.27 (m, 1 H) 2.98-3.09 (m, 2 H) 2.70-2.86 (m, 1 H) 2.38-2.54 (m, 1 H) 2.22 (d, 3 H) 2.16-2.22 (m, 1 H) 2.06 (d, 3 H) 1.93-2.03 (m, 3 H) 1.75-1.89 (m, 4 H) 1.61-1.73 (m, 2 H); MS (ESI) m/z 433[M+H⁺].

Example 34

6-(butylsulfonyl)-N-[(3S)-5-pyridin-4-yl-3,4-dihydro-2H-chromen-3-yl]nicotinamide The title compound was synthesized according to method C starting from Amine 1 and methyl 6-(butylsulfonyl)nicotinate. $^1$H NMR (400 MHz, DMSO-d$_6$) δ ppm 9.08 (m, 1 H), 8.89 (d, 1 H), 8.64 (d, 2 H), 8.46 (m, 1 H), 8.13 (d, 1 H), 7.40 (d, 2 H), 7.25 (t, 1 H), 6.93 (d, 1 H), 6.85 (d, 1 H), 4.30 (m, 2 H), 4.02 (m, 1 H), 3.46 (m, 2 H), 2.85 (m, 2 H), 1.52 (m, 2 H), 1.34 (m, 2 H), 0.82 (t, 3 H); MS (ESI) m/z 452[M+H⁺].

Example 35

6-chloro-N-[(3S)-5-pyridin-4-yl-3,4-dihydro-2H-chromen-3-yl]nicotinamide

The title compound was synthesized according to method B1, starting from Amine 1 and Acid 16; $^1$H NMR (400 MHz, CD$_3$OD) δ ppm 8.72 (d, 1 H), 8.53-8.61 (m, 2 H), 8.13 (dd, 1 H), 7.52 (d, 1 H), 7.42-7.45 (m, 2 H), 7.24 (t, 1 H), 6.94 (dd, 1 H), 6.86 (dd, 1 H), 4.37-4.46 (m, 1 H), 4.28-4.35 (m, 1 H), 4.05-4.14 (m, 1 H), 2.94-3.03 (m, 1 H), 2.77-2.87 (m, 1 H); MS (ESI) m/z 366, 368[M+H$^+$].

Example 36

2-isopropoxy-N-[(3S)-5-pyridin-4-yl-3,4-dihydro-2H-chromen-3-yl]pyrimidine-5-carboxamide The title compound was synthesized according to method B1, starting from Amine 1 and Acid 17; $^1$H NMR (400 MHz, CD$_3$OD) δ ppm 8.79 (s, 2 H), 8.49 (br. s., 2 H), 7.32-7.37 (m, 2 H), 7.14 (t, 1 H), 6.84 (d, 1 H), 6.77 (d, 1 H), 5.20-5.32 (m, 1 H), 4.26-4.36 (m, 1 H), 4.18-4.26 (m, 1 H), 3.95-4.05 (m, 1 H), 2.84-2.94 (m, 1 H), 2.63-2.77 (m, 1 H), 1.28 (d, 6 H); MS (ESI) m/z 391[M+H$^+$].

Example 37

5-methoxy-N-[(3S)-5-pyridin-4-yl-3,4-dihydro-2H-chromen-3-yl]pyrazine-2-carboxamide The title compound was synthesized according to method B1, starting from Amine 1 and Acid 18; $^1$H NMR (400 MHz, CD$_3$OD) δ ppm 8.76 (d, 1 H), 8.57 (d, 2 H), 8.15 (d, 1 H), 7.41-7.44 (m, 2 H), 7.25 (t, 1 H), 6.95 (dd, 1 H), 6.87 (dd, 1 H), 4.41-4.50 (m, 1 H), 4.26-4.33 (m, 1 H), 4.11-4.18 (m, 1 H), 4.02 (s, 3 H), 2.97-3.05 (m, 1 H), 2.82 (dd, 1 H); MS (ESI) m/z 363[M+H$^+$].

Example 38

5-isopropoxy-N-[(3S)-5-pyridin-4-yl-3,4-dihydro-2H-chromen-3-yl]pyrazine-2-carboxamide The title compound was synthesized according to method D from corresponding chlorinated heterocycle (synthesized from Amine 1 and methyl 5-chloropyrazine-2-carboxylate, according to Method C) and isopropanol; $^1$H NMR (400 MHz, CD$_3$OD) δ ppm 8.73 (d, 1 H), 8.50-8.63 (m, 2 H), 8.06 (d, 1 H), 7.43 (d, 2 H), 7.25 (t, 1 H), 6.95 (dd, 1 H), 6.87 (dd, 1 H), 5.32-5.42 (m, 1 H), 4.39-4.50 (m, 1 H), 4.26-4.33 (m, 1 H), 4.12-4.18 (m, 1 H), 3.01 (dd, 1 H), 2.82 (dd, 1 H), 1.38 (d, 3 H), 1.36 (d, 3 H); MS (ESI) m/z 391[M+H$^+$].

Example 39

N-[(2R)-8-(3-fluoropyridin-4-yl)-1,2,3,4-tetrahydronaphthalen-2-yl]-6-isopropoxynicotinamide The title compound was synthesized according to method B1, starting from Amine 31 and Acid 6; $^1$H NMR (400 MHz, CD$_3$OD) δ ppm 8.56 (d, 1 H), 8.51 (d, 1 H), 8.44 (d, 1 H), 8.01 (dd, 1 H), 7.35-7.41 (m, 1 H), 7.24-7.30 (m, 2 H), 7.04-7.10 (m, 1 H), 6.73 (d, 1 H), 5.26-5.36 (m, 1 H), 4.15-4.27 (m, 1 H), 3.07 (dd, 2 H), 2.75-2.85 (m, 1 H), 2.61-2.70 (m, 1 H), 2.14-2.24 (m, 1 H), 1.80-1.94 (m, 1 H), 1.33 (d, 6 H); MS (ESI) m/z 406[M+H$^+$].

Example 40

N-[(2R)-8-(3-fluoropyridin-4-yl)-1,2,3,4-tetrahydronaphthalen-2-yl]-6-(2,2,2-trifluoroethoxy)nicotinamide The title compound was synthesized according to method B1, starting from Amine 31 and Acid 4; $^1$H NMR (400 MHz, CD$_3$OD) δ ppm 8.60 (d, 1 H), 8.50 (d, 1 H), 8.43 (d, 1 H), 8.12 (dd, 1 H), 7.35-7.40 (m, 1 H), 7.23-7.30 (m, 2 H), 7.04-7.09 (m, 1 H), 6.93 (d, 1 H), 4.88-4.95 (m, 2 H), 4.16-4.27 (m, 1 H), 3.02-3.09 (m, 2 H), 2.74-2.83 (m, 1 H), 2.59-2.71 (m, 1 H), 2.15-2.24 (m, 1 H), 1.79-1.92 (m, 1 H); MS (ESI) m/z 446 [M+H$^+$].

Example 41

N-[(3S)-5-pyridin-4-yl-3,4-dihydro-2H-chromen-3-yl]quinoxaline-2-carboxamide

The title compound was synthesized according to method A, starting from Amine 1 and quinoxaline-2-carbonyl chloride; $^1$H NMR (400 MHz, CD$_3$OD) δ ppm 9.47 (s, 1 H), 8.49-8.59 (m, 2 H), 8.11-8.20 (m, 2 H), 7.87-7.97 (m, 2 H), 7.41-7.47 (m, 2 H), 7.26 (t, 1 H), 6.98 (dd, 1 H), 6.88 (dd, 1 H), 4.49-4.58 (m, 1 H), 4.33-4.40 (m, 1 H), 4.21 (dd, 1 H), 3.00-3.09 (m, 1 H), 2.89-2.98 (m, 1 H); MS (ESI) m/z 383 [M+H$^+$].

Example 42

5-isopropoxy-N-[(3S)-5-pyridin-3-yl-3,4-dihydro-2H-chromen-3-yl]pyrazine-2-carboxamide The title compound was synthesized according to method D from corresponding chlorinated heterocycle (synthesized from Amine 3 and methyl 5-chloropyrazine-2-carboxylate, according to Method C) and isopropanol; $^1$H NMR (400 MHz, CD$_3$OD) δ ppm 8.73 (d, 1 H), 8.48-8.54 (m, 2 H), 8.06 (d, 1 H), 7.84 (dt, 1 H), 7.50 (dd, 1 H), 7.24 (t, 1 H), 6.94 (dd, 1 H), 6.86 (dd, 1 H), 5.32-5.40 (m, 1 H), 4.41-4.49 (m, 1 H), 4.26-4.32 (m, 1 H), 4.10-4.17 (m, 1 H), 2.97 (dd, 1 H), 2.79 (dd, 1 H), 1.37 (d, 3 H), 1.35 (d, 3 H); MS (ESI) m/z 391[M+H$^+$].

Example 43

N-[(3S)-5-pyridin-3-yl-3,4-dihydro-2H-chromen-3-yl]-5-(3,3,3-trifluoropropoxy)pyrazine-2-carboxamide The title compound was synthesized according to method B1, starting from Amine 3 and Acid 20; $^1$H NMR (400 MHz, CD$_3$OD) δ ppm 8.67 (d, 1 H), 8.37-8.45 (m, 2 H), 8.08 (d, 1 H), 7.74 (dt, 1 H), 7.40 (dd, 1 H), 7.14 (t, 1 H), 6.84 (dd, 1 H), 6.76 (dd, 1 H), 4.54 (t, 2 H), 4.31-4.40 (m, 1 H), 4.16-4.22 (m, 1 H), 4.04 (dd, 1 H), 2.82-2.91 (m, 1 H), 2.58-2.74 (m, 3 H); MS (ESI) m/z 445[M+H$^+$].

Example 44

5-methoxy-N-[(3S)-5-pyridin-3-yl-3,4-dihydro-2H-chromen-3-yl]pyrazine-2-carboxamide The title compound was synthesized according to method B1, starting from Amine 3 and Acid 18; $^1$H NMR (400 MHz, CD$_3$OD) δ ppm 8.66 (d, 1 H), 8.39-8.45 (m, 2 H), 8.05 (d, 1 H), 7.72-7.76 (m, 1 H), 7.40 (dd, 1 H), 7.14 (t, 1 H), 6.82-6.86 (m, 1 H), 6.76 (dd, 1 H), 4.31-4.40 (m, 1 H), 4.17-4.22 (m, 1 H), 4.00-4.07 (m, 1 H), 3.92 (s, 3 H), 2.88 (dd, 1 H), 2.70 (dd, 1 H); MS (ESI) m/z 363[M+H$^+$].

Example 45

N-[(3S)-5-pyridin-3-yl-3,4-dihydro-2H-chromen-3-yl]-1,8-naphthyridine-2-carboxamide The title compound was synthesized according to method B1, starting from Amine 3 and Acid 21; $^1$H NMR (400 MHz, CD$_3$OD) δ ppm 9.07-9.13 (m, 1 H), 8.60 (d, 1 H), 8.50-8.56 (m, 3 H), 8.31 (d, 1 H), 7.87 (dt, 1 H), 7.72 (dd, 1 H), 7.51 (dd, 1 H), 7.26 (t, 1 H), 6.96 (d, 1 H), 6.87 (d, 1 H), 4.49-4.58 (m, 1 H), 4.32-4.39 (m, 1 H), 4.22-4.29 (m, 1 H), 3.08 (dd, 1 H), 2.88 (dd, 1 H); MS (ESI) m/z 383[M+H$^+$].

Example 46

N-[(3S)-5-pyridin-3-yl-3,4-dihydro-2H-chromen-3-yl]-1,5-naphthyridine-2-carboxamide The title compound was synthesized according to method B1, starting from Amine 3 and Acid 22; $^1$H NMR (400 MHz, CD$_3$OD) δ ppm 9.01 (dd, 1 H), 8.47-8.57 (m, 4 H), 8.40 (d, 1 H), 7.76-7.88 (m, 2 H), 7.50 (dd, 1 H), 7.25 (t, 1 H), 6.96 (d, 1 H), 6.86 (d, 1 H), 4.46-4.56 (m, 1 H), 4.32-4.39 (m, 1 H), 4.20 (dd, 1 H), 2.96-3.05 (m, 1 H), 2.85-2.94 (m, 1 H); MS (ESI) m/z 383[M+H$^+$].

Example 47

2-methyl-N-[(3S)-5-pyridin-3-yl-3,4-dihydro-2H-chromen-3-yl]-1,6-naphthyridine-3-carboxamide The title compound was synthesized according to method B1, starting from Amine 3 and Acid 23; $^1$H NMR (400 MHz, CD$_3$OD) δ ppm 9.27 (s, 1 H), 8.69 (d, 1 H), 8.55 (dd, 1 H), 8.50-8.53 (m, 1 H), 8.44 (s, 1 H), 7.82-7.88 (m, 2 H), 7.52 (dd, 1 H), 7.24 (t, 1 H), 6.92-6.96 (m, 1 H), 6.86 (dd, 1 H), 4.44-4.51 (m, 1 H), 4.32-4.38 (m, 1 H), 4.23-4.30 (m, 1 H), 3.09 (dd, 1 H), 2.77 (dd, 1 H), 2.72 (s, 3 H); MS (ESI) m/z 397[M+H$^+$].

Example 48

N-[(3S)-5-(6-methoxypyridin-3-yl)-3,4-dihydro-2H-chromen-3-yl]-5-(3,3,3-trifluoropropoxy)pyrazine-2-carboxamide The title compound was synthesized according to method B1, starting from Amine 11 and Acid 20; $^1$H NMR (400 MHz, CD$_3$OD) δ ppm 8.78 (d, 1 H), 8.19 (d, 1 H), 8.07 (d, 1 H), 7.66 (dd, 1 H), 7.20 (t, 1 H), 6.87-6.91 (m, 1 H), 6.81-6.87 (m, 2 H), 4.65 (t, 2 H), 4.41-4.50 (m, 1 H), 4.24-4.32 (m, 1 H), 4.13 (dd, 1 H), 3.93 (s, 3 H), 2.93-3.02 (m, 1 H), 2.68-2.84 (m, 3 H); MS (ESI) m/z 475[M+H$^+$].

Example 49

5-methoxy-N-[(3S)-5-(6-methoxypyridin-3-yl)-3,4-dihydro-2H-chromen-3-yl]pyrazine-2-carboxamide The title compound was synthesized according to method B1, starting from Amine 11 and Acid 18; $^1$H NMR (400 MHz, CD$_3$OD) δ ppm 8.72-8.78 (m, 1 H), 8.13-8.17 (m, 1 H), 8.06 (d, 1 H), 7.66 (dd, 1 H), 7.20 (t, 1 H), 6.80-6.91 (m, 3 H), 4.37-4.49 (m, 1 H), 4.23-4.31 (m, 1 H), 4.13 (dd, 1 H), 4.02 (s, 3 H), 3.93 (s, 3 H), 2.98 (dd, 1 H), 2.80 (dd, 1 H); MS (ESI) m/z 393[M+H$^+$].

Example 50

6-isopropoxy-N-[(3S)-5-pyridin-3-yl-3,4-dihydro-2H-chromen-3-yl]nicotinamide

The title compound was synthesized according to method B1, starting from Amine 3 and Acid 6; $^1$H NMR (400 MHz, DMSO-d$_6$) δ ppm 8.54-8.62 (m, 3 H), 8.39 (d, 1 H), 8.06 (dd, 1 H), 7.79-7.83 (m, 1 H), 7.45-7.51 (m, 1 H), 7.24 (t, 1 H), 6.91 (dd, 1 H), 6.85 (dd, 1 H), 6.77 (dd, 1 H), 5.23-5.33 (m, 1 H), 4.17-4.30 (m, 2 H), 3.88-3.97 (m, 1 H), 2.73-2.87 (m, 2 H), 1.29 (d, 6 H); MS (ESI) m/z 390[M+H$^+$].

Example 51

N-[(3S)-5-pyridin-3-yl-3,4-dihydro-2H-chromen-3-yl]-6-(3,3,3-trifluoropropoxy)nicotinamide The title compound was synthesized according to method B1, starting from Amine 3 and Acid 5; $^1$H NMR (400 MHz, DMSO-d$_6$) δ ppm 8.61-8.64 (m, 1 H), 8.56-8.60 (m, 2 H), 8.45 (d, 1 H), 8.12 (dd, 1 H), 7.78-7.84 (m, 1 H), 7.44-7.51 (m, 1 H), 7.24 (t, 1 H), 6.91 (dd, 1 H), 6.88 (dd, 1 H), 6.85 (dd, 1 H), 4.53 (t, 2 H), 4.18-4.31 (m, 2 H), 3.90-3.98 (m, 1 H), 2.72-2.88 (m, 4 H); MS (ESI) m/z 444[M+H$^+$].

Example 52

2-isobutyl-5-methyl-N-[(3S)-5-pyridin-3-yl-3,4-dihydro-2H-chromen-3-yl]-2H-1,2,3-triazole-4-carboxamide The title compound was synthesized according to method C, starting from Amine 3 and ethyl 2-isobutyl-5-methyl-2H-1,2,3-triazole-4-carboxylate; $^1$H NMR (400 MHz, DMSO-d$_6$) δ ppm 8.65 (d, 1 H), 8.58 (dd, 1 H), 8.55 (dd, 1 H), 7.75-7.80 (m, 1 H), 7.45-7.50 (m, 1 H), 7.23 (t, 1 H), 6.90 (dd, 1 H), 6.85 (dd, 1 H), 4.09-4.30 (m, 5 H), 2.93 (dd, 1 H), 2.63-2.72 (m, 1 H), 2.18 (s, 3 H), 1.88-2.00 (m, 1 H), 0.75 (d, 3 H), 0.73 (d, 3 H); MS (ESI) m/z 392[M+H$^+$].

Example 53

6-isopropoxy-N-[(3S)-5-pyrimidin-5-yl-3,4-dihydro-2H-chromen-3-yl]nicotinamide

The title compound was synthesized according to method B1, starting from Amine 19 and Acid 6; $^1$H NMR (400 MHz, DMSO-d$_6$) δ ppm 9.22 (s, 1 H), 8.87 (s, 2 H), 8.60 (d, 1 H), 8.37 (d, 1 H), 8.06 (dd, 1 H), 7.28 (t, 1 H), 6.96 (dd, 1 H), 6.93 (dd, 1 H), 6.78 (d, 1 H), 5.23-5.33 (m, 1 H), 4.16-4.31 (m, 2 H), 3.91-3.99 (m, 1 H), 2.84 (d, 2 H), 1.29 (d, 6 H); MS (ESI) m/z 391[M+H$^+$].

Example 54

N-[(3S)-5-pyrimidin-5-yl-3,4-dihydro-2H-chromen-3-yl]-6-(3,3,3-trifluoropropoxy)nicotinamide The title compound was synthesized according to method B1, starting from Amine 19 and Acid 5; $^1$H NMR (400 MHz, DMSO-d$_6$) δ ppm 9.22 (s, 1 H), 8.87 (s, 2 H), 8.63 (dd, 1 H), 8.43 (d, 1 H), 8.12 (dd, 1 H), 7.28 (t, 1 H), 6.96 (dd, 1 H), 6.93 (dd, 1 H), 6.89 (dd, 1 H), 4.53 (t, 2 H), 4.19-4.31 (m, 2 H), 3.92-4.00 (m, 1 H), 2.73-2.89 (m, 4 H); MS (ESI) m/z 445[M+H$^+$].

Example 55

6-isopropoxy-N-[(3S)-5-(2-methoxypyrimidin-5-yl)-3,4-dihydro-2H-chromen-3-yl]nicotinamide The title compound was synthesized according to method B1, starting from Amine 20 and Acid 6; $^1$H NMR (400 MHz, DMSO-$d_6$) δ ppm 8.65 (s, 2 H), 8.60 (d, 1 H), 8.37 (d, 1 H), 8.07 (dd, 1 H), 7.24 (t, 1 H), 6.92 (dd, 1 H), 6.89 (dd, 1 H), 6.78 (d, 1 H), 5.25-5.32 (m, 1 H), 4.17-4.30 (m, 2 H), 3.96 (s, 3 H), 3.89-3.94 (m, 1 H), 2.80-2.86 (m, 2 H), 1.29 (d, 6 H); MS (ESI) m/z 421[M+H$^+$].

Example 56

N-[(3S)-5-(2-methoxypyrimidin-5-yl)-3,4-dihydro-2H-chromen-3-yl]-6-(3,3,3-trifluoropropoxy)nicotinamide The title compound was synthesized according to method B1, starting from Amine 20 and Acid 5; $^1$H NMR (400 MHz, DMSO-$d_6$) δ ppm 8.65 (s, 2 H), 8.62-8.64 (m, 1 H), 8.43 (d, 1 H), 8.13 (dd, 1 H), 7.24 (t, 1 H), 6.86-6.94 (m, 3 H), 4.53 (t, 2 H), 4.19-4.31 (m, 2 H), 3.96 (s, 3 H), 3.91-3.95 (m, 1 H), 2.74-2.87 (m, 4 H); MS (ESI) m/z 475[M+H$^+$].

Example 57

N-[(3S)-5-pyridin-3-yl-3,4-dihydro-2H-chromen-3-yl]-6-(2,2,2-trifluoroethoxy)nicotinamide The title compound was synthesized according to method B1, starting from Amine 3 and Acid 4; $^1$H NMR (400 MHz, DMSO-$d_6$) δ ppm 8.63 (dd, 1 H), 8.57-8.60 (m, 2 H), 8.51 (d, 1 H), 8.19 (dd, 1 H), 7.78-7.83 (m, 1 H), 7.45-7.51 (m, 1 H), 7.24 (t, 1 H), 7.05 (dd, 1 H), 6.91 (dd, 1 H), 6.85 (dd, 1 H), 5.05 (q, 2 H), 4.19-4.32 (m, 2 H), 3.90-3.99 (m, 1 H), 2.78-2.84 (m, 2 H); MS (ESI) m/z 430[M+H$^+$].

Example 58

6-isopropoxy-N-[(3S)-5-(2-methoxypyridin-4-yl)-3,4-dihydro-2H-chromen-3-yl]nicotinamide The title compound was synthesized according to method B1, starting from Amine 9 and Acid 6; $^1$H NMR (400 MHz, DMSO-$d_6$) δ ppm 8.60 (dd, 1 H), 8.39 (d, 1 H), 8.22 (dd, 1 H), 8.07 (dd, 1 H), 7.22 (t, 1 H), 6.98 (dd, 1 H), 6.90 (dd, 1 H), 6.83 (dd, 1 H), 6.75-6.80 (m, 2 H), 5.23-5.33 (m, 1 H), 4.17-4.29 (m, 2 H), 3.89-3.96 (m, 1 H), 3.88 (s, 3 H), 2.73-2.88 (m, 2 H), 1.29 (d, 6 H); MS (ESI) m/z 420[M+H$^+$].

Example 59

N-[(3S)-5-(2-methoxypyridin-4-yl)-3,4-dihydro-2H-chromen-3-yl]-6-(3,3,3-trifluoropropoxy)nicotinamide The title compound was synthesized according to method B1, starting from Amine 9 and Acid 5; $^1$H NMR (400 MHz, DMSO-$d_6$) δ ppm 8.63 (dd, 1 H), 8.45 (d, 1 H), 8.22 (dd, 1 H), 8.13 (dd, 1 H), 7.22 (t, 1 H), 6.98 (dd, 1 H), 6.86-6.92 (m, 2 H), 6.83 (dd, 1 H), 6.77-6.80 (m, 1 H), 4.53 (t, 1 H), 4.18-4.30 (m, 2 H), 3.90-3.97 (m, 1 H), 3.88 (s, 3 H), 2.72-2.89 (m, 5 H); MS (ESI) m/z 474[M+H$^+$].

Example 60

6-isopropoxy-N-[(3S)-5-(2-methylpyrimidin-5-yl)-3,4-dihydro-2H-chromen-3-yl]nicotinamide The title compound was synthesized according to method B1, starting from Amine 21 and Acid 6; $^1$H NMR (400 MHz, DMSO-$d_6$) δ ppm 8.73 (s, 2 H), 8.59-8.61 (m, 1 H), 8.37 (d, 1 H), 8.06 (dd, 1 H), 7.26 (t, 1 H), 6.94 (dd, 1 H), 6.90 (dd, 1 H), 6.78 (dd, 1 H), 5.23-5.33 (m, 1 H), 4.18-4.31 (m, 2 H), 3.91-3.98 (m, 1 H), 2.81-2.86 (m, 2 H), 2.67 (s, 3 H), 1.29 (d, 6 H); MS (ESI) m/z 405[M+H$^+$].

Example 61

N-[(3S)-5-(2-methylpyrimidin-5-yl)-3,4-dihydro-2H-chromen-3-yl]-6-(3,3,3-trifluoropropoxy)nicotinamide The title compound was synthesized according to method B1, starting from Amine 21 and Acid 5; $^1$H NMR (400 MHz, DMSO-$d_6$) δ ppm 8.73 (s, 2 H), 8.62-8.64 (m, 1 H), 8.42 (d, 1 H), 8.12 (dd, 1 H), 7.26 (t, 1 H), 6.94 (dd, 1 H), 6.86-6.92 (m, 2 H), 4.53 (t, 2 H), 4.18-4.32 (m, 2 H), 3.91-3.99 (m, 1 H), 2.73-2.87 (m, 4 H), 2.67 (s, 3 H); MS (ESI) m/z 459[M+H$^+$].

Example 62

N-[(3S)-5-(2-fluoropyridin-4-yl)-3,4-dihydro-2H-chromen-3-yl]-6-isopropoxynicotinamide The title compound was synthesized according to method B1, starting from Amine 8 and Acid 6; $^1$H NMR (400 MHz, DMSO-$d_6$) δ ppm 8.58-8.62 (m, 1 H), 8.39 (d, 1 H), 8.31 (d, 1 H), 8.06 (dd, 1 H), 7.36-7.40 (m, 1 H), 7.26 (t, 1 H), 7.20-7.23 (m, 1 H), 6.95 (dd, 1 H), 6.88 (dd, 1 H), 6.78 (dd, 1 H), 5.23-5.34 (m, 1 H), 4.17-4.31 (m, 2 H), 3.90-3.99 (m, 1 H), 2.77-2.89 (m, 2 H), 1.29 (d, 6 H); MS (ESI) m/z 408[M+H$^+$].

Example 63

N-[(3S)-5-(2-fluoropyridin-4-yl)-3,4-dihydro-2H-chromen-3-yl]-6-(3,3,3-trifluoropropoxy)nicotinamide The title compound was synthesized according to method B1, starting from Amine 8 and Acid 5; $^1$H NMR (400 MHz, DMSO-$d_6$) δ ppm 8.63 (dd, 1 H), 8.45 (d, 1 H), 8.31 (d, 1 H), 8.12 (dd, 1 H), 7.37-7.40 (m, 1 H), 7.26 (t, 1 H), 7.21-7.23 (m, 1 H), 6.95 (dd, 1 H), 6.86-6.91 (m, 2 H), 4.53 (t, 2 H), 4.20-4.30 (m, 2 H), 3.92-3.99 (m, 1 H), 2.73-2.86 (m, 4 H); MS (ESI) m/z 462[M+H$^+$].

Example 64

N-[(3S)-5-pyridin-3-yl-3,4-dihydro-2H-chromen-3-yl]quinoxaline-2-carboxamide The title compound was synthesized according to method A, starting from Amine 3 and quinoxaline-2-carbonyl chloride; $^1$H NMR (400 MHz, DMSO-$d_6$) δ ppm 9.44 (s, 1 H), 8.99 (d, 1 H), 8.55-8.60 (m, 2 H), 8.14-8.24 (m, 2 H), 7.92-8.02 (m, 2 H), 7.78-7.84 (m, 1 H), 7.45-7.50 (m, 1 H), 7.26 (t, 1 H), 6.95 (dd, 1 H), 6.88 (dd, 1 H), 4.35-4.45 (m, 1 H), 4.27-4.34 (m, 1 H), 4.10 (dd, 1 H), 3.04 (dd, 1 H), 2.81 (dd, 1 H); MS (ESI) m/z 383[M+H$^+$].

Example 65

N-[(3S)-5-pyridin-3-yl-3,4-dihydro-2H-chromen-3-yl]quinoline-2-carboxamide

The title compound was synthesized according to method B1, starting from Amine 3 and Acid 24; $^1$H NMR (400 MHz, DMSO-d$_6$) δ ppm 8.84 (d, 1 H), 8.54-8.60 (m, 3 H), 8.13 (d, 2 H), 8.08 (d, 1 H), 7.84-7.89 (m, 1 H), 7.80-7.84 (m, 1 H), 7.68-7.74 (m, 1 H), 7.45-7.50 (m, 1 H), 7.26 (t, 1 H), 6.96 (dd, 1 H), 6.88 (dd, 1 H), 4.34-4.44 (m, 1 H), 4.27-4.33 (m, 1 H), 4.09-4.16 (m, 1 H), 3.03 (dd, 1 H), 2.83 (dd, 1 H); MS (ESI) m/z 382[M+H$^+$].

Example 66

6-isopropoxy-N-[(3S)-5-(3-methylpyridin-4-yl)-3,4-dihydro-2H-chromen-3-yl]nicotinamide The title compound was synthesized according to method B1, starting from Amine 10 and Acid 6; $^1$H NMR (400 MHz, DMSO-d$_6$) δ ppm 8.56-8.60 (m, 1 H), 8.53 (d, 1 H), 8.42-8.46 (m, 1 H), 8.35 (t, 1 H), 8.01-8.07 (m, 1 H), 7.22 (t, 1 H), 7.16 (dd, 1 H), 6.87-6.93 (m, 1 H), 6.77 (d, 1 H), 6.70 (td, 1 H), 5.23-5.31 (m, 1 H), 4.19-4.31 (m, 2 H), 3.80-3.89 (m, 1 H), 2.52-2.68 (m, 1 H), 2.31-2.48 (m, 1 H), 2.03 (s, 3 H), 1.28 (d, 6 H); MS (ESI) m/z 404[M+H$^+$].

Example 67

N-[(3S)-5-(6-fluoropyridin-3-yl)-3,4-dihydro-2H-chromen-3-yl]-6-isopropoxynicotinamide The title compound was synthesized according to method B1, starting from Amine 12 and Acid 6; $^1$H NMR (400 MHz, DMSO-d$_6$) δ ppm 8.58-8.61 (m, 1 H), 8.38 (d, 1 H), 8.22-8.25 (m, 1 H), 8.06 (dd, 1 H), 8.02 (td, 1 H), 7.28 (dd, 1 H), 7.24 (t, 1 H), 6.92 (dd, 1 H), 6.86 (dd, 1 H), 6.78 (dd, 1 H), 5.23-5.33 (m, 1 H), 4.18-4.29 (m, 2 H), 3.90-3.97 (m, 1 H), 2.75-2.82 (m, 2 H), 1.29 (d, 6 H); MS (ESI) m/z 408[M+H$^+$].

Example 68

N-[(3S)-5-(3-methylpyridin-4-yl)-3,4-dihydro-2H-chromen-3-yl]-6-(3,3,3-trifluoropropoxy)nicotinamide The title compound was synthesized according to method B1, starting from Amine 10 and Acid 5; $^1$H NMR (400 MHz, DMSO-d$_6$) δ ppm 8.59-8.64 (m, 1 H), 8.53 (d, 1 H), 8.43-8.46 (m, 1 H), 8.41 (t, 1 H), 8.07-8.13 (m, 1 H), 7.23 (t, 1 H), 7.16 (dd, 1 H), 6.85-6.93 (m, 2 H), 6.70 (td, 1 H), 4.50-4.55 (m, 2 H), 4.22-4.32 (m, 2 H), 3.81-3.89 (m, 1 H), 2.73-2.86 (m, 2 H), 2.53-2.64 (m, 1 H), 2.31-2.48 (m, 1 H), 2.03 (d, 3 H); MS (ESI) m/z 458[M+H$^+$].

Example 69

N-[(3S)-5-(6-fluoropyridin-3-yl)-3,4-dihydro-2H-chromen-3-yl]-6-(3,3,3-trifluoropropoxy)nicotinamide The title compound was synthesized according to method B1, starting from Amine 12 and Acid 5; $^1$H NMR (400 MHz, DMSO-d$_6$) δ ppm 8.61-8.64 (m, 1 H), 8.44 (d, 1 H), 8.24 (d, 1 H), 8.12 (dd, 1 H), 8.02 (td, 1 H), 7.28 (dd, 1 H), 7.24 (t, 1 H), 6.92 (dd, 1 H), 6.84-6.90 (m, 2 H), 4.53 (t, 2 H), 4.19-4.29 (m, 2 H), 3.91-3.98 (m, 1 H), 2.73-2.86 (m, 4 H); MS (ESI) m/z 462[M+H$^+$].

Example 70

6-(2,4-dimethoxyphenyl)-N-[(3S)-5-pyridin-4-yl-3,4-dihydro-2H-chromen-3-yl]nicotinamide The title compound was synthesized according to method B1, starting from Amine 1 and Acid 62; $^1$H NMR (400 MHz, DMSO-d$_6$) δ ppm 8.96-9.00 (m, 1 H), 8.63-8.66 (m, 2 H), 8.60 (d, 1 H), 8.12 (dd, 1 H), 7.91 (dd, 1 H), 7.81 (d, 1 H), 7.39-7.42 (m, 2 H), 7.25 (t, 1 H), 6.93 (dd, 1 H), 6.85 (dd, 1 H), 6.65-6.70 (m, 2 H), 4.23-4.33 (m, 2 H), 3.95-4.02 (m, 1 H), 3.85 (s, 3 H), 3.83 (s, 3 H), 2.82-2.87 (m, 2 H); MS (ESI) m/z 468[M+H$^+$].

Example 71

6-isopropoxy-N-[(3S)-5-(2-methoxypyridin-3-yl)-3,4-dihydro-2H-chromen-3-yl]nicotinamide The title compound was synthesized according to method B1, starting from Amine 14 and Acid 6; $^1$H NMR (400 MHz, DMSO-d$_6$) δ ppm 8.59 (d, 1 H), 8.36 (br. s., 1 H), 8.21 (dd, 1 H), 8.06 (dd, 1 H), 7.57 (dd, 1 H), 7.17 (t, 1 H), 7.08 (dd, 1 H), 6.86 (dd, 1 H), 6.72-6.79 (m, 2 H), 5.22-5.33 (m, 1 H), 4.25 (br. s., 2 H), 3.83-3.93 (m, 1 H), 3.83 (s, 3 H), 2.61-2.79 (m, 2 H), 1.28 (d, 6 H); MS (ESI) m/z 420[M+H$^+$].

Example 72

N-[(3S)-5-(2-methoxypyridin-3-yl)-3,4-dihydro-2H-chromen-3-yl]-6-(3,3,3-trifluoropropoxy)nicotinamide The title compound was synthesized according to method B1, starting from Amine 14 and Acid 5; $^1$H NMR (400 MHz, DMSO-d$_6$) δ ppm 8.62 (d, 1 H), 8.43 (br. s., 1 H), 8.21 (dd, 1 H), 8.11 (dd, 1 H), 7.57 (dd, 1 H), 7.17 (t, 1 H), 7.08 (dd, 1 H), 6.84-6.90 (m, 2 H), 6.74 (dd, 1 H), 4.52 (t, 2 H), 4.26 (br. s., 2 H), 3.83-3.92 (m, 1 H), 3.82 (s, 3 H), 2.72-2.87 (m, 4 H); MS (ESI) m/z 474[M+H$^+$].

Example 73

6-isopropoxy-N-[(2S)-8-(2-methoxypyrimidin-5-yl)-1,2,3,4-tetrahydronaphthalen-2-yl]nicotinamide The title compound was synthesized according to method B1, starting from Amine 35 and Acid 6; $^1$H NMR (400 MHz, DMSO-d$_6$) δ ppm 8.58-8.62 (m, 3 H), 8.36 (d, 1 H), 8.07 (dd, 1 H), 7.19-7.29 (m, 2 H), 7.09 (dd, 1 H), 6.77 (d, 1 H), 5.23-5.34 (m, 1 H), 4.01-4.12 (m, 1 H), 3.95 (s, 3 H), 2.90-3.02 (m, 2 H), 2.65-2.82 (m, 2 H), 2.01-2.11 (m, 1 H), 1.70-1.83 (m, 1 H), 1.29 (d, 6 H); MS (ESI) m/z 419[M+H$^+$].

Example 74

N-[(2R)-8-(2-fluoropyridin-3-yl)-1,2,3,4-tetrahydronaphthalen-2-yl]-6-isopropoxynicotinamide The title compound was synthesized according to method B1, starting from Amine 32 and Acid 6; $^1$H NMR (400 MHz, DMSO-d$_6$) δ ppm 8.59 (d, 1 H), 8.36 (d, 1 H), 8.25-8.29 (m, 1 H), 8.05 (dd, 1 H), 7.85-7.93 (m, 1 H), 7.42-7.48 (m, 1 H), 7.22-7.28 (m, 2 H), 7.04-7.09 (m, 1 H), 6.76 (dd, 1 H), 5.22-5.33 (m, 1 H), 4.03-4.16 (m, 1 H), 2.90-3.04 (m, 2 H), 2.52-2.65 (m, 2 H), 2.01-2.10 (m, 1 H), 1.68-1.82 (m, 1 H), 1.28 (d, 6 H); MS (ESI) m/z 406[M+H$^+$].

Example 75

N-[(2R)-8-pyridazin-4-yl-1,2,3,4-tetrahydronaphthalen-2-yl]-6-(3,3,3-trifluoropropoxy)nicotinamide The title compound was synthesized according to method B1, starting from Amine 34 and Acid 5; $^1$H NMR (400 MHz, CD$_3$OD) δ ppm 9.14-9.24 (m, 2 H), 8.59 (d, 1 H), 8.06 (dd, 1 H), 7.68-7.77 (m, 1 H), 7.26-7.33 (m, 2 H), 7.06-7.17 (m, 1 H), 6.83 (d, 1 H), 4.58 (t, 2 H), 4.15-4.27 (m, 1 H), 3.01-3.11 (m, 2 H), 2.86-2.96 (m, 1 H), 2.62-2.83 (m, 3 H), 2.13-2.24 (m, 1 H), 1.82-1.95 (m, 1 H); MS (ESI) m/z 443[M+H$^+$].

Example 76

6-isopropoxy-N-[(3S)-5-(6-methoxypyridin-3-yl)-3,4-dihydro-2H-chromen-3-yl]nicotinamide The title compound was synthesized according to method B1, starting from Amine 11 and Acid 6; $^1$H NMR (400 MHz, CD$_3$OD) δ ppm 8.54 (d, 1 H), 8.08 (d, 1 H), 8.00 (dd, 1 H), 7.67 (dd, 1 H), 7.19 (t, 1 H), 6.84-6.89 (m, 2 H), 6.80-6.83 (m, 1 H), 6.72 (d, 1 H), 5.22-5.37 (m, 1 H), 4.34-4.41 (m, 1 H), 4.27-4.33 (m, 1 H), 4.02 (dd, 1 H), 3.93 (s, 3 H), 2.86-2.97 (m, 1 H), 2.74-2.84 (m, 1 H), 1.32 (d, 6 H); MS (ESI) m/z 420 [M+H$^+$].

Example 77

N-[(3S)-5-(6-methoxypyridin-3-yl)-3,4-dihydro-2H-chromen-3-yl]-6-(3,3,3-trifluoropropoxy)nicotinamide The title compound was synthesized according to method B1, starting from Amine 11 and Acid 5; $^1$H NMR (400 MHz, CD$_3$OD) δ ppm 8.58 (d, 1 H), 8.08 (d, 1 H), 8.05 (dd, 1 H), 7.67 (dd, 1 H), 7.19 (t, 1 H), 6.84-6.90 (m, 2 H), 6.82 (d, 2 H), 4.58 (t, 2 H), 4.34-4.43 (m, 1 H), 4.28-4.34 (m, 1 H), 4.03 (dd, 1 H), 3.94 (s, 3 H), 2.89-2.98 (m, 1 H), 2.77-2.85 (m, 1 H), 2.62-2.75 (m, 2 H); MS (ESI) m/z 474[M+H$^+$].

Example 78

6-isopropoxy-N-[(2R)-8-pyridazin-4-yl-1,2,3,4-tetrahydronaphthalen-2-yl]nicotinamide The title compound was synthesized according to method B1, starting from Amine 34 and Acid 6; $^1$H NMR (400 MHz, CD$_3$OD) δ ppm 9.22 (d, 2 H), 8.56 (d, 1 H), 8.01 (dd, 1 H), 7.71-7.76 (m, 1 H), 7.28-7.34 (m, 2 H), 7.09-7.15 (m, 1 H), 6.72 (d, 1 H), 5.25-5.36 (m, 1 H), 4.14-4.24 (m, 1 H), 3.02-3.09 (m, 2 H), 2.86-2.94 (m, 1 H), 2.72-2.81 (m, 1 H), 2.15-2.24 (m, 1 H), 1.83-1.96 (m, 1 H), 1.32 (d, 6 H); MS (ESI) m/z 389[M+H$^+$].

Example 79

N-[(3S)-5-(5-fluoro-6-methoxypyridin-3-yl)-3,4-dihydro-2H-chromen-3-yl]-5-methoxypyrazine-2-carboxamide The title compound was synthesized according to method B1, starting from Amine 15 and Acid 18; $^1$H NMR (400 MHz, CD$_3$OD) δ ppm 8.76 (s, 1 H), 8.15 (s, 1 H), 7.88 (d, 1 H), 7.51 (dd, 1 H), 7.20 (t, 1 H), 6.90 (d, 1 H), 6.85 (d, 1 H), 4.41-4.50 (m, 1 H), 4.28 (dd, 1 H), 4.12 (dd, 1 H), 4.02 (s, 6 H), 2.93-3.06 (m, 1 H), 2.73-2.88 (m, 1 H); MS (ESI) m/z 411 [M+H$^+$].

Example 80

N-[(3S)-5-pyridazin-4-yl-3,4-dihydro-2H-chromen-3-yl]-6-(2,2,2-trifluoroethoxy)nicotinamide The title compound was synthesized according to method B1, starting from Amine 26 and Acid 4; $^1$H NMR (400 MHz, CD$_3$OD) δ ppm 9.14-9.30 (m, 2 H), 8.59 (d, 1 H), 8.11 (dd, 1 H), 7.78 (dd, 1 H), 7.30 (t, 1 H), 7.01 (d, 1 H), 6.94 (d, 2 H), 4.91-4.96 (m, 2 H), 4.38-4.48 (m, 1 H), 4.30-4.37 (m, 1 H), 4.13 (dd, 1 H), 3.03 (dd, 1 H), 2.81-2.91 (m, 1 H); MS (ESI) m/z 431[M+H$^+$].

Example 81

N-[(3S)-5-pyridazin-4-yl-3,4-dihydro-2H-chromen-3-yl]-6-(3,3,3-trifluoropropoxy)nicotinamide The title compound was synthesized according to method B1, starting from Amine 26 and Acid 5; $^1$H NMR (400 MHz, CD$_3$OD) δ ppm 9.26 (s, 1 H), 9.24 (d, 1 H), 8.57 (d, 1 H), 8.04 (dd, 1 H), 7.77 (dd, 1 H), 7.30 (t, 1 H), 7.01 (d, 1 H), 6.94 (d, 1 H), 6.82 (d, 1 H), 4.57 (t, 2 H), 4.36-4.44 (m, 1 H), 4.29-4.37 (m, 1 H), 4.12 (dd, 1 H), 2.97-3.05 (m, 1 H), 2.81-2.91 (m, 1 H), 2.62-2.75 (m, 2 H); MS (ESI) m/z 445[M+H$^+$].

Example 82

6-isopropoxy-N-[(2R)-8-(2-methoxypyrimidin-5-yl)-1,2,3,4-tetrahydronaphthalen-2-yl]nicotinamide The title compound was synthesized according to method B1, starting from Amine 36 and Acid 6; $^1$H NMR (400 MHz, DMSO-d$_6$) δ ppm 8.57-8.63 (m, 3 H), 8.36 (d, 1 H), 8.07 (dd, 1 H), 7.19-7.28 (m, 2 H), 7.09 (dd, 1 H), 6.77 (dd, 1 H), 5.23-5.34 (m, 1 H), 4.01-4.12 (m, 1 H), 3.95 (s, 3 H), 2.87-3.03 (m, 2 H), 2.65-2.82 (m, 2 H), 2.02-2.11 (m, 1 H), 1.70-1.83 (m, 1 H), 1.29 (d, 6 H); MS (ESI) m/z 419[M+H$^+$].

Example 83

5-methoxy-N-[(3S)-5-(2-methoxypyrimidin-5-yl)-3,4-dihydro-2H-chromen-3-yl]pyrazine-2-carboxamide The title compound was synthesized according to method B1, starting from Amine 20 and Acid 18; $^1$H NMR (400 MHz, DMSO-d$_6$) δ ppm 8.76 (d, 1 H), 8.63 (s, 2 H), 8.53 (d, 1 H), 8.31 (d, 1 H), 7.25 (t, 1 H), 6.88-6.95 (m, 2 H), 4.28-4.37 (m, 1 H), 4.23 (dd, 1 H), 4.04 (dd, 1 H), 3.98 (s, 3 H), 3.95 (s, 3 H), 2.92-3.00 (m, 1 H), 2.79-2.87 (m, 1 H); MS (ESI) m/z 394 [M+H$^+$].

Example 84

N-[(2R)-8-(2-methoxypyrimidin-5-yl)-1,2,3,4-tetrahydronaphthalen-2-yl]-6-(3,3,3-trifluoropropoxy)nicotinamide The title compound was synthesized according to method B1, starting from Amine 36 and Acid 5; $^1$H NMR (400 MHz, DMSO-d$_6$) δ ppm 8.62-8.64 (m, 1 H), 8.60 (s, 2 H), 8.43 (d, 1 H), 8.13 (dd, 1 H), 7.20-7.28 (m, 2 H), 7.09 (dd, 1 H), 6.88 (dd, 1 H), 4.53 (t, 2 H), 4.00-4.08 (m, 1 H), 3.95 (s, 3 H), 2.92-3.00 (m, 2 H), 2.64-2.88 (m, 4 H), 2.03-2.12 (m, 1 H), 1.70-1.82 (m, 1 H); MS (ESI) m/z 473[M+H$^+$].

Example 85

N-[(2R)-8-(2-methoxypyrimidin-5-yl)-1,2,3,4-tetrahydronaphthalen-2-yl]-6-(2,2,2-trifluoroethoxy)nicotinamide The title compound was synthesized according to method B1, starting from Amine 36 and Acid 4; $^1$H NMR (400 MHz, DMSO-d$_6$) δ ppm 8.62-8.68 (m, 1 H), 8.61 (s, 2 H), 8.50 (d, 1 H), 8.21 (dd, 1 H), 7.20-7.29 (m, 2 H), 7.10 (dd, 1 H), 7.06 (dd, 1 H), 5.06 (q, 2 H), 4.03-4.14 (m, 1 H), 3.96 (s, 3 H), 2.90-3.02 (m, 2 H), 2.65-2.84 (m, 2 H), 2.04-2.13 (m, 1 H), 1.71-1.84 (m, 1 H); MS (ESI) m/z 459[M+H$^+$].

Example 86

N-[(3S)-5-(2-methoxypyrimidin-5-yl)-3,4-dihydro-2H-chromen-3-yl]-6-(2,2,2-trifluoroethoxy)nicotinamide The title compound was synthesized according to method B1, starting from Amine 20 and Acid 4; $^1$H NMR (400 MHz, DMSO-d$_6$) δ ppm 8.61-8.66 (m, 3 H), 8.51 (d, 1 H), 8.20 (dd, 1 H), 7.25 (t, 1 H), 7.04-7.08 (m, 1 H), 6.86-6.95 (m, 2 H), 5.05 (q, 2 H), 4.19-4.32 (m, 2 H), 3.96 (s, 3 H), 3.91-3.98 (m, 1 H), 2.85 (d, 2 H); MS (ESI) m/z 461[M+H$^+$].

Example 87

N-[(2R)-8-(2-fluoropyridin-3-yl)-1,2,3,4-tetrahydronaphthalen-2-yl]-6-(2,2,2-trifluoroethoxy)nicotinamide The title compound was synthesized according to method B1, starting from Amine 32 and Acid 4; $^1$H NMR (400 MHz, DMSO-d$_6$) δ ppm 8.60 (d, 1 H), 8.19-8.23 (m, 1 H), 8.12 (dd, 1 H), 7.78-7.87 (m, 1 H), 7.37-7.43 (m, 1 H), 7.22-7.27 (m, 2 H), 7.03-7.08 (m, 1 H), 6.94 (d, 1 H), 4.91 (q, 2 H), 4.22 (br. s., 1 H), 3.00-3.10 (m, 2 H), 2.54-2.84 (m, 2 H), 2.14-2.26 (m, 1 H), 1.78-1.94 (m, 1 H); MS (ESI) m/z 446[M+H$^+$].

Example 88

N-[(3S)-5-(5-fluoro-6-methoxypyridin-3-yl)-3,4-dihydro-2H-chromen-3-yl]-6-(2,2,2-trifluoroethoxy)nicotinamide The title compound was synthesized according to method B1, starting from Amine 15 and Acid 4; $^1$H NMR (400 MHz, DMSO-d$_6$) δ ppm 8.59-8.61 (m, 1 H), 8.12 (dd, 1 H), 7.90 (d, 1 H), 7.52 (dd, 1 H), 7.20 (t, 1 H), 6.92-6.96 (m, 1 H), 6.90 (dd, 1 H), 6.84 (dd, 1 H), 4.91 (q, 2 H), 4.35-4.43 (m, 1 H), 4.28-4.35 (m, 1 H), 4.03-4.08 (m, 1 H), 4.03 (s, 3 H), 2.91-3.01 (m, 1 H), 2.77-2.87 (m, 1 H); MS (ESI) m/z 478[M+H$^+$].

Example 89

N-[(3S)-5-(2-methoxypyrimidin-5-yl)-3,4-dihydro-2H-chromen-3-yl]-4-methyl-2-(2,2,2-trifluoroethoxy)pyrimidine-5-carboxamide The title compound was synthesized according to method B1, starting from Amine 20 and Acid 25; $^1$H NMR (400 MHz, DMSO-d$_6$) δ ppm 8.62-8.68 (m, 3 H), 8.57 (s, 1 H), 7.24 (t, 1 H), 6.86-6.94 (m, 2 H), 5.06 (q, 2 H), 4.20-4.29 (m, 2 H), 4.00-4.07 (m, 1 H), 3.96 (s, 3 H), 2.93 (dd, 1 H), 2.69-2.78 (m, 1 H), 2.45 (s, 3 H); MS (ESI) m/z 476[M+H$^+$].

Example 90

N-[(2R)-8-(2-methoxypyrimidin-5-yl)-1,2,3,4-tetrahydronaphthalen-2-yl]-4-methyl-2-(2,2,2-trifluoroethoxy)pyrimidine-5-carboxamide The title compound was synthesized according to method B1, starting from Amine 36 and Acid 25; $^1$H NMR (400 MHz, DMSO-d$_6$) δ ppm 8.57-8.62 (m, 4 H), 7.20-7.28 (m, 2 H), 7.09 (dd, 1 H), 5.06 (q, 2 H), 4.02-4.12 (m, 1 H), 3.96 (s, 3 H), 2.90-3.02 (m, 2 H), 2.77-2.86 (m, 1 H), 2.67 (dd, 1 H), 2.46 (s, 3 H), 2.04-2.13 (m, 1 H), 1.71-1.81 (m, 1 H); MS (ESI) m/z 474[M+H$^+$].

Example 91

N-[(3S)-5-imidazo[1,2-a]pyridin-6-yl-3,4-dihydro-2H-chromen-3-yl]-6-(2,2,2-trifluoroethoxy)nicotinamide The title compound was synthesized according to method B1, starting from Amine 30 and Acid 4; $^1$H NMR (400 MHz, DMSO-d$_6$) δ ppm 8.63 (d, 1 H), 8.56-8.59 (m, 2 H), 8.19 (dd, 1 H), 7.94 (s, 1 H), 7.60-7.63 (m, 2 H), 7.21-7.27 (m, 2 H), 7.04 (d, 1 H), 6.92 (d, 2 H), 5.01-5.07 (m, 2 H), 4.20-4.30 (m, 2 H), 3.91-3.96 (m, 1 H), 2.80-2.92 (m, 2 H); MS (APPI/APCI) m/z 469[M+H$^+$].

Example 92

2-isopropoxy-N-[(3S)-5-(2-methoxypyrimidin-5-yl)-3,4-dihydro-2H-chromen-3-yl]-4-methylpyrimidine-5-carboxamide The title compound was synthesized according to method C, starting from Amine 20 and methyl 2-isopropoxy-4-methylpyrimidine-5-carboxylate; $^1$H NMR (400 MHz, DMSO-d$_6$) δ ppm 8.63 (s, 2 H), 8.53 (d, 1 H), 8.47 (s, 1 H), 7.24 (t, 1 H), 6.87-6.93 (m, 2 H), 5.15-5.24 (m, 1 H), 4.19-4.29 (m, 2 H), 3.98-4.05 (m, 1 H), 3.96 (s, 3 H), 2.91 (dd, 1 H), 2.68-2.77 (m, 1 H), 2.40 (s, 3 H), 1.29 (d, 6 H); MS (ESI) m/z 436[M+H$^+$].

Example 93

N-[(3S)-5-(2-ethoxypyrimidin-5-yl)-3,4-dihydro-2H-chromen-3-yl]-6-(2,2,2-trifluoroethoxy)nicotinamide The title compound was synthesized according to method B1, starting from Amine 24 and Acid 4; $^1$H NMR (400 MHz, DMSO-d$_6$) δ ppm 8.64 (m, 3 H), 8.51 (d, 1 H), 8.19 (dd, 1 H), 7.24 (t, 1 H), 7.06 (d, 1 H), 6.88-6.94 (m, 2 H), 5.05 (m, 2 H), 4.37-4.42 (m, 2 H), 4.20-4.30 (m, 2 H), 3.95 (m, 1 H), 2.85 (d, 2 H), 1.36 (t, 3 H); MS (ESI) m/z 475[M+H$^+$].

Example 94

6-(cyclobutyloxy)-N-[(3S)-5-(5-fluoro-6-methoxypyridin-3-yl)-3,4-dihydro-2H-chromen-3-yl]nicotinamide The title compound was synthesized according to method B1, starting from Amine 15 and Acid 14; $^1$H NMR (400 MHz, DMSO-d$_6$) δ ppm 8.58 (d, 1 H), 8.40 (d, 1 H), 8.03-8.11 (dd, 1 H), 7.98 (d, 1 H), 7.73-7.83 (dd, 1 H), 7.22 (t, 1 H), 6.78-6.95 (m, 3 H), 5.10-5.21 (m, 1 H), 4.15-4.33 (m, 2 H), 3.98 (s, 3 H), 3.91 (t, 1 H), 2.74-2.90 (m, 2 H), 2.34-2.44 (m, 2 H), 1.96-2.12 (m, 2 H), 1.77 (q, 1 H), 1.56-1.70 (m, 1 H); MS (APCI) m/z 450[M+H$^+$].

Example 95

N-[(3S)-5-(2-ethylpyrimidin-5-yl)-3,4-dihydro-2H-chromen-3-yl]-6-(2,2,2-trifluoroethoxy)nicotinamide The title compound was synthesized according to method B1, starting from Amine 22 and Acid 4; $^1$H NMR (400 MHz, DMSO-d$_6$) δ ppm 8.77 (s, 2 H), 8.64 (d, 1 H), 8.50 (d, 1 H), 8.14-8.25 (dd, 1 H), 7.26 (t, 1 H), 7.06 (d, 1 H), 6.88-6.99 (m, 2 H), 5.05 (q, 2 H), 4.16-4.34 (m, 2 H), 3.96 (t, 1 H), 2.95 (q, 2 H), 2.85 (m, 2 H), 1.32 (t, 3 H); MS (APCI) m/z 459[M+H$^+$].

Example 96

N-[(3S)-5-(2-cyclopropylpyrimidin-5-yl)-3,4-dihydro-2H-chromen-3-yl]-6-(3-fluoropropoxy)nicotinamide The title compound was synthesized according to method B1, starting from Amine 23 and Acid 19; $^1$H NMR (400 MHz, CDCl$_3$) δ ppm 8.52 (s, 2 H) 8.46 (d, 1 H), 7.92 (dd, 1 H), 7.23-7.29 (m, 1 H), 6.98 (dd, 1 H), 6.86 (dd, 1 H), 6.74 (d, 1 H), 6.30 (d, 1 H), 4.67 (t, 2 H), 4.55 (t, 1 H), 4.46 (t, 2 H), 4.23-4.33 (m, 2 H) 3.11 (dd, 1 H), 2.70 (dd, 1 H), 2.25-2.34 (m, 1 H), 2.16-2.23 (m, 1 H), 2.09-2.16 (m, 1 H), 1.15-1.22 (m, 2 H), 1.10-1.16 (m, 2 H); MS (APCI) m/z 449[M+H$^+$].

Example 97

N-[(3S)-5-(5-fluoro-6-methoxypyridin-3-yl)-3,4-dihydro-2H-chromen-3-yl]-6-(3,3,3-trifluoropropoxy)nicotinamide The title compound was synthesized according to method B1, starting from Amine 15 and Acid 5; $^1$H NMR (400 MHz, DMSO-d$_6$) δ ppm 8.64 (d, 1 H), 8.45 (d, 1 H), 8.08-8.19 (dd, 1 H), 7.98 (d, 1 H), 7.73-7.84 (dd, 1 H), 7.15-7.26 (m, 1 H), 6.82-6.95 (m, 3 H), 4.53 (t, 2 H), 4.17-4.33 (m, 2 H), 3.98 (s, 3 H), 3.92 (t, 1 H), 2.71-2.90 (m, 4 H); MS (APCI) m/z 492[M+H$^+$].

Example 98

N-[(3S)-5-(3,6-dimethoxypyridazin-4-yl)-3,4-dihydro-2H-chromen-3-yl]-6-(2,2,2-trifluoroethoxy)nicotinamide The title compound was synthesized according to method B1, starting from Amine 27 and Acid 4; $^1$H NMR (400 MHz, CDCl$_3$) δ ppm 8.48 (d, 1 H), 8.01 (dd, 1 H), 7.22-7.27 (m, 1 H), 6.99 (dd, 1 H), 6.89 (d, 1 H), 6.78-6.82 (m, 2 H), 6.36 (d, 1 H), 4.78 (q, 2 H), 4.64 (br. s., 1 H), 4.30-4.35 (m, 1 H), 4.22-4.27 (m, 1 H), 4.09 (s, 3 H), 3.97 (br. s., 3 H), 3.00 (br. s., 1 H), 2.59 (br. s., 1 H); MS (APCI) m/z 491[M+H$^+$].

Example 99

N-[(3S)-5-(6-methylpyrazin-2-yl)-3,4-dihydro-2H-chromen-3-yl]-6-(2,2,2-trifluoroethoxy)nicotinamide The title compound was synthesized according to method B1, starting from Amine 28 and Acid 4; $^1$H NMR (400 MHz, DMSO-d$_6$) δ ppm 8.64 (d, 1 H), 8.60 (s, 1 H), 8.54-8.53 (m, 2 H), 8.20 (dd, 1 H), 7.26 (t, 1 H), 7.06-7.03 (m, 2 H), 6.96 (dd, 1 H), 5.08-5.01 (m, 2 H), 4.31-4.24 (m, 2 H), 4.00-3.95 (m, 1 H), 3.00-2.92 (m, 2 H), 2.55 (s, 3 H); MS (APCI) m/z 445 [M+H$^+$].

Example 100

6-(3-fluoropropoxy)-N-[(3S)-5-(2-methoxypyrimidin-5-yl)-3,4-dihydro-2H-chromen-3-yl]nicotinamide The title compound was synthesized according to method B1, starting from Amine 20 and Acid 19; $^1$H NMR (400 MHz, DMSO-d$_6$) δ ppm 8.65 (s, 2 H), 8.62 (d, 1 H), 8.42 (d, 1 H), 8.10 (dd, 1 H), 7.24 (t, 1 H), 6.93-6.86 (m, 3 H), 4.65 (t, 1 H), 4.53 (t, 1 H), 4.39 (t, 2 H), 4.29-4.20 (m, 2 H), 3.96-3.91 (m, 4 H), 2.90-2.80 (m, 2 H), 2.17-2.04 (m, 2 H); MS (APCI) m/z 439[M+H$^+$].

Example 101

6-(3-fluoropropoxy)-N-[(3S)-5-(2-methylpyrimidin-5-yl)-3,4-dihydro-2H-chromen-3-yl]nicotinamide The title compound was synthesized according to method B1, starting from Amine 21 and Acid 19; $^1$H NMR (400 MHz, DMSO-d$_6$) δ ppm 8.73 (s, 2 H), 8.62 (d, 1 H), 8.40 (d, 1 H), 8.10 (dd, 1 H), 7.26 (t, 1 H), 6.95-6.86 (m, 3 H), 4.64 (t, 1 H), 4.53 (t, 1 H), 4.39 (t, 2 H), 4.30-4.21 (m, 2 H), 3.97-3.92 (m, 1 H), 2.90-2.80 (m, 2 H), 2.67 (s, 3 H), 2.17-2.04 (m, 2 H); MS (APCI) m/z 423[M+H$^+$].

Example 102

N-[(3S)-5-(2-methylpyrimidin-5-yl)-3,4-dihydro-2H-chromen-3-yl]-6-(2,2,2-trifluoroethoxy)nicotinamide The title compound was synthesized according to method B1, starting from Amine 21 and Acid 4; $^1$H NMR (400 MHz, DMSO-d$_6$) δ ppm 8.74 (s, 2 H), 8.65 (d, 1 H), 8.50 (d, 1 H), 8.16-8.25 (dd, 1 H), 7.27 (t, 1 H), 7.07 (d, 1 H), 6.88-6.99 (m, 2 H), 5.06 (q, 2 H), 4.19-4.34 (m, 2 H), 3.96 (t, 1 H), 2.85 (m, 2 H), 2.68 (s, 3 H); MS (APCI) m/z 445[M+H$^+$].

Example 103

2-isopropoxy-N-[(2R)-8-(2-methoxypyrimidin-5-yl)-1,2,3,4-tetrahydronaphthalen-2-yl]isonicotinamide The title compound was synthesized according to method B1, starting from Amine 36 and Acid 26; $^1$H NMR (400 MHz, DMSO-d$_6$) δ ppm 8.53-8.63 (m, 3 H), 8.22 (d, 1 H), 7.18-7.30 (m, 3 H), 7.05-7.13 (m, 2 H), 5.18-5.30 (m, 1 H), 4.00-4.12 (m, 1 H), 3.95 (s, 3 H), 2.87-3.01 (m, 2 H), 2.69-2.78 (m, 2 H), 1.98-2.11 (m, 1 H), 1.71-1.84 (m, 1 H), 1.28 (d, 6 H); MS (APCI) m/z 419[M+H$^+$].

Example 104

2-isopropoxy-N-[(3S)-5-(2-methylpyrimidin-5-yl)-3,4-dihydro-2H-chromen-3-yl]isonicotinamide The title compound was synthesized according to method B1, starting from Amine 21 and Acid 26; $^1$H NMR (400 MHz, DMSO-d$_6$) δ ppm 8.73 (s, 2 H), 8.58 (d, 1 H), 8.23 (d, 1 H), 7.21-7.31 (m, 2 H), 7.10 (s, 1 H), 6.86-6.98 (m, 2 H), 5.18-

5.31 (m, 1 H), 4.16-4.30 (m, 2 H), 3.91-4.03 (m, 1 H), 2.84 (m, 2 H), 2.67 (s, 3 H), 1.28 (d, 6 H); MS (APCI) m/z 405[M+H$^+$].

Example 105

6-(cyclobutyloxy)-N-[(3S)-5-(2-methylpyrimidin-5-yl)-3,4-dihydro-2H-chromen-3-yl]nicotinamide The title compound was synthesized according to method B1, starting from Amine 21 and Acid 14; $^1$H NMR (400 MHz, DMSO-d$_6$) δ ppm 8.73 (s, 2 H), 8.58 (d, 1 H), 8.38 (d, 1 H), 8.03-8.11 (dd, 1 H), 7.26 (t, 1 H), 6.86-6.99 (m, 2 H), 6.82 (d, 1 H), 5.10-5.21 (m, 1 H), 4.17-4.30 (m, 2 H), 3.90-3.98 (m, 1 H), 2.83 (m, 2 H), 2.67 (s, 3 H), 2.35-2.44 (m, 2 H), 1.99-2.10 (m, 2 H), 1.73-1.84 (m, 1 H), 1.59-1.71 (m, 1H); MS (APCI) m/z 417[M+H$^+$].

Example 106

6-(cyclobutyloxy)-N-[(3S)-5-(2-methoxypyrimidin-5-yl)-3,4-dihydro-2H-chromen-3-yl]nicotinamide The title compound was synthesized according to method B1, starting from Amine 20 and Acid 14; $^1$H NMR (400 MHz, DMSO-d$_6$) δ ppm 8.64 (s, 2 H), 8.58 (d, 1 H), 8.38 (d, 1 H), 8.03-8.13 (dd, 1 H), 7.24 (t, 1 H), 6.85-6.96 (m, 2 H), 6.82 (d, 1 H), 5.10-5.21 (m, 1 H), 4.17-4.31 (m, 2 H), 3.87-4.02 (m, 4 H), 2.83 (m, 2 H), 2.34-2.46 (m, 2 H), 1.96-2.13 (m, 2 H), 1.71-1.85 (m, 1 H), 1.58-1.71 (m, 1 H); MS (APCI) m/z 433[M+H$^+$].

Example 107

2-isopropoxy-N-[(3S)-5-(2-methoxypyrimidin-5-yl)-3,4-dihydro-2H-chromen-3-yl]isonicotinamide The title compound was synthesized according to method B1, starting from Amine 20 and Acid 26; $^1$H NMR (400 MHz, CDCl$_3$) δ ppm 8.48 (s, 2 H), 8.21 (d, 1 H), 7.24-7.30 (m, 1 H), 7.09 (dd, 1 H), 6.99 (dd, 1 H), 6.84-6.90 (m, 2 H), 6.40 (d, 1 H), 5.26-5.36 (m, 1 H), 4.63-4.71 (m, 1 H), 4.21-4.32 (m, 2 H), 4.07 (s, 3 H), 3.11 (dd, 1 H), 2.69 (d, 1 H), 1.33 (dd, 6 H); MS (ESI) m/z 421[M+H$^+$].

Example 108

N-[(3S)-5-(3,5-dimethylpyrazin-2-yl)-3,4-dihydro-2H-chromen-3-yl]-6-(3-fluoropropoxy)nicotinamide The title compound was synthesized according to method B1, starting from Amine 29 and Acid 19; $^1$H NMR (400 MHz, DMSO-d$_6$) δ ppm 8.60 (d, 1 H), 8.41 (s, 1 H), 8.40 (d, 1 H), 8.09 (dd, 1 H), 7.23 (t, 1 H), 6.93 (dd, 1 H), 6.86 (d, 1 H), 6.83 (dd, 1 H), 4.64 (t, 1 H), 4.52 (t, 1 H), 4.38 (t, 2 H), 4.30-4.23 (m, 2 H), 3.87-3.82 (m, 1 H), 2.70-2.52 (m, 2 H), 2.50 (s, overlapped with solvent signal, 3 H), 2.29 (s, 3 H), 2.16-2.04 (m, 2 H); MS (APCI) m/z 437[M+H$^+$].

Example 109

N-[(3S)-5-(2-cyclopropylpyrimidin-5-yl)-3,4-dihydro-2H-chromen-3-yl]-6-(2,2,2-trifluoroethoxy)nicotinamide The title compound was synthesized according to method B1, starting from Amine 23 and Acid 4; $^1$H NMR (400 MHz, DMSO-d$_6$) δ ppm 8.77 (s, 1 H), 8.66-8.70 (m, 1 H), 8.64 (d, 1 H), 8.46-8.55 (m, 1 H), 8.16-8.23 (m, 1 H), 7.20-7.30 (m, 1 H), 7.06 (d, 1 H), 6.84-6.97 (m, 2 H), 5.05 (q, 2 H), 4.17-4.31 (m, 2 H), 3.89-4.00 (m, 1 H), 2.79-2.87 (m, 2 H), 2.19-2.29 (m, 1 H), 1.76-1.89 (m, 1 H), 1.01-1.13 (m, 2 H), 0.96 (t, 1 H); MS (APCI) m/z 471[M+H$^+$].

Example 110

N$^5$-[(3S)-5-(2-methoxypyrimidin-5-yl)-3,4-dihydro-2H-chromen-3-yl]-N$^2$,N$^2$-dipropylpyridine-2,5-dicarboxamide The title compound was synthesized according to method B1, starting from Amine 20 and Acid 27; $^1$H NMR (400 MHz, DMSO-d$_6$) δ ppm 8.92-8.95 (m, 1 H), 8.72 (d, 1 H), 8.65 (s, 2 H), 8.26 (dd, 1 H), 7.58 (dd, 1 H), 7.25 (t, 1 H), 6.87-6.95 (m, 2 H), 4.20-4.32 (m, 2 H), 3.97-4.12 (m, 1 H), 3.96 (s, 3 H), 3.35-3.40 (m, 2 H), 3.10-3.15 (m, 2 H), 2.87 (d, 2 H), 1.55-1.65 (m, 2 H), 1.40-1.52 (m, 2 H), 0.90 (t, 3H), 0.63 (t, 3 H); MS (APPI/APCI) m/z 490[M+H$^+$].

Example 111

N$^5$-[(3S)-5-(2-methoxypyrimidin-5-yl)-3,4-dihydro-2H-chromen-3-yl]-N$^2$-(3-methylbutyl)pyridine-2,5-dicarboxamide The title compound was synthesized according to method B1, starting from Amine 20 and Acid 28; $^1$H NMR (400 MHz, DMSO-d$_6$) δ ppm 8.95-8.98 (m, 1 H), 8.80-8.85 (m, 1 H), 8.75 (d, 1 H), 8.65 (s, 2 H), 8.34 (dd, 1 H), 8.08 (d, 1 H), 7.25 (t, 1 H), 6.87-6.95 (m, 2 H), 4.25-4.35 (m, 2 H), 3.98-4.02 (m, 1 H), 3.96 (s, 3 H), 3.20-3.45 (m, 2 H, obscured by H$_2$O), 2.85-2.90 (m, 2 H), 1.54-1.63 (m, 1 H), 1.40-1.47 (m, 2 H), 0.89 (d, 6 H); MS (APPI/APCI) m/z 476[M+H$^+$].

Example 112

N$^2$-isobutyl-N$^5$-[(3S)-5-(2-methoxypyrimidin-5-yl)-3,4-dihydro-2H-chromen-3-yl]-N$^2$-methylpyridine-2,5-dicarboxamide The title compound was synthesized according to method B1, starting from Amine 20 and Acid 29; $^1$H NMR (400 MHz, DMSO-d$_6$) δ ppm 8.92-8.97 (m, 1 H), 8.70-8.75 (m, 1 H), 8.66 (s, 2 H), 8.23-8.29 (m, 1 H), 7.56-7.61 (m, 1 H), 7.25 (t, 1 H), 6.87-6.95 (m, 2 H), 4.22-4.32 (m, 2 H), 3.98-4.10 (m, 1 H), 3.96 (s, 3 H), 3.30 (d, 1 H), 3.10 (d, 1 H), 2.98 (s, 1.5 H), 2.87 (m, 2 H), 2.84 (s, 1.5 H), 1.96-2.08 (m, 1 H), 1.80-1.90 (m, 1 H), 0.91 (d, 3 H), 0.67 (d, 3 H); MS (APPI/APCI) m/z 476[M+H$^+$].

Example 113

N-[(3S)-5-pyridin-4-yl-3,4-dihydro-2H-chromen-3-yl]-6-(pyrrolidin-1-ylcarbonyl)nicotinamide The title compound was synthesized according to method C, starting from Amine 1 and methyl 6-(pyrrolidin-1-ylcarbonyl)nicotinate; $^1$H NMR (400 MHz, CD$_3$OD) δ ppm 8.93 (d, 1 H), 8.58 (d, 2 H), 8.24 (dd, 1 H), 7.77 (d, 1 H), 7.42-7.46 (m, 2 H), 7.25 (t, 1 H), 6.93-6.97 (m, 1 H), 6.87 (dd, 1 H), 4.38-4.48 (m, 1 H), 4.27-4.38 (m, 1 H), 4.08-4.17 (m, 1 H), 3.62 (t, 4 H), 2.95-3.06 (m, 1 H), 2.77-2.88 (m, 1 H), 1.87-2.00 (m, 4 H); MS (ESI) m/z 429[M+H$^+$].

Example 114

N-[(3S)-5-pyridin-4-yl-3,4-dihydro-2H-chromen-3-yl]-6-(1,3-thiazol-2-ylmethoxy)nicotinamide The title compound was synthesized according to method B2 starting from Amine 1 and Acid 36; $^1$H NMR (400 MHz, DMSO-$d_6$) δ ppm 8.61 (m, 3 H), 8.47 (d, 1 H), 8.16 (dd, 1 H), 7.82 (d, 1 H), 7.74 (d, 1 H), 7.37-7.42 (m, 2 H), 7.24 (t, 1H), 6.99 (d, 1 H), 6.92 (d, 1 H), 6.84 (d, 1 H), 5.70 (s, 2 H), 4.20-4.30 (m, 2 H), 3.93-3.98 (m, 1 H), 2.82 (d, 2 H); MS (APPI/APCI) m/z 445[M+H$^+$].

Example 115

6-[(5-methylisoxazol-3-yl)methoxy]-N-[(3S)-5-pyridin-4-yl-3,4-dihydro-2H-chromen-3-yl]nicotinamide The title compound was synthesized according to method B2 starting from Amine 1 and Acid 37; $^1$H NMR (400 MHz, DMSO-$d_6$) δ ppm 8.60-8.70 (m, 3 H), 8.45 (d, 1 H), 8.13 (dd, 1 H), 7.36-7.44 (m, 2 H), 7.24 (t, 1 H), 6.90-6.97 (m, 2 H), 6.81-6.87 (m, 1 H), 6.27 (s, 1 H), 5.41 (s, 2 H), 4.20-4.35 (m, 2 H), 3.96 (t, 1 H), 2.84 (d, 2 H), 2.38 (s, 3 H); MS (APPI/APCI) m/z 443[M+H$^+$].

Example 116

6-[(1-methyl-1H-imidazol-2-yl)methoxy]-N-[(3S)-5-pyridin-4-yl-3,4-dihydro-2H-chromen-3-yl]nicotinamide The title compound was synthesized according to method B2 starting from Amine 1 and Acid 38; $^1$H NMR (400 MHz, DMSO-$d_6$) δ ppm 8.62-8.68 (m, 3 H), 8.45 (d, 1 H), 8.12 (dd, 1 H), 7.37-7.43 (m, 2 H), 7.25 (t, 1 H), 7.17 (s, 1 H), 6.89-6.95 (m, 2 H), 6.82-6.88 (m, 2 H), 5.38 (s, 2 H), 4.20-4.32 (m, 2 H), 3.93-3.98 (m, 1 H), 3.68 (s, 3 H), 2.83 (d, 2 H); MS (APPI/APCI) m/z 442[M+H$^+$].

Example 117

6-(cyclopentylsulfonyl)-N-[(3S)-5-pyridin-4-yl-3,4-dihydro-2H-chromen-3-yl]nicotinamide The title compound was synthesized according to method B2 starting from Amine 1 and Acid 42; $^1$H NMR (400 MHz, DMSO-$d_6$) δ ppm 9.07-9.10 (m, 1 H), 8.89 (d, 1 H), 8.64 (d, 2 H), 8.46 (dd, 1 H), 8.14 (d, 1 H), 7.40 (d, 2 H), 7.25 (t, 1 H), 6.93 (d, 1 H), 6.85 (d, 1 H), 4.25-4.35 (m, 2 H), 3.99-4.10 (m, 2 H), 2.77-2.92 (m, 2 H), 1.75-1.90 (m, 4 H), 1.50-1.70 (m, 4 H); MS (APPI/APCI) m/z 464[M+H$^+$].

Example 118

N-[(3S)-5-pyridin-4-yl-3,4-dihydro-2H-chromen-3-yl]-6-(pyridin-2-ylmethoxy)nicotinamide The title compound was synthesized according to method B2 starting from Amine 1 and Acid 39; $^1$H NMR (400 MHz, DMSO-$d_6$) δ ppm 8.61-8.65 (m, 2 H), 8.59 (d, 1 H), 8.55 (d, 1 H), 8.43 (d, 1 H), 8.13 (dd, 1 H), 7.79 (td, 1 H), 7.43 (d, 1 H), 7.37-7.41 (m, 2 H), 7.29-7.34 (m, 1 H), 7.24 (t, 1 H), 6.99 (d, 1 H), 6.92 (dd, 1 H), 6.84 (dd, 1 H), 5.46 (s, 2 H), 4.20-4.30 (m, 2 H), 3.92-3.98 (m, 1 H), 2.82 (d, 2 H); MS (APPI/APCI) m/z 439[M+H$^+$].

Example 119

N-[(3S)-5-pyridin-4-yl-3,4-dihydro-2H-chromen-3-yl]-6-(pyridin-3-ylmethoxy)nicotinamide The title compound was synthesized according to method B2 starting from Amine 1 and Acid 40; $^1$H NMR (400 MHz, DMSO-$d_6$) δ ppm 8.66-8.69 (m, 1 H), 8.61-8.65 (m, 3 H), 8.53 (dd, 1 H), 8.44 (d, 1 H), 8.12 (dd, 1 H), 7.84-7.89 (m, 1 H), 7.37-7.44 (m, 3 H), 7.24 (t, 1 H), 6.93 (t, 2 H), 6.84 (d, 1 H), 5.44 (s, 2 H), 4.20-4.30 (m, 2 H), 3.93-3.97 (m, 1 H), 2.82 (d, 2H); MS (APPI/APCI) m/z 439[M+H$^+$].

Example 120

6-(pyrazin-2-ylmethoxy)-N-[(3S)-5-pyridin-4-yl-3,4-dihydro-2H-chromen-3-yl]nicotinamide The title compound was synthesized according to method B2 starting from Amine 1 and Acid 41; $^1$H NMR (400 MHz, DMSO-$d_6$) δ ppm 8.74-8.76 (m, 1 H), 8.61-8.65 (m, 3 H), 8.57-8.61 (m, 2 H), 8.44 (d, 1 H), 8.14 (dd, 1 H), 7.36-7.42 (m, 2 H), 7.24 (t, 1 H), 7.00 (d, 1 H), 6.92 (d, 1 H), 6.84 (d, 1 H), 5.54 (s, 2 H), 4.20-4.30 (m, 2 H), 3.93-3.97 (m, 1 H), 2.82 (d, 2 H); MS (APPI/APCI) m/z 440[M+H$^+$].

Example 121

N-[(3S)-5-(2-methoxypyrimidin-5-yl)-3,4-dihydro-2H-chromen-3-yl]-6-(tetrahydrofuran-2-ylmethoxy)nicotinamide The title compound was synthesized according to method B2 starting from Amine 20 and Acid 44; $^1$H NMR (400 MHz, DMSO-$d_6$) δ ppm 8.64 (s, 2 H), 8.60 (d, 1 H), 8.39 (d, 1 H), 8.10 (dd, 1 H), 7.24 (t, 1 H), 6.84-6.94 (m, 3 H), 4.20-4.32 (m, 4 H), 4.12-4.18 (m, 1 H), 3.96 (s, 3 H), 3.92-3.95 (m, 1 H), 3.74-3.79 (m, 1 H), 3.63-3.68 (m, 1 H), 2.85 (d, 2 H), 1.92-2.02 (m, 1 H), 1.75-1.90 (m, 2 H), 1.60-1.67 (m, 1 H); MS (ESI) m/z 463 [M+H$^+$].

Example 122

N-[(3S)-5-(2-methoxypyrimidin-5-yl)-3,4-dihydro-2H-chromen-3-yl]-6-(tetrahydro-2H-pyran-2-ylmethoxy)nicotinamide The title compound was synthesized according to method B2 starting from Amine 20 and Acid 43; $^1$H NMR (400 MHz, DMSO-$d_6$) δ ppm 8.64 (s, 2 H), 8.60 (d, 1 H), 8.39 (d, 1 H), 8.09 (dd, 1 H), 7.24 (t, 1 H), 6.85-6.94 (m, 3 H), 4.20-4.30 (m, 4 H), 3.96 (s, 3 H), 3.85-3.95 (m, 2 H), 3.57-3.65 (m, 1 H), 3.20-3.40 (m, 1 H, obscured by H$_2$O), 2.85 (d, 2 H), 1.77-1.85 (m, 1 H), 1.61 (d, 1 H), 1.45-1.50 (m, 3 H), 1.25-1.35 (m, 1 H); MS (ESI) m/z 477[M+H$^+$].

Example 123

N-[(3S)-5-(2-methoxypyrimidin-5-yl)-3,4-dihydro-2H-chromen-3-yl]-6-(tetrahydro-2H-pyran-4-ylmethoxy)nicotinamide The title compound was synthesized according to method B2 starting from Amine 20 and Acid 49; $^1$H NMR (400 MHz, DMSO-$d_6$) δ ppm 8.64 (s, 2 H), 8.59-8.62 (m, 1 H), 8.38 (d, 1 H), 8.10 (dd, 1H), 7.24 (t, 1 H), 6.83-6.94 (m, 3 H), 4.20-4.30 (m, 2 H), 4.16 (d, 2 H), 3.96 (s, 3 H), 3.92-3.95 (m, 1 H), 3.86 (dd, 2 H), 3.20-2.45 (m, 2 H, obscured by H2O), 2.84 (d, 2 H), 1.95-2.05 (m, 1 H), 1.60-1.67 (m, 2 H), 1.25-1.37 (m, 2 H); MS (ESI) m/z 477[M+H$^+$].

Example 124

6-(but-2-yn-1-yloxy)-N-[(3S)-5-(2-methoxypyrimidin-5-yl)-3,4-dihydro-2H-chromen-3-yl]nicotinamide The title compound was synthesized according to method B2 starting from Amine 20 and Acid 52; $^1$H NMR (400 MHz, DMSO-d$_6$) δ ppm 8.64 (s, 2 H), 8.62 (d, 1 H), 8.44 (d, 1 H), 8.12 (dd, 1 H), 7.24 (t, 1 H), 6.70-6.94 (m, 3 H), 4.97 (m, 2 H), 4.20-4.30 (m, 2 H), 3.96 (s, 3 H); 3.90-3.95 (m, 1 H), 2.84 (d, 2 H), 1.80-1.84 (m, 3 H); MS (ESI) m/z 431[M+H$^+$].

Example 125

N$^5$-[(3S)-5-(2-methoxypyrimidin-5-yl)-3,4-dihydro-2H-chromen-3-yl]-N$^2$-(3,3,3-trifluoropropyl)pyridine-2,5-dicarboxamide The title compound was synthesized according to method B1 starting from Amine 20 and Acid 30; $^1$H NMR (400 MHz, DMSO-d$_6$) δ ppm 9.08 (t, 1 H), 8.96-9.0 (m, 1 H), 8.77 (d, 1 H), 8.65 (s, 2 H), 8.36 (dd, 1 H), 8.10 (d, 1 H), 7.25 (t, 1 H), 6.87-6.95 (m, 2 H), 4.25-4.33 (m, 2 H), 3.98-4.04 (m, 1 H), 3.96 (s, 3 H), 3.53-3.58 (m, 2 H), 2.85-2.89 (m, 2 H), 2.53-2.64 (m, 2 H); MS (APPI/APCI) m/z 502[M+H$^+$].

Example 126

6-(2-methoxyethoxy)-N-[(3S)-5-pyridin-4-yl-3,4-dihydro-2H-chromen-3-yl]nicotinamide The title compound was synthesized according to method B1 starting from Amine 1 and Acid 50; $^1$H NMR (400 MHz, CD$_3$OD) δ ppm 8.57 (d, 2 H), 8.54 (d, 1 H), 8.02 (dd, 1 H), 7.43 (d, 2 H), 7.23 (t, 1 H), 6.93 (d, 1 H), 6.85 (d, 1 H), 6.81 (d, 1 H), 4.43-4.48 (m, 2 H), 4.34-4.42 (m, 1 H), 4.29-4.34 (m, 1 H), 4.01-4.07 (m, 1 H), 3.70-3.75 (m, 2 H), 3.39 (s, 3 H), 2.90-3.00 (m, 1 H), 2.79-2.88 (m, 1 H); MS (ESI) m/z 406 [M+H$^+$].

Example 127

6-(oxetan-2-ylmethoxy)-N-[(3S)-5-pyridin-4-yl-3,4-dihydro-2H-chromen-3-yl]nicotinamide The title compound was synthesized according to method B1 starting from Amine 1 and Acid 45; $^1$H NMR (400 MHz, CD$_3$OD) δ ppm 8.58 (d, 2 H), 8.56 (d, 1 H), 8.05 (dd, 1 H), 7.43 (d, 2 H), 7.24 (t, 1 H), 6.94 (dd, 1 H), 6.83-6.89 (m, 2 H), 5.10-5.18 (m, 1 H), 4.66-4.73 (m, 1 H), 4.58-4.65 (m, 1 H), 4.50 (d, 2 H), 4.35-4.43 (m, 1 H), 4.28-4.35 (m, 1 H), 4.02-4.09 (m, 1 H), 2.92-2.99 (m, 1 H), 2.71-2.89 (m, 2 H), 2.57-2.70 (m, 1 H); MS (ESI) m/z 418[M+H$^+$].

Example 128

6-{[(2R)-2-methoxypropyl]oxy}-N-[(3S)-5-pyridin-4-yl-3,4-dihydro-2H-chromen-3-yl]nicotinamide The title compound was synthesized according to method B1 starting from Amine 1 and Acid 51; $^1$H NMR (400 MHz, CD$_3$OD) δ ppm 8.58 (d, 2 H), 8.55 (d, 1 H), 8.04 (dd, 1 H), 7.44 (d, 2 H), 7.24 (t, 1 H), 6.94 (d, 1 H), 6.84 (dd, 2 H), 4.24-4.44 (m, 4 H), 4.01-4.10 (m, 1 H), 3.68-3.79 (m, 1 H), 3.40 (s, 3 H), 2.90-3.01 (m, 1 H), 2.77-2.88 (m, 1 H), 1.23 (d, 3 H); MS (ESI) m/z 420[M+H$^+$].

Example 129

N-[(3S)-5-pyridin-4-yl-3,4-dihydro-2H-chromen-3-yl]-6-(tetrahydro-2H-pyran-4-yloxy)nicotinamide The title compound was synthesized according to method B1 starting from Amine 1 and Acid 53; $^1$H NMR (400 MHz, CD$_3$OD) δ ppm 8.56-8.60 (m, 2 H), 8.55 (d, 1 H), 8.03 (dd, 1 H), 7.41-7.46 (m, 2 H), 7.24 (t, 1 H), 6.94 (dd, 1 H), 6.86 (dd, 1 H), 6.79 (d, 1 H), 5.24-5.32 (m, 1 H), 4.36-4.45 (m, 1 H), 4.29-4.35 (m, 1 H), 4.02-4.10 (m, 1 H), 3.89-3.98 (m, 2 H), 3.54-3.65 (m, 2 H), 2.91-3.00 (m, 1 H), 2.77-2.87 (m, 1 H), 2.02-2.11 (m, 2 H), 1.67-1.80 (m, 2 H); MS (ESI) m/z 432 [M+H$^+$].

Example 130

N$^5$-[(3S)-5-pyridin-4-yl-3,4-dihydro-2H-chromen-3-yl]-N$^2$-(tetrahydro-2H-pyran-4-yl)pyridine-2,5-dicarboxamide The title compound was synthesized according to method C starting from Amine 1 and methyl 6-(tetrahydro-2H-pyran-4-ylcarbamoyl)nicotinate; $^1$H NMR (400 MHz, CD$_3$OD) δ ppm 8.95 (d, 1 H), 8.58 (d, 2 H), 8.26 (dd, 1 H), 8.12 (d, 1 H), 7.44 (d, 2 H), 7.24 (t, 1 H), 6.95 (d, 1 H), 6.87 (d, 1 H), 4.39-4.49 (m, 1 H), 4.30-4.37 (m, 1 H), 4.07-4.17 (m, 2 H), 3.95-4.02 (m, 1 H), 3.53 (td, 2 H), 2.97-3.05 (m, 1 H), 2.84 (dd, 1 H), 1.84-1.93 (m, 2 H), 1.65-1.78 (m, 2 H); MS (ESI) m/z 459[M+H$^+$].

Example 131

N$^5$-[(3S)-5-pyridin-4-yl-3,4-dihydro-2H-chromen-3-yl]-N$^2$-(2,2,2-trifluoroethyl)pyridine-2,5-dicarboxamide The title compound was synthesized according to method C starting from Amine 1 and methyl 6-[(2,2,2-trifluoroethyl)carbamoyl]nicotinate; $^1$H NMR (400 MHz, CD$_3$OD) δ ppm 8.96-9.00 (m, 1 H), 8.57-8.60 (m, 2 H), 8.28 (dd, 1 H), 8.14-8.18 (m, 1 H), 7.42-7.47 (m, 2 H), 7.25 (t, 1 H), 6.95 (dd, 1 H), 6.87 (dd, 1 H), 4.40-4.48 (m, 1 H), 4.32-4.38 (m, 1 H), 4.08-4.16 (m, 3 H), 2.97-3.06 (m, 1 H), 2.81-2.88 (m, 1 H); MS (ESI) m/z 457[M+H$^+$].

Example 132

N$^5$-[(3S)-5-pyridin-3-yl-3,4-dihydro-2H-chromen-3-yl]-N$^2$-(3,3,3-trifluoropropyl)pyridine-2,5-dicarboxamide The title compound was synthesized according to method C starting from Amine 3 and methyl 6-[(3,3,3-trifluoropropyl)carbamoyl]nicotinate; $^1$H NMR (400 MHz, CD$_3$OD) δ ppm 8.95 (d, 1 H), 8.47-8.56 (m, 2 H), 8.26 (dd, 1 H), 8.12 (d, 1 H), 7.85 (dt, 1 H), 7.52 (dd, 1 H), 7.24 (t, 1 H), 6.94 (d, 1 H), 6.86 (d, 1 H), 4.40-4.47 (m, 1 H), 4.30-4.37 (m, 1 H), 4.09-4.14 (m, 1 H), 3.67 (t, 2 H), 2.93-3.01 (m, 1 H), 2.76-2.85 (m, 1 H), 2.45-2.59 (m, 2 H); MS (ESI) m/z 471[M+H$^+$].

Example 133

N-[(3S)-5-pyridin-3-yl-3,4-dihydro-2H-chromen-3-yl]-5-(tetrahydro-2H-pyran-4-yloxy)pyrazine-2-carboxamide The title compound was synthesized according to method D from corresponding chlorinated heterocycle (synthesized from Amine 3 and methyl 5-chloropyrazine-2-carboxylate, according to Method C) and tetrahydro-2H-pyran-4-ol; $^1$H NMR (400 MHz, CD$_3$OD) δ ppm 8.70-8.74 (m, 1 H), 8.47-8.56 (m, 2 H), 8.09-8.14 (m, 1 H), 7.84 (dt, 1 H), 7.50 (dd, 1 H), 7.24 (t, 1 H), 6.93 (d, 1 H), 6.86 (d, 1 H), 5.27-5.38 (m, 1 H), 4.41-4.50 (m, 1 H), 4.30 (dd, 1 H), 4.14 (dd, 1 H), 3.90-3.99 (m, 2 H), 3.55-3.65 (m, 2 H), 2.98 (dd, 1 H), 2.79 (dd, 1 H), 2.03-2.13 (m, 2 H), 1.71-1.83 (m, 2 H); MS (ESI) m/z 433[M+H$^+$].

Example 134

N-[(3S)-5-(6-methoxypyridin-3-yl)-3,4-dihydro-2H-chromen-3-yl]-6-(tetrahydro-2H-pyran-4-yloxy)nicotinamide The title compound was synthesized according to method B1 starting from Amine 11 and Acid 53; $^1$H NMR (400 MHz, CD$_3$OD) δ ppm 8.55 (d, 1 H), 8.08 (d, 1 H), 8.03 (dd, 1 H), 7.67 (dd, 1 H), 7.19 (t, 1 H), 6.83-6.90 (m, 2 H), 6.75-6.83 (m, 2 H), 5.22-5.31 (m, 1 H), 4.33-4.42 (m, 1 H), 4.27-4.33 (m, 1 H), 4.02 (dd, 1 H), 3.90-3.98 (m, 5 H), 3.54-3.63 (m, 2 H), 2.87-2.97 (m, 1 H), 2.75-2.85 (m, 1 H), 2.01-2.10 (m, 2 H), 1.67-1.80 (m, 2 H); MS (ESI) m/z 462[M+H$^+$].

Example 135

N-[(3S)-5-(6-methoxypyridin-3-yl)-3,4-dihydro-2H-chromen-3-yl]-6-(tetrahydro-2H-pyran-3-yloxy)nicotinamide The title compound was synthesized according to method B1 starting from Amine 11 and Acid 46; $^1$H NMR (400 MHz, CD$_3$OD) δ ppm 8.54 (d, 1 H), 8.07 (d, 1 H), 8.02 (dd, 1 H), 7.67 (dd, 1 H), 7.19 (t, 1 H), 6.86 (t, 2 H), 6.76-6.83 (m, 2 H), 5.05-5.14 (m, 1 H), 4.33-4.42 (m, 1 H), 4.26-4.33 (m, 1 H), 4.02 (dd, 1 H), 3.93 (s, 3 H), 3.90 (dd, 1 H), 3.59-3.75 (m, 3 H), 2.87-2.97 (m, 1 H), 2.76-2.85 (m, 1 H), 2.01-2.12 (m, 1 H), 1.77-1.95 (m, 2 H), 1.55-1.66 (m, 1 H); MS (ESI) m/z 462[M+H$^+$].

Example 136

N-[(3S)-5-pyridin-4-yl-3,4-dihydro-2H-chromen-3-yl]-6-(tetrahydro-2H-pyran-3-yloxy)nicotinamide The title compound was synthesized according to method B1 starting from Amine 1 and Acid 46; $^1$H NMR (400 MHz, CD$_3$OD) δ ppm 8.56-8.60 (m, 2 H), 8.54 (d, 1 H), 8.02 (dd, 1 H), 7.41-7.46 (m, 2 H), 7.24 (t, 1 H), 6.91-6.96 (m, 1 H), 6.86 (dd, 1 H), 6.79 (d, 1 H), 5.07-5.14 (m, 1 H), 4.35-4.42 (m, 1 H), 4.30-4.35 (m, 1 H), 4.06 (dd, 1 H), 3.90 (dd, 1 H), 3.60-3.74 (m, 3 H), 2.91-2.99 (m, 1 H), 2.79-2.88 (m, 1 H), 2.01-2.12 (m, 1 H), 1.77-1.94 (m, 2 H), 1.54-1.67 (m, 1 H); MS (ESI) m/z 432[M+H$^+$].

Example 137

6-(2-methoxyethoxy)-N-[(3S)-5-pyridin-3-yl-3,4-dihydro-2H-chromen-3-yl]nicotinamide The title compound was synthesized according to method B1 starting from Amine 3 and Acid 50; $^1$H NMR (400 MHz, DMSO-d$_6$) δ ppm 8.54-8.61 (m, 3 H), 8.42 (d, 1 H), 8.09 (dd, 1 H), 7.77-7.83 (m, 1 H), 7.45-7.51 (m, 1 H), 7.24 (t, 1 H), 6.83-6.94 (m, 3 H), 4.38-4.43 (m, 2 H), 4.19-4.30 (m, 2 H), 3.90-3.98 (m, 1 H), 3.63-3.67 (m, 2 H), 3.28 (s, 3 H), 2.73-2.88 (m, 2 H); MS (ESI) m/z 406[M+H].

Example 138

2-(2-methoxyethyl)-5-methyl-N-[(3S)-5-pyridin-3-yl-3,4-dihydro-2H-chromen-3-yl]-2H-1,2,3-triazole-4-carboxamide The title compound was synthesized according to method C starting from Amine 3 and ethyl 2-(2-methoxyethyl)-5-methyl-2H-1,2,3-triazole-4-carboxylate; $^1$H NMR (400 MHz, CD$_3$OD) δ ppm 8.51 (br. s., 2 H), 7.79-7.85 (m, 1 H), 7.46-7.53 (m, 1 H), 7.22 (t, 1 H), 6.91 (dd, 1 H), 6.84 (dd, 1 H), 4.48 (t, 2 H), 4.34-4.43 (m, 1 H), 4.23-4.30 (m, 1 H), 4.04-4.12 (m, 1 H), 3.81 (t, 2 H), 3.27 (s, 3 H), 2.87-2.95 (m, 1 H), 2.74-2.82 (m, 1 H), 2.41 (s, 3 H); MS (ESI) m/z 394[M+H$^+$].

Example 139

6-(oxetan-2-ylmethoxy)-N-[(3S)-5-pyridin-3-yl-3,4-dihydro-2H-chromen-3-yl]nicotinamide The title compound was synthesized according to method B1 starting from Amine 3 and Acid 45; $^1$H NMR (400 MHz, DMSO-d$_6$) δ ppm 8.57-8.62 (m, 3 H), 8.43 (d, 1 H), 8.12 (dd, 1 H), 7.79-7.83 (m, 1 H), 7.46-7.50 (m, 1 H), 7.24 (t, 1 H), 6.89-6.93 (m, 2 H), 6.85 (dd, 1 H), 4.96-5.04 (m, 1 H), 4.38-4.56 (m, 4 H), 4.19-4.31 (m, 2 H), 3.90-3.98 (m, 1 H), 2.75-2.88 (m, 2 H), 2.63-2.73 (m, 1 H); MS (ESI) m/z 418 [M+H$^+$].

Example 140

6-(2-methoxyethoxy)-N-[(3S)-5-(2-methoxypyridin-4-yl)-3,4-dihydro-2H-chromen-3-yl]nicotinamide The title compound was synthesized according to method B1 starting from Amine 9 and Acid 50; $^1$H NMR (400 MHz, DMSO-d$_6$) δ ppm 8.57-8.62 (m, 1 H), 8.42 (d, 1 H), 8.22 (dd, 1 H), 8.10 (dd, 1 H), 7.22 (t, 1 H), 6.98 (dd, 1 H), 6.90 (dd, 1 H), 6.85-6.89 (m, 1 H), 6.83 (dd, 1 H), 6.77-6.80 (m, 1 H), 4.39-4.44 (m, 2 H), 4.19-4.29 (m, 2 H), 3.90-3.96 (m, 1 H), 3.88 (s, 3 H), 3.63-3.67 (m, 2 H), 3.28 (s, 3 H), 2.77-2.88 (m, 2 H); MS (ESI) m/z 436[M+H$^+$].

Example 141

6-(2-methoxyethoxy)-N-[(3S)-5-(2-methylpyrimidin-5-yl)-3,4-dihydro-2H-chromen-3-yl]nicotinamide The title compound was synthesized according to method B1 starting from Amine 21 and Acid 50; $^1$H NMR (400 MHz, DMSO-d$_6$) δ ppm 8.73 (s, 2 H), 8.59-8.62 (m, 1 H), 8.40 (d, 1 H), 8.10 (dd, 1 H), 7.26 (t, 1 H), 6.86-6.96 (m, 3 H), 4.39-4.43 (m, 2 H), 4.18-4.31 (m, 2 H), 3.91-3.98 (m, 1 H), 3.62-3.67 (m, 2 H), 3.28 (s, 3 H), 2.81-2.86 (m, 2 H), 2.67 (s, 3 H); MS (ESI) m/z 421[M+H$^+$].

Example 142

6-(2-methoxyethoxy)-N-[(3S)-5-(3-methylpyridin-4-yl)-3,4-dihydro-2H-chromen-3-yl]nicotinamide The title compound was synthesized according to method B1 starting from Amine 10 and Acid 50; $^1$H NMR (400 MHz, DMSO-d$_6$) δ ppm 8.56-8.61 (m, 1 H), 8.53 (d, 1 H), 8.45 (dd, 1 H), 8.38 (t, 1 H), 8.03-8.11 (m, 1 H), 7.23 (t, 1 H), 7.16 (dd, 1 H), 6.88-6.93 (m, 1 H), 6.84-6.88 (m, 1 H), 6.70 (td, 1 H), 4.38-4.43 (m, 2 H), 4.20-4.31 (m, 2 H), 3.81-3.89 (m, 1 H), 3.62-3.67 (m, 2 H), 3.28 (s, 3 H), 2.52-2.64 (m, 1 H), 2.34-2.48 (m, 1 H), 2.03 (d, 3 H); MS (ESI) m/z 420[M+H$^+$].

Example 143

N-[(3S)-5-(6-fluoropyridin-3-yl)-3,4-dihydro-2H-chromen-3-yl]-6-(2-methoxyethoxy)nicotinamide The title compound was synthesized according to method B1 starting from Amine 12 and Acid 50; $^1$H NMR (400 MHz, DMSO-d$_6$) δ ppm 8.57-8.62 (m, 1 H), 8.41 (d, 1 H), 8.24 (d, 1 H), 8.09 (dd, 1 H), 8.02 (td, 1 H), 7.28 (dd, 1 H), 7.24 (t, 1 H), 6.92 (dd, 1 H), 6.84-6.89 (m, 2 H), 4.38-4.43 (m, 2 H), 4.18-4.29 (m, 2 H), 3.90-3.98 (m, 1 H), 3.61-3.67 (m, 2 H), 3.28 (s, 3 H), 2.76-2.82 (m, 2 H); MS (ESI) m/z 424[M+H$^+$].

Example 144

N-[(2R)-8-(2-fluoropyridin-3-yl)-1,2,3,4-tetrahydronaphthalen-2-yl]-6-(2-methoxyethoxy)nicotinamide The title compound was synthesized according to method B1 starting from Amine 32 and Acid 50; $^1$H NMR (400 MHz, DMSO-d$_6$) δ ppm 8.59 (d, 1 H), 8.35-8.42 (m, 1 H), 8.23-8.28 (m, 1 H), 8.08 (dd, 1 H), 7.86-7.93 (m, 1 H), 7.42-7.48 (m, 1 H), 7.21-7.28 (m, 2 H), 7.07 (dd, 1 H), 6.86 (dd, 1 H), 4.38-4.43 (m, 2 H), 4.03-4.15 (m, 1 H), 3.62-3.67 (m, 2 H), 3.28 (s, 3 H), 2.92-3.02 (m, 2 H), 2.59 (br. s., 2 H), 2.02-2.10 (m, 1 H), 1.70-1.81 (m, 1 H); MS (ESI) m/z 422[M+H$^+$].

Example 145

N-[(2R)-8-(2-fluoropyridin-3-yl)-1,2,3,4-tetrahydronaphthalen-2-yl]-6-(tetrahydro-2H-pyran-4-yloxy)nicotinamide The title compound was synthesized according to method B1 starting from Amine 32 and Acid 53; $^1$H NMR (400 MHz, DMSO-d$_6$) δ ppm 8.57-8.60 (m, 1 H), 8.34-8.41 (m, 1 H), 8.25-8.29 (m, 1 H), 8.08 (dd, 1 H), 7.86-7.93 (m, 1 H), 7.42-7.48 (m, 1 H), 7.21-7.28 (m, 2 H), 7.04-7.09 (m, 1 H), 6.82 (d, 1 H), 5.18-5.26 (m, 1 H), 4.03-4.15 (m, 1 H), 3.81-3.88 (m, 2 H), 3.45-3.54 (m, 2 H), 2.88-3.01 (m, 2 H), 2.58 (br. s., 2 H), 1.94-2.09 (m, 3 H), 1.69-1.81 (m, 1 H), 1.56-1.68 (m, 2 H); MS (ESI) m/z 448[M+H$^+$].

Example 146

N-[(2R)-8-pyridazin-4-yl-1,2,3,4-tetrahydronaphthalen-2-yl]-6-(tetrahydro-2H-pyran-3-yloxy)nicotinamide The title compound was synthesized according to method B1 starting from Amine 34 and Acid 46; $^1$H NMR (400 MHz, CD$_3$OD) δ ppm 9.18-9.25 (m, 2 H), 8.56 (d, 1 H), 8.04 (dd, 1 H), 7.70-7.76 (m, 1 H), 7.27-7.34 (m, 2 H), 7.07-7.16 (m, 1 H), 6.80 (d, 1 H), 5.08-5.15 (m, 1 H), 4.14-4.24 (m, 1 H), 3.91 (dd, 1 H), 3.59-3.75 (m, 3 H), 3.03-3.10 (m, 2 H), 2.86-2.94 (m, 1 H), 2.72-2.81 (m, 1 H), 2.16-2.24 (m, 1 H), 2.03-2.12 (m, 1 H), 1.79-1.96 (m, 3 H), 1.56-1.67 (m, 1 H); MS (ESI) m/z 431[M+H$^+$].

Example 147

N-[(2R)-8-(6-methylpyridin-3-yl)-1,2,3,4-tetrahydronaphthalen-2-yl]-2-(tetrahydro-2H-pyran-3-yloxy)pyrimidine-5-carboxamide The title compound was synthesized according to method D from corresponding chlorinated heterocycle (synthesized from Amine 33 and Acid 61, according to Method B) and tetrahydro-2H-pyran-3-ol; $^1$H NMR (400 MHz, CD$_3$OD) δ ppm 8.91 (s, 2 H), 8.31 (d, 1 H), 7.68 (dd, 1 H), 7.35 (d, 1 H), 7.16-7.27 (m, 2 H), 7.03 (dd, 1 H), 5.07-5.16 (m, 1 H), 4.12-4.24 (m, 1 H), 3.91 (dd, 1 H), 3.61-3.75 (m, 3 H), 3.04 (dd, 2 H), 2.88 (dd, 1 H), 2.66 (dd, 1 H), 2.56 (s, 3 H), 2.06-2.24 (m, 2 H), 1.79-2.00 (m, 3 H), 1.53-1.69 (m, 1 H); MS (ESI) m/z 445[M+H$^+$].

Example 148

1-butyl-N-[(3S)-5-(5-fluoro-6-methoxypyridin-3-yl)-3,4-dihydro-2H-chromen-3-yl]-2-oxo-1,2-dihydropyridine-4-carboxamide The title compound was synthesized according to method B1 starting from Amine 15 and Acid 59; $^1$H NMR (400 MHz, CD$_3$OD) δ ppm 7.89 (d, 1 H), 7.69 (d, 1 H), 7.51 (dd, 1 H), 7.20 (t, 1 H), 6.89 (d, 1 H), 6.84 (d, 1 H), 6.81 (d, 1 H), 6.61 (dd, 1 H), 4.31-4.39 (m, 1 H), 4.29 (d, 1 H), 4.03 (s, 3 H), 3.95-4.08 (m, 3 H), 2.88-2.99 (m, 1 H), 2.73-2.84 (m, 1 H), 1.64-1.77 (m, 2 H), 1.26-1.42 (m, 2 H), 0.96 (t, 3 H); MS (ESI) m/z 452[M+H$^+$].

Example 149

N-[(3S)-5-(5-fluoro-6-methoxypyridin-3-yl)-3,4-dihydro-2H-chromen-3-yl]-2-(tetrahydrofuran-3-yloxy)pyrimidine-5-carboxamide The title compound was synthesized according to method D from corresponding chlorinated heterocycle (synthesized from Amine 15 and methyl 2-chloropyrimidine-5-carboxylate, according to Method C) and tetrahydrofuran-3-ol; $^1$H NMR (400 MHz, CD$_3$OD) δ ppm 8.91 (s, 2 H), 7.90 (d, 1 H), 7.52 (dd, 1 H), 7.21 (t, 1 H), 6.90 (d, 1 H), 6.85 (d, 1 H), 5.56-5.69 (m, 1 H), 4.35-4.45 (m, 1 H), 4.26-4.35 (m, 1 H), 4.03 (s, 3 H), 3.85-4.10 (m, 5 H), 2.90-3.04 (m, 1 H), 2.81 (dd, 1 H), 2.25-2.38 (m, 1 H), 2.10-2.23 (m, 1 H); MS (ESI) m/z 467[M+H$^+$].

Example 150

1-butyl-N-[(3S)-5-(2-methoxypyrimidin-5-yl)-3,4-dihydro-2H-chromen-3-yl]-2-oxo-1,2-dihydropyridine-4-carboxamide The title compound was synthesized according to method B1 starting from Amine 20 and Acid 59; $^1$H NMR (400 MHz, CD$_3$OD) δ ppm 8.57 (s, 2 H), 7.69 (d, 1 H), 7.24 (t, 1 H), 6.93 (d, 1 H), 6.87 (d, 1 H), 6.75-6.82 (m, 1 H), 6.60 (dd, 1 H), 4.32-4.40 (m, 1 H), 4.23-4.32 (m, 1 H), 4.06-4.11 (m, 1 H), 4.05 (s, 3 H), 3.99 (t, 2 H), 2.97 (dd, 1 H), 2.71-2.85 (m, 1 H), 1.63-1.77 (m, 2 H), 1.30-1.44 (m, 2 H), 0.96 (t, 3 H); MS (ESI) m/z 435[M+H$^+$].

Example 151

N-[(3S)-5-(6-fluoro-5-methylpyridin-3-yl)-3,4-dihydro-2H-chromen-3-yl]-6-(tetrahydro-2H-pyran-3-yloxy)nicotinamide The title compound was synthesized according to method B1 starting from Amine 16 and Acid 46; $^1$H NMR (400 MHz, CD$_3$OD) δ ppm 8.55 (d, 1 H), 8.03 (dd, 1 H), 7.96 (s, 1 H), 7.78 (d, 1 H), 7.21 (t, 1 H), 6.91 (d, 1 H), 6.76-6.86 (m, 2 H), 5.03-5.16 (m, 1 H), 4.33-4.42 (m, 1 H), 4.27-4.34 (m, 1 H), 4.04 (dd, 1 H), 3.90 (dd, 1 H), 3.58-3.75 (m, 3 H), 2.87-2.96 (m, 1 H), 2.73-2.83 (m, 1 H), 2.34 (s, 3 H), 2.02-2.12 (m, 1 H), 1.79-1.97 (m, 2 H), 1.52-1.68 (m, 1 H); MS (ESI) m/z 464 [M+H$^+$].

Example 152

1-butyl-N-[(3S)-5-(6-fluoro-5-methylpyridin-3-yl)-3,4-dihydro-2H-chromen-3-yl]-2-oxo-1,2-dihydropyridine-4-carboxamide The title compound was synthesized according to method B1 starting from Amine 16 and Acid 59; $^1$H NMR (400 MHz, CD$_3$OD) δ ppm 7.95 (s, 1 H), 7.77 (d, 1 H), 7.70 (d, 1 H), 7.21 (t, 1 H), 6.91 (d, 1 H), 6.78-6.86 (m, 2 H), 6.60 (dd, 1 H), 4.31-4.39 (m, 1 H), 4.23-4.31 (m, 1 H), 4.02-4.08 (m, 1 H), 3.99 (t, 2 H), 2.85-2.96 (m, 1 H), 2.70-2.82 (m, 1 H), 2.34 (s, 3 H), 1.64-1.75 (m, 2 H), 1.30-1.42 (m, 2 H), 0.96 (t, 3 H); MS (ESI) m/z 436[M+H$^+$].

Example 153

N-[(3S)-5-(6-fluoro-5-methylpyridin-3-yl)-3,4-dihydro-2H-chromen-3-yl]-2-(tetrahydro-2H-pyran-3-yloxy)pyrimidine-5-carboxamide The title compound was synthesized according to method D from corresponding chlorinated heterocycle (synthesized from Amine 16 and Acid 61, according to Method B) and tetrahydro-2H-pyran-3-ol; $^1$H NMR (400 MHz, CD$_3$OD) δ ppm 8.91 (s, 2 H), 7.96 (s, 1 H), 7.72-7.83 (m, 1 H), 7.22 (t, 1 H), 6.92 (d, 1 H), 6.84 (d, 1 H), 5.09-5.18 (m, 1 H), 4.36-4.44 (m, 1 H), 4.28-4.34 (m, 1 H), 4.07 (dd, 1 H), 3.92 (dd, 1 H), 3.66-3.75 (m, 3 H), 2.96 (dd, 1 H), 2.72-2.82 (m, 1 H), 2.34 (s, 3 H), 2.06-2.16 (m, 1 H), 1.85-2.01 (m, 2 H), 1.58-1.69 (m, 1 H); MS (ESI) m/z 465[M+H$^+$].

Example 154

N-[(2S)-8-(2-methoxypyrimidin-5-yl)-1,2,3,4-tetrahydronaphthalen-2-yl]-6-(tetrahydro-2H-pyran-4-yloxy)nicotinamide The title compound was synthesized according to method B1 starting from Amine 35 and Acid 53; $^1$H NMR (400 MHz, DMSO-d$_6$) δ ppm 8.60 (s, 3 H), 8.37 (d, 1 H), 8.10 (dd, 1 H), 7.19-7.28 (m, 2 H), 7.09 (dd, 1 H), 6.84 (dd, 1 H), 5.18-5.28 (m, 1 H), 4.00-4.12 (m, 1 H), 3.95 (s, 3 H), 3.81-3.88 (m, 2 H), 3.45-3.53 (m, 2 H), 2.88-3.01 (m, 2 H), 2.65-2.81 (m, 2 H), 1.95-2.10 (m, 3 H), 1.70-1.82 (m, 1 H), 1.55-1.68 (m, 2 H); MS (ESI) m/z 461[M+H$^+$].

Example 155

N-[(3S)-5-(2-methylpyrimidin-5-yl)-3,4-dihydro-2H-chromen-3-yl]-6-(tetrahydro-2H-pyran-4-yloxy)nicotinamide The title compound was synthesized according to method B1 starting from Amine 20 and Acid 53; $^1$H NMR (400 MHz, DMSO-d$_6$) δ ppm 8.73 (s, 2 H), 8.59 (dd, 1 H), 8.38 (d, 1 H), 8.09 (dd, 1 H), 7.26 (t, 1 H), 6.88-6.95 (m, 2 H), 6.84 (dd, 1 H), 5.18-5.28 (m, 1 H), 4.17-4.30 (m, 2 H), 3.91-3.98 (m, 1 H), 3.81-3.88 (m, 2 H), 3.45-3.53 (m, 2 H), 2.79-2.86 (m, 2 H), 2.67 (s, 3 H), 1.94-2.03 (m, 2 H), 1.57-1.68 (m, 2 H); MS (ESI) m/z 447 [M+H$^+$].

Example 156

N-[(2R)-8-(2-methoxypyrimidin-5-yl)-1,2,3,4-tetrahydronaphthalen-2-yl]-6-(tetrahydro-2H-pyran-4-yloxy)nicotinamide The title compound was synthesized according to method B1 starting from Amine 36 and Acid 53; $^1$H NMR (400 MHz, DMSO-d$_6$) δ ppm 8.58-8.61 (m, 3 H), 8.37 (d, 1 H), 8.10 (dd, 1 H), 7.19-7.28 (m, 2 H), 7.09 (dd, 1 H), 6.84 (dd, 1 H), 5.18-5.27 (m, 1 H), 4.01-4.12 (m, 1 H), 3.95 (s, 3 H), 3.81-3.88 (m, 2 H), 3.46-3.53 (m, 2 H), 2.90-2.99 (m, 2 H), 2.65-2.81 (m, 2 H), 1.95-2.11 (m, 3 H), 1.71-1.83 (m, 1 H), 1.56-1.67 (m, 2 H); MS (ESI) m/z 461[M+H$^+$].

Example 157

N-[(3S)-5-(2-methoxypyrimidin-5-yl)-3,4-dihydro-2H-chromen-3-yl]-6-(tetrahydro-2H-pyran-3-yloxy)nicotinamide The title compound was synthesized according to method B1 starting from Amine 20 and Acid 46; $^1$H NMR (400 MHz, DMSO-d$_6$) δ ppm 8.65 (s, 2 H), 8.60 (d, 1 H), 8.40 (d, 1 H), 8.10 (dd, 1 H), 7.24 (t, 1 H), 6.87-6.94 (m, 2 H), 6.85 (d, 1 H), 5.02-5.08 (m, 1 H), 4.18-4.30 (m, 2 H), 3.96 (s, 3 H), 3.90-3.95 (m, 1 H), 3.80-3.86 (m, 1 H), 3.58-3.66 (m, 1 H), 3.48-3.57 (m, 2 H), 2.81-2.87 (m, 2 H), 1.98-2.06 (m, 1 H), 1.69-1.84 (m, 2 H), 1.48-1.59 (m, 1 H); MS (ESI) m/z 463[M+H$^+$].

Example 158

N-[(3S)-5-(2-methoxypyrimidin-5-yl)-3,4-dihydro-2H-chromen-3-yl]-6-(tetrahydrofuran-3-yloxy)nicotinamide The title compound was synthesized according to method B1 starting from Amine 20 and Acid 47; $^1$H NMR (400 MHz, DMSO-d$_6$) δ ppm 8.65 (s, 2 H), 8.61 (d, 1 H), 8.41 (d, 1 H), 8.10 (dd, 1 H), 7.24 (t, 1 H), 6.84-6.94 (m, 3 H), 5.51-5.56 (m, 1 H), 4.18-4.29 (m, 2 H), 3.96 (s, 3 H), 3.88-3.95 (m, 2 H), 3.80-3.87 (m, 1 H), 3.70-3.78 (m, 2 H), 2.84 (d, 2 H), 2.17-2.29 (m, 1 H), 1.93-2.03 (m, 1 H); MS (ESI) m/z 449[M+H$^+$].

Example 159

N-[(2R)-8-(2-methylpyrimidin-5-yl)-1,2,3,4-tetrahydronaphthalen-2-yl]-6-(tetrahydrofuran-3-yloxy)nicotinamide The title compound was synthesized according to method B1 starting from Amine 37 and Acid 47; $^1$H NMR (400 MHz, DMSO-d$_6$) δ ppm 8.69 (s, 2 H), 8.61 (dd, 1 H), 8.40 (d, 1 H), 7.21-7.30 (m, 2 H), 7.10 (dd, 1 H), 6.86 (dd, 1 H), 5.51-5.56 (m, 1 H), 4.00-4.12 (m, 1 H), 3.91 (dd, 1 H), 3.80-3.87 (m, 1 H), 3.71-3.79 (m, 2 H), 2.92-3.00 (m, 2 H), 2.70-2.76 (m, 2 H), 2.66 (s, 3 H), 2.51-2.57 (m, 1 H), 2.18-2.29 (m, 1 H), 2.03-2.11 (m, 1 H), 1.94-2.03 (m, 1 H), 1.71-1.83 (m, 1 H); MS (ESI) m/z 431[M+H$^+$].

Example 160

N-[(2R)-8-(2-methylpyrimidin-5-yl)-1,2,3,4-tetrahydronaphthalen-2-yl]-6-(tetrahydro-2H-pyran-3-yloxy)nicotinamide The title compound was synthesized according to method B1 starting from Amine 37 and Acid 46; $^1$H NMR (400 MHz, DMSO-d$_6$) δ ppm 8.69 (s, 2 H), 8.56-8.60 (m, 1 H), 8.39 (d, 1 H), 8.09 (dd, 1 H), 7.21-7.30 (m, 2 H), 7.10 (dd, 1 H), 6.84 (dd, 1 H), 3.99-4.11 (m, 1 H), 3.83 (dd, 1 H), 3.58-3.66 (m, 1 H), 3.47-3.57 (m, 2 H), 2.92-3.03 (m, 2 H), 2.70-2.76 (m, 2 H), 2.66 (s, 3 H), 2.51-2.57 (m, 1 H), 1.95-2.11 (m, 2 H), 1.68-1.83 (m, 3 H), 1.48-1.59 (m, 1 H); MS (ESI) m/z 445 [M+H$^+$].

Example 161

N-[(2R)-8-(2-methylpyrimidin-5-yl)-1,2,3,4-tetrahydronaphthalen-2-yl]-6-(tetrahydrofuran-2-ylmethoxy)nicotinamide The title compound was synthesized according to method B1 starting from Amine 37 and Acid 44; $^1$H NMR (400 MHz, DMSO-d$_6$) δ ppm 8.67-8.72 (m, 2 H), 8.58-8.61 (m, 1 H), 8.40 (d, 1 H), 8.10 (dd, 1 H), 7.21-7.30 (m, 2 H), 7.10 (dd, 1 H), 6.86 (dd, 1 H), 4.20-4.32 (m, 2 H), 4.01-4.19 (m, 2 H), 3.73-3.80 (m, 1 H), 3.62-3.69 (m, 1 H), 2.93-3.02 (m, 2 H), 2.67-2.78 (m, 2 H), 2.66 (s, 3 H), 2.03-2.11 (m, 1 H), 1.92-2.02 (m, 1 H), 1.71-1.92 (m, 3 H), 1.58-1.69 (m, 1 H); MS (ESI) m/z 445[M+H$^+$].

Example 162

N-[(2R)-8-(2-methoxypyrimidin-5-yl)-1,2,3,4-tetrahydronaphthalen-2-yl]-6-[2-(2,2,2-trifluoroethoxy)ethoxy]nicotinamide The title compound was synthesized according to method B1 starting from Amine 36 and Acid 54; $^1$H NMR (400 MHz, DMSO-d$_6$) δ ppm 8.59-8.63 (m, 3 H), 8.41 (d, 1 H), 8.11 (dd, 1 H), 7.20-7.28 (m, 2 H), 7.09 (dd, 1 H), 6.89 (dd, 1 H), 4.45 (dd, 2 H), 4.13 (q, 2 H), 4.02-4.10 (m, 1 H), 3.91-3.97 (m, 5 H), 2.92-2.99 (m, 2 H), 2.65-2.81 (m, 2 H), 2.03-2.11 (m, 1 H), 1.70-1.83 (m, 1 H); MS (APPI/APCI) m/z 503[M+H$^+$].

Example 163

N-[(3S)-5-(2-methoxypyrimidin-5-yl)-3,4-dihydro-2H-chromen-3-yl]-6-[2-(2,2,2-trifluoroethoxy)ethoxy]nicotinamide The title compound was synthesized according to method B1 starting from Amine 20 and Acid 54; $^1$H NMR (400 MHz, DMSO-d$_6$) δ ppm 8.65 (s, 2 H), 8.61-8.62 (m, 1 H), 8.43 (d, 1 H), 8.11 (dd, 1 H), 7.24 (t, 1 H), 6.87-6.94 (m, 3 H), 4.43-4.47 (m, 2 H), 4.19-4.30 (m, 2 H), 4.13 (q, 2 H), 3.96 (s, 3 H), 3.91-3.95 (m, 3 H), 2.81-2.87 (m, 2 H), 2.51-2.55 (m, 1 H); MS (APPI/APCI) m/z 503[M+H$^+$].

Example 164

6-(1,4-dioxan-2-ylmethoxy)-N-[(2R)-8-(2-fluoropyridin-3-yl)-1,2,3,4-tetrahydronaphthalen-2-yl]nicotinamide The title compound was synthesized according to method B1 starting from Amine 32 and Acid 48; $^1$H NMR (400 MHz, DMSO-d$_6$) δ ppm 8.59 (d, 1 H), 8.41 (d, 1 H), 8.27 (d, 1 H), 8.09 (dd, 1 H), 7.90 (t, 1 H), 7.45 (t, 1 H), 7.18-7.30 (m, 2 H), 7.07 (dd, 1 H), 6.87 (d, 1 H), 4.19-4.32 (m, 2 H), 4.09 (br. s., 1 H), 3.69-3.91 (m, 3 H), 3.54-3.69 (m, 2 H), 3.43-3.53 (m, 1 H), 3.35-3.41 (m, 1 H), 2.88-3.05 (m, 2 H), 2.59 (br. s., 2 H), 2.01-2.12 (m, 1 H), 1.67-1.83 (m, 1 H); MS (ESI) m/z 464 [M+H$^+$].

Example 165

6-(1,4-dioxan-2-ylmethoxy)-N-[(3S)-5-(2-methoxypyridin-4-yl)-3,4-dihydro-2H-chromen-3-yl]nicotinamide The title compound was synthesized according to method B1 starting from Amine 9 and Acid 48; $^1$H NMR (400 MHz, DMSO-d$_6$) δ ppm 8.60 (d, 1 H), 8.44 (d, 1 H), 8.22 (d, 1 H), 8.11 (dd, 1 H), 7.22 (t, 1 H), 6.98 (dd, 1 H), 6.86-6.95 (m, 2 H), 6.75-6.86 (m, 2 H), 4.16-4.37 (m, 4 H), 3.82-4.00 (m, 4 H), 3.70-3.82 (m, 2 H), 3.55-3.70 (m, 2 H), 3.43-3.54 (m, 1 H), 3.34-3.43 (m, 1 H), 3.16 (d, 1 H), 2.73-2.90 (m, 2 H); MS (ESI) m/z 478[M+H$^+$].

Example 166

6-(1,4-dioxan-2-ylmethoxy)-N-[(3S)-5-(5-fluoro-6-methoxypyridin-3-yl)-3,4-dihydro-2H-chromen-3-yl]nicotinamide The title compound was synthesized according to method B1 starting from Amine 15 and Acid 48; $^1$H NMR (400 MHz, DMSO-d$_6$) δ ppm 8.61 (d, 1 H), 8.43 (d, 1 H), 8.11 (dd, 1 H), 7.98 (d, 1 H), 7.78 (dd, 1 H), 7.22 (t, 1 H), 6.79-6.96 (m, 3 H), 4.16-4.34 (m, 4 H), 3.70-4.03 (m, 6 H), 3.54-3.70 (m, 2 H), 3.42-3.53 (m, 1 H), 3.34-3.43 (m, 1 H), 3.16 (d, 1 H), 2.75-2.89 (m, 2 H); MS (ESI) m/z 496[M+H$^+$].

Example 167

N$^5$-[(2R)-8-(2-methoxypyrimidin-5-yl)-1,2,3,4-tetrahydronaphthalen-2-yl]-N$^2$-(3,3,3-trifluoropropyl)pyridine-2,5-dicarboxamide The title compound was synthesized according to method B1 starting from Amine 36 and Acid 30; $^1$H NMR (400 MHz, DMSO-d$_6$) δ ppm 9.11 (t, 1 H), 8.99 (dd, 1 H), 8.77 (d, 1 H), 8.61 (s, 2 H), 8.36 (dd, 1 H), 8.10 (dd, 1 H), 7.20-7.28 (m, 2 H), 7.10 (dd, 1 H), 4.15-4.25 (m, 1 H), 3.95 (s, 3 H), 3.53-3.58 (m, 2 H), 2.90-3.05 (m, 2 H), 2.70-2.85 (m, 2 H), 2.52-2.64 (m, 2 H), 2.05-2.15 (m, 1 H), 1.75-1.85 (m, 1 H); MS (ESI) m/z 500[M+H$^+$].

Example 168

6-(but-2-yn-1-yloxy)-N-[(2R)-8-(2-methoxypyrimidin-5-yl)-1,2,3,4-tetrahydronaphthalen-2-yl]nicotinamide The title compound was synthesized according to method B1 starting from Amine 36 and Acid 52; $^1$H NMR (400 MHz, DMSO-d$_6$) δ ppm 8.62 (dd, 1 H), 8.60 (s, 2 H), 8.44 (d, 1 H), 8.12 (dd, 1 H), 7.20-7.28 (m, 2 H), 7.09 (dd, 1 H), 6.89 (d, 1 H), 4.95-5.0 (m, 2 H), 4.02-4.15 (m, 1 H), 3.95 (s, 3 H), 2.90-3.03 (m, 2 H), 2.65-2.80 (m, 2 H), 2.02-2.11 (m, 1 H), 1.81 (t, 3 H), 1.72-1.79 (m, 1 H); MS (ESI) m/z 429[M+H$^+$].

Example 169

N-[(3S)-5-imidazo[1,2-a]pyridin-6-yl-3,4-dihydro-2H-chromen-3-yl]-6-(tetrahydro-2H-pyran-4-yloxy)nicotinamide The title compound was synthesized according to method B1 starting from Amine 30 and Acid 53; $^1$H NMR (400 MHz, DMSO-d$_6$) δ ppm 8.59 (dd, 1 H), 8.55-8.56 (m, 1 H), 8.42 (d, 1 H), 8.09 (dd, 1 H), 7.94 (s, 1 H), 7.58-7.64 (m, 2 H), 7.21-7.28 (m, 2 H), 6.91 (d, 2 H), 6.83 (dd, 1 H), 5.18-5.25 (m, 1 H), 4.20-4.30 (m, 2 H), 3.90-3.95 (m, 1 H), 3.80-3.87 (m, 2 H), 3.45-3.52 (m, 2 H), 2.79-2.90 (m, 2 H), 1.95-2.05 (m, 2 H), 1.56-1.65 (m, 2 H); MS (APPI/APCI) m/z 471[M+H$^+$].

Example 170

N$^2$-(4,4-difluorocyclohexyl)-N$^5$-[(3S)-5-(2-methoxypyrimidin-5-yl)-3,4-dihydro-2H-chromen-3-yl]pyridine-2,5-dicarboxamide The title compound was synthesized according to method B1 starting from Amine 20 and Acid 33; $^1$H NMR (400 MHz, DMSO-d$_6$) δ ppm 8.98 (dd, 1 H), 8.79 (m, 2 H), 8.66 (s, 2 H), 8.36 (dd, 1 H), 8.09 (dd, 1 H), 7.25 (t, 1 H), 6.88-6.95 (m, 2 H), 4.25-4.35 (m, 2 H), 3.95-4.05 (m, 5 H), 2.87 (d, 2 H), 1.70-2.10 (m, 8 H); MS (ESI) m/z 524[M+H$^+$].

Example 171

N$^5$-[(3S)-5-(2-methoxypyrimidin-5-yl)-3,4-dihydro-2H-chromen-3-yl]-N$^2$-(4,4,4-trifluorobutyl)pyridine-2,5-dicarboxamide The title compound was synthesized according to method B1 starting from Amine 20 and Acid 34; $^1$H NMR (400 MHz, DMSO-d$_6$) δ ppm 9.07 (t, 1 H), 8.98 (dd, 1 H), 8.78 (d, 1 H), 8.65 (s, 2 H), 8.35 (dd, 1 H), 8.09 (dd, 1 H), 7.25 (t, 1 H), 6.87-6.95 (m, 2 H), 4.25-4.34 (m, 2 H), 3.95-4.02 (m, 4 H), 3.33-3.39 (m, 2 H), 2.87 (d, 2 H), 2.21-2.34 (m, 2 H), 1.72-1.79 (m, 2 H); MS (ESI) m/z 516[M+H$^+$].

Example 172

N-[(3S)-5-(2-methoxypyrimidin-5-yl)-3,4-dihydro-2H-chromen-3-yl]-2-[2-(2,2,2-trifluoroethoxy)ethoxy]isonicotinamide The title compound was synthesized according to method B1 starting from Amine 20 and Acid 58; $^1$H NMR (400 MHz, CDCl$_3$) δ ppm 8.47 (s, 2 H), 8.19 (d, 1 H), 7.24-7.30 (m, 1 H), 7.14 (dd, 1 H), 6.96-7.01 (m, 2 H), 6.87 (dd, 1 H), 6.46 (d, 1 H), 4.62-4.70 (m, 1 H), 4.47-4.52 (m, 2 H), 4.21-4.31 (m, 2 H), 4.06 (s, 3 H), 3.96-3.98 (m, 2 H), 3.89-3.95 (m, 2 H), 3.11 (dd, 1 H), 2.70 (dd, 1 H); MS (ESI) m/z 505[M+H$^+$].

Example 173

N$^2$-methyl-N$^5$-[(3S)-5-(2-methylpyrimidin-5-yl)-3,4-dihydro-2H-chromen-3-yl]-N$^2$-(2,2,2-trifluoroethyl)pyridine-2,5-dicarboxamide The title compound was synthesized according to method B1 starting from Amine 21 and Acid 32; $^1$H NMR (400 MHz, DMSO-d$_6$) δ ppm 8.90-9.04 (m, 1 H), 8.74 (s, 3 H), 8.25-8.36 (dd, 1 H), 7.64-7.80 (m, 1 H), 7.27 (t, 1 H), 6.85-6.99 (m, 2 H), 4.60 (q, 1 H), 4.39 (q, 1 H), 4.22-4.34 (m, 2 H), 3.94-4.05 (m, 1 H), 2.98-3.17 (m, 3 H), 2.87 (m, 2 H), 2.67 (s, 3 H); MS (APCI) m/z 486[M+H$^+$].

Example 174

N$^5$-[(3S)-5-(2-ethylpyrimidin-5-yl)-3,4-dihydro-2H-chromen-3-yl]-N$^2$-(3,3,3-trifluoropropyl)pyridine-2,5-dicarboxamide The title compound was synthesized according to method B1 starting from Amine 22 and Acid 30; $^1$H NMR (400 MHz, DMSO-d$_6$) δ ppm 9.00 (t, 1 H), 8.86 (d, 1 H), 8.66 (m, 3 H), 8.17-8.28 (dd, 1 H), 7.99 (d, 1 H), 7.15 (t, 1 H), 6.74-6.87 (m, 2 H), 4.11-4.26 (m, 2 H), 3.88 (t, 1 H), 3.37-3.50 (m, 2 H), 2.83 (q, 2 H), 2.76 (m, 2 H), 2.44-2.52 (m, 2 H), 1.20 (t, 3 H); MS (APCI) m/z 500[M+H$^+$].

Example 175

N-{(3S)-5-[6-(methylsulfonyl)pyridin-3-yl]-3,4-dihydro-2H-chromen-3-yl}-6-[2-(2,2,2-trifluoroethoxy)ethoxy]nicotinamide The title compound was synthesized according to method E starting from the corresponding chromane borate (synthesized from Intermediate example I-15 and Acid 54, according to method B) and 5-bromo-2-(methylsulfonyl)pyridine; $^1$H NMR (400 MHz, CDCl$_3$) δ ppm 8.68 (d, 1 H), 8.46 (d, 1 H), 8.15 (d, 1 H), 7.94 (dd, 1 H), 7.90 (dd, 1 H), 7.31 (t, 1 H), 7.04 (dd, 1 H), 6.88 (dd, 1 H), 6.80 (d, 1 H), 6.29 (d, 1 H), 4.72-4.64 (m, 1 H), 4.54-4.52 (m, 2 H), 4.32-4.27 (m, 2 H), 3.99-3.97 (m, 2 H), 3.96-3.90 (m, 2 H), 3.30 (s, 3 H), 3.14-3.08 (m, 1 H), 2.71-2.66 (m, 1 H); MS (APCI) m/z 552[M+H$^+$].

Example 176

N-[(3S)-5-(6-cyanopyridin-3-yl)-3,4-dihydro-2H-chromen-3-yl]-6-[2-(2,2,2-trifluoroethoxy)ethoxy]nicotinamide The title compound was synthesized according to method E starting from the corresponding chromane borate (synthesized from Intermediate example I-15 and Acid 54, according to method B) and 5-bromopyridine-2-carbonitrile; $^1$H NMR (400 MHz, DMSO-d$_6$) δ ppm 8.79 (m, 1 H), 8.60 (d, 1 H), 8.43 (d, 1 H), 8.16-8.09 (m, 3 H), 7.28 (t, 1 H), 6.96 (dd, 1 H), 6.92-6.89 (m, 2 H), 4.46-4.43 (m, 2 H), 4.29-4.20 (m, 2 H), 4.16-4.09 (m, 2 H), 3.99-3.91 (m, 3 H), 2.87-2.76 (m, 2 H); MS (APCI) m/z 499[M+H$^+$].

Example 177

N-[(3S)-5-(2-cyclopropylpyrimidin-5-yl)-3,4-dihydro-2H-chromen-3-yl]-6-[2-(2,2,2-trifluoroethoxy)ethoxy]nicotinamide The title compound was synthesized according to method B1 starting from Amine 23 and Acid 54; $^1$H NMR (400 MHz, CDCl$_3$) δ ppm 8.53 (s, 2 H), 8.46 (d, 1 H), 7.93 (dd, 1 H), 7.23-7.30 (m, 1 H), 6.98 (dd, 1 H), 6.86 (dd, 1 H), 6.79 (d, 1 H), 6.32 (d, 1 H), 4.63-4.71 (m, 1 H), 4.49-4.54 (m, 2 H), 4.27 (d, 2 H), 3.95-4.00 (m, 2 H), 3.88-3.96 (m, 2 H), 3.11 (dd, 1 H), 2.70 (dd, 1 H), 2.25-2.34 (m, 1 H), 1.16-1.20 (m, 2 H), 1.10-1.16 (m, 2 H); MS (APCI) m/z 515[M+H$^+$].

Example 178

N-[(3S)-5-(2-ethylpyrimidin-5-yl)-3,4-dihydro-2H-chromen-3-yl]-6-[2-(2,2,2-trifluoroethoxy)ethoxy]nicotinamide The title compound was synthesized according to method B1 starting from Amine 22 and Acid 54; $^1$H NMR (400 MHz, DMSO-d$_6$) δ ppm 8.77 (s, 2 H), 8.61 (d, 1 H), 8.42 (d, 1 H), 8.06-8.16 (dd, 1 H), 7.26 (t, 1 H), 6.86-6.99 (m, 3 H), 4.38-4.51 (m, 2 H), 4.18-4.34 (m, 2 H), 4.13 (q, 2 H), 3.88-3.99 (m, 3 H), 2.95 (q, 2 H), 2.79-2.90 (m, 2 H), 1.32 (t, 3 H); MS (APCI) m/z 503[M+H$^+$].

Example 179

N$^5$-[(3S)-5-(5-fluoro-6-methoxypyridin-3-yl)-3,4-dihydro-2H-chromen-3-yl]-N$^2$-(3,3,3-trifluoropropyl)pyridine-2,5-dicarboxamide The title compound was synthesized according to method B1 starting from Amine 15 and Acid 30; $^1$H NMR (400 MHz, DMSO-d$_6$) δ ppm 9.12 (t, 1 H), 8.98 (d, 1 H), 8.80 (d, 1 H), 8.31-8.41 (dd, 1 H), 8.10 (d, 1 H), 7.99 (d, 1 H), 7.74-7.85 (dd, 1 H), 7.23 (t, 1 H), 6.80-6.97 (m, 3 H), 4.21-4.35 (m, 2 H), 3.90-4.04 (m, 4 H), 3.50-3.62 (m, 2 H), 2.86 (m, 2 H), 2.54-2.66 (m, 2 H); MS (APCI) m/z 519[M+H$^+$].

Example 180

N-[(3S)-5-(5-fluoro-6-methoxypyridin-3-yl)-3,4-dihydro-2H-chromen-3-yl]-6-[2-(2,2,2-trifluoroethoxy)ethoxy]nicotinamide The title compound was synthesized according to method B1 starting from Amine 15 and Acid 54; $^1$H NMR (400 MHz, DMSO-d$_6$) δ ppm 8.62 (d, 1 H), 8.44 (d, 1 H), 8.05-8.19 (dd, 1 H), 7.98 (d, 1 H), 7.72-7.85 (dd, 1 H), 7.22 (t, 1 H), 6.81-6.95 (m, 3 H), 4.36-4.53 (m, 2 H), 4.18-4.34 (m, 2 H), 4.13 (q, 2 H), 3.84-4.05 (m, 6 H), 2.74-2.91 (m, 2 H); MS (APCI) m/z 522[M+H$^+$].

Example 181

6-(cyclopentylsulfonyl)-N-[(3S)-5-(2-methoxypyrimidin-5-yl)-3,4-dihydro-2H-chromen-3-yl]nicotinamide The title compound was synthesized according to method B1 starting from Amine 20 and Acid 42; $^1$H NMR (400 MHz, DMSO-d$_6$) δ ppm 9.10 (dd, 1 H), 8.91 (d, 1 H), 8.65 (s, 2 H), 8.46 (dd, 1 H), 8.15 (dd, 1 H), 7.25 (t, 1 H), 6.93 (dd, 1 H), 6.90 (dd, 1 H), 4.31-4.25 (m, 2 H), 4.11-3.98 (m, 2 H), 3.96 (s, 3 H), 2.94-2.81 (m, 2 H), 1.90-1.80 (m, 4 H), 1.67-1.52 (m, 4 H); MS (APCI) m/z 495[M+H$^+$].

Example 182

N-[(3S)-5-(6-methylpyrazin-2-yl)-3,4-dihydro-2H-chromen-3-yl]-6-[2-(2,2,2-trifluoroethoxy)ethoxy]nicotinamide The title compound was synthesized according to method B1 starting from Amine 28 and Acid 54; $^1$H NMR (400 MHz, DMSO-d$_6$) δ ppm 8.62 (d, 1 H), 8.60 (s, 1 H), 8.53 (s, 1 H), 8.45 (d, 1 H), 8.11 (dd, 1 H), 7.26 (t, 1 H), 7.04 (dd, 1 H), 6.96 (dd, 1 H), 6.90 (d, 1 H), 4.46-4.43 (m, 2 H), 4.30-4.22 (m, 2 H), 4.16-4.09 (m, 2 H), 3.99-3.92 (m, 3 H), 2.97-2.95 (m, 2 H), 2.55 (s, 3 H); MS (APCI) m/z 489[M+H$^+$].

Example 183

N$^5$-[(3S)-5-(2-methylpyrimidin-5-yl)-3,4-dihydro-2H-chromen-3-yl]-N$^2$-(3,3,3-trifluoropropyl)pyridine-2,5-dicarboxamide The title compound was synthesized according to method B1 starting from Amine 21 and Acid 30; $^1$H NMR (400 MHz, DMSO-d$_6$) δ ppm 9.12 (t, 1 H), 8.98 (dd, 1 H), 8.80 (d, 1 H), 8.74 (s, 2 H), 8.36 (dd, 1 H), 8.10 (dd, 1 H), 7.27 (t, 1 H), 6.95 (dd, 1 H), 6.91 (dd, 1 H), 4.32-4.24 (m, 2 H), 4.02-3.97 (m, 1 H), 3.58-3.53 (m, 2 H), 2.90-2.82 (m, 2 H), 2.67 (s, 3 H), 2.64-2.52 (m, 2 H); MS (APCI) m/z 486[M+H$^+$].

Example 184

6-(2-isopropoxyethoxy)-N-[(3S)-5-(2-methoxypyrimidin-5-yl)-3,4-dihydro-2H-chromen-3-yl]nicotinamide The title compound was synthesized according to method B1 starting from Amine 20 and Acid 55; $^1$H NMR (400 MHz, DMSO-d$_6$) δ ppm 8.65 (s, 2 H), 8.61 (d, 1 H), 8.40 (d, 1 H), 8.10 (dd, 1 H), 7.24 (t, 1 H), 6.93-6.87 (m, 3 H), 4.39-4.36 (m, 2 H), 4.29-4.20 (m, 2 H), 3.96-3.91 (m, 4 H), 3.69-3.67 (m, 2 H), 3.63-3.57 (m, 1 H), 2.90-2.80 (m, 2 H), 1.08 (d, 6 H); MS (APCI) m/z 465[M+H$^+$].

Example 185

6-(2-isopropoxyethoxy)-N-[(3S)-5-(2-methylpyrimidin-5-yl)-3,4-dihydro-2H-chromen-3-yl]nicotinamide The title compound was synthesized according to method B1 starting from Amine 21 and Acid 55; $^1$H NMR (400 MHz, DMSO-d$_6$) δ ppm 8.73 (s, 2 H), 8.60 (d, 1 H), 8.40 (d, 1 H), 8.10 (dd, 1 H), 7.26 (t, 1 H), 6.96-6.87 (m, 3 H), 4.39-4.36 (m, 2 H), 4.29-4.21 (m, 2 H), 3.97-3.92 (m, 1 H), 3.69-3.67 (m, 2 H), 3.63-3.56 (m, 1 H), 2.90-2.80 (m, 2 H), 2.67 (s, 3 H), 1.08 (d, 6 H); MS (APCI) m/z 449[M+H$^+$].

Example 186

N$^2$-(3-isopropoxypropyl)-N$^5$-[(3S)-5-(2-methylpyrimidin-5-yl)-3,4-dihydro-2H-chromen-3-yl]pyridine-2,5-dicarboxamide The title compound was synthesized according to method B1 starting from Amine 21 and Acid 35; $^1$H NMR (400 MHz, DMSO-d$_6$) δ ppm 8.96 (dd, 1 H), 8.94 (t, 1 H), 8.78 (d, 1 H), 8.74 (s, 2 H), 8.34 (dd, 1 H), 8.08 (dd, 1 H), 7.26 (t, 1 H), 6.95 (dd, 1 H), 6.91 (dd, 1 H), 4.32-4.25 (m, 2 H), 4.01-3.97 (m, 1 H), 3.55-3.49 (m, 1 H), 3.43 (t, 2 H), 3.39-3.32 (m, 2 H, partly overlapped with water peak), 2.88-2.86 (m, 2 H), 2.67 (s, 3 H), 1.77-1.71 (m, 2 H), 1.09 (d, 6 H); MS (APCI) m/z 490 [M+H$^+$].

Example 187

N$^2$-(3-isopropoxypropyl)-N$^5$-[(3S)-5-(2-methoxypyrimidin-5-yl)-3,4-dihydro-2H-chromen-3-yl]pyridine-2,5-dicarboxamide The title compound was synthesized according to method B1 starting from Amine 20 and Acid 35; $^1$H NMR (400 MHz, DMSO-d$_6$) δ ppm 8.97 (dd, 1 H), 8.94 (t, 1 H), 8.79 (d, 1 H), 8.65 (s, 2 H), 8.35 (dd, 1 H), 8.09 (dd, 1 H), 7.25 (t, 1 H), 6.93 (dd, 1 H), 6.90 (dd, 1 H), 4.32-4.25 (m, 2 H), 4.01-3.96 (m, 4 H), 3.55-3.49 (m, 1 H), 3.43 (t, 2 H), 3.39-3.32 (m, 2 H, partly overlapped with water peak), 2.90-2.82 (m, 2 H), 1.77-1.71 (m, 2 H), 1.09 (d, 6 H); MS (APCI) m/z 506[M+H$^+$].

Example 188

N$^5$-[(3S)-5-(2-methylpyrimidin-5-yl)-3,4-dihydro-2H-chromen-3-yl]-N$^2$-(4,4,4-trifluorobutyl)pyridine-2,5-dicarboxamide The title compound was synthesized according to method B1 starting from Amine 20 and Acid 34; $^1$H NMR (400 MHz, DMSO-d$_6$) δ ppm 9.08 (t, 1 H), 8.98 (dd, 1 H), 8.78 (d, 1 H), 8.74 (s, 2 H), 8.34 (dd, 1 H), 8.09 (dd, 1 H), 7.26 (t, 1 H), 6.95 (dd, 1 H), 6.91 (dd, 1 H), 4.32-4.25 (m, 2 H), 4.02-3.97 (m, 1 H), 3.39-3.31 (2 H, partly overlapped with water peak), 2.88-2.86 (m, 2 H), 2.67 (s, 3 H), 2.34-2.21 (m, 2 H), 1.80-1.72 (m, 2 H); MS (APCI) m/z 500[M+H$^+$].

Example 189

N-[(3S)-5-(2-methylpyrimidin-5-yl)-3,4-dihydro-2H-chromen-3-yl]-6-[2-(2,2,2-trifluoroethoxy)ethoxy]nicotinamide The title compound was synthesized according to method B1 starting from Amine 21 and Acid 54; $^1$H NMR (400 MHz, DMSO-d$_6$) δ ppm 8.73 (s, 2 H), 8.61 (d, 1 H), 8.41 (d, 1 H), 8.07-8.15 (dd, 1 H), 7.26 (t, 1 H), 6.86-6.98 (m, 3 H), 4.39-4.50 (m, 2 H), 4.18-4.35 (m, 2 H), 4.13 (q, 2 H), 3.89-4.02 (m, 3 H), 2.79-2.91 (m, 2 H), 2.67 (s, 3 H); MS (APCI) m/z 489[M+H$^+$].

Example 190

N-[(2R)-8-(2-methoxypyrimidin-5-yl)-1,2,3,4-tetrahydronaphthalen-2-yl]-2-[2-(2,2,2-trifluoroethoxy)ethoxy]isonicotinamide The title compound was synthesized according to method B1 starting from Amine 36 and Acid 58; $^1$H NMR (400 MHz, DMSO-d$_6$) δ ppm 8.55-8.66 (m, 3 H), 8.24 (d, 1 H), 7.29-7.36 (dd, 1 H), 7.19-7.29 (m, 3 H), 7.06-7.13 (m, 1 H), 4.38-4.48 (m, 2 H), 4.00-4.20 (m, 3 H), 3.88-4.00 (m, 5 H), 2.89-3.03 (m, 2 H), 2.69-2.82 (m, 2 H), 1.99-2.13 (m, 1 H), 1.69-1.85 (m, 1 H); MS (APCI) m/z 503[M+H$^+$].

Example 191

N$^5$-[(3S)-5-(2-methoxypyrimidin-5-yl)-3,4-dihydro-2H-chromen-3-yl]-N$^2$-methyl-N$^2$-(2,2,2-trifluoroethyl)pyridine-2,5-dicarboxamide The title compound was synthesized according to method B1 starting from Amine 20 and Acid 32; $^1$H NMR (400 MHz, DMSO-d$_6$) δ ppm 8.93-9.02 (m, 1 H), 8.71-8.81 (m, 1 H), 8.66 (s, 2 H), 8.26-8.36 (dd, 1 H), 7.65-7.79 (m, 1 H), 7.25 (t, 1 H), 6.86-6.97 (m, 2 H), 4.53-4.67 (m, 1 H), 4.39 (q, 1 H), 4.22-4.34 (m, 2 H), 3.91-4.04 (m, 4 H), 2.98-3.16 (m, 3 H), 2.82-2.94 (m, 2 H); MS (APCI) m/z 502[M+H$^+$].

Example 192

N$^5$-[(3S)-5-(5-fluoro-6-methoxypyridin-3-yl)-3,4-dihydro-2H-chromen-3-yl]-N$^2$-methyl-N$^2$-(2,2,2-trifluoroethyl)pyridine-2,5-dicarboxamide The title compound was synthesized according to method B1 starting from Amine 15 and Acid 32; $^1$H NMR (400 MHz, DMSO-d$_6$) δ ppm 8.93-9.02 (m, 1 H), 8.71-8.82 (m, 1 H), 8.25-8.37 (dd, 1 H), 7.99 (d, 1 H), 7.61-7.86 (m, 2 H), 7.22 (t, 1 H), 6.82-6.98 (m, 2 H), 4.53-4.69 (m, 1 H), 4.39 (q, 1 H), 4.20-4.34 (m, 2 H), 3.98 (m, 4 H), 2.95-3.18 (m, 3 H), 2.86 (m, 2 H); MS (APCI) m/z 519[M+H$^+$].

Example 193

N-[(3S)-5-(5-fluoro-6-methoxypyridin-3-yl)-3,4-dihydro-2H-chromen-3-yl]-6-[(2,2,2-trifluoroethoxy)methyl]nicotinamide The title compound was synthesized according to method B1 starting from Amine 15 and Acid 57; $^1$H NMR (400 MHz, DMSO-d$_6$) δ ppm 8.93 (d, 1 H), 8.65 (d, 1 H), 8.22 (dd, 1 H), 7.98 (d, 1 H), 7.79 (dd, 1 H), 7.50 (d, 1 H), 7.22 (t, 1 H), 6.81-6.97 (m, 2 H), 4.80 (s, 2 H), 4.14-4.39 (m, 4 H), 3.86-4.05 (m, 4 H), 2.74-2.94 (m, 2 H); MS (APCI) m/z 492[M+H$^+$].

Example 194

N-[(3S)-5-(2-methoxypyrimidin-5-yl)-3,4-dihydro-2H-chromen-3-yl]-6-[(2,2,2-trifluoroethoxy)methyl]nicotinamide The title compound was synthesized according to method B1 starting from Amine 20 and Acid 57; $^1$H NMR (400 MHz, DMSO-d$_6$) δ ppm 8.93 (d, 1 H), 8.57-8.70 (m, 3 H), 8.22 (dd, 1 H), 7.51 (d, 1 H), 7.25 (t, 1 H), 6.85-6.98 (m, 2 H), 4.80 (s, 2 H), 4.15-4.37 (m, 4 H), 3.89-4.02 (m, 4 H), 2.86 (d, 2 H); MS (APCI) m/z 475[M+H$^+$].

Example 195

N-[(3S)-5-(2-methoxypyrimidin-5-yl)-3,4-dihydro-2H-chromen-3-yl]-2-[(3,3,3-trifluoropropyl)amino]pyrimidine-5-carboxamide The title compound was synthesized according to method B1 starting from Amine 20 and Acid 56; $^1$H NMR (400 MHz, DMSO-d$_6$) δ ppm 8.67-8.79 (m, 2 H), 8.65 (s, 2 H), 8.26 (d, 1 H), 7.94 (t, 1 H), 7.24 (t, 1 H), 6.84-6.96 (m, 2 H), 4.12-4.34

(m, 2 H), 3.85-4.02 (m, 4 H), 3.54 (q, 2 H), 2.82 (d, 2 H), 2.51-2.61 (m, 2 H); MS (APCI) m/z 475[M+H$^+$].

Example 196

N$^5$-[(3S)-5-(2-cyclopropylpyrimidin-5-yl)-3,4-dihydro-2H-chromen-3-yl]-N$^2$-methyl-N$^2$-(2,2,2-trifluoroethyl)pyridine-2,5-dicarboxamide The title compound was synthesized according to method B1 starting from Amine 23 and Acid 32; $^1$H NMR (400 MHz, DMSO-d$_6$) δ ppm 8.90-9.04 (m, 1 H), 8.77, 8.67 (s+s, 2 H), 8.72-8.77 (m, 1 H), 8.31 (dd, 1 H), 7.76, 7.69 (d+d, 1 H), 7.18-7.31 (m, 1 H), 6.85-6.98 (m, 2 H), 4.60, 4.39 (q+q, 2 H), 4.17-4.34 (m, 2 H), 3.89-4.05 (m, 1 H), 3.13, 3.02 (s+s, 3 H), 2.81-2.94, 1.74-1.87 (m+m, 3 H), 2.18-2.30 (m, 1 H), 1.01-1.14 (m, 3 H); MS (APCI) m/z 512[M+H$^+$].

Example 197

N$^5$-[(3S)-5-(2-cyclopropylpyrimidin-5-yl)-3,4-dihydro-2H-chromen-3-yl]-N$^2$-(3,3,3-trifluoropropyl)pyridine-2,5-dicarboxamide The title compound was synthesized according to method B1 starting from Amine 23 and Acid 30; $^1$H NMR (400 MHz, DMSO-d$_6$) δ ppm 9.12 (t, 1 H), 8.96-9.01 (m, 1 H), 8.75-8.83 (m, 1 H), 8.67 (s, 1 H), 8.35 (dd, 1 H), 8.10 (d, 1 H), 7.21-7.30 (m, 1 H), 6.86-6.99 (m, 2 H), 4.21-4.35 (m, 2 H), 3.94-4.05 (m, 1 H), 3.55 (q, 2 H), 2.81-2.93 (m, 2 H), 2.52-2.65 (m, 2 H), 2.20-2.30 (m, 1 H), 1.76-1.88 (m, 1 H), 1.00-1.13 (m, 3 H), 0.96 (t, 1 H); MS (APCI) m/z 512[M+H$^+$].

Example 198

N$^5$-[(3S)-5-(2-cyclopropylpyrimidin-5-yl)-3,4-dihydro-2H-chromen-3-yl]-N$^2$-methyl-N$^2$-(3,3,3-trifluoropropyl)pyridine-2,5-dicarboxamide The title compound was synthesized according to method B1 starting from Amine 23 and Acid 31; $^1$H NMR (400 MHz, DMSO-d$_6$) δ ppm 8.93-8.99 (m, 1 H), 8.70-8.75 (m, 1 H), 8.67 (s, 1 H), 8.24-8.32 (m, 1 H), 7.65 (dd, 1 H), 7.21-7.29 (m, 1 H), 6.85-6.98 (m, 2 H), 4.21-4.35 (m, 2 H), 3.93-4.04 (m, 1 H), 3.70 (t, 1 H), 3.49-3.57 (m, 1 H), 3.02 (s, 1 H), 2.82-2.96 (m, 4 H), 2.58-2.79 (m, 2 H), 2.20-2.29 (m, 1 H), 1.75-1.88 (m, 1 H), 1.00-1.13 (m, 3 H), 0.96 (t, 1 H); MS (APCI) m/z 526[M+H$^+$].

Example 199

N-[(3S)-5-(2-cyclopropylpyrimidin-5-yl)-3,4-dihydro-2H-chromen-3-yl]-2-oxo-1-(3,3,3-trifluoropropyl)-1,2-dihydropyridine-4-carboxamide The title compound was synthesized according to method B1 starting from Amine 23 and Acid 60; $^1$H NMR (400 MHz, DMSO-d$_6$) δ ppm 8.76 (s, 1 H), 8.66 (s, 1 H), 8.54-8.61 (m, 1 H), 7.80 (d, 1 H), 7.20-7.29 (m, 1 H), 6.90-6.95 (m, 1 H), 6.87-6.90 (m, 1 H), 6.80-6.82 (m, 1 H), 6.48-6.54 (m, 1 H), 4.19-4.27 (m, 1 H), 4.10-4.16 (m, 2 H), 3.88-3.99 (m, 1 H), 2.87-2.94 (m, 1 H), 2.79-2.85 (m, 2 H), 2.63-2.78 (m, 2 H), 2.18-2.29 (m, 1 H), 1.77-1.86 (m, 1 H), 1.00-1.13 (m, 2 H), 0.96 (t, 1 H); MS (APCI) m/z 485[M+H$^+$].

Example 200

N-[(3S)-5-(5-fluoro-6-methoxypyridin-3-yl)-3,4-dihydro-2H-chromen-3-yl]-2-[(3,3,3-trifluoropropyl)amino]pyrimidine-5-carboxamide The title compound was synthesized according to method B1 starting from Amine 15 and Acid 56; $^1$H NMR (400 MHz, DMSO-d$_6$) δ ppm 8.62-8.79 (m, 2 H), 8.27 (d, 1 H), 7.98 (d, 1 H), 7.93 (t, 1 H), 7.78 (dd, 1 H), 7.22 (t, 1 H), 6.80-6.93 (m, 2 H), 4.12-4.31 (m, 2 H), 3.98 (s, 3 H), 3.89 (t, 1 H), 3.54 (q, 2 H), 2.75-2.85 (m, 2 H), 2.53-2.61 (m, 2 H); MS (APCI) m/z 492[M+H$^+$].

Example 201

N-[(3S)-5-(2-methylpyrimidin-5-yl)-3,4-dihydro-2H-chromen-3-yl]-2-[(3,3,3-trifluoropropyl)amino]pyrimidine-5-carboxamide The title compound was synthesized according to method B1 starting from Amine 21 and Acid 56; $^1$H NMR (400 MHz, DMSO-d$_6$) δ ppm 8.58-8.80 (m, 4 H), 8.26 (d, 1 H), 7.94 (t, 1 H), 7.26 (t, 1 H), 6.85-6.99 (m, 2 H), 4.13-4.33 (m, 2 H), 3.92 (t, 1 H), 3.54 (q, 2 H), 2.82 (d, 2 H), 2.67 (s, 3 H), 2.51-2.61 (m, 2 H); MS (APCI) m/z 459[M+H$^+$].

Example 202

N-[(3S)-5-(3,5-dimethylpyrazin-2-yl)-3,4-dihydro-2H-chromen-3-yl]-6-[2-(2,2,2-trifluoroethoxy)ethoxy]nicotinamide The title compound was synthesized according to method B1 starting from Amine 29 and Acid 54; $^1$H NMR (400 MHz, CDCl$_3$) δ ppm 8.47 (d, 1 H), 8.33 (s, 1 H), 7.93 (dd, 1 H), 7.26 (t, 1 H), 6.98 (dd, 1 H), 6.86 (dd, 1 H), 6.79 (d, 1 H), 6.42 (d, 1 H), 4.65-4.60 (m, 1 H), 4.54-4.52 (m, 2 H), 4.31-4.20 (m, 2 H), 3.99-3.97 (m, 2 H), 3.96-3.90 (m, 2 H), 2.94-2.89 (m, 1 H), 2.59 (s, 3 H), 2.55-2.49 (m, 1 H), 2.35 (s, 3 H); MS (APCI) m/z 503[M+H$^+$].

Example 203

N-[(3S)-5-(2-methylpyrimidin-5-yl)-3,4-dihydro-2H-chromen-3-yl]-6-[(2,2,2-trifluoroethoxy)methyl]nicotinamide The title compound was synthesized according to method B1 starting from Amine 21 and Acid 57; $^1$H NMR (400 MHz, CD$_3$OD) δ ppm 8.87 (d, 1 H), 8.71 (s, 2 H), 8.20 (dd, 1 H), 7.59 (d, 1 H), 7.26 (t, 1 H), 6.96 (d, 1 H), 6.89 (d, 1 H), 4.81 (s, 2 H), 4.37-4.51 (m, 1 H), 4.33 (dd, 1 H), 4.00-4.20 (m, 3 H), 2.93-3.08 (m, 1 H), 2.83 (dd, 1 H), 2.74 (s, 3 H); MS (APCI) m/z 459[M+H$^+$].

Example 204

2-methoxy-N,N-dimethyl-5-[(3S)-3-({[6-(tetrahydro-2H-pyran-4-yloxy)pyridin-3-yl]carbonyl}amino)-3,4-dihydro-2H-chromen-5-yl]nicotinamide The title compound was synthesized according to method B1 starting from Amine 17 and Acid 53; $^1$H NMR (400 MHz, DMSO-d$_6$) δ ppm 8.60 (d, 1 H), 8.42 (d, 1 H), 8.22 (d, 1 H), 8.10 (dd, 1 H), 7.66 (d, 1 H), 7.21 (t, 1 H), 6.84-6.90 (m, 3 H), 5.20-5.26 (m, 1 H), 4.21-4.27 (m, 2 H), 3.90-3.96 (m, 4 H), 3.82-3.87 (m, 2 H), 3.46-3.52 (m, 2 H), 2.98 (s, 3 H), 2.80-2.85 (m, 5 H), 1.95-2.05 (m, 2 H), 1.58-1.67 (m, 2 H); MS (ESI) m/z 533 [M+H$^+$].

Example 205

5-[(3S)-3-{[(6-isopropoxypyridin-3-yl)carbonyl]amino}-3,4-dihydro-2H-chromen-5-yl]-2-methoxy-N-methylnicotinamide The title compound was synthesized according to method B1 starting from Amine 18 and Acid 6; $^1$H NMR (400 MHz, DMSO-d$_6$) δ ppm 8.60 (dd, 1 H), 8.41 (d, 1 H), 8.27-8.33 (m, 2 H), 8.09 (d, 1 H), 8.06 (dd, 1 H), 7.22 (t, 1 H), 6.89 (dd, 1 H), 6.84 (dd, 1 H), 6.77 (dd, 1 H), 5.42-5.32 (m, 1 H), 4.20-4.28 (m, 2 H), 4.01 (s, 3 H), 3.92-3.97 (m, 1 H), 2.75-2.85 (m, 5 H), 1.29 (d, 6 H); MS (ESI) m/z 477[M+H$^+$].

Example 206

2-methoxy-N-methyl-5-[(3S)-3-({[6-(tetrahydro-2H-pyran-4-yloxy)pyridin-3-yl]carbonyl}amino)-3,4-dihydro-2H-chromen-5-yl]nicotinamide The title compound was synthesized according to method B1 starting from Amine 18 and Acid 53; $^1$H NMR (400 MHz, DMSO-d$_6$) δ ppm 8.59 (m, 1 H), 8.42 (d, 1 H), 8.27-8.33 (m, 2 H), 8.09 (td, 2 H), 7.22 (t, 1 H), 6.89 (dd, 1 H), 6.82-6.86 (m, 2 H), 5.18-5.27 (m, 1 H), 4.20-4.28 (m, 2 H), 4.01 (s, 3 H), 3.91-3.97 (m, 1 H), 3.82-3.87 (m, 2 H) 3.40-3.52 (m, 2 H), 2.75-2.85 (m, 5 H), 1.95-2.03 (m, 2 H), 1.57-1.66 (m, 2 H); MS (ESI) m/z 519[M+H$^+$].

Example 207

5-[(3S)-3-{[(6-isopropoxypyridin-3-yl)carbonyl]amino}-3,4-dihydro-2H-chromen-5-yl]-2-methoxy-N,N-dimethylnicotinamide The title compound was synthesized according to method B1 starting from Amine 17 and Acid 6; $^1$H NMR (400 MHz, DMSO-d$_6$) δ ppm 8.60 (dd, 1 H), 8.40 (d, 1 H), 8.22 (d, 1 H), 8-07 (dd, 1 H), 7.66 (d, 1 H), 7.21 (t, 1 H), 6.83-6.90 (m, 2 H), 6.78 (dd, 1 H), 5.25-5.31 (m, 1 H), 4.22-4.28 (m, 2 H), 3.91-3.96 (m, 4 H), 2.98 (s, 3 H), 2.80-2.85 (m, 5 H), 1.29 (d, 6 H); MS (ESI) m/z 491[M+H$^+$].

Example 208

2-methoxy-N,N-dimethyl-5-[(3S)-3-({[6-(2,2,2-trifluoroethoxy)pyridin-3-yl]carbonyl}amino)-3,4-dihydro-2H-chromen-5-yl]nicotinamide The title compound was synthesized according to method B1 starting from Amine 17 and Acid 4; $^1$H NMR (400 MHz, DMSO-d$_6$) δ ppm 8.64 (dd, 1 H), 8.53 (d, 1 h), 8.22 (d, 1 H), 8.19 (dd, 1 H), 7.66 (d, 1 H), 7.21 (t, 1 H), 7.06 (d, 1 H), 6.83-6.90 (m, 2 H), 5.02-5.08 (m, 2 H), 4.22-4.28 (m, 2 H), 3.90-3.97 (m, 4 H), 2.98 (s, 3 H), 2.80-2.90 (m, 5 H); MS (ESI) m/z 531[M+H$^+$].

Example 209

N,N-dimethyl-5-{(3S)-3-[({6-[2-(2,2,2-trifluoroethoxy)ethoxy]pyridin-3-yl}carbonyl)amino]-3,4-dihydro-2H-chromen-5-yl}pyrimidine-2-carboxamide The title compound was synthesized according to method B1 starting from Amine 25 and Acid 54; $^1$H NMR (400 MHz, DMSO-d$_6$) δ ppm 8.94 (s, 2 H), 8.61 (d, 1 H), 8.44 (d, 1 H), 8.12 (dd, 1 H), 7.29 (t, 1 H), 6.98 (d, 2 H), 6.90 (d, 1 H), 4.46-4.43 (m, 2 H), 4.31-4.20 (m, 2 H), 4.16-4.09 (m, 2 H), 3.98-3.91 (m, 3 H), 3.04 (s, 3 H), 2.91-2.89 (m, 2 H), 2.85 (s, 3 H); MS (APPI/APCI) m/z 546[M+H$^+$].

Example 210

N-{(3S)-5-[6-(hydroxymethyl)pyridin-3-yl]-3,4-dihydro-2H-chromen-3-yl}-6-[2-(2,2,2-trifluoroethoxy)ethoxy]nicotinamide The title compound was synthesized according to method B1 starting from Amine 13 and Acid 54; $^1$H NMR (400 MHz, DMSO-d$_6$) δ ppm 8.60 (d, 1 H), 8.47 (d, 1 H), 8.44 (d, 1 H), 8.10 (dd, 1 H), 7.81 (dd, 1 H), 7.54 (d, 1 H), 7.23 (t, 1 H), 6.92-6.88 (m, 2 H), 6.84 (dd, 1 H), 5.47 (t, 1 H), 4.60 (d, 2 H), 4.45-4.43 (m, 2 H), 4.29-4.20 (m, 2 H), 4.16-4.09 (m, 2 H), 3.96-3.91 (m, 3 H), 2.87-2.75 (m, 2 H); MS (APPI/APCI) m/z 504[M+H$^+$].

Example 211

6-(3-fluoropropoxy)-N-{(3S)-5-[6-(hydroxymethyl)pyridin-3-yl]-3,4-dihydro-2H-chromen-3-yl}nicotinamide The title compound was synthesized according to method B1 starting from Amine 13 and Acid 19; $^1$H NMR (400 MHz, DMSO-d$_6$) δ ppm 8.61 (d, 1 H), 8.47 (d, 1 H), 8.43 (d, 1 H), 8.10 (dd, 1 H), 7.81 (dd, 1 H), 7.54 (d, 1 H), 7.23 (t, 1 H), 6.91-6.83 (m, 3 H), 5.47 (t, 1 H), 4.64 (t, 1 H), 4.60 (d, 2 H), 4.52 (t, 1 H), 4.38 (t, 2 H), 4.29-4.20 (m, 2 H), 3.96-3.91 (m, 1 H), 2.87-2.75 (m, 2 H), 2.16-2.04 (m, 2 H); MS (APPI/APCI) m/z 438[M+H$^+$].

Example 212

N-{(3S)-5-[6-(hydroxymethyl)pyridin-3-yl]-3,4-dihydro-2H-chromen-3-yl}-6-(2,2,2-trifluoroethoxy)nicotinamide The title compound was synthesized according to method B1 starting from Amine 13 and Acid 4; $^1$H NMR (400 MHz, DMSO-d$_6$) δ ppm 8.64 (dd, 1 H), 8.52 (d, 1 H), 8.47 (d, 1 H), 8.19 (dd, 1 H), 7.80 (dd, 1 H), 7.54 (d, 1 H), 7.23 (t, 1 H), 7.05 (dd, 1 H), 6.90 (dd, 1 H), 6.85 (dd, 1 H), 5.47 (t, 1 H), 5.08-5.01 (m, 2 H), 4.61-4.60 (d, 2 H), 4.30-4.20 (m, 2 H), 3.97-3.92 (m, 1 H), 2.88-2.75 (m, 2 H); MS (APPI/APCI) m/z 460[M+H$^+$].

Example 213

N-{(3S)-5-[5-(hydroxymethyl)pyrazin-2-yl]-3,4-dihydro-2H-chromen-3-yl}-6-[2-(2,2,2-trifluoroethoxy)ethoxy]nicotinamide The title compound was synthesized according to method E starting from the corresponding chromane borate (synthesized from Intermediate example I-15 and Acid 54, according to method B) and (5-chloropyrazin-2-yl)methanol (described in Intermediate example I-79); $^1$H NMR (400 MHz, DMSO-d$_6$) δ ppm 8.76 (m, 1 H), 8.72 (d, 1 H), 8.61 (d, 1 H), 8.46 (d, 1 H), 8.12 (dd, 1 H), 7.28 (t, 1 H), 7.08 (dd, 1 H), 6.97 (dd, 1 H), 6.90 (d, 1 H), 5.65 (t, 1 H), 4.68 (d, 2 H), 4.46-4.43 (m, 2 H), 4.30-4.22 (m, 2 H), 4.16-4.09 (m, 2 H), 3.98-3.91 (m, 3 H), 3.05-2.92 (m, 2 H); MS (APPI/APCI) m/z 505[M+H$^+$].

Synthesis of Intermediates

Intermediate Example I-1

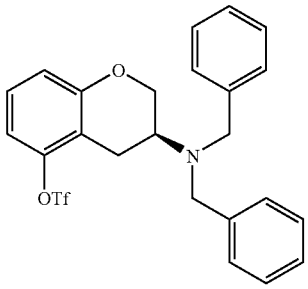

(3S)-3-(Dibenzylamino)-3,4-dihydro-2H-chromen-5-yl trifluoromethanesulfonate

Triethylamine (8.8 mL, 63.2 mmol) was added to a cooled (−40° C.) solution of (3S)-3-(dibenzylamino)chroman-5-ol (15.6 g, 45.2 mmol, described in WO9914212A1) in anhydrous dichloromethane (250 mL) under an atmosphere of nitrogen. A solution of trifluoromethanesulfonic anhydride (9.4 mL, 56.5 mmol) in anhydrous dichloromethane (70 mL) was added dropwise to the reaction mixture over 25 min. The cooling was removed, the reaction mixture was stirred until it reached ambient temperature, cooled again to 0° C. and saturated aqueous sodium bicarbonate was added. The aqueous layer was extracted with dichloromethane and the combined organic layers were dried over magnesium sulfate and concentrated in vacuo. Purification by column chromatography, using a gradient of ethyl acetate in heptane, gave 20.0 g (93%) of the title compound: $^1$H NMR (CDCl$_3$) δ 7.36-7.44 (m, 4 H), 7.33 (t, 4 H), 7.21-7.27 (m, 2 H), 7.13 (t, 1 H), 6.82 (t, 2 H), 4.29-4.37 (m, 1 H), 4.02 (t, 1 H), 3.77 (s, 4 H), 3.20-3.31 (m, 1 H), 3.00-3.10 (m, 1 H), 2.86-2.97 (m, 1 H); MS (ESI) m/z 478[M+H$^+$].

Intermediate Example I-2

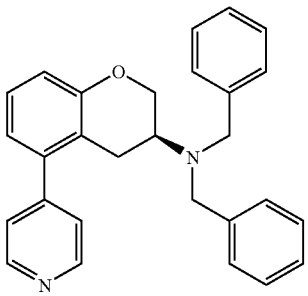

(3S)-N,N-Dibenzyl-5-pyridin-4-ylchroman-3-amine

A mixture of (3S)-3-(dibenzylamino)-3,4-dihydro-2H-chromen-5-yl trifluoromethanesulfonate (1.00 g, 2.1 mmol), pyridine-4-boronic acid (644 mg, 5.2 mmol), 1,1′-bis(diphenylphosphino)ferrocene palladium(II) dichloride (256 mg, 0.3 mmol) and potassium phosphate (1.34 g, 6.3 mmol) in dioxane (15 mL) was irradiated in a microwave at 150° C. for 2.5 h. The mixture was filtered through a pad of celite and concentrated in vacuo. Purification by column chromatography, using a gradient of ethyl acetate in heptane as the eluent, gave 707 mg (83%) of the title compound: MS (ESI) m/z 407[M+H$^+$].

Intermediate Example I-3

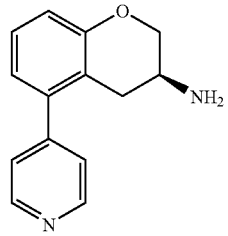

Amine 1: (3S)-5-Pyridin-4-ylchroman-3-amine

10% Palladium on charcoal (212 mg, 30 w %) and ammonium formate (1.100 g, 17.4 mmol) were added to a solution of (3S)-N,N-dibenzyl-5-pyridin-4-ylchroman-3-amine (707 mg, 1.74 mmol) in anhydrous methanol. The mixture was heated to reflux under an atmosphere of nitrogen for 20 h. The mixture was filtered through a pad of celite and concentrated in vacuo. The residue was dissolved in ethyl acetate and washed with aqueous ammonia and brine. The organic phase was dried over sodium sulfate and concentrated in vacuo to give 280 mg (71%) of the title compound: $^1$H NMR (DMSO-d$_6$) δ 8.63 (d, 2 H) 7.32-7.45 (m, 2 H) 7.18 (t, 1 H) 6.73-6.88 (m, 2 H) 4.06-4.29 (m, 1 H) 3.69-3.88 (m, 1 H) 3.64 (t, 0.5 H) 2.98-3.08 (m, 0.5 H) 2.58-2.81 (m, 1 H) 2.36-2.47 (m, 1 H); MS (ESI) m/z 227[M+H$^+$].

Intermediate Example I-4

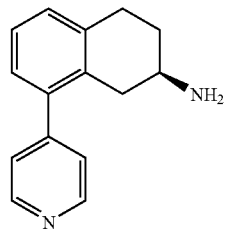

Amine 2: (2R)-8-Pyridin-4-yl-1,2,3,4-tetrahydronaphthalen-2-amine

A mixture of pyridine-4-boronic acid (54 mg, 0.44 mmol), dichloro[1,1′-bis(di-tert-butylphosphino)ferrocene]palladium(II) (14 mg, 0.022 mmol), (2R)-8-bromo-1,2,3,4-tetrahydronaphthalen-2-amine (50 mg, 0.22 mmol) and aqueous potassium carbonate (2 M, 0.19 mL, 0.37 mmol) in dioxane (0.8 mL) was irradiated in the microwave at 140° C. for 10 min. The mixture was filtered through a pad of celite and concentrated in vacuo. Purification by column chromatography, using a gradient of dichloromethane in methanol containing 1% triethylamine as the eluent, gave 48 mg (97%) of the title compound: $^1$H NMR (CDCl$_3$) δ 8.57-8.67 (m, 2 H), 7.14-7.26 (m, 4 H), 6.93-7.05 (m, 1 H), 3.01-3.18 (m, 1 H), 2.82-3.02 (m, 2 H), 2.71-2.83 (m, 1 H), 2.37-2.70 (m, 2 H), 1.97-2.21 (m, 1 H); MS (ESI) m/z 225[M+H$^+$].

Intermediate Example I-5

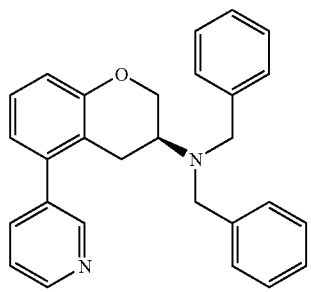

(3S)-N,N-dibenzyl-5-pyridin-3-ylchroman-3-amine

Palladium-tetrakis(triphenylphosphine) (48 mg, 0.042 mmol) and (3S)-3-(dibenzylamino)-3,4-dihydro-2H-chromen-5-yl trifluoromethanesulfonate (200 mg, 0.42 mmol) in dioxane (4 mL) were added to 3-(tri-N-butylstannyl)pyridine (232 mg, 0.63 mmol) under an atmosphere of argon and the resulting reaction mixture was irradiated in a microwave at 120-140° C. for 1.5 h. More palladium-tetrakis(triphenylphosphine) (48 mg, 0.042 mmol) was added and the irradiation was continued at 140° C. for 1 h. Water (20 mL) was added and the mixture was extracted with ethyl acetate. The organic phases was dried over sodium sulfate, the solvent was evaporated in vacuo and the residue purified by column chromatography, using a gradient of ethyl acetate in heptanes as the eluent, gave 63 mg (74%) of the title compound: MS (ES) m/z 407[M+H$^+$].

Intermediate Example I-6

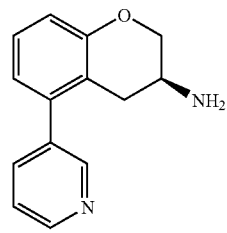

Amine 3: (3S)-5-pyridin-3-ylchroman-3-amine

Ammonium formate (195 mg, 3 mmol) and 10% palladium on charcoal (13 mg) were added to a solution of (3S)-N,N-dibenzyl-5-pyridin-3-ylchroman-3-amine (63 mg, 0.15 mmol) in methanol (10 mL). The reaction mixture was heated to reflux for 3.5 h, additional amounts of ammonium formate (195 mg, 3 mmol) and 10% palladium on charcoal (13 mg) were added and the mixture was heated to reflux for another 2.5 h. The mixture was cooled to ambient temperature, filtered through a pad of celite and concentrated in vacuo. The residue was partitioned between 2 M aqueous ammonia saturated with sodium chloride (20 mL) and ethyl acetate (20 mL), and the aqueous phase was extracted with ethyl acetate. The combined organic phases were dried over sodium sulfate and concentrated in vacuo to give 35 mg (quantitative yield) of the title compound: $^1$H NMR (CDCl$_3$) δ 8.54-8.64 (m, 2 H), 7.60-7.68 (m, 1 H), 7.31-7.39 (m, 1 H), 7.14-7.24 (m, 1 H), 6.86-6.95 (m, 1 H), 6.76-6.86 (m, 1 H), 4.14-4.30 (m, 1 H), 3.79-3.89 (m, 1 H), 3.24-3.35 (m, 1 H), 2.80-2.90 (m, 1 H), 2.38-2.48 (m, 1 H); MS (ES) m/z 227[M+H$^+$].

Intermediate Example I-7

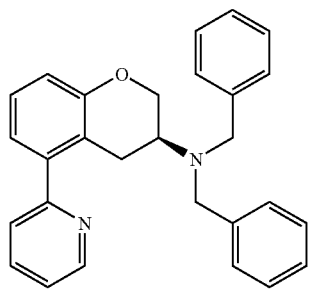

(3S)-N,N-dibenzyl-5-pyridin-2-ylchroman-3-amine

The title compound was synthesized as described for Intermediate example I-5 in 23% yield, starting from (3S)-3-(dibenzylamino)-3,4-dihydro-2H-chromen-5-yl trifluoromethanesulfonate and 2-(tri-N-butylstannyl)pyridine, but irradiated in a microwave at 140° C. for a total of 3 h; MS (ES) m/z 407[M+H$^+$].

Intermediate Example I-8

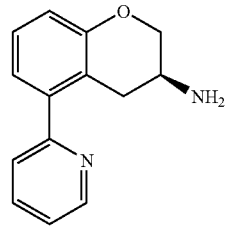

Amine 4: (3S)-5-pyridin-2-ylchroman-3-amine

The title compound was synthesized as described for Intermediate example I-6 in 86% yield, starting from (3S)-N,N-dibenzyl-5-pyridin-2-ylchroman-3-amine: $^1$H NMR (CDCl$_3$) δ 8.63-8.72 (m, 1 H), 7.69-7.81 (m, 1 H), 7.39 (d, 1 H), 7.16-7.31 (m, 2 H), 6.94-7.02 (m, 1 H), 6.88-6.94 (m, 1 H), 4.15-4.23 (m, 1 H), 3.80-3.90 (m, 1 H), 3.24-3.34 (m, 1 H), 2.96-3.09 (m, 1 H), 2.55-2.66 (m, 1 H): MS (ES) m/z 227[M+H$^+$].

Intermediate Example I-9

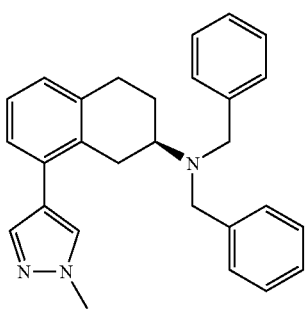

(2R)-N,N-Dibenzyl-8-(1-methyl-1 H-pyrazol-4-yl)-1,2,3,4-tetrahydronaphthalen-2-amine The title compound was synthesized as described for Intermediate example I-2 in 96% yield, starting from 1-methyl-4-(4,4,5,5-tetramethyl-1,3,2-dioxaborolan-2-yl)-1h-pyrazole and (2R)-N,N-dibenzyl-8-bromo-1,2,3,4-tetrahydronaphthalen-2-amine: MS (ESI) m/z 408[M+H$^+$].

Intermediate Example I-10

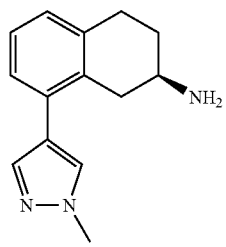

Amine 5: (2R)-8-(1-Methyl-1 H-pyrazol-4-yl)-1,2,3,4-tetrahydronaphthalen-2-amine The title compound was synthesized as described for Intermediate example I-3 in 71% yield, starting from (2R)-N,N-dibenzyl-8-(1-methyl-1 H-pyrazol-4-yl)-1,2,3,4-tetrahydronaphthalen-2-amine: $^1$H NMR (CD$_3$OD) δ 7.70 (s, 1 H), 7.56 (s, 1 H), 7.08-7.15 (m, 2 H), 6.97-7.06 (m, 1 H), 3.93 (s, 3 H), 2.99-3.10 (m, 2 H), 2.82-3.00 (m, 2 H), 2.54 (dd, 1 H), 2.02-2.12 (m, 1 H), 1.51-1.70 (m, 1 H); MS (ESI) m/z 228 [M+H$^+$].

Intermediate Example I-11

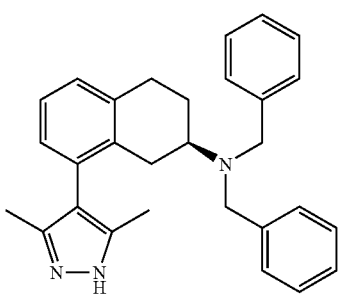

(2R)-N,N-Dibenzyl-8-(3,5-dimethyl-1 H-pyrazol-4-yl)-1,2,3,4-tetrahydronaphthalen-2-amine The title compound was synthesized as described for Intermediate example I-4 in 58% yield, starting from 3,5-dimethyl-4-(4,4,5,5-tetramethyl-1,3,2-dioxaborolan-2-yl)-1 H-pyrazole and (2R)-N,N-dibenzyl-8-bromo-1,2,3,4-tetrahydronaphthalen-2-amine (described in WO9905134A1): MS (ESI) m/z 422[M+H$^+$].

Intermediate Example I-12

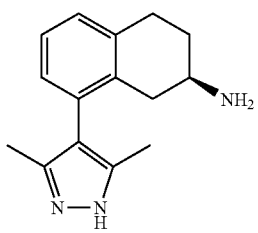

Amine 6: (2R)-8-(3,5-Dimethyl-1 H-pyrazol-4-yl)-1,2,3,4-tetrahydronaphthalen-2-amine The title compound was synthesized as described for Intermediate example I-3 in 82% yield, starting from (2R)-N,N-dibenzyl-8-(3,5-dimethyl-1 H-pyrazol-4-yl)-1,2,3,4-tetrahydronaphthalen-2-amine: $^1$H NMR (CD$_3$OD) δ 7.05-7.18 (m, 2 H), 6.89 (dd, 1 H), 2.98-3.07 (m, 1 H), 2.81-2.97 (m, 2 H), 2.60-2.73 (m, 1 H), 2.13-2.23 (m, 1 H), 2.03-2.07 (m, 1 H), 2.03 (s, 6 H), 1.49-1.63 (m, 1 H); MS (ESI) m/z 242[M+H$^+$].

Intermediate Example I-13

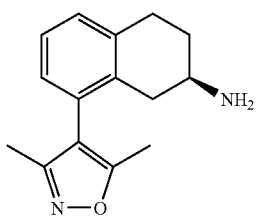

Amine 7: (2R)-8-(3,5-dimethylisoxazol-4-yl)-1,2,3,4-tetrahydronaphthalen-2-amine The title compounds was synthesized as described for Intermediate example I-4 in 80% yield, starting from 3,5-dimethylisoxazole-4-boronic acid and (2R)-8-bromo-1,2,3,4-tetrahydronaphthalen-2-amine: $^1$H NMR (CD$_3$OD) δ 7.14-7.23 (m, 2 H), 6.90-6.99 (m, 1 H), 2.99-3.11 (m, 1 H), 2.90-2.98 (m, 2 H), 2.59-2.74 (m, 1 H), 2.15-2.26 (m, 4 H), 2.05 (s, 3 H), 2.00-2.09 (m, 1 H), 1.50-1.66 (m, 1 H); MS (ESI) m/z 243[M+H$^+$].

Intermediate Example I-14

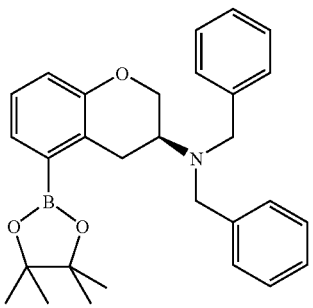

(3S)-N,N-dibenzyl-5-(4,4,5,5-tetramethyl-1,3,2-dioxaborolan-2-yl)chroman-3-amine A mixture of (3S)-3-(dibenzylamino)-3,4-dihydro-2H-chromen-5-yl trifluoromethanesulfonate (1500 mg, 3.14 mmol), bis(pinacolato)diboron (1595 mg, 6.28 mmol), 1,1'-bis(diphenylphosphino)ferrocene palladium(II) dichloride (128 mg, 0.16 mmol) and potassium acetate (925 mg, 9.42 mmol) in dioxane (3 mL) was irradiated under an atmosphere of nitrogen in a microwave at 150° C. for 1 h. The mixture was filtered through a pad of celite which was then washed with methanol. The filtrate was concentrated in vacuo and the crude partioned between ethyl acetate and 1M sodium hydroxide. The organic layer was dried over magnesium sulfate and concentrated in vacuo. Purification by column chromatography, using a gradient of ethyl acetate in heptane affording 1182 mg (83%) of the title compound as a colorless oil: $^1$H NMR (400 MHz, DMSO-$d_6$) δ ppm 7.27-7.39 (m, 8 H), 7.21 (t, 2 H), 7.16 (d, 1 H), 7.03 (t, 1 H), 6.81 (d, 1 H), 4.26 (d, 1 H), 3.97 (t, 1 H), 3.74 (s, 4 H), 3.14-3.27 (m, 1 H), 2.99-3.09 (m, 2 H), 1.30 (d, 12 H); MS (ESI) m/z 456, 457 [M+H$^+$].

Intermediate Example I-15

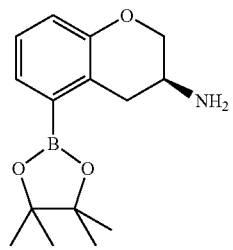

(3S)-5-(4,4,5,5-tetramethyl-1,3,2-dioxaborolan-2-yl)chroman-3-amine

The title compound was synthesized as described for Intermediate example I-3 in 67% yield, starting from (3S)-N,N-dibenzyl-5-(4,4,5,5-tetramethyl-1,3,2-dioxaborolan-2-yl)chroman-3-amine using 47 w % of 10% palladium on charcoal. The reaction mixture was heated to 55° C. for 1.5 h; $^1$H NMR (400 MHz, DMSO-$d_6$) δ ppm 7.19 (dd, 1 H), 7.04 (t, 1 H), 6.83 (dd, 1 H), 4.00-4.06 (m, 1 H), 3.50-3.59 (m, 1 H), 3.14-3.23 (m, 1 H), 2.98-3.12 (m, 1 H), 2.52-2.60 (m, 1 H), 1.29 (s, 12 H), 1.06 (s, 2 H); MS (APPI/APCI) m/z 276[M+H$^+$].

Intermediate Example I-16

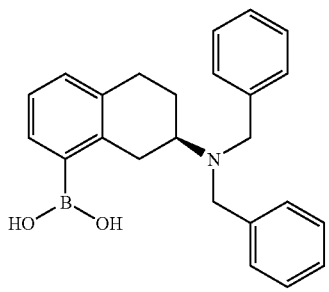

[(7R)-7-(dibenzylamino)-5,6,7,8-tetrahydronaphthalen-1-yl]boronic acid

To a solution of (2R)-N,N-dibenzyl-8-bromo-1,2,3,4-tetrahydronaphthalen-2-amine (1000 mg, 2.46 mmol) in dry tetrahydrofuran (10 mL) under an atmosphere of nitrogen, n-butyllithium (1.6M, 2.3 mL, 3.69 mmol) was added over 5 min at −70° C. The reaction mixture was stirred at 0° C. for 10 min before triethyl borate (0.50 mL, 2.95 mmol) was added. The reaction mixture was stirred for additional 5 min at 0° C. and then allowed to reach ambient temperature and stirred for another 2 h. The reaction mixture was quenched with saturated ammonium chloride (aq) and a white precipitate was filtered off. The filtrate was extracted with ethyl acetate, the organic layer was dried over magnesium sulfate and concentrated in vacuo to yield 612 mg (67%) of the title compound as a solid: $^1$H NMR (400 MHz, CDCl$_3$) δ ppm 8.31 (d, 1 H), 7.39-7.45 (m, 4 H), 7.28-7.37 (m, 2 H), 7.02-7.26 (m, 6 H), 3.65-3.92 (m, 4 H), 3.34-3.45 (m, 1 H), 2.70-3.19 (m, 4 H), 2.16 (br. s., 1 H), 1.66-1.79 (m, 1 H); MS (ESI) m/z 371, 372[M+H$^+$].

Intermediate Example I-17

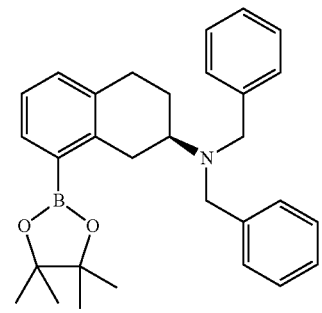

(2R)-N,N-dibenzyl-8-(4,4,5,5-tetramethyl-1,3,2-dioxaborolan-2-yl)-1,2,3,4-tetrahydronaphthalen-2-amine The title compound was synthesized as described for Intermediate example I-14 in 56% yield, starting from (2R)-N,N- dibenzyl-8-bromo-1,2,3,4-tetrahydronaphthalen-2-amine and bis(pinacolato)diboron using 2M potassium carbonate as base and isopropanol as solvent. The reaction mixture was irradiated in a microwave at 140° C. for 30 min; MS (APPI/APCI) m/z 454, 455[M+H$^+$].

Intermediate Example I-18

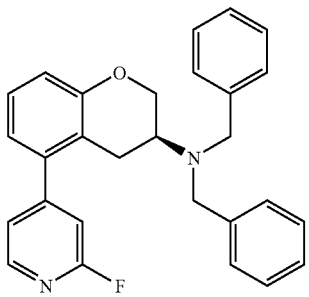

(3S)-N,N-dibenzyl-5-(2-fluoropyridin-4-yl)chroman-3-amine

The title compound was synthesized as described for Intermediate example I-2 in 68% yield, starting from 2-fluoro-4-pyridinylboronic acid and (3S)-3-(dibenzylamino)-3,4-dihydro-2H-chromen-5-yl trifluoromethanesulfonate. The reaction was irradiated in a microwave at 150° C. for 3 h; $^1$H NMR (400 MHz, DMSO-d$_6$) δ ppm 8.30 (d, 1 H), 7.33-7.37 (m, 1 H), 7.24-7.33 (m, 8 H), 7.15-7.22 (m, 4 H), 6.79-6.87 (m, 2 H), 4.32-4.38 (m, 1 H), 4.04-4.10 (m, 1 H), 3.61-3.74 (m, 4 H), 2.93-3.10 (m, 2 H), 2.42-2.48 (m, 1 H); MS (ESI) m/z 425[M+H$^+$].

Intermediate Example I-19

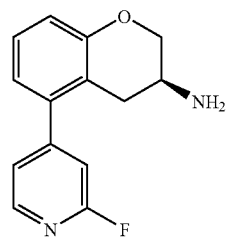

Amine 8: (3S)-5-(2-fluoropyridin-4-yl)chroman-3-amine

The title compound was synthesized as described for Intermediate example I-3 in 79% yield, starting from (3S)-N,N-dibenzyl-5-(2-fluoropyridin-4-yl)chroman-3-amine using 20 equiv of ammonium formate and 20 w % of 10% palladium on charcoal; $^1$H NMR (400 MHz, DMSO-d$_6$) δ ppm 8.30 (d, 1 H), 7.32-7.39 (m, 1 H), 7.13-7.23 (m, 2 H), 6.82-6.89 (m, 2 H), 4.06-4.14 (m, 1 H), 3.59-3.68 (m, 1 H), 2.97-3.09 (m, 1 H), 2.59-2.69 (m, 1 H), 2.36-2.48 (m, 1 H), 1.72 (br. s., 2 H); MS (ESI) m/z 245[M+H$^+$].

Intermediate Example I-20

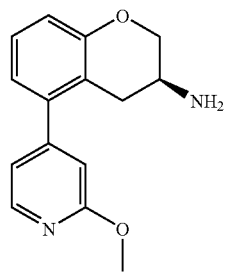

(3S)-N,N-dibenzyl-5-(2-methoxypyridin-4-yl)chroman-3-amine

The title compound was synthesized as described for Intermediate example I-2 in 100% yield, starting from 2-methoxypyridine-4-boronic acid and (3S)-3-(dibenzylamino)-3,4-dihydro-2H-chromen-5-yl trifluoromethanesulfonate; $^1$H NMR (400 MHz, DMSO-d$_6$) δ ppm 8.22 (d, 1 H), 7.23-7.34 (m, 8 H), 7.09-7.23 (m, 3 H), 6.96 (dd, 1 H), 6.80 (dd, 1 H), 6.70-6.78 (m, 2 H), 4.31-4.37 (m, 1 H), 4.03-4.10 (m, 1 H), 3.91 (s, 3 H), 3.62-3.73 (m, 4 H), 2.90-3.07 (m, 2 H), 2.43-2.49 (m, 1 H); MS (ESI) m/z 437[M+H$^+$].

Intermediate Example I-21

Amine 9: (3S)-5-(2-methoxypyridin-4-yl)chroman-3-amine

The title compound was synthesized as described for Intermediate example I-3 in 70% yield, starting from (3S)-N,N-dibenzyl-5-(2-methoxypyridin-4-yl)chroman-3-amine, using 20 equiv of ammonium formate and 20 w % of 10% palladium on charcoal; $^1$H NMR (400 MHz, DMSO-d$_6$) δ ppm 8.21 (d, 1 H), 7.17 (t, 1 H), 6.95 (dd, 1 H), 6.81-6.84 (m, 1 H), 6.78 (dd, 1 H), 6.73-6.76 (m, 1 H), 4.07-4.12 (m, 1 H), 3.89 (s, 3 H), 3.64 (dd, 1 H), 2.99-3.09 (m, 1 H), 2.60-2.69 (m, 1 H), 2.41 (dd, 1 H); MS (ESI) m/z 257[M+H$^+$].

Intermediate Example I-22

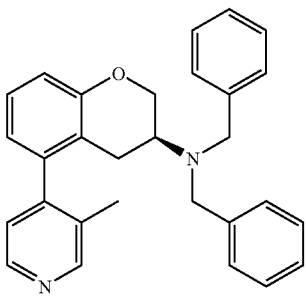

(3S)-N,N-dibenzyl-5-(3-methylpyridin-4-yl)chroman-3-amine

The title compound was synthesized as described for Intermediate example I-2 in 76% yield, starting from 3-methylpyridine-4-boronic acid and (3S)-3-(dibenzylamino)-3,4-dihydro-2H-chromen-5-yl trifluoromethanesulfonate; $^1$H NMR (400 MHz, DMSO-$d_6$) δ ppm 8.54 (d, 1 H), 8.46 (dd, 1 H), 7.25-7.32 (m, 8 H), 7.05-7.24 (m, 4 H), 6.76-6.83 (m, 1 H), 6.59-6.64 (m, 1 H), 4.26-4.34 (m, 1 H), 4.04-4.13 (m, 1 H), 3.55-3.68 (m, 4 H), 2.93-3.07 (m, 1 H), 2.34-2.43 (m, 1 H), 2.08-2.22 (m, 1 H), 1.92-2.02 (m, 3 H); MS (ESI) m/z 421 [M+H$^+$].

Intermediate Example I-23

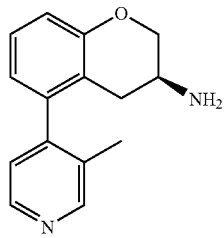

Amine 10: (3S)-5-(3-methylpyridin-4-yl)chroman-3-amine

The title compound was synthesized as described for Intermediate example I-3 in 90% yield, starting from (3S)-N,N-dibenzyl-5-(3-methylpyridin-4-yl)chroman-3-amine using 20 equiv of ammonium formate and 20 w % of 10% palladium on charcoal; $^1$H NMR (400 MHz, DMSO-$d_6$) δ ppm 8.52 (d, 1 H), 8.44 (d, 1 H), 7.05-7.20 (m, 2 H), 6.82 (d, 1 H), 6.58-6.67 (m, 1 H), 4.02-4.12 (m, 1 H), 3.49-3.64 (m, 1 H), 2.95-3.09 (m, 1 H), 2.21-2.46 (m, 1 H), 2.02 (d, 3 H), 1.89-2.17 (m, 1 H), 1.61 (br. s., 2 H); MS (ESI) m/z 241[M+H$^+$].

Intermediate Example I-24

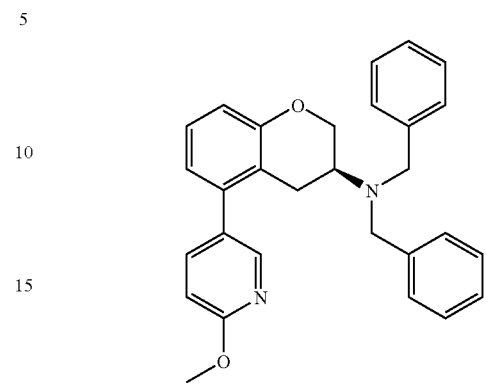

(3S)-N,N-dibenzyl-5-(6-methoxypyridin-3-yl)chroman-3-amine

The title compound was synthesized as described for Intermediate example I-2 in 84% yield, starting from 2-methoxy-5-pyridineboronic acid (1.7 equiv) and (3S)-3-(dibenzylamino)-3,4-dihydro-2H-chromen-5-yl trifluoromethanesulfonate; MS (ESI) m/z 437[M+H$^+$].

Intermediate Example I-25

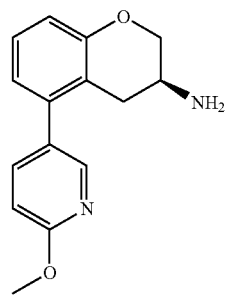

Amine 11: (3S)-5-(6-methoxypyridin-3-yl)chroman-3-amine

The title compound was synthesized as described for Intermediate example I-3 in 89% yield, starting from (3S)-N,N-dibenzyl-5-(6-methoxypyridin-3-yl)chroman-3-amine using 10 equiv of ammonium formate and 20 w % of 10% palladium on charcoal: $^1$H NMR (400 MHz, CD$_3$OD) δ ppm 8.05 (d, 1 H), 7.65 (dd, 1 H), 7.15 (t, 1 H), 6.85 (d, 1 H), 6.82 (dd, 1 H), 6.78 (dd, 1 H), 4.14-4.20 (m, 1 H), 3.94 (s, 3 H), 3.78 (dd, 1 H), 3.12-3.20 (m, 1 H), 2.78-2.86 (m, 1 H), 2.47 (dd, 1 H); MS (ESI) m/z 257[M+H$^+$].

Intermediate Example I-26

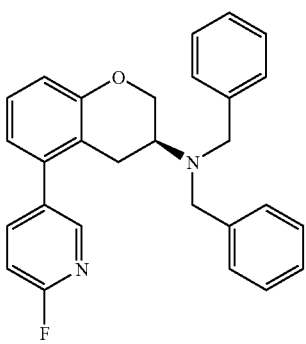

(3S)-N,N-dibenzyl-5-(6-fluoropyridin-3-yl)chroman-3-amine

The title compound was synthesized as described for Intermediate example I-2 in 64% yield, starting from 2-fluoro-5-pyridylboronic acid and (3S)-3-(dibenzylamino)-3,4-s dihydro-2H-chromen-5-yl trifluoromethanesulfonate; $^1$H NMR (400 MHz, DMSO-$d_6$) δ ppm 8.22 (d, 1 H), 7.95-8.03 (m, 1 H), 7.23-7.34 (m, 9 H), 7.11-7.23 (m, 3 H), 6.75-6.84 (m, 2 H), 4.30-4.38 (m, 1 H), 4.04 (t, 1 H), 3.61-3.73 (m, 4 H), 2.92-3.07 (m, 2 H), 2.40-2.49 (m, 1 H); MS (ESI) m/z 425 [M+H$^+$].

Intermediate Example I-27

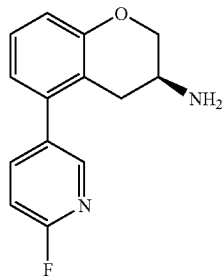

Amine 12: (3S)-5-(6-fluoropyridin-3-yl)chroman-3-amine

The title compound was synthesized as described for Intermediate example I-3 in 94% yield, starting from (3S)-N,N-dibenzyl-5-(6-fluoropyridin-3-yl)chroman-3-amine using 20 equiv of ammonium formate and 20 w % of 10% palladium on charcoal; $^1$H NMR (400 MHz, DMSO-$d_6$) δ ppm 8.21 (d, 1 H), 7.91-8.05 (m, 1 H), 7.27 (dd, 1 H), 7.18 (t, 1 H), 6.75-6.87 (m, 2 H), 4.06-4.15 (m, 1 H), 3.64 (t, 1 H), 2.95-3.10 (m, 1 H), 2.62 (dd, 1 H), 2.33-2.44 (m, 1 H); MS (ESI) m/z 245[M+H$^+$].

Intermediate Example I-28

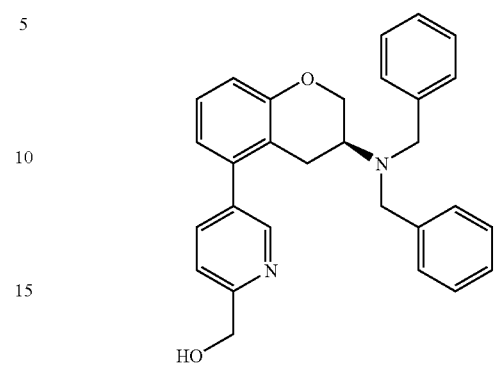

{5-[(3S)-3-(dibenzylamino)-3,4-dihydro-2H-chromen-5-yl]pyridin-2-yl}methanol

A mixture of (5-bromopyridin-2-yl)methanol (0.205 g, 1.09 mmol), (3S)-N,N-dibenzyl-5-(4,4,5,5-tetramethyl-1,3,2-dioxaborolan-2-yl)chroman-3-amine (0.13 M in isopropanol, 8.4 mL, 1.09 mmol), 1,1'-bis(diphenylphosphino)ferrocene-palladium(ii)dichloride dichloromethane complex (0.045 g, 0.05 mmol), and 2 M potassium carbonate (1.64 mL, 3.28 mmol) was irradiated in a microwave synthesizer at 140° C. for 20 min. The solution was filtered through a pad of celite and concentrated in vacuo. The residue was purified by column chromatography using a gradient of ethyl acetate in heptane. The crude was dissolved in chloroform and insoluble material was removed. The solvent was evaporated in vacuo yielding an oil, 0.360 g (76%); $^1$H NMR (400 MHz, DMSO-$d_6$) δ ppm 8.46 (d, 1 H), 7.79 (dd, 1 H), 7.54 (d, 1 H), 7.24-7.34 (m, 8 H), 7.06-7.22 (m, 3 H), 6.69-6.83 (m, 2 H), 5.51 (t, 1 H), 4.64 (d, 2 H), 4.28-4.39 (m, 1 H), 3.99-4.10 (m, 1 H), 3.59-3.74 (m, 4 H), 2.86-3.11 (m, 1 H), 2.39-2.49 (m, 1 H); MS (APPI/APCI) m/z 437[M+H$^+$].

Intermediate Example I-29

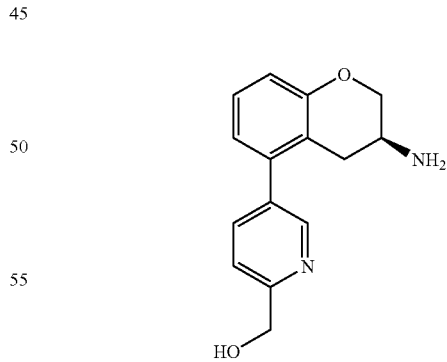

Amine 13: {5-[(3S)-3-amino-3,4-dihydro-2H-chromen-5-yl]pyridin-2-yl}methanol

The title compound was synthesized as described for Intermediate example I-3 in 73% yield, starting from {5-[(3S)-3-(dibenzylamino)-3,4-dihydro-2H-chromen-5-yl]pyridin-2-yl}methanol using 15 equiv of ammonium formate and 37 w % of 10% palladium on charcoal; ¹H NMR (400 MHz, DMSO-d₆) δ ppm 8.39-8.45 (m, 1 H), 7.78 (dd, 1 H), 7.53 (d, 1 H), 7.17 (t, 1 H), 6.75-6.84 (m, 2 H), 5.48 (t, 1 H), 4.61 (d, 2 H), 4.06-4.13 (m, 1 H), 3.56-3.66 (m, 1 H), 2.97-3.07 (m, 1 H), 2.56-2.66 (m, 1 H), 2.36-2.45 (m, 1 H); MS (ESI) m/z 257[M+H⁺].

Intermediate Example I-30

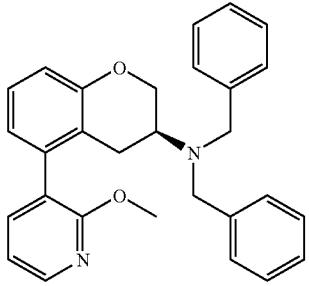

(3S)-N,N-dibenzyl-5-(2-methoxypyridin-3-yl)chroman-3-amine

The title compound was synthesized as described for Intermediate example I-2 in 93% yield, starting from 2-methoxypyridine-3-boronic acid and (3S)-3-(dibenzylamino)-3,4-dihydro-2H-chromen-5-yl trifluoromethanesulfonate. The reaction mixture was irradiated in a microwave at 150° C. for 1 h; ¹H NMR (400 MHz, DMSO-d₆) δ ppm 7.52 (dd, 1 H), 7.25-7.34 (m, 9 H), 7.16-7.24 (m, 2 H), 7.04-7.14 (m, 2 H), 6.76 (d, 1 H), 6.68 (d, 1 H), 4.25-4.35 (m, 1 H), 4.05 (t, 1 H), 3.80 (s, 3 H), 3.55-3.70 (m, 4 H), 2.93-3.04 (m, 1 H), 2.55-2.84 (m, 1 H), 2.27-2.38 (m, 1 H); MS (ESI) m/z 437[M+H⁺].

Intermediate Example I-31

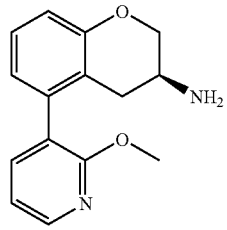

Amine 14: (3S)-5-(2-methoxypyridin-3-yl)chroman-3-amine

The title compound was synthesized as described for Intermediate example I-3 in 98% yield, starting from (3S)-N,N-dibenzyl-5-(2-methoxypyridin-3-yl)chroman-3-amine using 20 equiv of ammonium formate and 20 w % of 10% palladium on charcoal; ¹H NMR (400 MHz, DMSO-d₆) δ ppm 8.20 (dd, 1 H), 7.53 (dd, 1 H), 7.03-7.15 (m, 2 H), 6.77 (dd, 1 H), 6.69 (dd, 1 H), 4.05-4.10 (m, 1 H), 3.82 (s, 3 H), 3.56 (t, 1 H), 3.00 (br. s., 1 H), 2.02-2.46 (m, 2 H), 1.64 (br. s., 2 H); MS (ESI) m/z 257[M+H⁺].

Intermediate Example I-32

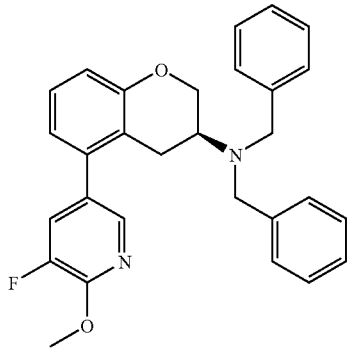

(3S)-N,N-dibenzyl-5-(5-fluoro-6-methoxypyridin-3-yl)chroman-3-amine

The title compound was synthesized as described for Intermediate example I-2 in 71% yield, starting from 5-fluoro-6-methoxypyridin-3-ylboronic acid (1.7 equiv) and (3S)-3-(dibenzylamino)-3,4-dihydro-2H-chromen-5-yl trifluoromethanesulfonate (1 equiv): ¹H NMR (400 MHz, DMSO-d₆) δ ppm 7.96 (d, 1 H), 7.73 (dd, 1 H), 7.23-7.37 (m, 8 H), 7.06-7.22 (m, 3 H), 6.78 (dd, 2 H), 4.34 (d, 1 H), 3.92-4.08 (m, 4 H), 3.60-3.79 (m, 4 H), 3.18-3.30 (m, 1 H), 2.89-3.10 (m, 2 H); MS (ESI) m/z 455[M+H⁺].

Intermediate Example I-33

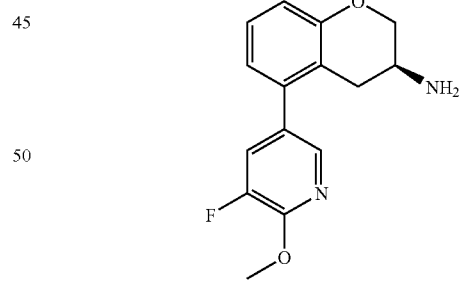

Amine 15: (3S)-5-(5-fluoro-6-methoxypyridin-3-yl)chroman-3-amine

The title compound was synthesized as described for Intermediate example I-3 in 75% yield, starting from (3S)-N,N-dibenzyl-5-(5-fluoro-6-methoxypyridin-3-yl)chroman-3-amine using 20 w % of 10% palladium on charcoal: ¹H NMR (400 MHz, CDCl₃) δ ppm 7.89 (d, 1 H), 7.33 (dd, 1 H), 7.19 (t, 1 H), 6.90 (dd, 1 H), 6.82 (dd, 1 H), 4.19 (ddd, 1 H), 4.08

(s, 3 H), 3.84 (ddd, 1 H), 3.27-3.36 (m, 1 H), 2.87 (ddd, 1 H), 2.44 (dd, 1 H); MS (ESI) m/z 275[M+H⁺].

Intermediate Example I-34

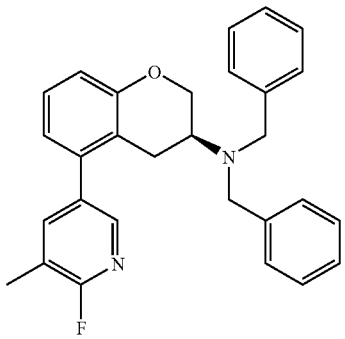

(3S)-N,N-dibenzyl-5-(6-fluoro-5-methylpyridin-3-yl)chroman-3-amine

The title compound was synthesized as described for Intermediate example I-2 in 79% yield, starting from 6-fluoro-5-methylpyridin-3-ylboronic acid (1.7 equiv) and (3S)-3-(dibenzylamino)-3,4-dihydro-2H-chromen-5-yl trifluoromethanesulfonate: ¹H NMR (400 MHz, CDCl₃) δ ppm 7.98 (s, 1 H), 7.50 (dd, 1 H), 7.28-7.36 (m, 8 H), 7.17-7.26 (m, 2 H), 7.14 (t, 1 H), 6.84 (d, 1 H), 6.74 (d, 1 H), 4.32-4.42 (m, 1 H), 4.03 (t, 1 H), 3.65-3.76 (m, 4 H), 3.11-3.25 (m, 1 H), 2.73-2.85 (m, 1 H), 2.61 (dd, 1 H), 2.36 (s, 3 H); MS (ESI) m/z 439[M+H⁺].

Intermediate Example I-35

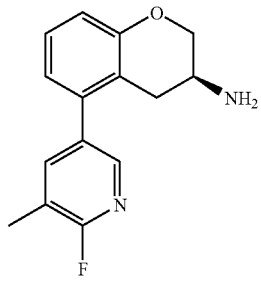

Amine 16: (3S)-5-(6-fluoro-5-methylpyridin-3-yl)chroman-3-amine

The title compound was synthesized as described for Intermediate example I-3 in 73% yield, starting from (3S)-N,N-dibenzyl-5-(6-fluoro-5-methylpyridin-3-yl)chroman-3-amine using 20 w % of 10% palladium on charcoal: ¹H NMR (400 MHz, CD₃OD) δ ppm 7.94 (s, 1 H), 7.76 (d, 1 H), 7.17 (t, 1 H), 6.86 (d, 1 H), 6.80 (d, 1 H), 4.15-4.21 (m, 1 H), 3.75-3.84 (m, 1 H), 3.12-3.22 (m, 1 H), 2.81 (dd, 1 H), 2.46 (dd, 1 H), 2.34 (s, 3 H); MS (ESI) m/z 259[M+H⁺].

Intermediate Example I-36

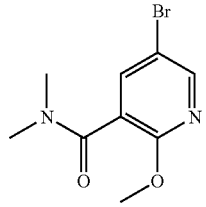

5-bromo-2-methoxy-N,N-dimethylnicotinamide

To a mixture of 5-bromo-2-methoxynicotinic acid (80 mg, 0.34 mmol), triethylamine (192 μl, 1.38 mmol) and 2-(1 H-benzotriazole-1-yl)-1,1,3,3-tetramethyluronium hexafluorophosphate in acetonitrile (1 mL) was added dimethylamine, 2 M in tetrahydrofuran (172 μl, 0.34 mmol). The reaction mixture was stirred at ambient temperature under an atmosphere of nitrogen for 3 h. The mixture was partitioned between water and ethyl acetate. The organic layer was dried over magnesium sulfate and concentrated in vacuo to give a crude product which was purified by column chromatography using a gradient of ethyl acetate in heptane affording 54 mg (60%) of the title compound as a white solid: ¹H NMR (400 MHz, DMSO-d₆) δ ppm 8.36 (d, 1 H), 7.91 (d, 1 H), 3.88 (s, 3 H), 2.96 (s, 3 H), 2.78 (s, 3 H); MS (ESI) m/z 259, 261[M+H⁺].

Intermediate Example I-37

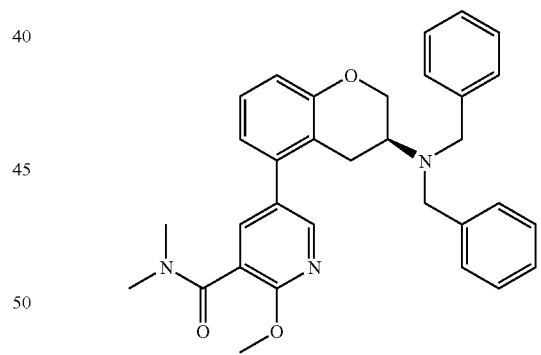

5-[(3S)-3-(dibenzylamino)-3,4-dihydro-2H-chromen-5-yl]-2-methoxy-N,N-dimethylnicotinamide The title compound was synthesized as described for Intermediate I-28 in 38% yield starting from (3S)-N,N-dibenzyl-5-(4,4,5,5-tetramethyl-1,3,2-dioxaborolan-2-yl)chroman-3-amine and 5-bromo-2-methoxy-N,N-dimethylnicotinamide. The reaction mixture was irradiated in a microwave at 140° C. for 45 min: ¹H NMR (400 MHz, DMSO-d₆) δ ppm 8.19 (d, 1 H), 7.68 (d, 1 H), 7.25-7.40 (m, 8 H), 7.11-7.22 (m, 3 H), 6.70-6.80 (m, 2 H), 4.32-4.38 (m, 1 H), 3.97-4.04 (m, 1

H), 3.96 (s, 3 H), 3.62-3.75 (m, 4 H), 3.02-3.13 (m, 2 H), 2.99 (s, 3 H), 2.91-2.98 (m, 1 H), 2.85 (s, 3 H); MS (ESI) m/z 508[M+H⁺].

Intermediate Example I-38

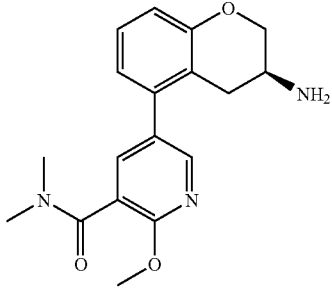

Amine 17: 5-[(3S)-3-amino-3,4-dihydro-2H-chromen-5-yl]-2-methoxy-N,N-dimethylnicotinamide The title compound was synthesized as described for Intermediate example I-3 in 93% yield, starting from 5-[(3S)-3-(dibenzylamino)-3,4-dihydro-2H-chromen-5-yl]-2-methoxy-N,N-dimethylnicotinamide using 55 w % of 10% palladium on charcoal; ¹H NMR (400 MHz, DMSO-$d_6$) δ ppm 8.19 (d, 1 H), 7.63 (d, 1 H), 7.15 (t, 1 H), 6.77-6.82 (m, 2 H), 4.05-4.12 (m, 1 H), 3.94 (s, 3 H), 3.54-3.67 (m, 1 H), 2.99-3.08 (m, 1 H), 2.98 (s, 3 H), 2.83 (s, 3 H), 2.61-2.69 (m, 1 H), 2.41 (dd, 1 H); MS (ESI) m/z 328[M+H⁺].

Intermediate Example I-39

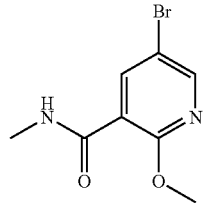

5-bromo-2-methoxy-N-methylnicotinamide

The title compound was synthesized as described for Intermediate example I-36 in 43% yield, starting from 5-bromo-2-methoxynicotinic acid and methylamine hydrochloride (4.3 equiv); ¹H NMR (400 MHz, DMSO-$d_6$) δ ppm 8.42 (d, 1 H), 8.26-8.35 (m, 1 H), 8.20 (d, 1 H), 3.95 (s, 3 H), 2.79 (d, 3 H); MS (APPI/APCI) m/z 245, 247[M+H⁺].

Intermediate Example I-40

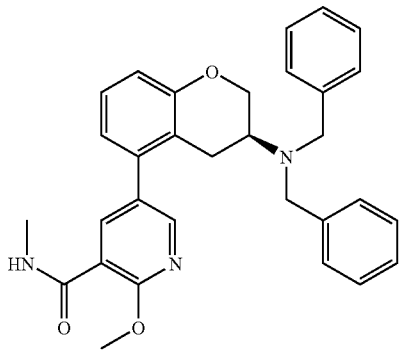

5-[(3S)-3-(dibenzylamino)-3,4-dihydro-2H-chromen-5-yl]-2-methoxy-N-methylnicotinamide The title compound was synthesized as described for Intermediate I-28 in 66% yield starting from (3S)-N,N-dibenzyl-5-(4,4,5,5-tetramethyl-1,3,2-dioxaborolan-2-yl)chroman-3-amine and 5-bromo-2-methoxy-N-methylnicotinamide; ¹H NMR (400 MHz, DMSO-$d_6$) δ ppm 8.33 (q, 1 H), 8.29 (d, 1 H), 8.06 (d, 1 H), 7.24-7.32 (m, 8 H), 7.11-7.21 (m, 3 H), 6.71-6.82 (m, 2 H), 4.26-4.38 (m, 1 H), 4.04 (s, 3 H), 4.01-4.11 (m, 1 H), 3.57-3.73 (m, 4 H), 2.87-3.09 (m, 2 H), 2.84 (d, 3 H), 2.46-2.54 (m, 1 H, obscured by DMSO); MS (ESI) m/z 494[M+H⁺].

Intermediate Example I-41

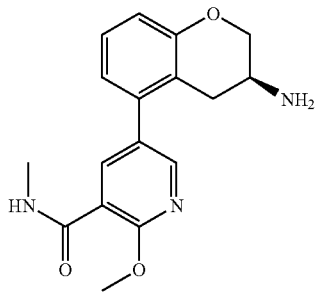

Amine 18: 5-[(3S)-3-amino-3,4-dihydro-2H-chromen-5-yl]-2-methoxy-N-methylnicotinamide The title compound was synthesized as described for Intermediate example I-3 in 91% yield, starting from 5-[(3S)-3-(dibenzylamino)-3,4-dihydro-2H-chromen-5-yl]-2-methoxy-N-methylnicotinamide using 55 w % of 10% palladium on charcoal; ¹H NMR (400 MHz, DMSO-$d_6$) δ ppm 8.31 (q, 1 H), 8.26 (d, 1 H), 8.05 (d, 1 H), 7.16 (t, 1 H), 6.77-6.83 (m, 2 H), 4.06-4.11 (m, 1 H), 4.02 (s, 3 H), 3.58-3.65 (m, 1 H), 2.97-3.06 (m, 1 H), 2.82 (d, 3 H), 2.55-2.69 (m, 1 H), 2.34-2.43 (m, 1 H); MS (APPI/APCI) m/z 314[M+H⁺].

Intermediate Example I-42

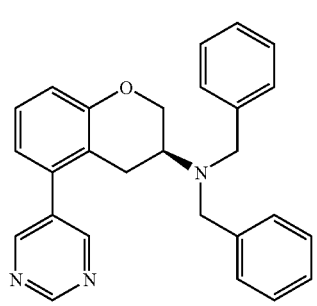

(3S)-N,N-dibenzyl-5-pyrimidin-5-ylchroman-3-amine

The title compound was synthesized as described for Intermediate example I-2 in 78% yield, starting from 5-pyrimidinylboronic acid and (3S)-3-(dibenzylamino)-3,4-dihydro-2H-chromen-5-yl trifluoromethanesulfonate; $^1$H NMR (400 MHz, DMSO-$d_6$) δ ppm 9.24 (s, 1 H), 8.86 (s, 2 H), 7.24-7.34 (m, 8 H), 7.15-7.23 (m, 3 H), 6.86 (d, 2 H), 4.32-4.38 (m, 1 H), 4.00-4.08 (m, 1 H), 3.61-3.75 (m, 4 H), 3.05-3.14 (m, 1 H), 2.93-3.03 (m, 1 H), 2.46-2.54 (m, 1 H, obscured by DSMO); MS (ESI) m/z 408[M+H$^+$].

Intermediate Example I-43

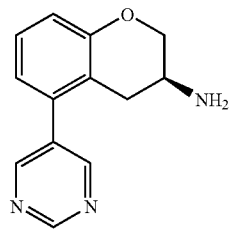

Amine 19: (3S)-5-pyrimidin-5-ylchroman-3-amine

The title compound was synthesized as described for Intermediate example I-3 in 79% yield, starting from (3S)-N,N-dibenzyl-5-pyrimidin-5-ylchroman-3-amine using 20 equiv of ammonium formate and 20 w % of 10% palladium on charcoal; $^1$H NMR (400 MHz, DMSO-$d_6$) δ ppm 9.21 (s, 1 H), 8.84 (s, 2 H), 7.22 (t, 1 H), 6.80-6.89 (m, 2 H), 4.07-4.13 (m, 1 H), 3.64 (dd, 1 H), 2.99-3.10 (m, 1 H), 2.60-2.69 (m, 1 H), 2.40-2.48 (m, 1 H), 1.67 (br. s., 2 H); MS (ESI) m/z 228[M+H$^+$].

Intermediate Example I-44

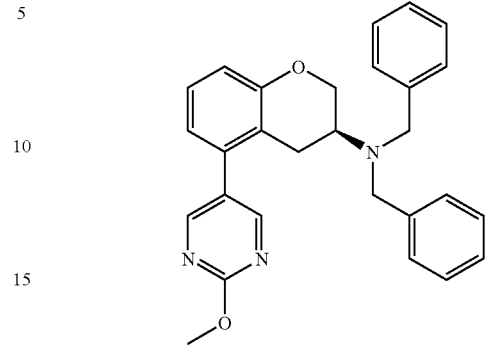

(3S)-N,N-dibenzyl-5-(2-methoxypyrimidin-5-yl)chroman-3-amine

The title compound was synthesized as described for Intermediate example I-2 in 93% yield, starting from 2-methoxy-5-pyrimidineboronic acid and (3S)-3-(dibenzylamino)-3,4-s dihydro-2H-chromen-5-yl trifluoromethanesulfonate; $^1$H NMR (400 MHz, DMSO-$d_6$) δ ppm 8.64 (s, 2 H), 7.24-7.36 (m, 8 H), 7.11-7.23 (m, 3 H), 6.82 (d, 2 H), 4.27-4.39 (m, 1 H), 4.00 (s, 3 H), 3.93-4.06 (m, 1 H), 3.57-3.76 (m, 4 H), 3.02-3.14 (m, 1 H), 2.91-3.01 (m, 1 H), 2.51-2.58 (m, 1 H); MS (ESI) m/z 438[M+H$^+$].

Intermediate Example I-45

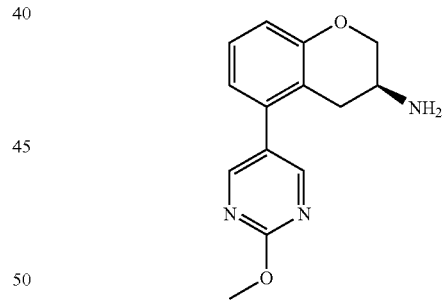

Amine 20: (3S)-5-(2-methoxypyrimidin-5-yl)chroman-3-amine

The title compound was synthesized as described for Intermediate example I-3 in 98% yield, starting from (3S)-N,N-dibenzyl-5-(2-methoxypyrimidin-5-yl)chroman-3-amine using 20 equiv of ammonium formate and 20 w % of 10% palladium on charcoal; $^1$H NMR (400 MHz, DMSO-$d_6$) δ ppm 8.62 (s, 2 H), 7.18 (t, 1 H), 6.81-6.86 (m, 2 H), 4.07-4.13 (m, 1 H), 3.97 (s, 3 H), 3.57-3.65 (m, 1 H), 2.99-3.09 (m, 1 H), 2.61-2.70 (m, 1 H), 2.43 (dd, 1 H), 1.64 (br. s., 2 H); MS (APPI/APCI) m/z 258[M+H$^+$].

Intermediate Example I-46

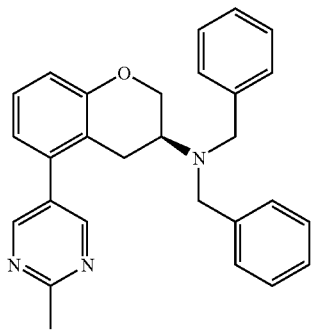

(3S)-N,N-dibenzyl-5-(2-methylpyrimidin-5-yl)chroman-3-amine

The title compound was synthesized as described for Intermediate example I-2 in 79% yield, starting from (2-methylpyrimidin-5-yl)boronic acid and (3S)-3-(dibenzylamino)-3,4-s dihydro-2H-chromen-5-yl trifluoromethanesulfonate; $^1$H NMR (400 MHz, DMSO-$d_6$) δ ppm 8.73 (s, 2 H), 7.24-7.35 (m, 8 H), 7.14-7.22 (m, 3 H), 6.80-6.86 (m, 2 H), 4.31-4.37 (m, 1 H), 4.04 (t, 1 H), 3.61-3.74 (m, 4 H), 3.04-3.14 (m, 1 H), 2.92-3.02 (m, 1 H), 2.71 (s, 3 H), 2.51-2.56 (m, 1 H, obscured by DMSO); MS (ESI) m/z 422[M+H$^+$].

Intermediate Example I-47

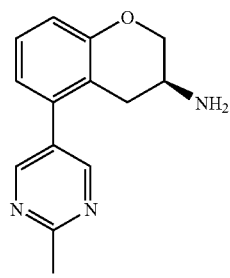

Amine 21: (3S)-5-(2-methylpyrimidin-5-yl)chroman-3-amine

The title compound was synthesized as described for Intermediate example I-3 in 81% yield, starting from (3S)-N,N-dibenzyl-5-(2-methylpyrimidin-5-yl)chroman-3-amine using 20 equiv of ammonium formate and 20 w % of 10% palladium on charcoal; $^1$H NMR (400 MHz, DMSO-$d_6$) δ ppm 8.71 (s, 2 H), 7.20 (t, 1 H), 6.80-6.88 (m, 2 H), 4.07-4.13 (m, 1 H), 3.63 (dd, 1 H), 2.98-3.10 (m, 1 H), 2.67 (s, 3 H), 2.60-2.67 (m, 1 H), 2.38-2.47 (m, 1 H); MS (ESI) m/z 242 [M+H$^+$].

Intermediate Example I-48

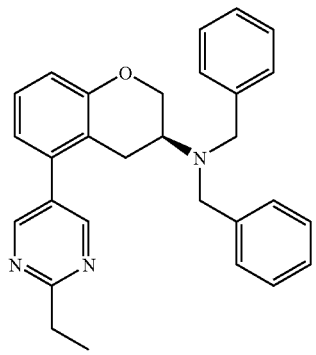

(3S)-N,N-dibenzyl-5-(2-ethylpyrimidin-5-yl)chroman-3-amine

A mixture of (3S)-N,N-dibenzyl-5-(4,4,5,5-tetramethyl-1,3,2-dioxaborolan-2-yl)chroman-3-amine (278 mg, 0.61 mmol), 5-bromo-2-ethylpyrimidine (114 mg, 0.61 mmol), dichloro[1,1'bis(di-tert-butylphosphino)ferrocene]palladium(II) (24 mg, 0.04 mmol) and 2M potassium carbonate (0.64 mL, 1.28 mmol) in dioxane (6 mL) was irradiated in a microwave under an atmosphere of argon at 140° C. for 1 h. The reaction mixture was filtered through a pad of celite, which was washed with methanol, and the filtrate was concentrated in vacuo. The crude was partioned between ethyl acetate and water and the organic layer was dried and concentrated in vacuo. Purification by column chromatography, using a gradient of ethyl acetate in heptane gave 145 mg (55%) of the desired compound, $^1$H NMR (400 MHz, DMSO-$d_6$) δ ppm 8.76 (s, 2 H), 7.23-7.35 (m, 8 H), 7.14-7.22 (m, 3 H), 6.78-6.87 (m, 2 H), 4.29-4.39 (m, 1 H), 4.04 (t, 1 H), 3.59-3.75 (m, 4 H), 3.03-3.14 (m, 1 H), 2.92-3.03 (m, 3 H), 2.52-2.57 (m, 1 H, obscured by DMSO), 1.36 (t, 3 H); MS (ESI) m/z 436[M+H$^+$].

Intermediate Example I-49

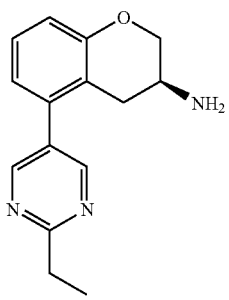

Amine 22: (3S)-5-(2-ethylpyrimidin-5-yl)chroman-3-amine

The title compound was synthesized as described for Intermediate example I-3 in 93% yield, starting from (3S)-N,N-dibenzyl-5-(2-ethylpyrimidin-5-yl)chroman-3-amine using 20 equiv of ammonium formate and 20 w % of 10% palladium on charcoal; ¹H NMR (400 MHz, CD₃OD) δ ppm 8.71 (s, 2 H), 7.22 (t, 1 H), 6.90 (dd, 1 H), 6.85 (dd, 1 H), 4.16-4.23 (m, 1 H), 3.82 (dd, 1 H), 3.13-3.24 (m, 1 H), 3.01 (q, 2 H), 2.76-2.89 (m, 1 H), 2.50 (dd, 1 H), 1.39 (t, 3 H); MS (ESI) m/z 256[M+H⁺].

Intermediate Example I-50

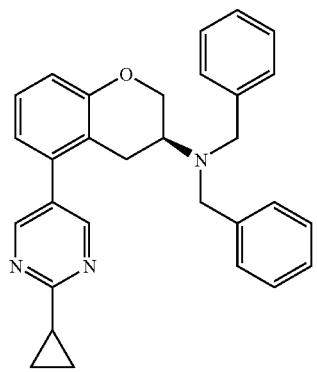

(3S)-N,N-dibenzyl-5-(2-cyclopropylpyrimidin-5-yl)chroman-3-amine

The title compound was synthesized as described for Intermediate example I-28 in 53% yield, starting from (3S)-N,N-dibenzyl-5-(4,4,5,5-tetramethyl-1,3,2-dioxaborolan-2-yl)chroman-3-amine and 5-bromo-2-cyclopropylpyrimidine (1.1 equiv); ¹H NMR (400 MHz, CDCl₃) δ ppm 8.55 (s, 2 H), 7.27-7.36 (m, 8 H), 7.13-7.26 (m, 3 H), 6.86 (dd, 1 H), 6.75 (dd, 1 H), 4.32-4.41 (m, 1 H), 4.02 (t, 1 H), 3.70 (s, 4 H), 3.14-3.25 (m, 1 H), 2.76-2.89 (m, 1 H), 2.59-2.69 (m, 1 H), 2.30-2.40 (m, 1 H), 1.22-1.28 (m, 2 H), 1.13-1.21 (m, 2 H); MS (ESI) m/z 448[M+H⁺].

Intermediate Example I-51

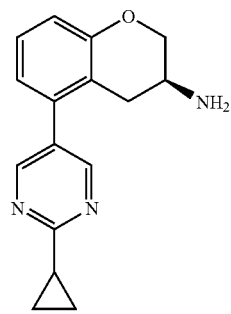

Amine 23: (3S)-5-(2-cyclopropylpyrimidin-5-yl)chroman-3-amine

In two 20 mL microwave vials, suspensions of 10% palladium on charcoal (100 mg) and ammonium formate (265 mg, 4.20 mmol) in ethanol (4 mL) was stirred for 2 min under an atmosphere of argon. (3S)-N,N-dibenzyl-5-(2-cyclopropylpyrimidin-5-yl)chroman-3-amine (235 mg, 0.525 mmol) dissolved in ethanol (6 mL) was added to each vial which were then capped. The reaction mixtures were irradiated in a microwave at 110° C. for 10 min. The crude mixtures were allowed to cool down to ambient temperature and were filtered through pads of celite which were washed with methanol. The filtrate was concentrated in vacuo and purified by column chromatography using a system of chloroform/methanol/ammonia (7M in methanol) 900/90/10. The fractions containing the product were pooled, and concentrated in vacuo together to yield the 189 mg (67%) of the desired product; ¹H NMR (400 MHz, CDCl₃) δ ppm 8.65 (s, 1 H), 8.55 (s, 1 H), 7.12-7.26 (m, 1 H), 6.89-6.98 (m, 1 H), 6.74-6.86 (m, 1 H), 4.17-4.24 (m, 1 H), 3.79-3.92 (m, 1 H), 3.30-3.38 (m, 1 H), 2.97-3.03 (m, 1 H), 2.83-2.93 (m, 1 H), 2.39-2.51 (m, 1 H), 2.25-2.36 (m, 1 H), 1.85-1.97 (m, 1 H), 1.10-1.22 (m, 1 H), 1.05 (t, 1 H); MS (ESI) m/z 268[M+H⁺].

Intermediate Example I-52

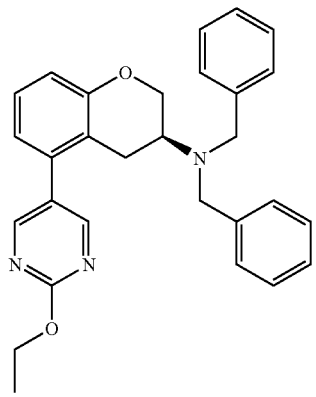

(3S)-N,N-dibenzyl-5-(2-ethoxypyrimidin-5-yl)chroman-3-amine

The title compound was synthesized as described for Intermediate example I-28 in 62% yield starting from (3S)-N,N-dibenzyl-5-(4,4,5,5-tetramethyl-1,3,2-dioxaborolan -2-yl)chroman-3-amine and 5-bromo-2-ethoxypyrimidine. The reaction mixture was irradiated in a microwave at 140° C. for 20 min; MS (ESI) m/z 452[M+H⁺].

Intermediate Example I-53

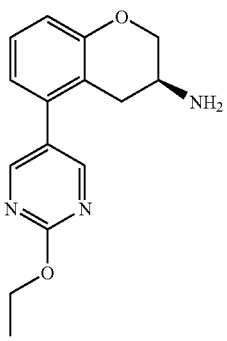

Amine 24: (3S)-5-(2-ethoxypyrimidin-5-yl)chroman-3-amine

The title compound was synthesized as described for Intermediate example I-3 in 86% yield, starting from (3S)-N,N-dibenzyl-5-(2-ethoxypyrimidin-5-yl)chroman-3-amine using 47 w % of 10% palladium on charcoal; MS (ESI) m/z 272[M+H$^+$].

Intermediate Example I-54

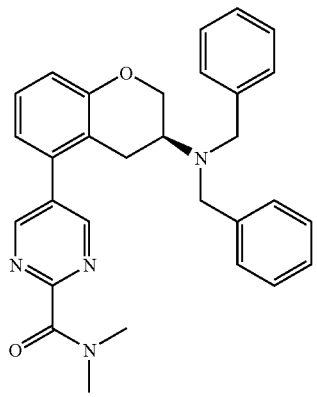

5-[(3S)-3-(dibenzylamino)-3,4-dihydro-2H-chromen-5-yl]-N,N-dimethylpyrimidine-2-carboxamide The title compound was synthesized as described for Intermediate example I-28 in 61% yield starting from (3S)-N,N-dibenzyl-5-(4,4,5,5-tetramethyl-1,3,2-dioxaborolan -2-yl)chroman-3-amine and 5-bromo-N,N-dimethylpyrimidine-2-carboxamide. The reaction mixture was irradiated in a microwave at 140° C. for 20 min; $^1$H NMR (400 MHz, DMSO-d$_6$) δ ppm 8.92 (s, 2 H), 7.23-7.34 (m, 8 H), 7.15-7.22 (m, 3 H), 6.84-6.93 (m, 2 H), 4.31-4.39 (m, 1 H), 4.05 (t, 1 H), 3.60-3.76 (m, 4 H), 3.08-3.15 (m, 1 H), 3.06 (s, 3 H), 2.94-3.05 (m, 1 H), 2.88 (s, 3 H), 2.52-2.59 (m, 1 H); MS (ESI) m/z 452[M+H$^+$].

Intermediate Example I-55

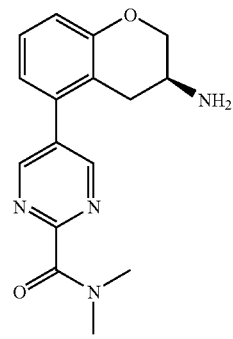

Amine 25: 5-[(3S)-3-amino-3,4-dihydro-2H-chromen-5-yl]-N,N-dimethylpyrimidine -2-carboxamide The title compound was synthesized as described for Intermediate example I-3 in 99% yield, starting from 5-[(3S)-3-(dibenzylamino)-3,4-dihydro-2H-chromen-5-yl]-N,N-dimethylpyrimidine -2-carboxamide using 15 equiv of ammonium formate and 35 w % of 10% palladium on charcoal; $^1$H NMR (400 MHz, DMSO-d$_6$) δ ppm 8.92 (s, 2 H), 7.23 (t, 1 H), 6.86-6.95 (m, 2 H), 4.08-4.16 (m, 1 H), 3.65 (dd, 1 H), 3.06-3.10 (m, 1 H), 3.04 (s, 3 H), 2.86 (s, 3 H), 2.65-2.74 (m, 1 H), 2.41-2.48 (m, 1 H); MS (ESI) m/z 272 [M+H$^+$].

Intermediate Example I-56

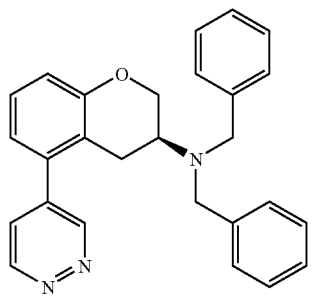

(3S)-N,N-dibenzyl-5-pyridazin-4-ylchroman-3-amine

The title compound was synthesized as described for Intermediate example I-48 in 62% yield starting from (3S)-N,N-dibenzyl-5-(4,4,5,5-tetramethyl-1,3,2-dioxaborolan -2-yl)chroman-3-amine and 4-bromopyridazine (1.2 equiv). The reaction was irradiated in microwave at 140° C. for 45 min: $^1$H NMR (400 MHz, CDCl$_3$) δ ppm 9.26 (dd, 1 H), 9.19-9.22 (m, 1 H), 7.38 (dd, 1 H), 7.26-7.34 (m, 8 H), 7.16-7.25 (m, 3 H), 6.91 (d, 1 H), 6.78 (dd, 1 H), 4.36-4.43 (m, 1 H), 4.06 (t, 1 H), 3.64-3.77 (m, 4 H), 3.15-3.25 (m, 1 H), 2.86 (dd, 1 H), 2.57 (ddd, 1 H); MS (ESI) m/z 408[M+H$^+$].

Intermediate Example I-57

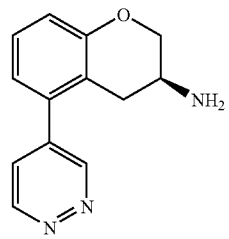

Amine 26: (3S)-5-pyridazin-4-ylchroman-3-amine

The title compound was synthesized as described for Intermediate example I-3 in 89% yield, starting from (3S)-N,N-dibenzyl-5-pyridazin-4-ylchroman-3-amine using 30 w % of 10% palladium on charcoal: $^1$H NMR (400 MHz, CD$_3$OD) δ ppm 9.14-9.27 (m, 2 H), 7.76 (dd, 1 H), 7.26 (t, 1 H), 6.93 (dd, 2 H), 4.18-4.26 (m, 1 H), 3.85 (dd, 1 H), 3.16-3.26 (m, 1 H), 2.87 (dd, 1 H), 2.55 (dd, 1 H); MS (ESI) m/z 228[M+H+].

Intermediate Example I-58

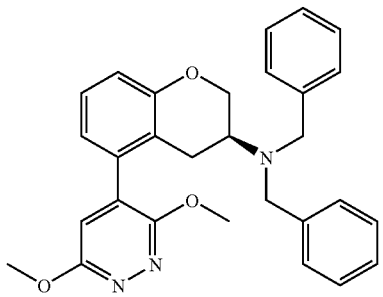

(3S)-N,N-dibenzyl-5-(3,6-dimethoxypyridazin-4-yl)chroman-3-amine

To tetrahydrofuran (2.0 mL) cooled to −20° C. a solution of n-butyllithium 2.5 M in hexane (0.644 mL, 1.61 mmol) was added via syringe. After 5 min diisopropylamine (0.227 mL, 1.61 mmol) was added and the reaction mixture was stirred for 15 min at that temperature and then cooled down to −78° C. A solution of 3,6-dimethoxypyridazine (0.098 g, 0.7 mmol) in tetrahydrofuran (2.0 mL) was added and the reaction mixture was stirred for 1 h at −78° C. Zinc chloride 1.0 M solution in diethylether (1.610 mL, 1.61 mmol) was added and the reaction mixture was allowed to warm up to ambient temperature. A solution of (3S)-3-(Dibenzylamino)-3,4-dihydro-2H-chromen-5-yl trifluoromethanesulfonate (0.368 g, 0.77 mmol) in tetrahydrofuran (2.0 mL) and tetrakis(triphenylphosphine)palladium(0) (0.032 g, 0.03 mmol) were added and the reaction mixture was heated to reflux for 16 hours. The reaction mixture was diluted with ethyl acetate and added saturated sodium bicarbonate solution. The organic layer was dried over sodium sulfate, concentrated in vacuo and purified by column chromatography using a gradient of ethyl acetate in heptane yielding 0.235 g (72%) of the desired compound as a colorless oil; $^1$H NMR (400 MHz, CDCl$_3$) δ ppm 7.25-7.36 (m, 8 H), 7.19-7.25 (m, 2 H), 7.15 (t, 1 H), 6.87 (dd, 1 H), 6.81 (s, 1 H), 6.71 (dd, 1 H), 4.34 (dd, 1 H), 4.14 (s, 3 H), 4.04-4.09 (m, 1 H), 4.03 (s, 3 H), 3.69 (s, 4 H), 3.23 (br. s., 1 H), 2.29-2.99 (m, 2 H); MS (APPI/APCI) m/z 468[M+H+].

Intermediate Example I-59

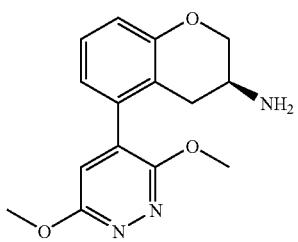

Amine 27: (3S)-5-(3,6-dimethoxypyridazin-4-yl)chroman-3-amine

The title compound was synthesized as described for Intermediate example I-3 in 86% yield, starting from (3S)-N,N-dibenzyl-5-(3,6-dimethoxypyridazin-4-yl)chroman-3-amine using 20 w % of 10% palladium on charcoal; $^1$H NMR (400 MHz, CDCl$_3$) δ ppm 7.20 (t, 1 H), 6.94 (dd, 1 H), 6.82 (s, 1 H), 6.76 (dd, 1 H), 4.16-4.22 (m, 1 H), 4.10 (s, 3 H), 4.04 (s, 3 H), 3.82-3.91 (m, 1 H), 3.35 (br. s., 1 H), 2.73 (br. s., 2 H), 2.35 (br. s., 2 H); MS (APPI/APCI) m/z 288[M+H+].

Intermediate Example I-60

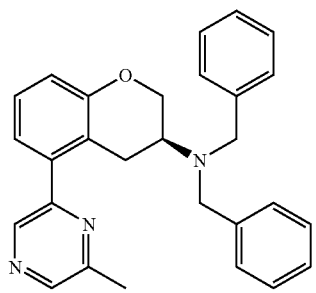

(3S)-N,N-dibenzyl-5-(6-methylpyrazin-2-yl)chroman-3-amine

The title compound was synthesized as described for Intermediate example I-28 in 83% yield starting from (S)-N,N-dibenzyl-5-(4,4,5,5-tetramethyl-1,3,2-dioxaborolan-2-yl)chroman-3-amine and 2-chloro-6-methylpyrazine (1.1 equiv); $^1$H NMR (400 MHz, DMSO-d$_6$) δ ppm 8.59 (s, 1 H), 8.54-8.56 (m, 1 H), 7.24-7.34 (m, 8 H), 7.16-7.22 (m, 3 H), 6.99 (dd, 1 H), 6.86 (dd, 1 H), 4.31-4.37 (m, 1 H), 4.07 (t, 1 H), 3.64-3.73 (m, 4 H), 3.12-3.21 (m, 1 H), 2.92-3.02 (m, 1 H), 2.64-2.73 (m, 1 H), 2.55 (s, 3 H); MS (APPI/APCI) m/z 422[M+H+].

Intermediate Example I-61

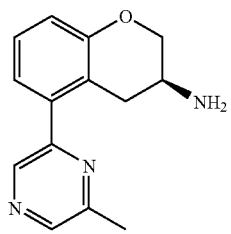

Amine 28: (3S)-5-(6-methylpyrazin-2-yl)chroman-3-amine

The title compound was synthesized as described for Intermediate example I-3 in 73% yield, starting from (3S)-N,N-dibenzyl-5-(6-methylpyrazin-2-yl)chroman-3-amine using 50 w % of 10% palladium on charcoal; $^1$H NMR (400 MHz, DMSO-d$_6$) δ ppm 8.56 (s, 1 H), 8.53 (s, 1 H), 7.20 (t, 1 H), 6.97 (dd, 1 H), 6.88 (dd, 1 H), 4.07-4.13 (m, 1 H), 3.64 (dd, 1

H), 2.98-3.09 (m, 1 H), 2.72-2.81 (m, 1 H), 2.55 (s, 3 H), 2.47-2.55 (m, 1 H, obscured by DMSO); MS (APPI/APCI) m/z 242[M+H⁺].

Intermediate Example I-62

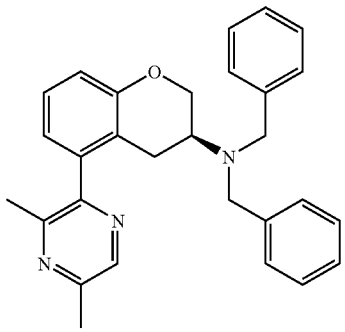

(3S)-N,N-dibenzyl-5-(3,5-dimethylpyrazin-2-yl)chroman-3-amine

The title compound was synthesized as described for Intermediate example I-28 in 72% yield starting from (S)-N,N-dibenzyl-5-(4,4,5,5-tetramethyl-1,3,2-dioxaborolan-2-yl)chroman-3-amine and 2-chloro-3,5-dimethylpyrazine (1.2 equiv); $^1$H NMR (400 MHz, DMSO-d$_6$) δ ppm 8.43 (s, 1 H), 7.24-7.31 (m, 8 H), 7.17-7.22 (m, 2 H), 7.11-7.17 (m, 1 H), 6.82 (dd, 1 H), 6.74 (dd, 1 H), 4.27-4.34 (m, 1 H), 4.07 (t, 1 H), 3.56-3.67 (m, 4 H), 2.95-3.05 (m, 1 H), 2.56-2.67 (m, 1 H), 2.54 (s, 3 H), 2.28-2.40 (m, 1 H), 2.24 (s, 3 H); MS (APPI/APCI) m/z 436[M+H⁺].

Intermediate Example I-63

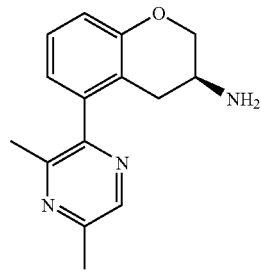

Amine 29: (3S)-5-(3,5-dimethylpyrazin-2-yl)chroman-3-amine

The title compound was synthesized as described for Intermediate example I-3 in 89% yield, starting from (3S)-N,N-dibenzyl-5-(3,5-dimethylpyrazin-2-yl)chroman-3-amine using 15 equiv of ammonium formate and 30 w % of 10% palladium on charcoal; MS (ESI) m/z 256[M+H⁺].

Intermediate Example I-64

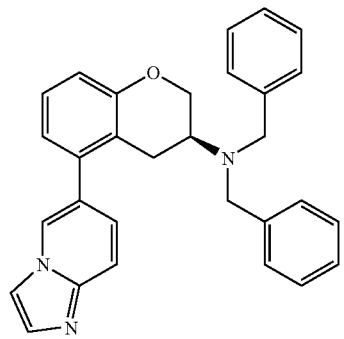

(3S)-N,N-dibenzyl-5-imidazo[1,2-a]pyridin-6-yl-chroman-3-amine

The title compound was synthesized as described for Intermediate example I-2 in 76% yield, starting from of imidazo[1,2-a]pyridine-6-boronic acid (1.5 equiv) and (3S3-(dibenzylamino)-3,4-dihydro-2H-chromen-5-yl trifluoromethanesulfonate but run in isopropanol (10 mL), using 2M potassium carbonate as base. The reaction mixture was irradiated in microwave at 140° C. for 15 min: $^1$H NMR (400 MHz, DMSO-d$_6$) δ ppm 8.51 (s, 1 H), 7.96 (s, 1 H), 7.59-7.64 (m, 2 H), 7.23-7.30 (m, 9 H), 7.13-7.17 (m, 3 H), 6.80-6.85 (m, 2 H), 4.33-4.36 (m, 1 H), 4.00-4.09 (m, 1 H), 3.63-3.72 (m, 4 H), 2.99-3.02 (m, 2 H), 2.53-2.55 (m, 1 H); MS (APPI/APCI) m/z 446[M+H⁺].

Intermediate Example I-65

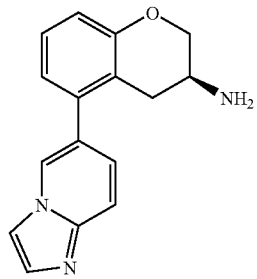

Amine 30: (3S)-5-imidazo[1,2-a]pyridin-6-ylchroman-3-amine

The title compound was synthesized as described for Intermediate example I-3 in 86% yield, starting from (3S)-N,N-dibenzyl-5-imidazo[1,2-c]pyridin-6-ylchroman-3-amine using 68 w % of 10% palladium on charcoal: $^1$H NMR (400 MHz, DMSO-d$_6$) δ ppm 8.55 (s, 1 H), 7.95 (s, 1 H), 7.59-7.61 (m, 2 H), 7.23 (dd, 1 H), 7.17 (t, 1 H), 6.82-6.87 (m, 2 H), 4.07-4.12 (m, 1 H), 3.63 (t, 1 H), 3.02-3.07 (m, 1 H), 2.71 (dd, 1 H), 2.43 (dd, 1 H); MS (APPI/APCI) m/z 266[M+H⁺].

Intermediate Example I-66

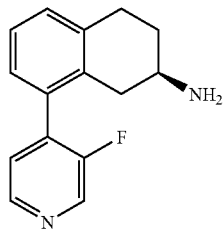

Amine 31: (2R)-8-(3-fluoropyridin-4-yl)-1,2,3,4-tetrahydronaphthalen-2-amine

The title compound was synthesized as described for Intermediate I-4 in 71% yield starting from 3-fluoropyridine-4-boronic acid and (2R)-8-bromo-1,2,3,4-tetrahydronaphthalen-2-amine using 3 equiv of 2M potassium carbonate: $^1$H NMR (400 MHz, CD$_3$OD) δ ppm 8.54 (d, 1 H), 8.47 (d, 1 H), 7.39 (dd, 1 H), 7.25-7.32 (m, 2 H), 7.05-7.14 (m, 1 H), 2.96-3.07 (m, 3 H), 2.72-2.84 (m, 1 H), 2.46-2.62 (m, 1 H), 2.12-2.22 (m, 1 H), 1.70-1.84 (m, 1 H); MS (ESI) m/z 243 [M+H$^+$].

Intermediate Example I-67

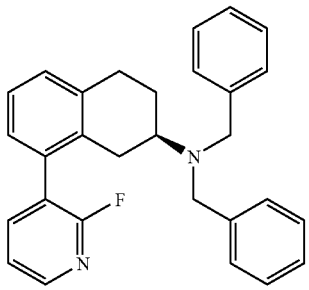

(2R)-N,N-dibenzyl-8-(2-fluoropyridin-3-yl)-1,2,3,4-tetrahydronaphthalen-2-amine

The title compound was synthesized as described for Intermediate example I-4 in 75% yield, starting from (2R)-N,N-dibenzyl-8-bromo-1,2,3,4-tetrahydronaphthalen-2-amine and 2-fluoropyridine-3-boronic acid; $^1$H NMR (400 MHz, DMSO-d$_6$) δ ppm 8.29-8.34 (m, 1 H), 7.78-7.89 (m, 1 H), 7.41-7.52 (m, 1 H), 7.21-7.30 (m, 8 H), 7.11-7.21 (m, 4 H), 7.01 (dd, 1 H), 3.51-3.61 (m, 4 H), 2.89-3.00 (m, 1 H), 2.83 (br. s., 1 H), 2.59-2.78 (m, 2 H), 2.34-2.46 (m, 1 H), 2.00-2.12 (m, 1 H), 1.64-1.79 (m, 1 H); MS (ESI) m/z 424[M+H$^+$].

Intermediate Example I-68

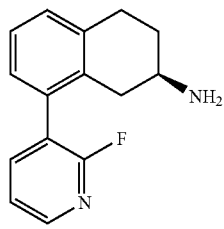

Amine 32: (2R)-8-(2-fluoropyridin-3-yl)-1,2,3,4-tetrahydronaphthalen-2-amine

The title compound was synthesized as described for Intermediate example I-3 in 91% yield, starting from (2R)-N,N-dibenzyl-8-(2-fluoropyridin-3-yl)-1,2,3,4-tetrahydronaphthalen-2-amine using 20 equiv of ammonium formate and 20 w % of 10% palladium on charcoal; $^1$H NMR (400 MHz, DMSO-d$_6$) δ ppm 8.24-8.31 (m, 1 H), 7.80-7.92 (m, 1 H), 7.41-7.52 (m, 1 H), 7.14-7.24 (m, 2 H), 6.96-7.08 (m, 1 H), 2.74-2.98 (m, 3 H), 2.42-2.57 (m, 1 H), 2.07-2.26 (m, 1 H), 1.80-1.94 (m, 1 H), 1.64 (br. s., 2 H), 1.31-1.51 (m, 1 H); MS (ESI) m/z 242[M+H$^+$].

Intermediate Example I-69

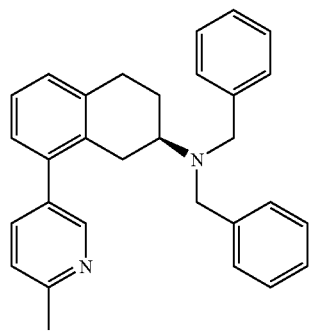

(2R)-N,N-dibenzyl-8-(6-methylpyridin-3-yl)-1,2,3,4-tetrahydronaphthalen-2-amine

The title compound was synthesized as described for Intermediate example I-48 in 63% yield starting from [(7R)-7-(dibenzylamino)-5,6,7,8-tetrahydronaphthalen-1-yl]boronic acid and 5-bromo-2-methylpyridine (1.6 equiv): $^1$H NMR (400 MHz, CDCl$_3$) δ ppm 8.45 (d, 1 H), 7.48 (dd, 1 H), 7.30-7.36 (m, 4 H), 7.23-7.29 (m, 5 H), 7.07-7.23 (m, 4 H), 7.00 (d, 1 H), 3.63 (s, 4 H), 2.90-3.04 (m, 2 H), 2.74-2.86 (m, 1 H), 2.68-2.73 (m, 2 H), 2.67 (s, 3 H), 2.11-2.19 (m, 1 H), 1.67-1.82 (m, 1 H); MS (ESI) m/z 420[M+H$^+$].

Intermediate Example I-70

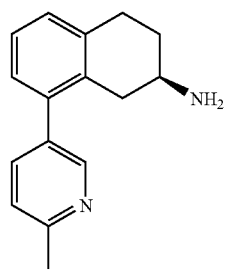

Amine 33: (2R)-8-(6-methylpyridin-3-yl)-1,2,3,4-tetrahydronaphthalen-2-amine

The title compound was synthesized as described for Intermediate example I-3 in 95% yield, starting from (2R)-N,N-dibenzyl-8-(6-methylpyridin-3-yl)-1,2,3,4-tetrahydronaphthalen-2-amine using 20 w % of 10% palladium on charcoal:

¹H NMR (400 MHz, CD₃OD) δ ppm 8.31 (d, 1 H), 7.68 (dd, 1 H), 7.37 (d, 1 H), 7.12-7.23 (m, 2 H), 7.01 (dd, 1 H), 2.86-3.06 (m, 3 H), 2.76 (dd, 1 H), 2.58 (s, 3 H), 2.42 (dd, 1 H), 1.97-2.11 (m, 1 H), 1.53-1.67 (m, 1 H); MS (ESI) m/z 239[M+H⁺].

Intermediate Example I-71

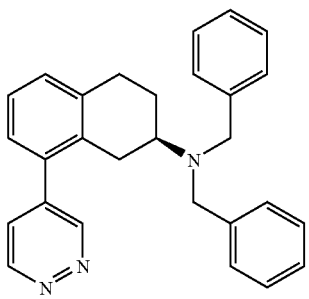

(2R)-N,N-dibenzyl-8-pyridazin-4-yl-1,2,3,4-tetrahydronaphthalen-2-amine

The title compound was synthesized as described for Intermediate example I-48 in 45% yield starting from [(7R)-7-(dibenzylamino)-5,6,7,8-tetrahydronaphthalen-1-yl]boronic acid and 4-bromopyridazine (1 equiv): ¹H NMR (400 MHz, CDCl₃) δ ppm 9.24 (dd, 1 H), 9.17 (dd, 1 H), 7.31-7.36 (m, 5 H), 7.25-7.30 (m, 4 H), 7.15-7.24 (m, 4 H), 7.00 (dd, 1 H), 3.59-3.70 (m, 4 H), 2.92-3.08 (m, 2 H), 2.69-2.89 (m, 2 H), 2.51-2.62 (m, 1 H), 2.13-2.25 (m, 1 H), 1.71-1.86 (m, 1 H); MS (ESI) m/z 406[M+H⁺].

Intermediate Example I-72

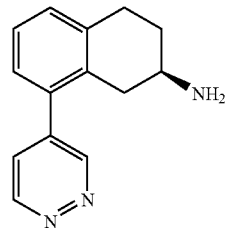

Amine 34: (2R)-8-pyridazin-4-yl-1,2,3,4-tetrahydronaphthalen-2-amine

The title compound was synthesized as described for Intermediate example I-6 in 47% yield, starting from (2R)-N,N-dibenzyl-8-pyridazin-4-yl-1,2,3,4-tetrahydronaphthalen-2-amine using 10 equiv of ammonium formate. After refluxing for 20 h, additional 10 equiv of ammonium formate and 5 w % of 10% palladium on charcoal were added: ¹H NMR (400 MHz, CD₃OD) δ ppm 9.19-9.24 (m, 2 H), 7.72 (dd, 1 H), 7.23-7.30 (m, 2 H), 7.07-7.12 (m, 1 H), 2.87-3.08 (m, 3 H), 2.73-2.80 (m, 1 H), 2.51 (dd, 1 H), 2.02-2.11 (m, 1 H), 1.55-1.70 (m, 1 H); MS (ESI) m/z 226[M+H⁺].

Intermediate Example I-73

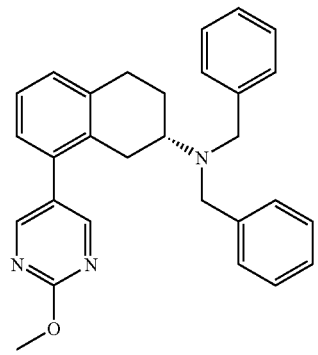

(2S)-N,N-dibenzyl-8-(2-methoxypyrimidin-5-yl)-1,2,3,4-tetrahydronaphthalen-2-amine The title compound was synthesized as described for Intermediate example I-4 in 80% yield starting from (S)-N,N-dibenzyl-8-bromo-1,2,3,4-tetrahydronaphthalen-2-amine and 2-methoxypyrimidine-5-boronic acid (1.9 equiv) and. The reaction mixture was irradiated in a microwave under an atmosphere of argon at 140° C. for 1 h; ¹H NMR (400 MHz, DMSO-d₆) δ ppm 8.59 (s, 2 H), 7.22-7.32 (m, 8 H), 7.09-7.20 (m, 4 H), 7.00-7.04 (m, 1 H), 4.00 (s, 3 H), 3.53-3.70 (m, 4 H), 2.87-3.00 (m, 2 H), 2.64-2.85 (m, 2 H), 2.45-2.54 (m, 1 H, obscured by DMSO), 2.05-2.14 (m, 1 H), 1.62-1.78 (m, 1 H); MS (ESI) m/z 436[M+H⁺].

Intermediate Example I-74

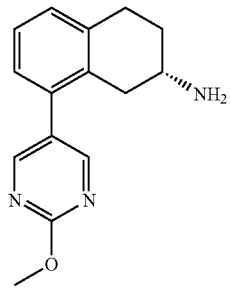

Amine 35: (2S)-8-(2-methoxypyrimidin-5-yl)-1,2,3,4-tetrahydronaphthalen-2-amine

The title compound was synthesized as described for Intermediate example I-3 in 88% yield, starting from (2S)-N,N-dibenzyl-8-(2-methoxypyrimidin-5-yl)-1,2,3,4-tetrahydronaphthalen-2-amine using 20 equiv of ammonium formate and 20 w % of 10% palladium on charcoal; ¹H NMR (400 MHz, DMSO-d₆) δ ppm 8.58 (s, 2 H), 7.12-7.24 (m, 2 H), 7.05 (dd, 1 H), 3.97 (s, 3 H), 2.87-2.97 (m, 2 H), 2.74-2.86

(m, 1 H), 2.63 (dd, 1 H), 2.34 (dd, 1 H), 1.83-1.91 (m, 1 H), 1.58 (br. s., 2 H), 1.36-1.51 (m, 1 H); MS (ESI) m/z 256[M+H⁺].

Intermediate Example I-75

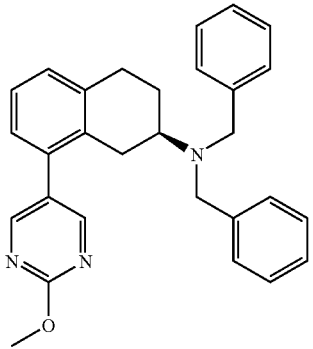

(2R)-N,N-dibenzyl-8-(2-methoxypyrimidin-5-yl)-1,2,3,4-tetrahydronaphthalen-2-amine The title compound was synthesized as described for Intermediate example I-2 in 63% yield, starting from 2-methoxypyrimidine-5-boronic acid and (2R)-N,N-dibenzyl-8-bromo-1,2,3,4-tetrahydronaphthalen-2-amine. The reaction mixture was irradiated in a microwave at 150° C. for 1 h; ¹H NMR (400 MHz, DMSO-d₆) δ ppm 8.59 (s, 2 H), 7.21-7.33 (m, 8 H), 7.08-7.21 (m, 4 H), 7.02 (dd, 1 H), 4.00 (s, 3 H), 3.53-3.70 (m, 4 H), 2.87-3.01 (m, 2 H), 2.64-2.84 (m, 2 H), 2.43-2.53 (m, 1 H, obscured by DMSO), 2.03-2.15 (m, 1 H), 1.62-1.77 (m, 1 H); MS (ESI) m/z 436[M+H⁺].

Intermediate Example I-76

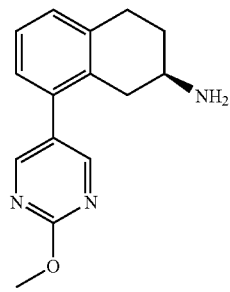

Amine 36: (2R)-8-(2-methoxypyrimidin-5-yl)-1,2,3,4-tetrahydronaphthalen-2-amine

The title compound was synthesized as described for Intermediate example I-3 in 81% yield, starting from (2R)-N,N-dibenzyl-8-(2-methoxypyrimidin-5-yl)-1,2,3,4-tetrahydronaphthalen-2-amine using 20 equiv of ammonium formate and 20 w % of 10% palladium on charcoal; ¹H NMR (400 MHz, DMSO-d₆) δ ppm 8.58 (s, 2 H), 7.12-7.22 (m, 2 H), 7.05 (dd, 1 H), 3.97 (s, 3 H), 2.86-2.96 (m, 2 H), 2.75-2.85 (m, 1 H), 2.63 (dd, 1 H), 2.34 (dd, 1 H), 1.83-1.91 (m, 1 H), 1.56 (br. s., 2 H), 1.36-1.50 (m, 1 H); MS (ESI) m/z 256[M+H⁺].

Intermediate Example I-77

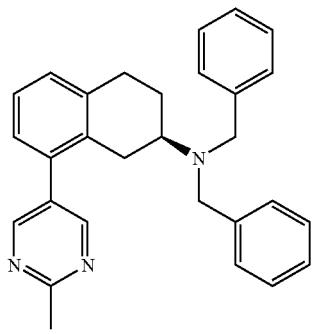

(2R)-N,N-dibenzyl-8-(2-methylpyrimidin-5-yl)-1,2,3,4-tetrahydronaphthalen-2-amine The title compound was synthesized as described for Intermediate example I-2 in 58% yield, starting from (2-methylpyrimidin-5-yl)boronic acid and (2R)-N,N-dibenzyl-8-bromo-1,2,3,4-tetrahydronaphthalen-2-amine; ¹H NMR (400 MHz, DMSO-d₆) δ ppm 8.68 (s, 2 H), 7.22-7.32 (m, 8 H), 7.11-7.21 (m, 4 H), 7.03 (dd, 1 H), 3.50-3.70 (m, 4 H), 2.88-3.02 (m, 2 H), 2.71 (s, 3 H), 2.66-2.83 (m, 2 H), 2.42-2.53 (m, 1 H, obscured by DMSO), 2.05-2.14 (m, 1 H), 1.64-1.79 (m, 1 H); MS (ESI) m/z 420[M+H⁺].

Intermediate Example I-78

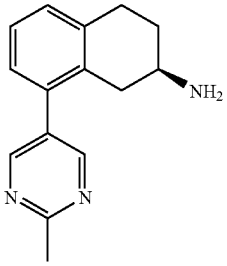

Amine 37: (2R)-8-(2-methylpyrimidin-5-yl)-1,2,3,4-tetrahydronaphthalen-2-amine

The title compound was synthesized as described for Intermediate example I-3 in 55% yield, starting (2R)-N,N-dibenzyl-8-(2-methylpyrimidin-5-yl)-1,2,3,4-tetrahydronaphthalen-2-amine using 20 equiv of ammonium formate and 20 w % of 10% palladium on charcoal; ¹H NMR (400 MHz, CD₃OD) δ ppm 8.63 (s, 2 H), 7.15-7.28 (m, 2 H), 7.03 (dd, 1 H), 2.80-3.05 (m, 3 H), 2.69-2.80 (m, 4 H), 2.45 (dd, 1 H), 1.98-2.08 (m, 1 H), 1.53-1.67 (m, 1 H); MS (ESI) m/z 240 [M+H⁺].

Intermediate Example I-79

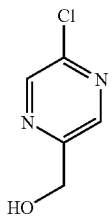

(5-chloropyrazin-2-yl)methanol

Diisobutylaluminum hydride (4.29 mL, 4.29 mmol) was added dropwise over 5 min to a solution of methyl 5-chloropyrazine-2-carboxylate (185 mg, 1.07 mmol) in tetrahydrofuran (10 mL) at −70° C. under an atmosphere of nitrogen. The reaction mixture was stirred at −70° C. for 5 min and then allowed to reach ambient temperature and stirred over night. The reaction mixture was cooled on ice and approximately 2 mL of 1 M sodium hydroxide was added dropwise while stirring. The reaction mixture was diluted with diethyl ether and stirred for 45 min at ambient temperature and then filtered. The filtrate was concentrated in vacuo and the residue was purified by column chromatography using a gradient of ethyl acetate in heptane to yield 43 mg (28%) of the title product; $^1$H NMR (400 MHz, DMSO-d$_6$) δ ppm 8.72 (d, 1 H), 8.52-8.55 (m, 1 H), 5.71 (t, 1 H), 4.64 (d, 2 H);

Intermediate Example I-80

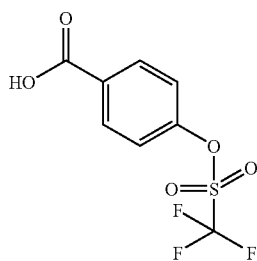

Acid 3: 4-{[(Trifluoromethyl)sulfonyl]oxy}benzoic acid

A suspension of 4-(trifluoromethanesulfonyloxy)benzaldehyde (5.2 g, 20.5 mmol, described in *JACS*, 1987, 109, 5478) and potassium dichromate (2.5 g) in sulfuric acid (30%, 47 mL) was heated at 65° C. for 1 h. The mixture was allowed to cool to ambient temperature and then poured on ice. The formed precipitate was filtered off and washed with several portions of water. The crude product was recrystallized from water/ethanol (1:1) affording 2.63 g (47% yield) of the title compound: mp 178-180° C.; $^1$H NMR (400 MHz, DMSO-d$_6$) δ 8.11 (d, 2 H), 7.64 (d, 2 H).

Intermediate Example I-81

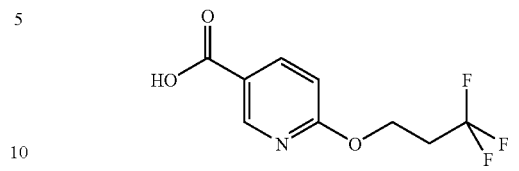

Acid 5: 6-(3,3,3-trifluoropropoxy)nicotinic acid

To a solution of potassium tert-butoxide (0.864 g, 7.7 mmol) in tetrahydrofuran (10 mL) 3,3,3-trifluoropropan-1-ol (0.878 g, 7.7 mmol) was added at 0° C. After 5 min 6-chloronicotinate (1.3 g, 7.0 mmol) was added to the stirred solution. The mixture was allowed to reach ambient temperature and stirred for additional 2 h. Brine was added and the mixture was extracted with ethyl acetate. The organic phase was dried over anhydrous sodium sulphate, filtered and concentrated in vacuo. The residue as a yellow oil (1.26 g, 4.8 mmol) was dissolved in a mixture of tetrahydrofuran (4 mL) and water (1 mL) and treated with lithium hydroxide (0.126 g, 3.0 mmol). The mixture was stirred at ambient temperature for 16 h then the tetrahydrofuran was removed in vacuo. The residue was diluted by water (5 mL) and the pH was adjusted to 2 by 4M hydrochloric acid. The resulting precipitate was collected by filtration, washed with water and dried in vacuo affording the title product as a white solid (0.913 g, 81%). $^1$H NMR (400 MHz, DMSO-d$_6$) δ ppm 8.72 (d, 1 H), 8.16 (dd, 1 H), 6.91 (d, 1 H), 4.56 (t, 2 H), 2.81 (dd, 2 H); MS (ESI) m/z 236[M+H$^+$].

Intermediate Example I-82

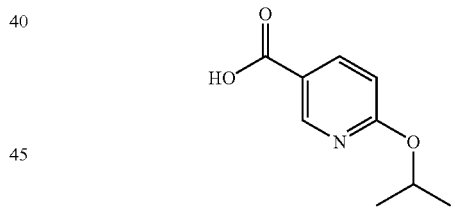

Acid 6: 6-isopropoxynicotinic acid

To a solution of potassium tert-butoxide (0.891 g, 7.94 mmol) in tetrahydrofuran (40 mL) at 0° C. was isopropanol (0.608 mL, 7.94 mmol) added. 6-chloronicotinonitrile (1.0 g, 7.22 mmol) was added after stirring for 5 min and the reaction mixture was allowed to reach ambient temperature. The reaction mixture was concentrated in vacuo, water (50 mL) was added and the resulting mixture extracted with ethyl acetate (3×50 mL). The crude was suspended in 4M sodium hydroxide (30 mL) and heated to reflux over night. The reaction mixture was concentrated in vacuo and 1M hydrochloric acid was added until an acidic pH was reached. The formed precipitate was collected by filtration and washed with water to yield 1.140 g (85%) of the title compound; $^1$H NMR (400 MHz, DMSO-d$_6$) δ ppm 12.99 (s, 1 H), 8.70 (d, 1 H), 8.10 (dd, 1 H), 6.82 (d, 1 H), 5.21-5.40 (m, 1 H), 1.31 (d, 6 H); MS (ESI) m/z 182[M+H$^+$].

Intermediate Example I-83

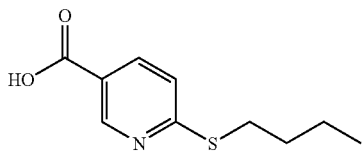

6-(Butylthio)nicotinic acid

A suspension of buthanethiol (150 mg, 1.68 mmol) in 1 M sodium hydroxide (0.7 mL) was added to a solution of 6-chloronicotinic acid (265 mg, 1.68 mmol) in a 1 M sodium hydroxide (2 mL). Tetrahydrofuran (2 mL) was added, and the mixture was stirred at 60° C. overnight. Another 150 mg of buthanethiol and 2 mL of ethanol were added, and the mixture was heated at 70° C. for 24 h. The volatiles were removed and the residue was partitioned between ethyl acetate and water. 1 M solution of hydrochloric acid was added to adjust pH of the aqueous phase to 5. The organic phase was dried over magnesium sulfate and concentrated in vacuo to leave a crude product which was purified by column chromatography using a gradient of ethyl acetate in heptane affording 74 mg of the title compound (21%) as a white solid. MS (ESI) m/z 212[M+H$^+$].

Intermediate Example I-84

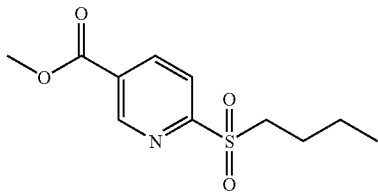

Methyl 6-(butylsulfonyl)nicotinate

A mixture of 6-(butylthio)nicotinic acid (61 mg, 0.29 mmol) and m-chloroperbenzoic acid (60%, 175 mg, 0.61 mmol) in N,N-dimethylformamide (1.5 mL) was stirred at ambient temperature over night. The solvent was removed in vacuo, the residue was dissolved in methanol. Concentrated sulfuric acid (0.15 mL) was added, and the solution was heated to reflux for 4 h. The volatiles were removed, and the residue was dissolved with diethyl ether and washed with a 1 M solution of sodium hydroxide. The organic phase was dried over magnesium sulfate and concentrated in vacuo. The crude product was purified by column chromatography using a gradient of ethyl acetate in heptane (50 to 100%) affording 36 mg (48%) of a white solid. $^1$H NMR (400 MHz, DMSO-d$_6$) δ (ppm) 9.24 (m, 1 H), 8.62 (d, 1 H), 8.20 (d, 1 H), 3.94 (s, 3 H), 3.49 (m, 2 H), 1.56 (m, 2 H), 1.36 (m, 2 H), 0.83 (t, 3 H); MS (ESI) m/z 258[M+H$^+$].

Intermediate Example I-85

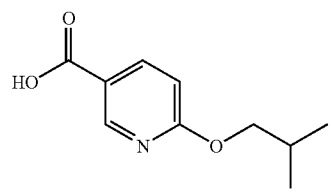

Acid 9: 6-isobutoxynicotinic acid

The title compound was synthesized as described for Intermediate example I-81 in 25% yield starting from ethyl 6-chloronicotinate and 2-methylpropan-1-ol. The reduction was performed using 3 equiv of lithium hydroxide, the reaction mixture was stirred at 35° C. over night. The product contains 58% of 6-ethoxynicotinic acid; MS (ESI) m/z 194[M–H$^+$].

Intermediate Example I-86

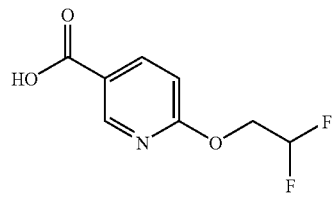

Acid 11: 6-(2,2-difluoroethoxy)nicotinic acid

The title compound was synthesized as described for Intermediate example I-81 in 79% yield starting from ethyl 6-chloronicotinate and 2,2,2-trifluoroethanol. The reduction was performed using 3 equiv of lithium hydroxide, the reaction mixture was stirred at ambient temperature over night; $^1$H NMR (400 MHz, DMSO-d$_6$) δ ppm 8.73 (d, 1 H), 8.20 (dd, 1 H), 7.02 (d, 1 H), 6.21-6.57 (m, 1 H), 4.65 (dt, 2 H); MS (ESI) m/z 202[M–H$^+$].

Intermediate Example I-87

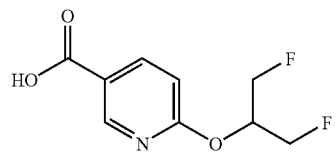

Acid 12: 6-[2-fluoro-1-(fluoromethyl)ethoxy]nicotinic acid

The title compound was synthesized as described for Intermediate example I-81 in 47% yield starting from ethyl 6-chloronicotinate and 1,3-difluoro-2-propanol. The reduction was performed using 3 equiv of lithium hydroxide, the reaction mixture was stirred at ambient temperature over night; $^1$H NMR (400 MHz, DMSO-$d_6$) δ ppm 8.71 (d, 1 H), 8.19 (dd, 1 H), 6.99 (d, 1 H), 5.62-5.80 (m, 1 H), 4.77-4.87 (m, 2 H), 4.65-4.75 (m, 2 H); MS (ESI) m/z 216[M−H$^+$].

Intermediate Example I-88

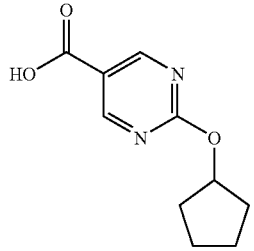

Acid 13: 2-(cyclopentyloxy)pyrimidine-5-carboxylic acid

The title compound was synthesized as described for Intermediate example I-81 in 32% yield starting from methyl 2-chloropyrimidine-5-carboxylate and cyclopentanol. The reduction was performed using 3 equiv of lithium hydroxide, the reaction mixture was stirred at ambient temperature over night; $^1$H NMR (400 MHz, DMSO-$d_6$) δ ppm 8.99 (s, 2 H), 5.38-5.48 (m, 1 H), 1.89-2.04 (m, 2 H), 1.67-1.83 (m, 4 H), 1.55-1.67 (m, 2 H); MS (ESI) m/z 207[M−H$^+$].

Intermediate Example I-89

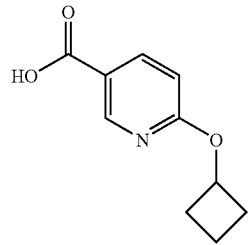

Acid 14: 6-(cyclobutyloxy)nicotinic acid

The title compound was synthesized as described for Intermediate example I-82 in 62% yield starting from 6-chloronicotinonitrile and cyclobutanol. The final acidic solution was extracted with ethyl acetate in order to collect the product; $^1$H NMR (400 MHz, DMSO-$d_6$) δ ppm 8.69 (d, 1 H), 8.14 (dd, 1 H), 6.87 (d, 1 H), 5.13-5.26 (m, 1 H), 2.37-2.47 (m, 2 H), 2.00-2.14 (m, 2 H), 1.73-1.86 (m, 1 H), 1.54-1.73 (m, 1 H); MS (ESI) m/z 192[M+H$^+$].

Intermediate Example I-90

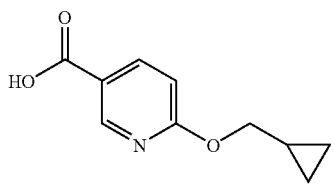

Acid 15: 6-(cyclopropylmethoxy)nicotinic acid

The title compound was synthesized as described for Intermediate example I-89 in 57% yield starting from 6-chloronicotinonitrile and cyclopropanemethanol; $^1$H NMR (400 MHz, DMSO-$d_6$) δ ppm 8.69 (d, 1 H), 8.12 (dd, 1 H), 6.89 (d, 1 H), 4.17 (d, 2 H), 1.12-1.34 (m, 1 H), 0.47-0.61 (m, 2 H), 0.27-0.38 (m, 2 H); MS (ESI) m/z 192[M+H$^+$].

Intermediate Example I-91

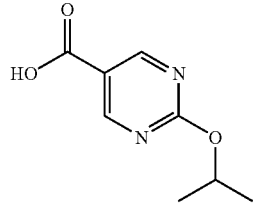

Acid 17: 2-isopropoxypyrimidine-5-carboxylic acid

The title compound was synthesized as described for Intermediate example I-81 in 14% yield starting from methyl 2-chloropyrimidine-5-carboxylate and isopropanol.

The hydrolysis was performed while heating to 75° C. for 2 h and additional 12 h at 40° C. and the product was collected by extraction of the acidic water layer with ethyl acetate. The organic layer was dried over magnesium sulfate and concentrated to give the title compound; $^1$H NMR (400 MHz, CD$_3$OD) δ ppm 9.05 (s, 2 H), 5.29-5.51 (m, 1 H), 1.41 (d, 6 H); MS (ESI) m/z 181[M−H$^+$].

Intermediate Example I-92

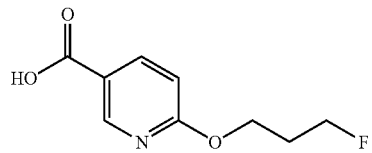

Acid 19: 6-(3-fluoropropoxy)nicotinic acid

Sodium hydride (0.220 g, 5.50 mmol) was added to a solution of 3-fluoropropan-1-ol (0.390 g, 5 mmol) in N,N-dimethylformamide (5 mL). The mixture was stirred under an atmosphere of nitrogen for 25 min and added a solution of ethyl 6-chloronicotinate (0.928 g, 5.00 mmol) in N,N-dimethylformamide (2.5 mL). The reaction mixture was stirred for 35 min and then quenched with water. The reaction mixture was extracted with ethyl acetate, the organic layer was washed with brine, dried over magnesium sulfate and evaporated in vacuo. Purification by column chromatography using a gradient of ethyl acetate in heptane yielded an oil. The crude was dissolved in 1M sodium hydroxide, (16.50 mL, 16.50 mmol) and ethanol (20 mL) and heated to 50° C. for 1.5 h. The organic solvent was removed in vacuo, and the residual aqueous solution was cooled on ice. 2 M hydrochloric acid was added until an acidic pH was reached. The obtained precipitate was filtered off, washed with ice-water, and dried in vacuo affording the title compound, 0.53 g (81%) as a white solid; $^1$H NMR (400 MHz, DMSO-$d_6$) δ ppm 8.71 (dd, 1 H), 8.14 (dd, 1 H), 6.90 (dd, 1 H), 4.65 (t, 1 H), 4.54 (t, 1 H), 4.43 (t, 2 H), 2.05-2.19 (m, 2 H); MS (APPI/APCI) m/z 228[M+H$^+$].

Intermediate Example I-93

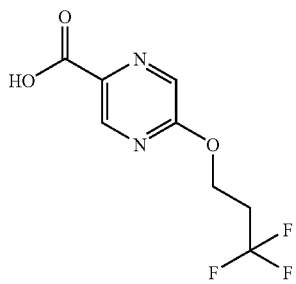

Acid 20:
5-(3,3,3-trifluoropropoxy)pyrazine-2-carboxylic acid

The title compound was synthesized as described for Intermediate example I-81 in 53% yield starting from methyl 5-chloropyrazine-2-carboxylate and 3,3,3-trifluoropropan-1-ol. 1 additional equivalent of 3,3,3-trifluoropropan-1-o deprotonated with potassium tert-butoxide was added at 0° C. after stirring 1 h at ambient temperature. Water must have been present because hydrolysis of the ester was performed without adding lithium hydroxide and water. The product was collected by extraction of the acidic water layer with ethyl acetate. The organic layer was dried over magnesium sulfate and concentrated in vacuo to give the title compound in a 74:26 mixture with 5-methoxypyrazine-2-carboxylic acid which was also formed in the reaction; $^1$H NMR (400 MHz, DMSO-$d_6$) δ ppm 8.81 (s, 1 H), 8.30-8.47 (m, 1 H), 4.62 (t, 2 H), 2.78-2.95 (m, 2 H); MS (ESI) m/z 237[M+H$^+$], m/z 235 [M−H];

Intermediate Example I-94

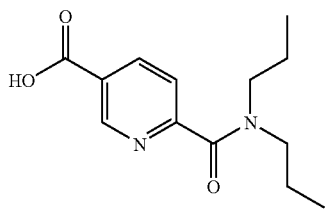

Acid 27: 6-(dipropylcarbamoyl)nicotinic acid

N,N'-carbonyldiimidazole (145 mg, 0.89 mmol) was added to a solution of 5-(methoxycarbonyl)pyridine-2-carboxylic acid (162 mg, 0.89 mmol) in N,N-dimethylformamide (2.5 mL) at 60° C. The reaction mixture was stirred at 60° C. for 10 min. Dipropylamine (90 mg, 0.89 mmol) in N,N-dimethylformamide (1 mL) was added, and the reaction mixture was stirred at ambient temperature over night. The mixture was partitioned between saturated sodium bicarbonate and ethyl acetate. The organic layer was washed with brine, dried over magnesium sulfate and concentrated in vacuo. Half the amount of the crude intermediate (83 mg, 0.31 mmol) was dissolved in ethanol (3 mL) and 1 M sodium hydroxide (3 mL, 3 mmol) and heated to 50° C. for 30 min. The solvents were removed in vacuo and the residue was dissolved in water (3 mL) and cooled on ice. A 6 M hydrochloric acid solution was added dropwise and the solvents were removed in vacuo. The residue was added acetonitrile followed by evaporation in vacuo in order to remove trace of water. The procedure was repeated twice. The material was suspended in N,N-dimethylformamide and filtered. The filtrate was concentrated in vacuo to give 80 mg (64% total yield); MS (APPI/APCI) m/z 251[M+H$^+$].

Intermediate Example I-95

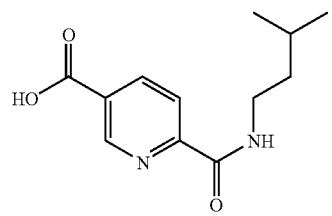

Acid 28: 6-[(3-methylbutyl)carbamoyl]nicotinic acid

The title compound was synthesized as described for Intermediate example I-94 in 58% yield starting from 5-(methoxycarbonyl)pyridine-2-carboxylic acid and 3-methylbutan-1-amine; MS (APPI/APCI) m/z 237[M+H$^+$].

Intermediate Example I-96

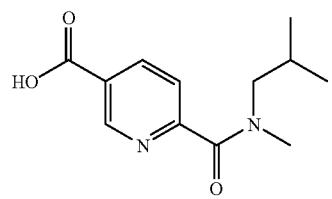

Acid 29: 6-[isobutyl(methyl)carbamoyl]nicotinic acid

The title compound was synthesized as described for Intermediate example I-94 in 75% yield starting from 5-(methoxycarbonyl)pyridine-2-carboxylic acid and n-methylisobutylamine; MS (APPI/APCI) m/z 237[M+H$^+$].

Intermediate Example I-97

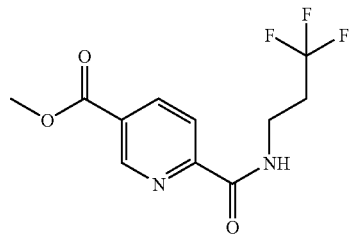

methyl 6-[(3,3,3-trifluoropropyl)carbamoyl]nicotinate 5-(methoxycarbonyl)pyridine-2-carboxylic acid (100 mg, 0.55 mmol) was dissolved in acetonitrile (1 mL). Triethylamine (0.230 mL, 1.66 mmol) and O-benzotriazol-1-yl-tetramethyluronium hexafluorophosphate (314 mg, 0.83 mmol) were added. The reaction mixture was stirred at rt for 5 min. 3,3,3-trifluoropropylamine hydrochloride (83 mg, 0.55 mmol) was added and the reaction mixture was stirred at ambient temperature for 2 h. The solvent was removed in vacuo and the crude was pardoned between ethyl acetate and 1M sodium hydroxide. The organic layer was dried over magnesium sulfate and concentrated in vacuo. The crude was purified by column chromatography using a gradient of ethyl acetate in heptane yielded 38 mg (25%) of the title compound as a white solid; $^1$H NMR (400 MHz, DMSO-d$_6$) δ ppm 9.17 (t, 1 H), 9.11 (d, 1 H), 8.48 (dd, 1 H), 8.18 (d, 1 H), 3.92 (s, 3 H), 3.53-3.60 (m, 2 H), 2.54-2.66 (m, 2 H); MS (ESI) m/z 277[M+H$^+$], m/z 275[M−H$^+$];

Intermediate Example I-98

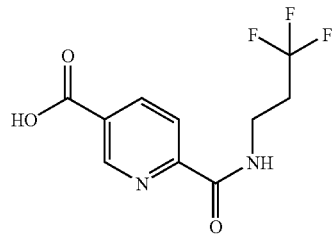

Acid 30: 6-[(3,3,3-trifluoropropyl)carbamoyl]nicotinic acid

A solution of methyl 6-[(3,3,3-trifluoropropyl)carbamoyl] nicotinate (0.265 g, 0.96 mmol), sodium hydroxide (9.60 ml, 9.60 mmol), and ethanol (10 mL) was heated to 50° C. for 3.5 h. The volatiles were removed in vacuo. The residue was suspended in water (20 mL) and insoluble material was filtered off. The filtrate was cooled on ice and 6 M hydrochloric acid was added while stirring until an acidic pH was reached. The precipitate was filtered off, washed with ice-water and dried in vacuo to yield 78 mg (31%); MS (APPI/APCI) m/z 263[M+H$^+$].

Intermediate Example I-99

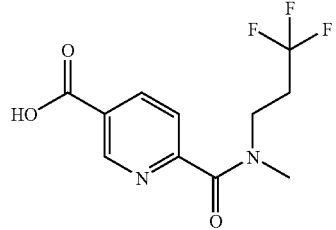

Acid 31: 6-[methyl(3,3,3-trifluoropropyl)carbamoyl] nicotinic acid

To a solution of methyl 6-[(3,3,3-trifluoropropyl)carbamoyl]nicotinate (2.4 g, 8.6 mmol) in N,N-dimethylformamide (10 mL) was added sodium hydride (60% suspension in mineral oil) (1.3 g). The reaction mixture was stirred at ambient temperature for 1 h. Methyl iodide (3.42 g, 5.0 mL, 24.1 mmol) was added and the reaction mixture was stirred overnight and then added water (20 mL). The reaction mixture was stirred for another 30 min and then extracted with ethyl acetate (2×50 mL). The aqueous layer was acidified with citric acid and the formed precipitate was filtered off and dried in vacuum oven to yield 1.12 g (47%) of the title compound; $^1$H NMR (400 MHz, CDCl$_3$) δ ppm 9.26 (d, 1 H), 8.49 (d, 1 H), 7.78-7.91 (dd, 1 H), 3.80 (t, 1 H), 3.61-3.73 (m, 1 H), 3.16 (d, 3 H), 2.46-2.76 (m, 2 H); MS (ESI) m/z 277[M+H$^+$].

Intermediate Example I-100

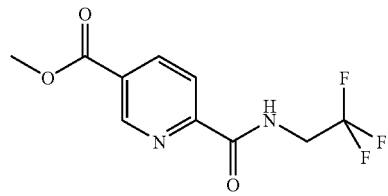

methyl 6-[(2,2,2-trifluoroethyl)carbamoyl]nicotinate 5-(methoxycarbonyl)pyridine-2-carboxylic acid (100 mg, 0.55 mmol) was dissolved in thionyl chloride (2 mL). The reaction mixture was stirred at ambient temperature for 5 min and a few drops of N,N-dimethylformamide was added. The reaction mixture was stirred at ambient temperature for 5 h. The solvent was removed in vacuo and the crude was added toluene which was evaporated again three times in order to get rid of all thionyl chloride. The crude was dissolved in dry dichloromethane (5 mL) and cooled to 0° C. A solution of 2,2,2-trifluoroethylamine (176 μL, 2.21 mmol) in dichloromethane (2 ml) and slowly added to the reaction mixture. The reaction mixture was stirred at ambient temperature overnight. The solvent was removed in vacuo and the crude was pardoned between ethyl acetate and 1M sodium hydroxide. The organic layer was washed with brine and dried over magnesium sulfate and concentrated in vacuo. Purification by column chromatography using a gradient of ethyl acetate in heptane to yield 89 mg (62%) of the title compound as a white solid; $^1$H NMR (400 MHz, DMSO-d$_6$) δ ppm 9.50 (t, 1 H), 9.14 (d, 1 H), 8.51 (dd, 1 H), 8.21 (d, 1 H), 4.03-4.16 (m, 2 H), 3.93 (s, 3 H); MS (ESI) m/z 263[M+H$^+$], m/z 261[M−H$^+$].

Intermediate Example I-101

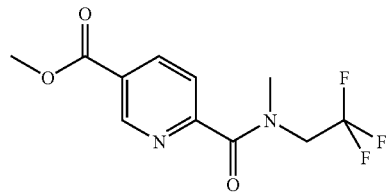

methyl 6-[methyl(2,2,2-trifluoroethyl)carbamoyl] nicotinate

To a solution of methyl 6-[(2,2,2-trifluoroethyl)carbamoyl]nicotinate (3.0 g, 11.5 mmol) in tetrahydrofuran (15 mL)

was added sodium hydride (60% suspension in mineral oil) (1.4 g) at ambient temperature. The reaction mixture was stirred for 1 h and methyl iodide (1.5 mL) was added. The reaction mixture was stirred over night and then quenched with water (20 mL). The mixture was extracted with ethyl acetate (3×50 mL) and the combined organic layer was washed with brine, dried over sodium sulfate, filtered and concentrated in vacuo to give 1.72 g (61%) of the title compound; $^1$H NMR (400 MHz, CDCl$_3$) δ ppm 8.43 (d, 1 H), 4.50 (q, 1 H), 4.23 (q, 1 H), 3.99 (s, 3 H), 3.24 (d, 3 H); MS (ESI) m/z 277[M+H$^+$].

Intermediate Example I-102

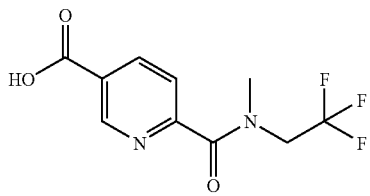

Acid 32:
6-[methyl(2,2,2-trifluoroethyl)carbamoyl]nicotinic acid

To methyl 6-(methyl(2,2,2-trifluoroethyl)carbamoyl)nicotinate (425 mg, 1.54 mmol) in tetrahydrofuran (17 mL) and water (8.5 mL) was lithium hydroxide monohydrate (193 mg, 4.60 mmol) added and the reaction mixture was stirred at ambient temperature over night. The organic solvent was evaporated, 1M hydrochloric acid added until an acidic pH was reached followed by extraction with ethyl acetate (3×25 mL). The organic layer was dried over sodium sulfate and concentrated in vacuo to yield 366 mg (91%) of the title compound as a solid; MS (APPI/APCI) m/z 263[M+H$^+$].

Intermediate Example I-103

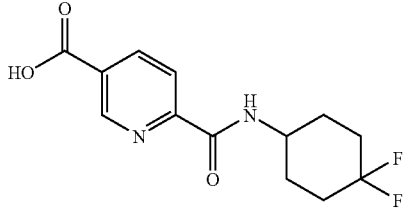

Acid 33:
6-[(4,4-difluorocyclohexyl)carbamoyl]nicotinic acid

The title compound was synthesized in two steps. The first as described for Intermediate example I-97, starting from 5-(methoxycarbonyl)pyridine-2-carboxylic acid and 4,4-difluorocyclohexylamine hydrochlorid, and the second as described for Intermediate example I-98 at 55° C., starting from the product received in the first step which was first purified by column chromatography using a gradient of ethyl acetate in heptane. Total yield (two steps) 65%; $^1$H NMR (400 MHz, DMSO-d$_6$) δ ppm 9.08 (dd, 1 H), 8.89 (d, 1 H), 8.43 (dd, 1 H), 8.13 (dd, 1 H), 3.95-4.07 (m, 1 H), 1.68-2.11 (m, 8 H); MS (ESI) m/z 285[M+H$^+$], m/z 283[M−H$^+$];

Intermediate Example I-104

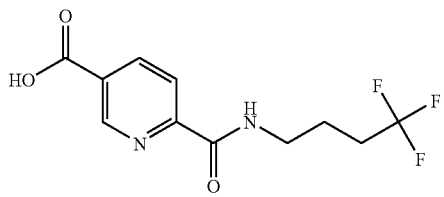

Acid 34: 6-[(4,4,4-trifluorobutyl)carbamoyl]nicotinic acid

The title compound was synthesized in two steps. The first as described for Intermediate example I-97, starting from 5-(methoxycarbonyl)pyridine-2-carboxylic acid and 4,4,4-trifluorobutan-1-amine, and the second as described for Intermediate example I-98 at 55° C., starting from the product received in the first step which was first purified by column chromatography using a gradient of ethyl acetate in heptane. Total yield (two steps) 34%; $^1$H NMR (400 MHz, DMSO-d$_6$) δ ppm 9.16 (t, 1 H), 9.09 (dd, 1 H), 8.44 (dd, 1 H), 8.14 (dd, 1 H), 3.38 (q, 2 H), 2.20-2.36 (m, 2 H), 1.71-1.81 (m, 2 H); MS (ESI) m/z 277[M+H$^+$], m/z 275[M−H$^+$];

Intermediate Example I-105

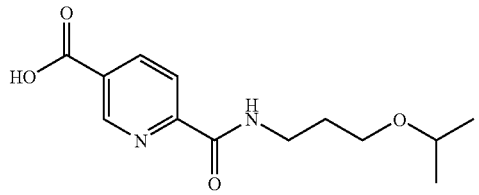

Acid 35:
6-[(3-isopropoxypropyl)carbamoyl]nicotinic acid

The title compound was synthesized in two steps. The first as described for Intermediate example I-97, starting from 5-(methoxycarbonyl)pyridine-2-carboxylic acid and 3-isopropoxypropylamine, and the second as described for Intermediate example I-98, starting from the product received in the first step which was first purified by column chromatography using a gradient of ethyl acetate in heptane. Total yield (two steps) 22%; $^1$H NMR (400 MHz, DMSO-d$_6$) δ ppm 9.06 (d, 1 H), 8.99 (t, 1 H), 8.43 (dd, 1 H), 8.13 (dd, 1 H), 3.48-3.56 (m, 1 H), 3.34-3.45 (m, 4 H, obscured by H$_2$O), 1.70-1.80 (m, 2 H), 1.09 (d, 6 H); MS (APPI/APCI) m/z 267[M+H$^+$].

Intermediate Example I-106

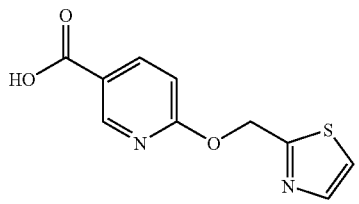

Acid 36: 6-(1,3-thiazol-2-ylmethoxy)nicotinic acid

The title compound was synthesized as described for Intermediate example I-81 in 21% yield starting from ethyl 6-chloronicotinate and 1,3-thiazol-2-ylmethanol. The deprotonation step was performed at ambient temperature and the intermediate product was purified by column chromatography using a gradient of ethyl acetate in heptane. The reduction step was carried out in sodium hydroxide:ethanol 50/50 heated to 50° C. for 1.5 h; $^1$H NMR (400 MHz, DMSO-d$_6$) δ ppm 8.74 (d, 1 H), 8.21 (dd, 1 H), 7.83 (d, 1 H), 7.76 (d, 1 H), 7.04 (d, 1 H), 5.74 (s, 2 H); MS (APPI/APCI) m/z 237[M+H$^+$].

Intermediate Example I-107

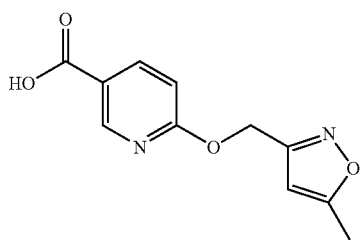

Acid 37: 6-[(5-methylisoxazol-3-yl)methoxy]nicotinic acid

The title compound was synthesized as described for Intermediate example I-106 in 10% yield starting from ethyl 6-chloronicotinate and 1,3-thiazol-2-ylmethanol; $^1$H NMR (400 MHz, DMSO-d$_6$) δ ppm 8.73 (d, 1 H), 8.18 (dd, 1 H), 6.98 (d, 1 H), 6.31 (s, 1 H), 5.45 (s, 2 H), 2.39 (s, 3 H); MS (APPI/APCI) m/z 235[M+H$^+$].

Intermediate Example I-108

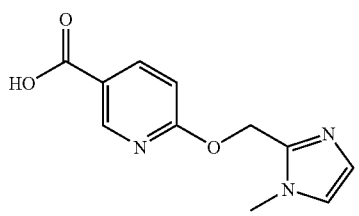

Acid 38: 6-[(1-methyl-1 H-imidazol-2-yl)methoxy]nicotinic acid

The title compound was synthesized as described for Intermediate example I-92 in 46% yield starting from ethyl 6-chloronicotinate and (1-methyl-1h-imidazol-2-yl)methanol; $^1$H NMR (400 MHz, DMSO-d$_6$) δ ppm 8.74 (d, 1 H), 8.24 (dd, 1 H), 7.58-7.74 (m, 2 H), 7.06 (d, 1 H), 5.69 (s, 2 H), 3.92 (s, 3 H); MS (APPI/APCI) m/z 234[M+H$^+$].

Intermediate Example I-109

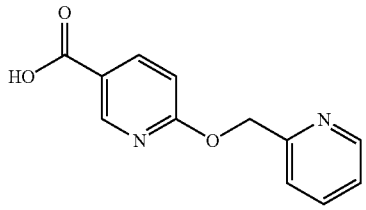

Acid 39: 6-(pyridin-2-ylmethoxy)nicotinic acid

The title compound was synthesized as described for Intermediate example I-92 in 56% yield starting from ethyl 6-chloronicotinate and (1-methyl-1h-imidazol-2-yl)methanol; $^1$H NMR (400 MHz, DMSO-d$_6$) δ ppm 8.71 (d, 1 H), 8.56 (d, 1 H), 8.19 (dd, 1 H), 7.81 (td, 1 H), 7.46 (d, 1 H), 7.34 (dd, 1 H), 7.03 (d, 1 H), 5.50 (s, 2 H).

Intermediate Example I-110

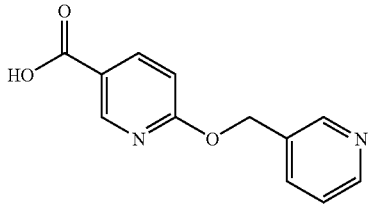

Acid 40: 6-(pyridin-3-ylmethoxy)nicotinic acid

The title compound was synthesized as described for Intermediate example I-92 in 66% yield starting from ethyl 6-chloronicotinate and pyridine-3-methanol; $^1$H NMR (400 MHz, DMSO-d$_6$) δ ppm 8.67-8.76 (m, 2 H), 8.54 (d, 1 H), 8.17 (dd, 1 H), 7.89 (d, 1 H), 7.42 (dd, 1 H), 6.98 (d, 1 H), 5.47 (s, 2 H); (APPI/APCI) m/z 231[M+H$^+$].

Intermediate Example I-111

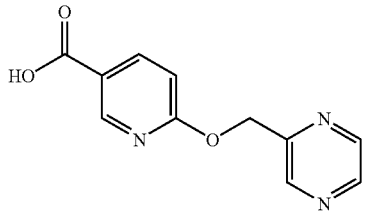

Acid 41: 6-(pyrazin-2-ylmethoxy)nicotinic acid

The title compound was synthesized as described for Intermediate example I-92 in 66% yield starting from ethyl 6-chloronicotinate and pyridine-3-methanol; ¹H NMR (400 MHz, DMSO-d₆) δ ppm 8.75-8.80 (m, 1 H), 8.70 (d, 1 H), 8.58-8.66 (m, 2 H), 8.19 (dd, 1 H), 7.04 (d, 1 H), 5.57 (s, 2 H); (APPI/APCI) m/z 232[M+H⁺].

Intermediate Example I-112

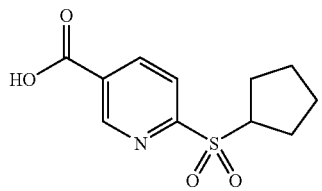

Acid 42: 6-(cyclopentylsulfonyl)nicotinic acid

Sodium hydride (0.022 g, 0.55 mmol) was added to a solution of cyclopentanethiol (0.053 mL, 0.50 mmol) in N,N-dimethylformamide (0.7 mL). The reaction mixture was stirred under an atmosphere of nitrogen for 5 min. Ethyl 6-chloronicotinate (0.093 g, 0.5 mmol) was added, and the reaction mixture was stirred at ambient temp over night. Water and ethyl acetate were added, and the organic layer was dried over magnesium sulfate and concentrated in vacuo. Purification by column chromatography using a gradient of ethyl acetate in heptane yielded a colourless oil. The crude was dissolved in N,N-dimethylformamide (1.7 mL) and added m-chloroperbenzoic acid (60%, 171 mg, 0.59 mmol. The reaction mixture was stirred at ambient temperature under nitrogen over night. The solvent was evaporated, and the residue was partitioned between 1 M sodium hydroxide and ethyl acetate. The organic layer was dried over magnesium sulfate and concentrated in vacuo. The formed intermediate was reduced to the title compound as described for Intermediate example I-97 yielding 58 mg (46%); ¹H NMR (400 MHz, DMSO-d₆) δ ppm 9.22 (d, 1 H), 8.58 (dd, 1 H), 8.18 (d, 1 H), 4.04-4.15 (m, 1 H), 1.79-1.93 (m, 4 H), 1.52-1.72 (m, 4 H); MS (APPI/APCI) m/z 256[M+H⁺].

Intermediate Example I-113

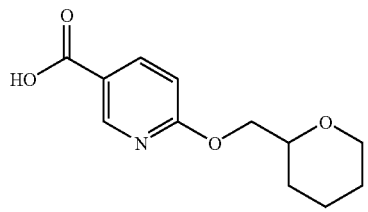

Acid 43: 6-(tetrahydro-2H-pyran-2-ylmethoxy)nicotinic acid

The title compound was synthesized as described for Intermediate example I-92 in 34% yield starting from ethyl 6-chloronicotinate and tetrahydro-2H-pyran-2-ylmethanol, the final reaction mixture was stirred for 1.5 h; ¹H NMR (400 MHz, DMSO-d₆) δ ppm 8.69 (d, 1 H), 8.13 (dd, 1 H), 4.26 (d, 2 H), 3.87 (d, 1 H), 3.58-3.68 (m, 1 H), 3.37-3.44 (m, 1 H, obscured by H₂O), 1.72-1.86 (m, 1 H), 1.62 (d, 1 H), 1.39-1.55 (m, 3 H), 1.23-1.36 (m, 1 H); MS (ESI) m/z 238 [M+H⁺].

Intermediate Example I-114

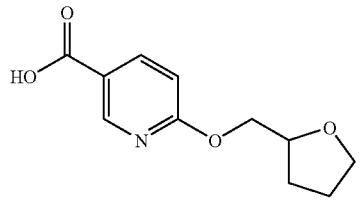

Acid 44: 6-(tetrahydrofuran-2-ylmethoxy)nicotinic acid

The title compound was synthesized as described for Intermediate example I-92 in 24% yield starting from ethyl 6-chloronicotinate and tetrahydrofuran-2-ylmethanol; ¹H NMR (400 MHz, DMSO-d₆) δ ppm 8.70 (d, 1 H), 8.14 (dd, 1 H), 6.90 (d, 1 H), 4.23-4.35 (m, 2 H), 4.10-4.21 (m, 1 H), 3.72-3.82 (m, 1 H), 3.61-3.71 (m, 1 H), 1.92-2.03 (m, 1 H), 1.74-1.93 (m, 2 H), 1.58-1.70 (m, 1 H); MS (ESI) m/z 224[M+H⁺], m/z 222[M−H⁺];

Intermediate Example I-115

Acid 45: 6-(oxetan-2-ylmethoxy)nicotinic acid

The title compound was synthesized as described for Intermediate example I-81 in 42% yield starting from ethyl 6-chloronicotinate and oxetan-2-ylmethanol. The reduction was performed using 3 equiv of lithium hydroxide while heating to 75° C. for 3.5 h. The final aqueous solution was extracted with ethyl acetate in order to collect the product; ¹H NMR (400 MHz, DMSO-d₆) δ ppm 8.71 (d, 1 H), 8.16 (dd, 1 H), 6.96 (dd, 1 H), 4.96-5.06 (m, 1 H), 4.41-4.57 (m, 4 H), 2.64-2.75 (m, 1 H), 2.46-2.56 (m, 1 H); S (ESI) m/z 210[M+H⁺], m/z 208[M−H⁺].

Intermediate Example I-116

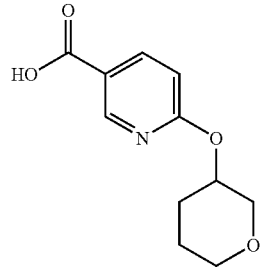

Acid 46: 6-(tetrahydro-2H-pyran-3-yloxy)nicotinic acid

The title compound was synthesized as described for Intermediate I-89 in 65% yield starting from 6-chloronicotinonitrile and tetrahydro-pyran-3-ol; $^1$H NMR (400 MHz, DMSO-d6) δ ppm 8.69 (d, 1 H), 8.13 (dd, 1 H), 6.88 (d, 1 H), 4.98-5.15 (m, 1 H), 3.84 (dd, 1 H), 3.48-3.65 (m, 3 H), 1.98-2.11 (m, 1 H), 1.70-1.86 (m, 2 H), 1.45-1.57 (m, 1 H); S (ESI) m/z 224[M+H$^+$], m/z 222[M−H$^+$].

Intermediate Example I-117

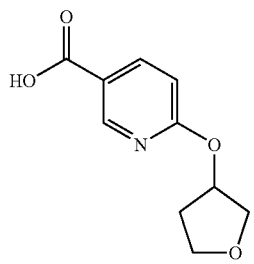

Acid 47: 6-(tetrahydrofuran-3-yloxy)nicotinic acid

The title compound was synthesized as described for Intermediate I-89 in 65% yield starting from 6-chloronicotinonitrile and 3-hydroxytetrahydrofuran; $^1$H NMR (400 MHz, DMSO-d6) δ ppm 8.70 (d, 1 H), 8.14 (dd, 1 H), 6.90 (d, 1 H), 5.52-5.61 (m, 1 H), 3.72-3.96 (m, 4 H), 2.17-2.32 (m, 1 H), 1.92-2.08 (m, 1 H) MS (ESI) m/z 210[M+H$^+$], m/z 208[M−H$^+$].

Intermediate Example I-118

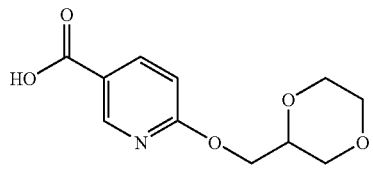

Acid 48: 6-(1,4-dioxan-2-ylmethoxy)nicotinic acid

The title compound was synthesized as described for Intermediate example I-81 in 58% yield starting from ethyl 6-chloronicotinate and 1,4-dioxan-2-ylmethanol. The reduction was performed using 3 equiv of lithium hydroxide. The final aqueous solution was extracted with ethyl acetate in order to collect the product; $^1$H NMR (400 MHz, DMSO-d6) δ ppm 8.70 (d, 1 H), 8.14 (dd, 1 H), 6.93 (d, 1 H), 4.28-4.32 (m, 2 H), 3.84-3.92 (m, 1 H), 3.72-3.83 (m, 2 H), 3.56-3.69 (m, 2 H), 3.44-3.55 (m, 1 H), 3.35-3.42 (m, 1 H); S (ESI) m/z 240[M+H$^+$], m/z 238[M−H$^+$];

Intermediate Example I-119

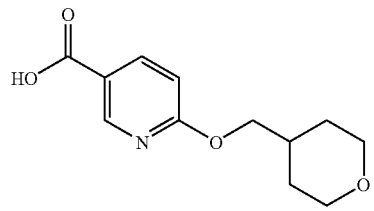

Acid 49: 6-(tetrahydro-2H-pyran-4-ylmethoxy)nicotinic acid

The title compound was synthesized as described for Intermediate example I-92 in 60% yield starting from ethyl 6-chloronicotinate and tetrahydro-2H-pyran-4-ylmethanol; $^1$H NMR (400 MHz, DMSO-d6) δ ppm 8.70 (d, 1 H), 8.13 (dd, 1 H), 6.89 (d, 1 H), 4.19 (d, 2 H), 3.86 (dd, 2 H), 3.09-3.50 (m, 2 H, obscured by H$_2$O), 1.95-2.10 (m, 1 H), 1.59-1.70 (m, 2 H), 1.25-1.40 (m, 2 H); MS (ESI) m/z 236[M−H$^+$].

Intermediate Example I-120

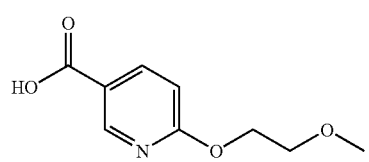

Acid 50: 6-(2-methoxyethoxy)nicotinic acid

The title compound was synthesized as described for Intermediate example I-81 in 67% yield starting from ethyl 6-chloronicotinate and 2-methoxyethanol. The reduction was performed using 3 equiv of lithium hydroxide while heating to 40° C. over weekend. The final aqueous solution was extracted with ethyl acetate in order to collect the product; $^1$H NMR (400 MHz, DMSO-d6) δ ppm 8.70 (d, 1 H), 8.13 (dd, 1 H), 6.91 (d, 1 H), 4.42-4.47 (m, 2 H), 3.62-3.68 (m, 2 H), 3.29 (s, 3 H); MS (ESI) m/z 198[M+H$^+$].

Intermediate Example I-121

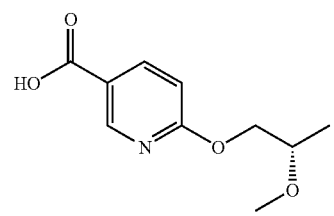

Acid 51: 6-{[(2S)-2-methoxypropyl]oxy}nicotinic acid

The title compound was synthesized as described for Intermediate example I-81 in 67% yield starting from ethyl 6-chloronicotinate and (s)-(+)-2-methoxypropanol. The reduction was performed using 3 equiv of lithium hydroxide while heating to 75° C. for 3 h. The final aqueous solution was extracted with ethyl acetate in order to collect the product; $^1$H NMR (400 MHz, CD$_3$OD) δ ppm 8.77 (d, 1 H), 8.21 (dd, 1 H), 6.87 (d, 1 H), 4.27-4.40 (m, 2 H), 3.69-3.81 (m, 1 H), 3.42 (s, 3 H), 1.24 (d, 3 H); MS (ESI) m/z 212[M+H$^+$], m/z 210 [M−H$^+$].

Intermediate Example I-122

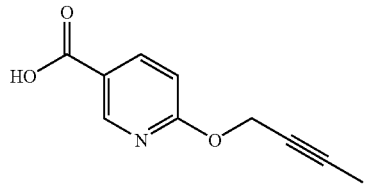

Acid 52: 6-(but-2-yn-1-yloxy)nicotinic acid

The title compound was synthesized as described for Intermediate example I-92 in 38% yield starting from ethyl 6-chloronicotinate and 2-butyn-1-ol; $^1$H NMR (400 MHz, DMSO-d$_6$) δ ppm 8.61-8.76 (m, 1 H), 8.03-8.23 (m, 1 H), 6.83-6.98 (m, 1 H), 4.94-5.05 (m, 2 H), 1.74-1.91 (m, 3 H); MS (ESI) m/z 192[M+H$^+$], m/z 190[M−H$^+$].

Intermediate Example I-123

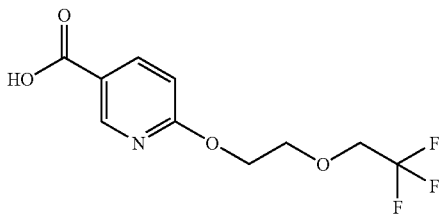

Acid 54: 6-[2-(2,2,2-trifluoroethoxy)ethoxy]nicotinic acid

The title compound was synthesized as described for Intermediate example I-92 in 71% yield starting from ethyl 6-chloronicotinate and 2-(2,2,2-trifluoroethoxy)ethanol. The reaction between sodium hydride and 2-(2,2,2-trifluoroethoxy)ethanol was performed at 0° C. for 3 min, then ambient temperature for 15 min and then cooled to 0° C. before ethyl 6-s chloronicotinate was added; $^1$H NMR (400 MHz, DMSO-d$_6$) δ ppm 8.71 (d, 1 H), 8.15 (dd, 1 H), 6.93 (d, 1 H), 4.42-4.52 (m, 2 H), 4.14 (q, 2 H), 3.92-3.97 (m, 2 H); MS (APPI/APCI) m/z 266[M+H$^+$].

Intermediate Example I-124

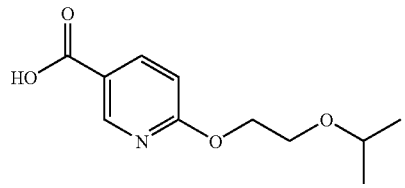

Acid 55: 6-(2-isopropoxyethoxy)nicotinic acid

The title compound was synthesized as described for Intermediate example I-92 in 51% yield starting from ethyl 6-chloronicotinate and 2-isopropoxyethanol; $^1$H NMR (400 MHz, DMSO-d$_6$) δ ppm 8.70 (dd, 1 H), 8.13 (dd, 1 H), 6.91 (dd, 1 H), 4.39-4.43 (m, 2 H), 3.67-3.71 (m, 2 H), 3.55-3.65 (m, 1 H), 1.09 (d, 6 H); MS (APPI/APCI) m/z 226[M+H$^+$].

Intermediate Example I-125

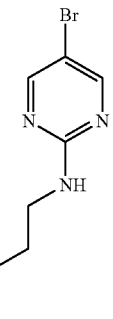

5-bromo-N-(3,3,3-trifluoropropyl)pyrimidin-2-amine

Sodium hydride (560 mg, 14.0 mmol) was added in portions to a solution of 3,3,3-trifluoro-propylamine (1.59 g, 14.0 mmol) in dry tetrahydrofuran at ambient temperature. The reaction mixture was stirred for 30 min and a solution of 5-bromo-2-iodopyrimidine (2.0 g, 7.0 mmol) in tetrahydrofuran was added. The reaction mixture was stirred for 30 min and then quenched with water (10 mL). The mixture was extracted with ethyl acetate and the organic layer was washed with brine, dried over sodium sulfate and concentrated in vacuo. The crude residue was purified by column chromatography using a gradient of ethyl acetate in hexane to yield 950 mg (48%) of the title compound; $^1$H NMR (400 MHz, CDCl$_3$) δ ppm 8.30 (s, 2 H), 5.42 (br. s, 1 H), 3.64 (m, 2 H), 2.41 (m, 2 H).

Intermediate Example I-126

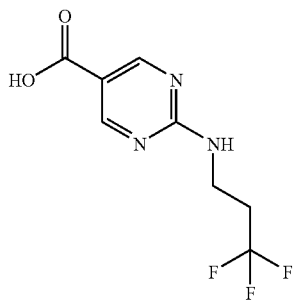

Acid 56: 2-[(3,3,3-trifluoropropyl)amino]pyrimidine-5-carboxylic acid

A solution of 5-bromo-N-(3,3,3-trifluoropropyl)pyrimidin-2-amine (500 mg, 1.8 mmol) in N,N-dimethylformamide/methanol (3:1) (6 ml) and triethylamine (1 mL, 7.2 mmol) was degassed for 1 h. Dichlorobis(triphenylphosphine)palladium(II) (0.1 equiv) was added and the reaction mixture was heated to 80° C. with carbon monoxide constantly bubbling through the mixture for 6 h. The reaction mixture was filtered through a pad of celite and the solvent was evaporated in vacuo. The crude product was purified by column chromatography using a gradient of ethyl acetate in hexane.

The intermediate product was dissolved in tetrahydrofuran/water (4:1) (8 mL), added lithium hydroxide (25.4 mg, 1 mmol) and stirred for 4 h at ambient temperature. The solvent was evaporated in vacuo and the residue redissolved in water and neutralized with citric acid. The formed precipitate was filtered off, washed with water and dried in a vacuum oven to yield 200 mg (88%); $^1$H NMR (400 MHz, DMSO-$d_6$) δ ppm 8.77 (br. s., 1 H), 8.71 (br. s., 1 H), 8.14 (t, 1 H), 3.58 (q, 2 H), 2.43-2.67 (m, 2 H); MS (ESI) m/z 236[M+H$^+$].

Intermediate Example I-127

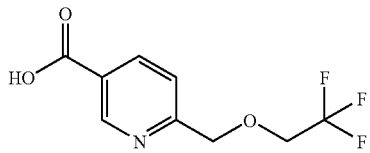

Acid 57: 6-[(2,2,2-trifluoroethoxy)methyl]nicotinic acid

To a solution of methyl 6-(hydroxymethyl)nicotinate (500 mg, 2.99 mmol) in tetrahydrofuran (30 mL) was added sodium hydride 60% dispersion in mineral oil (126 mg, 3.14 mmol) and the reaction mixture was stirred at ambient temperature for 5 min. 2,2,2-trifluoroethyl trifluoromethanesulphonate (729 mg, 3.14 mmol) was added and the reaction mixture was stirred at ambient temperature for 4 h. Additional sodium hydride (42 mg, 1.05 mmol) was added followed by 2,2,2-Trifluoroethyl trifluoromethanesulphonate (243 mg, 1.45 mmol) after 5 min. Water (20 mL) was added carefully followed by lithium hydroxide monohydrate (0.376 g, 8.97 mmol) and the formed reaction mixture was stirred at ambient temperature for 5.5 h. The solvent was partially removed in vacuo and 1M hydrochloric acid added until an acidic pH was reached. The mixture was extracted with ethyl acetate (3×25 mL) and the combined organic layer was dried over magnesium sulfate and concentrated in vacuo. Purification by column chromatography using a gradient of methanol in dichloromethane yielded 171 mg (24%) of the title compound; $^1$H NMR (400 MHz, DMSO-$d_6$) δ ppm 9.02 (dd, 1 H), 8.32 (dd, 1 H), 7.56 (dd, 1 H), 4.84 (s, 2 H), 4.26 (q, 2 H); MS (ESI) m/z 236[M+H$^+$].

Intermediate Example I-128

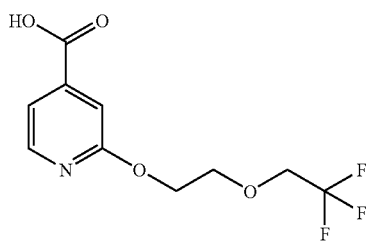

Acid 58: 2-[2-(2,2,2-trifluoroethoxy)ethoxy]isonicotinic acid

The title compound was synthesized as described for Intermediate example I-89 in 62% yield starting from 2-chloroisonicotinonitrile and 2-(2,2,2-trifluoroethoxy)ethanol; $^1$H NMR (400 MHz, CDCl$_3$) δ ppm 8.32 (dd, 1 H), 7.49 (dd, 1 H), 7.44 (s, 1 H), 4.50-4.61 (m, 2 H), 4.00-4.04 (m, 2 H), 3.97 (q, 2 H); MS (ESI) m/z 266[M+H$^+$], m/z 264[M−H$^+$].

Intermediate Example I-129

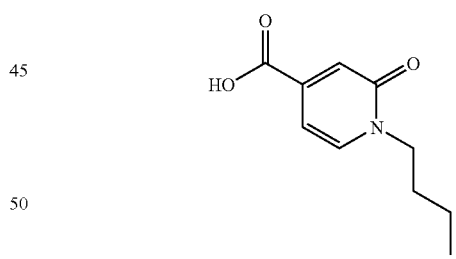

Acid 59: 1-butyl-2-oxo-1,2-dihydropyridine-4-carboxylic acid

To a solution of methyl isonicotinate (540 mg, 3.94 mmol) in dry acetone (5 mL) was added 1-iodobutane (1.35 mL, 11.8 mmol) followed by toluene (1 mL). The reaction mixture was stirred at ambient temperature for 3 h and then heated to 50° C. over night. Acetonitrile (5 ml) was added and the temperature was raised to 80° C. for 5 h. The reaction mixture was allowed to cool to ambient temperature and was stirred over the week end. The solvent was removed in vacuo and the crude was purified by column chromatography using a gradient of methanol in dichloromethane with 1% acetic acid.

615 mg of the intermediate product was dissolved in water (6 mL) and dropwise added a 10 M solution of sodium hydroxide (1.149 mL, 11.49 mmol) and a 1.25 M solution of potassium ferricyanide(III) (3.06 mL, 3.83 mmol) in hot water over 2 h. The reaction mixture was stirred at ambient temperature for 4 h. 3M hydrochloric acid was added until an acidic pH was reached. The reaction mixture was extracted with ethyl acetate and the organic layer was dried over magnesium sulfate and concentrated in vacuo to yield 235 mg (40% total yield) of the title compound as a solid; $^1$H NMR (400 MHz, DMSO-$d_6$) δ ppm 7.78 (d, 1 H), 6.82 (d, 1 H), 6.53 (dd, 1 H), 3.89 (t, 2 H), 1.52-1.65 (m, 2 H), 1.18-1.34 (m, 2 H), 0.89 (t, 3 H); MS (ESI) m/z 196[M+H$^+$], m/z 194[M−H$^+$].

Intermediate Example I-130

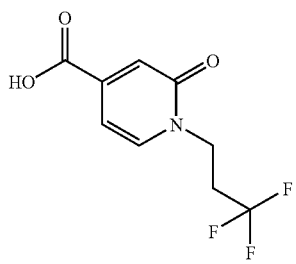

Acid 60: 2-oxo-1-(3,3,3-trifluoropropyl)-1,2-dihydropyridine-4-carboxylic acid

Methyl isonicotinate (1.02 g, 0.88 mL, 7.44 mmol) and 1,1,1-trifluoro-3-iodo-propane (5 g, 2.6 mL, 22.3 mmol) were dissolved in acetonitrile (12 mL). The reaction mixture was

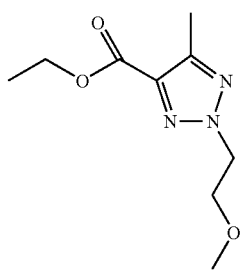

ethyl 2-(2-methoxyethyl)-5-methyl-2H-1,2,3-triazole-4-carboxylate

The title compound was synthesized as described for Intermediate example I-131 in 54% yield starting from ethyl 5-methyl-2H-1,2,3-triazole-4-carboxylate and 2-bromoethyl methyl ether; $^1$H NMR (400 MHz, CDCl$_3$) δ ppm 4.58 (t, 2 H), 4.42 (q, 2 H), 3.90 (t, 2 H), 3.35 (s, 3 H), 2.49-2.56 (m, 3 H), 1.34-1.46 (m, 3 H); MS (ESI) m/z 214[M+H$^+$].

Intermediate Example I-133

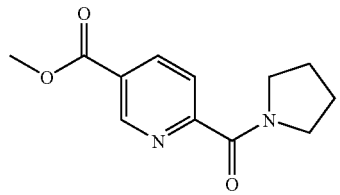

methyl 6-(pyrrolidin-1-ylcarbonyl)nicotinate

The title compound was synthesized as described for Intermediate example I-97 in 36% yield starting from 5-(methoxycarbonyl)pyridine-2-carboxylic acid and pyrrolidine. Purification by column chromatography using a gradient of ethyl acetate in heptane; $^1$H NMR (400 MHz, CD$_3$OD) δ ppm 9.15 (d, 1 H), 8.47 (dd, 1 H), 7.84 (d, 1 H), 3.97 (s, 3 H), 3.61-3.68 (m, 4 H), 1.90-2.03 (m, 4 H); MS (ESI) m/z 235 [M+H]$^+$.

Intermediate Example I-134

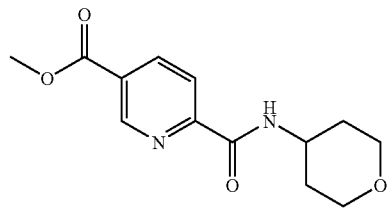

methyl 6-(tetrahydro-2H-pyran-4-ylcarbamoyl)nicotinate 5-(methoxycarbonyl)pyridine-2-carboxylic acid (100 mg, 0.55 mmol) was suspended in dry dichloromethane (3 mL) and oxalyl chloride (0.190 mL, 2.21 mmol) was added. The reaction mixture was stirred at rt for 30 min. The solvent and excess oxalyl chloride were irradiated in microwave for 10 h at 110° C. The solvent was removed in vacuo and the residue was co-evaporated with hexanes and ether several times.

A part of the intermediate product (210 mg, 0.58 mmol) was dissolved in water (1 mL). Sodium hydroxide (139 mg, 3.49 mmol) in water (1 mL) and potassium ferricyanide(III) (490 mg, 1.16 mmol) in water (1 mL) were added to the reaction mixture. The reaction mixture was stirred for 4 h and acidified with 6M hydrochloric acid. The mixture was extracted with ethyl acetate and the organic layer was washed with brine, dried over sodium sulfate and concentrated in vacuo. The crude was purified by column chromatography using a gradient of methanol in dichloromethane to yield 87 mg (total yield 29%); $^1$H NMR (CDCl$_3$, 400 MHz) δ ppm 7.4 (m, 2 H), 6.8 (d, 1 H), 4.2 (m, 2 H), 2.8 (m, 2 H); MS (ESI) m/z 236[M+H$^+$].

Intermediate Example I-131

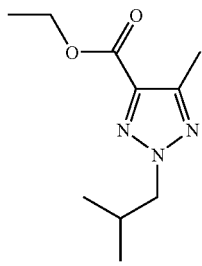

ethyl 2-isobutyl-5-methyl-2H-1,2,3-triazole-4-carboxylate

To av solution of ethyl 5-methyl-2H-1,2,3-triazole-4-carboxylate (0.5 g, 3.2 mmol) in acetonitrile (40 mL) were added 1-bromo-2-methylpropane (1.25 mL, 11.5 mmol), potassium carbonate (2.66 g, 19.2 mmol) and a catalytic amount of potassium iodide. The reaction mixture was heated to 60° C. for 22 h. The reaction mixture was allowed to cool to ambient temperature and was diluted with water (50 mL) and extracted with ethyl acetate (3×50 mL). The organic layer was dried over sodium sulfate and concentrated in vacuo to yield 293 mg (43%) of the title compound; MS (APPI/APCI) m/z 212[M+H$^+$].

Intermediate Example I-132 evaporated in vacuo and the crude was suspended in dry dichloromethane (3 mL) and added tetrahydro-2H-pyran-4-amine (112 mg, 1.10 mmol). The reaction mixture was stirred at ambient temperature for 30 min. The solvent was evaporated in vacuo and the crude was partioned between ethyl acetate and 1M sodium hydroxide. The organic layer was dried over magnesium sulfate and concentrated in vacuo to yield 30 mg (21%) of the title compound as a white solid; $^1$H NMR (400 MHz, CD$_3$OD) δ ppm 9.15-9.20 (m, 1 H), 8.51 (dd, 1 H), 8.18-8.21 (m, 1 H), 4.08-4.19 (m, 1 H), 3.98-4.03 (m, 2 H), 3.98 (s, 3 H), 3.55 (td, 2 H), 1.88-1.95 (m, 2 H), 1.67-1.80 (m, 2 H); MS (ESI) m/z 265[M+H$^+$].

Biological Tests

Expression of voltage-gated sodium channel in cell lines:

Gene(s) encoding the full-length protein of the voltage-gated sodium channel of interest are cloned and expressed under a suitable promoter in a suitable cell line, as well known in the art. The so constructed stable cell lines are used in screening assays to identify suitable compounds active on voltage-gated sodium channels. Suitable screening assays are as follows.

Li$^+$ Influx Assay

The cell line expressing the voltage-gated sodium channel of interest is plated in conventional 96 or 384 well tissue plates at a suitable cell density (for example 40000 cells/well in 96 well plate, or 20000 cells/well in 384 well plate). The cells are then repeatedly washed with a suitable Na free buffer using a suitable commercially available washer (for example EL-405 washer) until all tissue culture medium is removed from the wells. A suitable Na-free buffer could have the composition (mM) Choline chloride 137, KCl 5.4, MgSO$_4$ 0.81, CaCl$_2$ 0.95, glucose 5.55 and HEPES 25 at pH 7.4, but may also have other suitable composition. After completion of all wash steps, cells are incubated in the suitable Na free buffer for 15 min. Then, the Na free buffer is removed and cells are incubated with a buffer rich in LiCl for 60 min at 37° C. The LiCl buffer is also enriched in potassium ions, causing a depolarizing stimulus to the cells. Such a buffer may have the composition (mM): LiCl 100, KCl 50, MgSO$_1$ 0.81, CaCl$_2$ 0.95, glucose 5.55 and HEPES 25 at pH 7.4, but may also have other suitable composition. To enhance signal-to-noise ratio, an effective concentration (for example 100 μM) of the voltage-gated sodium channel opener veratridine, or any other suitable voltage-gated sodium channel opener, may be added to the medium to enhance signal detection. Furthermore, and also to enhance signal-to-noise ratio, an effective concentration (for example 10 μg/ml) of suitable scorpion venom may also be added to the medium to delay channel inactivation. In order to find a modulator of the voltage-gated sodium channel of interest, the assay can be complemented with compounds from a compound library. Compounds of interest are added to the Li-rich solution, one in each well. At the end of the incubation period cells are repeatedly washed with Na free buffer until all extracellular LiCl is removed. Cell lysis is obtained through incubation of cells with triton (1%) for 15 min, or any other suitable method. The resulting cell lysate is then introduced into an atomic absorption spectrophotometer, thus quantifying the amount of Li-influx during the procedure described above.

The described assay can be run with any atomic absorption spectrophotometer using plates of 96-well format, 384-well format, or any other conventional plate format. The described assay can be applied to cell lines expressing any given one or more of the voltage-gated sodium channel alpha subunits, as well as any given combination of one of the voltage-gated alpha subunits with any one or more beta subunit.

If needed the cell line of choice can be further hyperpolarised by expression of a suitable potassium leak ion channel, for example TREK-1, either by transient co-transfection or through establishment of a stable co-transfected cell line. The successful expression of a leak K current can be verified using traditional intracellular electrophysiology, either in whole cell patch-clamp, perforated patch-clamp or conventional two-electrode voltage-clamp. A cell line of choice modified to successfully express a voltage-gated sodium channel of interest together with a suitable potassium leak ion channel transfected can then be used for screening using atomic absorptions spectrometry, as described above.

Whole-Cell Voltage Clamp Electrophysiology Assay

Electrophysiological recordings of sodium currents in cells stably expressing the voltage-gated sodium channel of interest confirms activity and provides a functional measure of the potency of compounds that specifically inhibit such channels.

Electrophysiological studies can be performed using automated patch-clamp electrophysiology platforms, like IonWorks HT, IonWorks Quattro, PatchXpress, QPatch or any other suitable platform. The cell line expressing the voltage-gated sodium channel of interest is appropriately prepared as suggested by the manufacturer of the automated patch-clamp platforms. Suitable extracellular and intracellular buffer for such experiments are applied according to the instructions given by the manufacturer of the automated patch-clamp platforms. Cells that express the voltage-gated sodium channel protein of interest are exposed to drugs through the pipetting system integrated in the platforms. A suitable voltage stimulus protocol is used to activate the voltage-gated sodium channel proteins of interest through depolarisation from a defined holding potential.

Electrophysiological studies can also be performed using the whole cell configuration of the standard patch clamp technique. In this assay, cells that express the voltage-gated sodium channel protein of interest are exposed to the drugs by conventional microperfusion systems and a suitable voltage stimulus protocol is used to activate the voltage-gated sodium channels.

EXAMPLE

Title compounds of the above Examples were tested in the Whole-cell voltage clamp electrophysiology assay described above and were found to exhibit $IC_{50}$ values as shown in the table below.

| Example no | pIC50 |
|---|---|
| 1 | 6.4 |
| 2 | 6.9 |
| 3 | 6.6 |
| 4 | 5.9 |
| 5 | 5.8 |
| 6 | 6 |
| 7 | 6.7 |
| 8 | 5.8 |
| 9 | 5.2 |
| 10 | 5.4 |
| 11 | 6.2 |
| 12 | 7.2 |
| 13 | 7.4 |
| 14 | 6.6 |
| 15 | 7.6 |
| 16 | 5.7 |
| 17 | 5.4 |
| 18 | 7 |
| 19 | 7.1 |
| 20 | 6.8 |
| 21 | 7.2 |
| 22 | 5.2 |
| 23 | 5.9 |
| 24 | 6.9 |
| 25 | 5.7 |
| 26 | 6.2 |
| 27 | 6.2 |
| 28 | 7 |
| 29 | 6.8 |
| 30 | 6.7 |
| 31 | 5.6 |
| 32 | 5 |
| 33 | 6.5 |
| 34 | 6.2 |
| 35 | 6.2 |
| 36 | 5.9 |
| 37 | 6 |
| 38 | 6.2 |
| 39 | 6.9 |
| 40 | 7.3 |
| 41 | 5.3 |
| 42 | 6 |
| 43 | 6.3 |
| 44 | 6.2 |
| 45 | 5.9 |
| 46 | 5.5 |
| 47 | 5 |
| 48 | 6.2 |
| 49 | 5.9 |
| 50 | 7.2 |
| 51 | 7.4 |
| 52 | 5.4 |
| 53 | 6.6 |
| 54 | 7.2 |
| 55 | 6.5 |
| 56 | 7.1 |
| 57 | 7.1 |
| 58 | 6.4 |
| 59 | 6.9 |
| 60 | 6.8 |
| 61 | 7.3 |
| 62 | 6.6 |
| 63 | 7.1 |
| 64 | 5 |
| 65 | 5.3 |
| 66 | 6.8 |
| 67 | 6.3 |
| 68 | 7 |
| 69 | 7.1 |
| 70 | 6 |
| 71 | 5.7 |
| 72 | 6.3 |
| 73 | 5.4 |
| 74 | 6.6 |
| 75 | 6.2 |
| 76 | 6.4 |
| 77 | 6.9 |
| 78 | 5.5 |
| 79 | 5.9 |
| 80 | 5.6 |
| 81 | 6.4 |
| 82 | 5.6 |
| 83 | 5.3 |
| 84 | 6.4 |
| 85 | 6.3 |
| 86 | 7.1 |
| 87 | 6.7 |
| 88 | 6.4 |
| 89 | 5.7 |
| 90 | 5.8 |
| 91 | 7.1 |
| 92 | 5.3 |
| 93 | 6.2 |
| 94 | 6.1 |
| 95 | 6.8 |
| 96 | 7.3 |
| 97 | 6.4 |
| 98 | 5.2 |
| 99 | 6.4 |
| 100 | 6.4 |
| 101 | 6.8 |
| 102 | 7 |
| 103 | 5 |
| 104 | 5.6 |
| 105 | 7.2 |
| 106 | 6.6 |
| 107 | 5.4 |
| 108 | 5.4 |
| 109 | 6.9 |
| 110 | 5.7 |
| 111 | 6.6 |
| 112 | 5.8 |
| 113 | 5 |
| 114 | 6 |
| 115 | 6.5 |
| 116 | 5.7 |
| 117 | 6.3 |
| 118 | 5.8 |
| 119 | 5.7 |
| 120 | 5.8 |
| 121 | 5.3 |
| 122 | 5.7 |
| 123 | 6 |
| 124 | 6.8 |
| 125 | 6.5 |
| 126 | 5.7 |
| 127 | 5.5 |
| 128 | 6 |
| 129 | 6.7 |
| 130 | 5.4 |
| 131 | 6.2 |
| 132 | 7.1 |
| 133 | 6.1 |
| 134 | 6.5 |
| 135 | 6.5 |
| 136 | 6.5 |
| 137 | 6.1 |
| 138 | 5.5 |
| 139 | 5.8 |

| Example no | pIC50 |
|---|---|
| 140 | 6.2 |
| 141 | 5.4 |
| 142 | 5.5 |
| 143 | 5.8 |
| 144 | 5.5 |
| 145 | 6.7 |
| 146 | 5.1 |
| 147 | 5.8 |
| 148 | 6.1 |
| 149 | 5.2 |
| 150 | 6 |
| 151 | 6.6 |
| 152 | 5.9 |
| 153 | 6.2 |
| 154 | 5.2 |
| 155 | 5.9 |
| 156 | 5.7 |
| 157 | 6 |
| 158 | 5.4 |
| 159 | 5.2 |
| 160 | 5.5 |
| 161 | 5.1 |
| 162 | 6.3 |
| 163 | 7.4 |
| 164 | 6 |
| 165 | 6.8 |
| 166 | 6.3 |
| 167 | 6.4 |
| 168 | 5.2 |
| 169 | 6.7 |
| 170 | 6.6 |
| 171 | 6.9 |
| 172 | 6.7 |
| 173 | 5.8 |
| 174 | 6.7 |
| 175 | 5.6 |
| 176 | 6.9 |
| 177 | 7.3 |
| 178 | 7.2 |
| 179 | 6.7 |
| 180 | 6.5 |
| 181 | 6.3 |
| 182 | 7.2 |
| 183 | 6.5 |
| 184 | 6.3 |
| 185 | 6.5 |
| 186 | 5.7 |
| 187 | 5.8 |
| 188 | 6.6 |
| 189 | 7.1 |
| 190 | 5.1 |
| 191 | 6.1 |
| 192 | 6.2 |
| 193 | 6.8 |
| 194 | 6.7 |
| 195 | 6.4 |
| 196 | 6.3 |
| 197 | 6.8 |
| 198 | 6.3 |
| 199 | 6.3 |
| 200 | 6.5 |
| 201 | 6.4 |
| 202 | 6.1 |
| 203 | 6.7 |
| 204 | 5.1 |
| 205 | 5.9 |
| 206 | 5.5 |
| 207 | 5.4 |
| 208 | 5.8 |
| 209 | 5.1 |
| 210 | 7 |
| 211 | 6.7 |
| 212 | 7 |
| 213 | 6.5 |

The invention claimed is:

1. A compound of formula I or a pharmaceutically acceptable salt thereof, wherein:

formula I corresponds to:

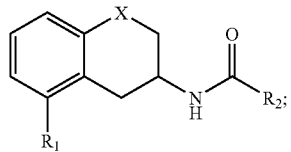

(I)

X is O or $CH_2$;

$R_1$ is pyridinyl, pyrazolyl, isoxazolyl, pyrimidinyl, pyridazinyl, imidazopyridinyl, or pyrazinyl, wherein:
any such group may be independently mono-, di-, or tri-substituted with $R_{11}$, $R_{12}$, and/or $R_{13}$;

$R_{11}$, $R_{12}$, and $R_{13}$ are independently selected from halogen, $C_{1-6}$alkyl, $C_{1-6}$alkoxy, $C_{3-6}$cycloalkyl, $C_{1-6}$hydroxyalkyl, $C_{3-6}$cycloalkyloxy, $C_{3-6}$cycloalkyl$C_{1-6}$alkoxy, cyano, hydroxy, $C_{1-6}$haloalkyl, $C_{1-6}$haloalkoxy, $C_{1-6}$haloalkoxy$C_{1-6}$alkoxy, $C_{1-6}$haloalkoxy$C_{1-6}$alkyl, $C_{1-6}$alkylsulfonic acid-, $C_{1-6}$haloalkylsulfonic acid-, $C_{3-6}$cycloalkylsulfonic acid-, $C_{3-6}$halocycloalkylsulfonic acid-, $C_{3-6}$cycloalkyl$C_{1-6}$alkylsulfonic acid-, $C_{3-6}$halocycloalkyl$C_{1-6}$alkylsulfonic acid-, $C_{1-6}$alkylsulfonyl-, $C_{1-6}$haloalkylsulfonyl-, $C_{3-6}$cycloalkylsulfonyl-, $C_{3-6}$halocycloalkylsulfonyl-, $C_{3-6}$cycloalkyl$C_{1-6}$alkylsulfonyl, $C_{3-6}$halocycloalkyl$C_{1-6}$alkyl-sulfonyl, phenyl, phenyl$C_{1-6}$alkyl-, phenoxy, $C_{1-6}$alkylphenyl-, $C_{1-6}$alkoxyphenyl-, $C_{1-6}$alkylamine, $C_{1-6}$haloalkylamine, —C(O)NHC$_{1-6}$alkyl, —C(O)N(C$_{1-6}$alkyl)$_2$, and —C(O)NH$_2$;

$R_2$ is pyrazinyl, phenyl, pyridinyl, quinoxalinyl, triazolyl, pyridonyl, naphthyridinyl, pyrimidinyl, or quinolinyl, wherein:
any such group may be independently mono-, di-, or tri-substituted with $R_{14}$, $R_{15}$, and/or $R_{16}$;

$R_{14}$, $R_{15}$, and $R_{16}$ are independently selected from halogen, $C_{1-6}$alkyl, $C_{2-6}$alkenyl, $C_{3-6}$alkynyl, $C_{1-6}$alkoxy, $C_{2-6}$alkenyloxy, $C_{3-6}$alkynyloxy, $C_{3-6}$cycloalkyl, $C_{3-6}$heterocycloalkyl, $C_{3-6}$cycloalkyloxy, $C_{3-6}$heterocycloalkyloxy, $C_{3-6}$cycloalkyl$C_{1-6}$alkoxy, $C_{1-6}$alkyl-$C_{3-6}$cycloalkyl$C_{1-6}$alkoxy, $C_{3-6}$heterocycloalkyl$C_{1-6}$alkoxy, $C_{1-6}$alkyl-$C_{3-6}$heterocycloalkyl$C_{1-6}$alkoxy, $C_{1-6}$alkoxy$C_{1-6}$alkoxy, $C_{1-6}$alkoxy$C_{1-6}$alkyl, $C_{1-6}$hydroxyalkyl, $C_{1-6}$haloalkyl, $C_{1-6}$haloalkoxy, $C_{1-6}$haloalkoxy$C_{1-6}$alkoxy, $C_{1-6}$haloalkoxy$C_{1-6}$alkyl, cyano, hydroxyl, $NR^4R^5$, $C_{1-6}$alkylsulfonic acid-, $C_{1-6}$haloalkylsulfonic acid-, $C_{3-6}$cycloalkylsulfonic acid-, $C_{3-6}$halocycloalkylsulfonic acid-, $C_{3-6}$cycloalkyl$C_{1-6}$alkylsulfonic acid-, $C_{3-6}$halocycloalkyl$C_{1-6}$alkylsulfonic acid-, $C_{1-6}$alkylsulfonyl-, $C_{1-6}$haloalkylsulfonyl-, $C_{3-6}$cycloalkylsulfonyl-, $C_{3-6}$halocycloalkylsulfonyl-, $C_{3-6}$cycloalkyl-$C_{1-6}$alkyl-sulfonyl, $C_{3-6}$halocycloalkyl-$C_{1-6}$alkyl-sulfonyl, phenyl, phenyl$C_{1-6}$alkyl-, phenoxy, $C_{1-6}$alkylphenyl-, $C_{1-6}$alkoxyphenyl-, —C(O) $NR^4R^5$, —C(O)$C_{3-6}$cycloalkyl, —C(O)$C_{3-6}$heterocycloalkyl, —C(O)$C_{3-6}$cycloalkyl$C_{1-6}$alkoxy, —C(O)$C_{3-6}$heterocycloalkyl$C_{1-6}$alkoxy, —C(O)$C_{3-6}$cycloalkyl$C_{1-6}$alkyl, and —C(O)$C_{3-6}$heterocycloalkyl$C_{1-6}$alkyl; and $R^4$ and $R^5$ are independently selected from hydrogen, $C_{1-6}$alkyl, $C_{1-6}$haloalkyl, $C_{1-6}$hydroxyalkyl, C$_{1-6}$alkoxyC$_{1-6}$alkyl, C$_{3-6}$cycloalkyl, C$_{3-6}$halocycloalkyl, C$_{3-6}$heterocycloalkyl, and C$_{3-6}$heterocycloalkylC$_{1-6}$alkyl.

2. A compound or pharmaceutically acceptable salt thereof according to claim 1, wherein:
R$_1$ is pyridinyl, pyrazolyl, isoxazolyl, pyrimidinyl, pyridazinyl, imidazopyridinyl, or pyrazinyl, wherein:
any such group may be independently mono- or di-substituted with R$_{11}$ and/or R$_{12}$;
R$_{11}$ and R$_{12}$ are independently selected from halogen, C$_{1-6}$alkyl, C$_{1-6}$alkoxy, C$_{3-6}$cycloalkyl, C$_{1-6}$hydroxyalkyl, cyano, C$_{1-6}$alkylsulfonyl-, —C(O)NHC$_{1-6}$alkyl, and —C(O)N(C$_{1-6}$alkyl)$_2$;
R$_2$ is pyrazinyl, phenyl, pyridinyl, quinoxalinyl, triazolyl, pyridonyl, naphthyridinyl, pyrimidinyl, or quinolinyl, wherein:
any such group may be independently mono- or di-substituted with R$_{14}$ and/or R$_{15}$;
R$_{14}$ and R$_{15}$ are independently selected from halogen, C$_{1-6}$alkyl, C$_{1-6}$alkoxy, C$_{3-6}$alkynyloxy, C$_{3-6}$cycloalkyloxy, C$_{3-6}$heterocycloalkyloxy, C$_{3-6}$cycloalkylC$_{1-6}$alkoxy, C$_{3-6}$heterocycloalkylC$_{1-6}$alkoxy, C$_{1-6}$alkyl-C$_{3-6}$heterocycloalkylC$_{1-6}$alkoxy, C$_{1-6}$alkoxyC$_{1-6}$alkoxy, C$_{1-6}$alkoxyC$_{1-6}$alkyl, C$_{1-6}$haloalkoxy, C$_{1-6}$haloalkoxyC$_{1-6}$alkoxy, NR$^4$R$^5$, C$_{1-6}$haloalkylsulfonic acid-, C$_{1-6}$alkylsulfonyl-, C$_{3-6}$cycloalkylsulfonyl-, phenyl, C$_{1-6}$alkoxyphenyl-, —C(O)NR$^4$R$^5$, and —C(O)C$_{3-6}$heterocycloalkyl; and
R$^4$ and R$^5$ are independently selected from hydrogen, C$_{1-6}$alkyl, C$_{1-6}$haloalkyl, C$_{1-6}$alkoxyC$_{1-6}$alkyl, C$_{3-6}$halocycloalkyl, and C$_{3-6}$heterocycloalkyl.

3. A compound or pharmaceutically acceptable salt thereof according to claim 1, wherein R$_1$ is pyridine-4-yl, pyridine-3-yl, pyridine-2-yl, pyrazole-4-yl, isoxazole-4-yl, pyrimidine-5-yl, pyridazine-4-yl, imidazo [1,2-a]pyridine-6-yl, or pyrazine-2-yl, wherein:
any such group may be independently mono-, di-, or tri-substituted with R$_{11}$, R$_{12}$, and/or R$_{13}$.

4. A compound or pharmaceutically acceptable salt thereof according to claim 1, wherein:
R$_1$ is pyridinyl, pyrazolyl, isoxazolyl, pyrimidinyl, pyridazinyl, imidazopyridinyl, or pyrazinyl, wherein:
any such group is independently mono-, di-, or tri-substituted with R$_{11}$, R$_{12}$, and/or R$_{13}$; and
R$_{11}$, R$_{12}$, and R$_{13}$ are independently selected from cyano, fluoro, iodo, chloro, bromo, methyl, ethyl, n-propyl, i-propyl, n-butyl, i-butyl, s-butyl, t-butyl, all isomeric forms of pentyl and hexyl, methoxy, ethoxy, hydroxymethyl, hydroxyethyl, hydroxypropyl, propoxy, i-propoxy, n-butoxy, t-butoxy, i-butoxy, methylsulfonyl, ethylsulfonyl, n-propylsulfonyl, i-propylsulfonyl, n-butylsulfonyl, i-butylsulfonyl, s-butylsulfonyl, t-butylsulfonyl, all isomeric forms of pentyl- and hexylsulfonyl, methylamide, dimethylamide, N-ethyl-N -methylamide, ethylamide, diethylamide, cyclopropyl, cyclobutyl, and cyclopentyl.

5. A compound or pharmaceutically acceptable salt thereof according to claim 1, wherein:
R$_1$ is pyridinyl, pyrazolyl, isoxazolyl, pyrimidinyl, pyridazinyl, imidazopyridinyl, or pyrazinyl, wherein:
any such group is independently mono- or di-substituted with R$_{11}$ and/or R$_{12}$; and
R$_{11}$ and R$_{12}$ are independently selected from cyano, fluoro, methyl, ethyl, methoxy, ethoxy, hydroxymethyl, methylsulfonyl, methylamide, dimethylamide, and cyclopropyl.

6. A compound or pharmaceutically acceptable salt thereof according to claim 1, wherein R$_2$ is pyrazine-2-yl, phenyl, pyridine-4-yl, pyridine-3-yl, quinoxaline-2-yl, 1,2,3-triazole-4-yl, 2-pyridone-4-yl, 1,8-naphthyridine-2-yl, 1,5-naphthyridine-2-yl, 1,6-naphthyridine-3-yl, pyrimidine-5-yl, or quinoline-2-yl wherein:
any such group may be independently mono-, di-, or tri-substituted with R$_{14}$, R$_{15}$, and/or R$_{16}$.

7. A compound of formula I or a pharmaceutically acceptable salt thereof, wherein:
formula I corresponds to:

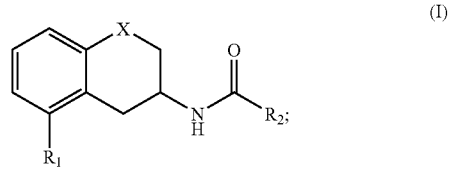

(I)

X is O or CH$_2$;
R$_1$ is pyridinyl, pyrazolyl, isoxazolyl, pyrimidinyl, pyridazinyl, imidazopyridinyl, or pyrazinyl, wherein:
any such group may be independently mono-, di-, or tri-substituted with R$_{11}$, R$_{12}$, and/or R$_{13}$;
R$_{11}$, R$_{12}$, and R$_{13}$, are independently selected from halogen, C$_{1-6}$alkyl, C$_{1-6}$alkoxy, C$_{3-6}$cycloalkyl, C$_{1-6}$hydroxyalkyl, C$_{3-6}$cycloalkloxy, C$_{3-6}$cycloalkylC$_{1-6}$alkoxy, cyano, hydroxy, C$_{1-6}$haloalkyl, C$_{1-6}$haloalkoxy, C$_{1-6}$haloalkoxy C$_{1-6}$alkoxy, C$_{1-6}$haloalkoxyC$_{1-6}$alkyl C$_{1-6}$alkylsulfonic acid-, C$_{1-6}$haloalkylsulfonic acid-, C$_{3-6}$cycloalkylsulfonic acid-, C$_{3-6}$halocycloalkylsulfonic acid- C$_{3-6}$cycloalkylC$_{1-6}$alkylsulfonic acid-, C$_{3-6}$halocycloalkylC$_{1-6}$alkylsulfonic acid- C$_{1-6}$alkylsulfonyl-, C$_{1-6}$haloalkylsulfonyl-, C$_{3-6}$cycloalkylsulfonyl-, C$_{3-6}$halocycloalkylsulfonyl-, C$_{3-6}$cycloalkylC$_{1-6}$alkylsulfonyl, C$_{3-6}$halocycloalkylC$_{1-6}$alkyl-sulfonyl, phenyl, phenylC$_{1-6}$alkyl-, phenoxy, C$_{1-6}$alkylphenyl-, C$_{1-6}$alkoxyphenyl-, C$_{1-6}$alkylamine, C$_{1-6}$haloalkylamine, —C(O)NHC$_{1-6}$alkyl, —C(O)N(C$_{1-6}$alkyl)$_2$, and —C(O)NH$_2$;

R$_2$ is pyrazinyl, phenyl, pyridinyl, quinoxalinyl, triazolyl, pyridonyl, naphthyridinyl, pyrimidinyl, or quinolinyl, wherein:
any such group is independently mono-, di-, or tri-substituted with R$_{14}$, R$_{15}$, and/or R$_{16}$; and
R$_{14}$, R$_{15}$, and R$_{16}$ are independently selected from fluoro, iodo, chloro, bromo, methyl, ethyl, n-propyl, i-propyl, n-butyl, i-butyl, s-butyl, t-butyl, all isomeric forms of pentyl and hexyl, methoxy, ethoxy, propoxy, i-propoxy, n-butoxy, t-butoxy, i-butoxy, propynyloxy, butynyloxy, pentynyloxy, methoxyethoxy, methoxypropoxy, ethoxymethoxy, ethoxyethoxy, ethoxypropoxy, propoxymethoxy, propoxyethoxy, propoxypropoxy, methoxymethyl, methoxyethyl, methoxypropyl, ethoxymethyl, ethoxyethyl, ethoxypropyl, propoxymethyl, propoxyethyl, propoxypropyl, fluoromethyl, difluoromethyl, trifluoromethyl, fluoroethyl, difluoroethyl, trifluoroethyl, fluoropropyl, difluoropropyl, trifluoropropyl, fluorobutyl, difluorobutyl, trifluorobutyl, bromopropyl, fluoromethoxy, difluoromethoxy, trifluoromethoxy, fluoroethoxy, difluoroethoxy, trifluoroethoxy, fluoropropoxy, difluoropropoxy, trifluoropropoxy, fluorobutoxy, difluorobutoxy, trifluorobutoxy, fluoropentoxy, difluoropentoxy, trifluoropentoxy, trifluoromethoxymethoxy, trifluoromethoxyethoxy, trifluoroethoxymethoxy, trifluoroethoxyethoxy, trifluoromethoxymethyl, trifluoromethoxyethyl, trifluoroethoxymethyl, trifluoroethoxyethyl, trifluoromethylamine, trifluoroethylamine, trifluoropropylamine, trifluoromethanesulfonic acid, difluoromethanesulfonic acid, fluoromethanesulfonic acid, methanesulfonyl, ethanesulfonyl, propanesulfonyl, butanesulfonyl, phenyl, cyclopropylsulfonyl, cyclobutylsulfonyl, cyclopentylsulfonyl, methylamide, ethylamide, propylamide, butylamide, pentylamide, dimethylamide, diethylamide, dipropylamide, N-methyl-N-ethylamide, N-methyl-N-propylamide, N-methyl-N-butylamide, N-methyl-N-pentylamide, N-ethyl-N-propylamide, N-ethyl-N-butylamide, N-ethyl-N-pentylamide, N-propyl-N-methylamide, N-propyl-N-ethylamide, N-propyl-N-butylamide, N-propyl-N-pentylamide, N-methoxymethylamide, N-methoxyethylamide, N-methoxypropylamide, N-methoxybutylamide, N-ethoxyethylamide, N-ethoxypropylamide, N-ethoxybutylamide, N-propoxymethylamide, N-propoxyethylamide, N-propoxypropylamide, N-propoxybutylamide, N-difluorocyclopropylamide, N-difluorocyclobutylamide, N-difluorocyclopentylamide, N-difluorocyclohexylamide, tetrahydropyranylamide, oxetanylamide, tetrahydrofuranylamide, oxepanylamide, dioxanylamide, trifluoromethylamide, trifluoroethylamide, trifluoropropylamide, trifluorobutylamide, N-trifluoromethyl-N-methylamide, N-trifluoromethyl-N-ethylamide, N-trifluoromethyl- N-propylamide, N-trifluoroethyl- N-methylamide, N-trifluoroethyl-N-ethylamide, N-trifluoroethyl- N-propylamide, N-trifluoropropyl- N-methylamide, N-trifluoropropyl-N-ethylamide, N-trifluoropropyl-N- propylamide, oxetanyl, tetrahydrofuranyl, tetrahydropyranyl, oxepanyl, dioxanyl, oxetanyloxy, tetrahydrofuranyloxy, tetrahydropyranyloxy, oxepanyloxy, dioxanyloxy, oxetanylmethoxy, tetrahydrofuranylmethoxy, tetrahydropyranylmethoxy, oxepanylmethoxy, dioxanylmethoxy, cyclopropylmethoxy, cyclopropylethoxy, cyclobutylmethoxy, cyclobutylethoxy, cyclopropyloxy, cyclopropyloxy, cyclobutyloxy, cyclopentyloxy, cyclohexyloxy, pyrrolidinyl, pyrrolidinyl-carbonyl, thiazolyl, thiazolylmethoxy, thiazolylethoxy, methyl-thiazolylmethoxy, methyl-thiazolylmethyl, isoxazolylmethoxy, isoxazolylethoxy, methyl-isoxazolylmethoxy, methyl-isoxazolylmethyl, imidazolyl, imidazolylmethoxy, imidazolylethoxy, methyl-imidazolylmethoxy, methyl-imidazolylmethyl, pyridinyl, pyridinylmethoxy, pyridinylethoxy, methyl-pyridinylmethoxy, methyl-pyridinylmethyl, pyrazinyl, pyrazinylmethoxy, pyrazinylethoxy, methylpyrazinylmethoxy, and methylpyrazinylmethyl.

8. A compound or pharmaceutically acceptable salt thereof according to claim 1, wherein:
   $R_2$ is pyrazinyl, phenyl, pyridinyl, quinoxalinyl, triazolyl, pyridonyl, naphthyridinyl, pyrimidinyl, or quinolinyl, wherein:
     any such group is independently mono- or di-substituted with $R_{14}$ and/or $R_{15}$; and
   $R_{14}$ and $R_{15}$ are independently selected from chloro, methyl, n-butyl, i-butyl, methoxy, ethoxy, i-propoxy, n-butoxy, i-butoxy, butynyloxy, methoxyethoxy, methoxypropoxy, propoxyethoxy, methoxyethyl, trifluoromethoxy, difluoroethoxy, trifluoroethoxy, fluoropropoxy, difluoropropoxy, trifluoropropoxy, trifluoroethoxyethoxy, trifluoroethoxymethyl, trifluoropropylamine, trifluoromethanesulfonic acid, butanesulfonyl, phenyl, cyclopentylsulfonyl, pentylamide, dipropylamide, N-methyl-N-butylamide, N-propoxypropylamide, N-difluorocyclohexylamide, tetrahydropyranylamide, trifluoroethylamide, trifluoropropylamide, trifluorobutylamide, N-trifluoroethyl-N-methylamide, N-trifluoropropyl- N-methylamide, tetrahydrofuranyloxy, tetrahydropyranyloxy, oxetanylmethoxy, tetrahydrofuranylmethoxy, tetrahydropyranylmethoxy, dioxanylmethoxy, cyclopropylmethoxy, cyclobutyloxy, cyclopentyloxy, pyrrolidinyl-carbonyl, thiazolylmethoxy, methyl-isoxazolylmethoxy, methyl-imidazolylmethoxy, pyridinylmethoxy, and pyrazinylmethoxy.

9. A compound or pharmaceutically acceptable salt thereof, wherein the compound is selected from:
   N-[(3S)-5-Pyridin-4-yl-3,4-dihydro-2H-chromen-3-yl]-4-(trifluoromethoxy)-benzamide;
   4-Butoxy-N-[(3S)-5-pyridin-4-yl-3,4-dihydro-2H-chromen-3-yl]benzamide;
   4-{[(2R)-8-Pyridin-4-yl-1,2,3,4-tetrahydronaphthalen-2-yl]carbamoyl}phenyl trifluoromethanesulfonate;
   N-[(3S)-5-Pyridin-3-yl-3,4-dihydro-2H-chromen-3-yl]-4-(trifluoromethoxy)-benzamide;
   N-[(3S)-5-Pyridin-2-yl-3,4-dihydro-2H-chromen-3-yl]-4-(trifluoromethoxy)-benzamide;
   N-[(2R)-8-(1-Methyl-1H-pyrazol-4-yl)-1,2,3,4-tetrahydronaphthalen-2-yl]-4-(trifluoromethoxy)-benzamide;
   4-{[(2R)-8-(1-Methyl-1H-pyrazol-4-yl)-1,2,3,4-tetrahydronaphthalen-2-yl]carbamoyl}phenyl trifluoromethanesulfonate;
   5-Methyl-N-[(2R)-8-(1-methyl-1H-pyrazol-4-yl)-1,2,3,4-tetrahydronaphthalen-2-yl]-2-phenyl-2H-1,2,3-triazole-4-carboxamide;
   N-[(2R)-8-(3,5-Dimethyl-1H-pyrazol-4-yl)-1,2,3,4-tetrahydronaphthalen-2-yl]-4-(trifluoromethoxy)-benzamide;
   N-[(2R)-8-(3,5-Dimethylisoxazol-4-yl)-1,2,3,4-tetrahydronaphthalen-2-yl]-4-(trifluoromethoxy)-benzamide;
   4-{[(2R)-8-(3,5-Dimethylisoxazol-4-yl)-1,2,3,4-tetrahydronaphthalen-2-yl]carbamoyl}phenyl trifluoromethanesulfonate;
   N-[(2R)-8-pyridin-4-yl-1,2,3,4-tetrahydronaphthalen-2-yl]-6-(2,2,2-trifluoroethoxy)nicotinamide;
   N-[(2R)-8-pyridin-4-yl-1,2,3,4-tetrahydronaphthalen-2-yl]-6-(3,3,3-trifluoropropoxy)nicotinamide;
   6-isopropoxy-N-[(2R)-8-pyridin-4-yl-1,2,3,4-tetrahydronaphthalen-2-yl]nicotin-amide;
   6-(cyclopentyloxy)-N-[(2R)-8-pyridin-4-yl-1,2,3,4-tetrahydronaphthalen-2-yl]nicotin -amide;
   2,4-dimethoxy-N-[(2R)-8-pyridin-4-yl-1,2,3,4-tetrahydronaphthalen-2-yl]-benzamide;
   5-methyl-2-phenyl-N-[(2R)-8-pyridin-4-yl-1,2,3,4-tetrahydronaphthalen-2-yl]-2H-1,2,3 -triazole-4-carboxamide;
   N-[(3S)-5-pyridin-4-yl-3,4-dihydro-2H-chromen-3-yl]-6-(2,2,2-trifluoroethoxy)nicotinamide;
   N-[(3S)-5-pyridin-4-yl-3,4-dihydro-2H-chromen-3-yl]-6-(3,3,3-trifluoropropoxy)nicotin-amide;
   6-isopropoxy-N-[(3S)-5-pyridin-4-yl-3,4-dihydro-2H-chromen-3-yl]nicotin-amide;
   6-(cyclopentyloxy)-N-[(3S)-5-pyridin-4-yl-3,4-dihydro-2H-chromen-3-yl]nicotin-amide;
   2,4-dimethoxy-N-[(3S)-5-pyridin-4-yl-3,4-dihydro-2H-chromen-3-yl]benzamide;
   5-methyl-2-phenyl-N-[(3S)-5-pyridin-4-yl-3,4-dihydro-2H-chromen-3-yl]-2H-1,2,3-triazole-4-carboxamide;

6-isobutoxy-N-[(3S)-5-pyridin-4-yl-3,4-dihydro-2H-chromen-3-yl]nicotin-amide;
6-ethoxy-N-[(3S)-5-pyridin-4-yl-3,4-dihydro-2H-chromen-3-yl]nicotin-amide;
6-(2,2-difluoroethoxy)-N-[(3S)-5-pyridin-4-yl-3,4-dihydro-2H-chromen-3-yl]nicotin-amide;
6-[2-fluoro-1-(fluoromethyl)ethoxy]-N-[(3S)-5-pyridin-4-yl-3,4-dihydro-2H-chromen-3-yl]nicotin-amide;
2-(cyclopentyloxy)-N-[(3S)-5-pyridin-4-yl-3,4-dihydro-2H-chromen-3-yl]pyrimidine-5-carboxamide;
6-(cyclobutyloxy)-N-[(3S)-5-pyridin-4-yl-3,4-dihydro-2H-chromen-3-yl]nicotin-amide;
6-(cyclopropylmethoxy)-N-[(3S)-5-pyridin-4-yl-3,4-dihydro-2H-chromen-3-yl]nicotin-amide;
N-[(2R)-8-(3,5-dimethylisoxazol-4-yl)-1,2,3,4-tetrahydronaphthalen-2-yl]-6-isopropoxy-nicotinamide;
6-(2,2-difluoroethoxy)-N-[(2R)-8-(3,5-dimethylisoxazol-4-yl)-1,2,3,4-tetrahydronaphthalen-2-yl]nicotin-amide;
2-(cyclopentyloxy)-N-[(2R)-8-(3,5-dimethylisoxazol-4-yl)-1,2,3,4-tetrahydronaphthalen-2-yl]pyrimidine-5-carboxamide;
6-(butylsulfonyl)-N-[(3S)-5-pyridin-4-yl-3,4-dihydro-2H-chromen-3-yl]nicotinamide;

10. A compound or pharmaceutically acceptable salt thereof, wherein the compound is selected from the group consisting of:
6-chloro-N-[(3S)-5-pyridin-4-yl-3,4-dihydro-2H-chromen-3-yl]nicotinamide;
2-isopropoxy-N-[(3S)-5-pyridin-4-yl-3,4-dihydro-2H-chromen-3-yl]pyrimidine-5-carboxamide;
5-methoxy-N-[(3S)-5-pyridin-4-yl-3,4-dihydro-2H-chromen-3-yl]pyrazine-2-carboxamide;
5-isopropoxy-N-[(3S)-5-pyridin-4-yl-3,4-dihydro-2H-chromen-3-yl]pyrazine-2-carboxamide;
N-[(2R)-8-(3-fluoropyridin-4-yl)-1,2,3,4-tetrahydronaphthalen-2-yl]-6-isopropoxynicotinamide;
N-[(2R)-8-(3-fluoropyridin-4-yl)-1,2,3,4-tetrahydronaphthalen-2-yl]-6-(2,2,2-trifluoroethoxy)nicotinamide;
N-[(3S)-5-pyridin-4-yl-3,4-dihydro-2H-chromen-3-yl]quinoxaline-2-carboxamide;
5-isopropoxy-N-[(3S)-5-pyridin-3-yl-3,4-dihydro-2H-chromen-3-yl]pyrazine-2-carboxamide;
N-[(3S)-5-pyridin-3-yl-3,4-dihydro-2H-chromen-3-yl]-5-(3,3,3-trifluoropropoxy)pyrazine-2-carboxamide;
5-methoxy-N-[(3S)-5-pyridin-3-yl-3,4-dihydro-2H-chromen-3-yl]pyrazine-2-carboxamide;
N-[(3S)-5-pyridin-3-yl-3,4-dihydro-2H-chromen-3-yl]-1,8-naphthyridine-2-carboxamide;
N-[(3S)-5-pyridin-3-yl-3,4-dihydro-2H-chromen-3-yl]-1,5-naphthyridine-2-carboxamide;
2-methyl-N-[(3S)-5-pyridin-3-yl-3,4-dihydro-2H-chromen-3-yl]-1,6-naphthyridine-3-carboxamide;
N-[(3S)-5-(6-methoxypyridin-3-yl)-3,4-dihydro-2H-chromen-3-yl]-5-(3,3,3-trifluoropropoxy)pyrazine-2-carboxamide;
5-methoxy-N-[(3S)-5-(6-methoxypyridin-3-yl)-3,4-dihydro-2H-chromen-3-yl]pyrazine-2-carboxamide;
6-isopropoxy-N-[(3S)-5-pyridin-3-yl-3,4-dihydro-2H-chromen-3-yl]nicotinamide;
N-[(3S)-5-pyridin-3-yl-3,4-dihydro-2H-chromen-3-yl]-6-(3,3,3-trifluoropropoxy)nicotinamide;
2-isobutyl-5-methyl-N-[(3S)-5-pyridin-3-yl-3,4-dihydro-2H-chromen-3-yl]-2H-1,2,3-triazole-4-carboxamide;
6-isopropoxy-N-[(3S)-5-pyrimidin-5-yl-3,4-dihydro-2H-chromen-3-yl]nicotinamide;
N-[(3S)-5-pyrimidin-5-yl-3,4-dihydro-2H-chromen-3-yl]-6-(3,3,3-trifluoropropoxy)nicotinamide;
6-isopropoxy-N-[(3S)-5-(2-methoxypyrimidin-5-yl)-3,4-dihydro-2H-chromen-3-yl]nicotinamide;
N-[(3S)-5-(2-methoxypyrimidin-5-yl)-3,4-dihydro-2H-chromen-3-yl]-6-(3,3,3-trifluoropropoxy)nicotinamide;
N-[(3S)-5-pyridin-3-yl-3,4-dihydro-2H-chromen-3-yl]-6-(2,2,2-trifluoroethoxy)nicotinamide;
6-isopropoxy-N-[(3S)-5-(2-methoxypyridin-4-yl)-3,4-dihydro-2H-chromen-3-yl]nicotinamide;
N-[(3S)-5-(2-methoxypyridin-4-yl)-3,4-dihydro-2H-chromen-3-yl]-6-(3,3,3-trifluoropropoxy)nicotinamide;
6-isopropoxy-N-[(3S)-5-(2-methylpyrimidin-5-yl)-3,4-dihydro-2H-chromen-3-yl]nicotinamide;
N-[(3S)-5-(2-methylpyrimidin-5-yl)-3,4-dihydro-2H-chromen-3-yl]-6-(3,3,3-trifluoropropoxy)nicotinamide;
N-[(3S)-5-(2-fluoropyridin-4-yl)-3,4-dihydro-2H-chromen-3-yl]-6-isopropoxynicotinamide;
N-[(3S)-5-(2-fluoropyridin-4-yl)-3,4-dihydro-2H-chromen-3-yl]-6-(3,3,3-trifluoropropoxy)nicotinamide;
N-[(3S)-5-pyridin-3-yl-3,4-dihydro-2H-chromen-3-yl]quinoxaline-2-carboxamide;
N-[(3S)-5-pyridin-3-yl-3,4-dihydro-2H-chromen-3-yl]quinoline-2-carboxamide;
6-isopropoxy-N-[(3S)-5-(3-methylpyridin-4-yl)-3,4-dihydro-2H-chromen-3-yl]nicotinamide;
N-[(3S)-5-(6-fluoropyridin-3-yl)-3,4-dihydro-2H-chromen-3-yl]-6-isopropoxynicotinamide;
N-[(3S)-5-(3-methylpyridin-4-yl)-3,4-dihydro-2H-chromen-3-yl]-6-(3,3,3-trifluoropropoxy)nicotinamide;
N-[(3S)-5-(6-fluoropyridin-3-yl)-3,4-dihydro-2H-chromen-3-yl]-6-(3,3,3-trifluoropropoxy)nicotinamide;
6-(2,4-dimethoxyphenyl)-N-[(3S)-5-pyridin-4-yl-3,4-dihydro-2H-chromen-3-yl]nicotinamide;
6-isopropoxy-N-[(3S)-5-(2-methoxypyridin-3-yl)-3,4-dihydro-2H-chromen-3-yl]nicotinamide;
N-[(3S)-5-(2-methoxypyridin-3-yl)-3,4-dihydro-2H-chromen-3-yl]-6-(3,3,3-trifluoropropoxy)nicotinamide;
6-isopropoxy-N-[(2S)-8-(2-methoxypyrimidin-5-yl)-1,2,3,4-tetrahydronaphthalen-2-yl]nicotinamide;
N-[(2R)-8-(2-fluoropyridin-3-yl)-1,2,3,4-tetrahydronaphthalen-2-yl]-6-isopropoxynicotinamide;
N-[(2R)-8-pyridazin-4-yl-1,2,3,4-tetrahydronaphthalen-2-yl]-6-(3,3,3-trifluoropropoxy)nicotinamide;
6-isopropoxy-N-[(3S)-5-(6-methoxypyridin-3-yl)-3,4-dihydro-2H-chromen-3-yl]nicotinamide;
N-[(3S)-5-(6-methoxypyridin-3-yl)-3,4-dihydro-2H-chromen-3-yl]-6-(3,3,3-trifluoropropoxy)nicotinamide;
6-isopropoxy-N-[(2R)-8-pyridazin-4-yl-1,2,3,4-tetrahydronaphthalen-2-yl]nicotinamide;
N-[(3S)-5-(5-fluoro-6-methoxypyridin-3-yl)-3,4-dihydro-2H-chromen-3-yl]-5-methoxypyrazine-2-carboxamide;
N-[(3S)-5-pyridazin-4-yl-3,4-dihydro-2H-chromen-3-yl]-6-(2,2,2-trifluoroethoxy)nicotinamide;
N-[(3S)-5-pyridazin-4-yl-3,4-dihydro-2H-chromen-3-yl]-6-(3,3,3-trifluoropropoxy)nicotinamide;
6-isopropoxy-N-[(2R)-8-(2-methoxypyrimidin-5-yl)-1,2,3,4-tetrahydronaphthalen-2-yl]nicotinamide;
5-methoxy-N-[(3S)-5-(2-methoxypyrimidin-5-yl)-3,4-dihydro-2H-chromen-3-yl]pyrazine-2-carboxamide;

N-[(2R)-8-(2-methoxypyrimidin-5-yl)-1,2,3,4-tetrahydronaphthalen-2-yl]-6-(3,3,3-trifluoropropoxy)nicotinamide;

N-[(2R)-8-(2-methoxypyrimidin-5-yl)-1,2,3,4-tetrahydronaphthalen-2-yl]-6-(2,2,2-trifluoroethoxy)nicotinamide;

N-[(3S)-5-(2-methoxypyrimidin-5-yl)-3,4-dihydro-2H-chromen-3-yl]-6-(2,2,2-trifluoroethoxy)nicotinamide;

N-[(2R)-8-(2-fluoropyridin-3-yl)-1,2,3,4-tetrahydronaphthalen-2-yl]-6-(2,2,2-trifluoroethoxy)nicotinamide;

N-[(3S)-5-(5-fluoro-6-methoxypyridin-3-yl)-3,4-dihydro-2H-chromen-3-yl]-6-(2,2,2-trifluoroethoxy)nicotinamide;

N-[(3S)-5-(2-methoxypyrimidin-5-yl)-3,4-dihydro-2H-chromen-3-yl]-4-methyl-2-(2,2,2-trifluoroethoxy)pyrimidine-5-carboxamide;

N-[(2R)-8-(2-methoxypyrimidin-5-yl)-1,2,3,4-tetrahydronaphthalen-2-yl]-4-methyl-2-(2,2,2-trifluoroethoxy)pyrimidine-5-carboxamide;

N-[(3S)-5-imidazo [1,2-a]pyridin-6-yl-3,4-dihydro-2H-chromen-3-yl]-6-(2,2,2-trifluoroethoxy)nicotinamide;

2-isopropoxy-N-[(3S)-5-(2-methoxypyrimidin-5-yl)-3,4-dihydro-2H-chromen-3-yl]-4-methylpyrimidine-5-carboxamide;

N-[(3S)-5-(2-ethoxypyrimidin-5-yl)-3,4-dihydro-2H-chromen-3-yl]-6-(2,2,2-trifluoroethoxy)nicotinamide;

6-(cyclobutyloxy)-N-[(3S)-5-(5-fluoro-6-methoxypyridin-3-yl)-3,4-dihydro-2H-chromen-3-yl]nicotinamide;

N-[(3S)-5-(2-ethylpyrimidin-5-yl)-3,4-dihydro-2H-chromen-3-yl]-6-(2,2,2-trifluoroethoxy)nicotinamide;

N-[(3S)-5-(2-cyclopropylpyrimidin-5-yl)-3,4-dihydro-2H-chromen-3-yl]-6-(3-fluoropropoxy)nicotinamide;

N-[(3S)-5-(5-fluoro-6-methoxypyridin-3-yl)-3,4-dihydro-2H-chromen-3-yl]-6-(3,3,3-trifluoropropoxy)nicotinamide;

N-[(3S)-5-(3,6-dimethoxypyridazin-4-yl)-3,4-dihydro-2H-chromen-3-yl]-6-(2,2,2-trifluoroethoxy)nicotinamide;

N-[(3S)-5-(6-methylpyrazin-2-yl)-3,4-dihydro-2H-chromen-3-yl]-6-(2,2,2-trifluoroethoxy)nicotinamide;

6-(3-fluoropropoxy)-N-[(3S)-5-(2-methoxypyrimidin-5-yl)-3,4-dihydro-2H-chromen-3-yl]nicotinamide;

6-(3-fluoropropoxy)-N-[(3S)-5-(2-methylpyrimidin-5-yl)-3,4-dihydro-2H-chromen-3-yl]nicotinamide;

N-[(3S)-5-(2-methylpyrimidin-5-yl)-3,4-dihydro-2H-chromen-3-yl]-6-(2,2,2-trifluoroethoxy)nicotinamide;

2-isopropoxy-N-[(2R)-8-(2-methoxypyrimidin-5-yl)-1,2,3,4-tetrahydronaphthalen-2-yl]isonicotinamide;

2-isopropoxy-N-[(3S)-5-(2-methylpyrimidin-5-yl)-3,4-dihydro-2H-chromen-3-yl]isonicotinamide;

6-(cyclobutyloxy)-N-[(3S)-5-(2-methylpyrimidin-5-yl)-3,4-dihydro-2H-chromen-3-yl]nicotinamide;

6-(cyclobutyloxy)-N-[(3S)-5-(2-methoxypyrimidin-5-yl)-3,4-dihydro-2H-chromen-3-yl]nicotinamide;

2-isopropoxy-N-[(3S)-5-(2-methoxypyrimidin-5-yl)-3,4-dihydro-2H-chromen-3-yl]isonicotinamide;

N-[(3S)-5-(3,5-dimethylpyrazin-2-yl)-3,4-dihydro-2H-chromen-3-yl]-6-(3-fluoropropoxy)nicotinamide;

N-[(3S)-5-(2-cyclopropylpyrimidin-5-yl)-3,4-dihydro-2H-chromen-3-yl]-6-(2,2,2-trifluoroethoxy)nicotinamide;

$N^5$-[(3S)-5-(2-methoxypyrimidin-5-yl)-3,4-dihydro-2H-chromen-3-yl]-$N^2$,$N^2$-dipropylpyridine-2,5-dicarboxamide;

$N^5$-[(3S)-5-(2-methoxypyrimidin-5-yl)-3,4-dihydro-2H-chromen-3-yl]-$N^2$-(3-methylbutyl)pyridine-2,5-dicarboxamide;

$N^2$-isobutyl-$N^5$-[(3S)-5-(2-methoxypyrimidin-5-yl)-3,4-dihydro-2H-chromen-3-yl]-$N^2$-methylpyridine-2,5-dicarboxamide;

N-[(3S)-5-pyridin-4-yl-3,4-dihydro-2H-chromen-3-yl]-6-(pyrrolidin-1-ylcarbonyl)nicotinamide;

N-[(3S)-5-pyridin-4-yl-3,4-dihydro-2H-chromen-3-yl]-6-(1,3-thiazol-2-ylmethoxy)nicotinamide;

6-[(5-methylisoxazol-3-yl)methoxy]-N-[(3S)-5-pyridin-4-yl-3,4-dihydro-2H-chromen-3-yl]nicotinamide;

6-[(1-methyl-1H-imidazol-2-yl)methoxy]-N-[(3S)-5-pyridin-4-yl-3,4-dihydro-2H-chromen-3-yl]nicotinamide;

6-(cyclopentylsulfonyl)-N-[(3S)-5-pyridin-4-yl-3,4-dihydro-2H-chromen-3-yl]nicotinamide;

N-[(3S)-5-pyridin-4-yl-3,4-dihydro-2H-chromen-3-yl]-6-(pyridin-2-ylmethoxy)nicotinamide;

N-[(3S)-5-pyridin-4-yl-3,4-dihydro-2H-chromen-3-yl]-6-(pyridin-3-ylmethoxy)nicotinamide;

6-(pyrazin-2-ylmethoxy)-N-[(3S)-5-pyridin-4-yl-3,4-dihydro-2H-chromen-3-yl]nicotinamide;

N-[(3S)-5-(2-methoxypyrimidin-5-yl)-3,4-dihydro-2H-chromen-3-yl]-6-(tetrahydrofuran -2-ylmethoxy)nicotinamide;

N-[(3S)-5-(2-methoxypyrimidin-5-yl)-3,4-dihydro-2H-chromen-3-yl]-6-(tetrahydro-2H -pyran-2-ylmethoxy)nicotinamide;

N-[(3S)-5-(2-methoxypyrimidin-5-yl)-3,4-dihydro-2H-chromen-3-yl]-6-(tetrahydro-2H -pyran-4-ylmethoxy)nicotinamide;

6-(but-2-yn-1-yloxy)-N-[(3S)-5-(2-methoxypyrimidin-5-yl)-3,4-dihydro-2H-chromen-3-yl]nicotinamide;

$N^5$-[(3S)-5-(2-methoxypyrimidin-5-yl)-3,4-dihydro-2H-chromen-3-yl]-$N^2$-(3,3,3-trifluoropropyl)pyridine-2,5-dicarboxamide;

6-(2-methoxyethoxy)-N-[(3S)-5-pyridin-4-yl-3,4-dihydro-2H-chromen-3-yl]nicotinamide;

6-(oxetan-2-ylmethoxy)-N-[(3S)-5-pyridin-4-yl-3,4-dihydro-2H-chromen-3-yl]nicotinamide;

6-{[(2R)-2-methoxypropyl]oxy}-N-[(3S)-5-pyridin-4-yl-3,4-dihydro-2H-chromen-3-yl]nicotinamide;

N-[(3S)-5-pyridin-4-yl-3,4-dihydro-2H-chromen-3-yl]-6-(tetrahydro-2H-pyran-4-yloxy)nicotinamide;

$N^5$-[(3S)-5-pyridin-4-yl-3,4-dihydro-2H-chromen-3-yl]-$N^2$-(tetrahydro-2H-pyran-4-yl)pyridine-2,5-dicarboxamide;

$N^5$-[(3S)-5-pyridin-4-yl-3,4-dihydro-2H-chromen-3-yl]-$N^2$-(2,2,2-trifluoroethyl)pyridine -2,5-dicarboxamide;

$N^5$-[(3S)-5-pyridin-3-yl-3,4-dihydro-2H-chromen-3-yl]-$N^2$-(3,3,3-trifluoropropyl)pyridine-2,5-dicarboxamide;

N-[(3S)-5-pyridin-3-yl-3,4-dihydro-2H-chromen-3-yl]-5-(tetrahydro-2H-pyran-4-yloxy)pyrazine-2-carboxamide;

N-[(3S)-5-(6-methoxypyridin-3-yl)-3,4-dihydro-2H-chromen-3-yl]-6-(tetrahydro-2H -pyran-4-yloxy)nicotinamide;

N-[(3S)-5-(6-methoxypyridin-3-yl)-3,4-dihydro-2H-chromen-3-yl]-6-(tetrahydro-2H -pyran-3-yloxy)nicotinamide;

N-[(3S)-5-pyridin-4-yl-3,4-dihydro-2H-chromen-3-yl]-6-(tetrahydro-2H-pyran-2-yloxy)nicotinamide;

6-(2-methoxyethoxy)-N-[(3S)-5-pyridin-3-yl-3,4-dihydro-2H-chromen-3-yl]nicotinamide;

2-(2-methoxyethyl)-5-methyl-N-[(3S)-5-pyridin-3-yl-3,4-dihydro-2H-chromen-3-yl]-2H -1,2,3-triazole-4-carboxamide;

6-(oxetan-2-ylmethoxy)-N-[(3S)-5-pyridin-3-yl-3,4-dihydro-2H-chromen-3-yl]nicotinamide;

6-(2-methoxyethoxy)-N-[(3S)-5-(2-methoxypyridin-4-yl)-3,4-dihydro-2H-chromen-3-yl]nicotinamide;
6-(2-methoxyethoxy)-N-[(3S)-5-(2-methylpyrimidin-5-yl)-3,4-dihydro-2H-chromen-3-yl]nicotinamide;
6-(2-methoxyethoxy)-N-[(3S)-5-(3-methylpyridin-4-yl)-3,4-dihydro-2H-chromen-3-yl]nicotinamide;
N-[(3S)-5-(6-fluoropyridin-3-yl)-3,4-dihydro-2H-chromen-3-yl]-6-(2-methoxyethoxy)nicotinamide;
N-[(2R)-8-(2-fluoropyridin-3-yl)-1,2,3,4-tetrahydronaphthalen-2-yl]-6-(2-methoxyethoxy)nicotinamide;
N-[(2R)-8-(2-fluoropyridin-3-yl)-1,2,3,4-tetrahydronaphthalen-2-yl]-6-(tetrahydro-2H-pyran-4-yloxy)nicotinamide;
N-[(2R)-8-pyridazin-4-yl-1,2,3,4-tetrahydronaphthalen-2-yl]-6-(tetrahydro-2H-pyran-3-yloxy)nicotinamide;
N-[(2R)-8-(6-methylpyridin-3-yl)-1,2,3,4-tetrahydronaphthalen-2-yl]-2-(tetrahydro-2H-pyran-3-yloxy)pyrimidine-5-carboxamide;
1-butyl-N-[(3S)-5-(5-fluoro-6-methoxypyridin-3-yl)-3,4-dihydro-2H-chromen-3-yl]-2-oxo-1,2-dihydropyridine-4-carboxamide;
N-[(3S)-5-(5-fluoro-6-methoxypyridin-3-yl)-3,4-dihydro-2H-chromen-3-yl]-2-(tetrahydrofuran-3-yloxy)pyrimidine-5-carboxamide;
1-butyl-N-[(3S)-5-(2-methoxypyrimidin-5-yl)-3,4-dihydro-2H-chromen-3-yl]-2-oxo-1,2-dihydropyridine-4-carboxamide;
N-[(3S)-5-(6-fluoro-5-methylpyridin-3-yl)-3,4-dihydro-2H-chromen-3-yl]-6-(tetrahydro-2H-pyran-3-yloxy)nicotinamide;
1-butyl-N-[(3S)-5-(6-fluoro-5-methylpyridin-3-yl)-3,4-dihydro-2H-chromen-3-yl]-2-oxo-1,2-dihydropyridine-4-carboxamide;
N-[(3S)-5-(6-fluoro-5-methylpyridin-3-yl)-3,4-dihydro-2H-chromen-3-yl]-2-(tetrahydro-2H-pyran-3-yloxy)pyrimidine-5-carboxamide;
N-[(2S)-8-(2-methoxypyrimidin-5-yl)-1,2,3,4-tetrahydronaphthalen-2-yl]-6-(tetrahydro-2H-pyran-4-yloxy)nicotinamide;
N-[(3S)-5-(2-methylpyrimidin-5-yl)-3,4-dihydro-2H-chromen-3-yl]-6-(tetrahydro-2H-pyran-4-yloxy)nicotinamide;
N-[(2R)-8-(2-methoxypyrimidin-5-yl)-1,2,3,4-tetrahydronaphthalen-2-yl]-6-(tetrahydro-2H-pyran-4-yloxy)nicotinamide;
N-[(3S)-5-(2-methoxypyrimidin-5-yl)-3,4-dihydro-2H-chromen-3-yl]-6-(tetrahydro-2H-pyran-3-yloxy)nicotinamide;
N-[(3S)-5-(2-methoxypyrimidin-5-yl)-3,4-dihydro-2H-chromen-3-yl]-6-(tetrahydrofuran-3-yloxy)nicotinamide;
N-[2R)-8-(2-methylpyrimidin-5-yl)-1,2,3,4-tetrahydronaphthalen-2-yl]-6-(tetrahydrofuran-3-yloxy)nicotinamide;
N-[(2R)-8-(2-methylpyrimidin-5-yl)-1,2,3,4-tetrahydronaphthalen-2-yl]-6-(tetrahydro-2H-pyran-3-yloxy)nicotinamide;
N-[2R)-8-(2-methylpyrimidin-5-yl)-1,2,3,4-tetrahydronaphthalen-2-yl]-6-(tetrahydrofuran-2-ylmethoxy)nicotinamide;
N-[(2R)-8-(2-methoxypyrimidin-5-yl)-1,2,3,4-tetrahydronaphthalen-2-yl]-6-[(2-(2,2,2-trifluoroethoxy)ethoxy]nicotinamide;
N-[(3S)-5-(2-methoxypyrimidin-5-yl)-3,4-dihydro-2H-chromen-3-yl]-6-[(2-(2,2,2-trifluoroethoxy)ethoxy]nicotinamide;
6-(1,4-dioxan-2-ylmethoxy)-N-[(2R)-8-(2-fluoropyridin-3-yl)-1,2,3,4-tetrahydronaphthalen-2-yl]nicotinamide;
6-(1,4-dioxan-2-ylmethoxy)-N-[(3S)-5-(2-methoxypyridin-4-yl)-3,4-dihydro-2H-chromen-3-yl]nicotinamide;
6-(1,4-dioxan-2-ylmethoxy)-N-[(3S)-5-(5-fluoro-6-methoxypyridin-3-yl)-3,4-dihydro-2H-chromen-3-yl]nicotinamide;
$N^5$-[(2R)-8-(2-methoxypyrimidin-5-yl)-1,2,3,4-tetrahydronaphthalen-2-yl]-$N^2$-(3,3,3-trifluoropropyl)pyridine-2,5-dicarboxamide;
6-(but-2-yn-1-yloxy)-N-[(2R)-8-(2-methoxypyrimidin-5-yl)-1,2,3,4-tetrahydronaphthalen-2-yl]nicotinamide;
N-[(3S)-5-imidazo[1,2-a]pyridin-6-yl-3,4-dihydro-2H-chromen-3-yl]-6-(tetrahydro-2H-pyran-4-yloxy)nicotinamide;
$N^2$-(4,4-difluorocyclohexyl)-$N^5$-[(3S)-5-(2-methoxypyrimidin-5-yl)-3,4-dihydro-2H-chromen-3-yl]pyridine-2,5-dicarboxamide;
$N^5$-[(3S)-5-(2-methoxypyrimidin-5-yl)-3,4-dihydro-2H-chromen-3-yl]-$N^2$-(4,4,4-trifluorobutyl)pyridine-2,5-dicarboxamide;
N-[(3S)-5-(2-methoxypyrimidin-5-yl)-3,4-dihydro-2H-chromen-3-yl]-2-[2-(2,2,2-trifluoroethoxy)ethoxy]isonicotinamide;
$N^2$-methyl-$N^5$-[(3S)-5-(2-methylpyrimidin-5-yl)-3,4-dihydro-2H-chromen-3-yl]-$N^2$-(2,2,2-trifluoroethyl)pyridine-2,5-dicarboxamide;
$N^5$-[(3S)-5-(2-ethylpyrimidin-5-yl)-3,4-dihydro-2H-chromen-3-yl]-$N^2$-(3,3,3-trifluoropropyl)pyridine-2,5-dicarboxamide;
N-{(3S)-5-[6-(methylsulfonyl)pyridin-3-yl]-3,4-dihydro-2H-chromen-3-yl}-6-[2-(2,2,2-trifluoroethoxy)ethoxy]nicotinamide;
N-[(3S)-5-(6-cyanopyridin-3-yl)-3,4-dihydro-2H-chromen-3-yl]-6-[2-(2,2,2-trifluoroethoxy)ethoxy]nicotinamide;
N-[(3S)-5-(2-cyclopropylpyrimidin-5-yl)-3,4-dihydro-2H-chromen-3-yl]-6-[2-(2,2,2-trifluoroethoxy)ethoxy]nicotinamide;
N-[(3S)-5-(2-ethylpyrimidin-5-yl)-3,4-dihydro-2H-chromen-3-yl]-6-[2-(2,2,2-trifluoroethoxy)ethoxy]nicotinamide;
$N^5$-[(3S)-5-(5-fluoro-6-methoxypyridin-3-yl)-3,4-dihydro-2H-chromen-3-yl]-$N^2$-(3,3,3-trifluoropropyl)pyridine-2,5-dicarboxamide;
N-[(3S)-5-(5-fluoro-6-methoxypyridin-3-yl)-3,4-dihydro-2H-chromen-3-yl]-6-[2-(2,2,2-trifluoroethoxy)ethoxy]nicotinamide;
6-(cyclopentylsulfonyl)-N-[(3S)-5-(2-methoxypyrimidin-5-yl)-3,4-dihydro-2H-chromen-3-yl]nicotinamide;
N-[(3S)-5-(6-methylpyrazin-2-yl)-3,4-dihydro-2H-chromen-3-yl]-6-[2-(2,2,2-trifluoroethoxy)ethoxy]nicotinamide;
$N^5$-[(3S)-5-(2-methylpyrimidin-5-yl)-3,4-dihydro-2H-chromen-3-yl]-$N^2$-(3,3,3-trifluoropropyl)pyridine-2,5-dicarboxamide;
6-(2-isopropoxyethoxy)-N-[(3S)-5-(2-methoxypyrimidin-5-yl)-3,4-dihydro-2H-chromen-3-yl]nicotinamide;
6-(2-isopropoxyethoxy)-N-[(3S)-5-(2-methylpyrimidin-5-yl)-3,4-dihydro-2H-chromen-3-yl]nicotinamide;
$N^2$-(3-isopropoxypropyl)-$N^5$-[(3S)-5-(2-methylpyrimidin-5-yl)-3,4-dihydro-2H-chromen-3-yl]pyridine-2,5-dicarboxamide;
$N^2$-(3-isopropoxypropyl)-$N^5$-[(3S)-5-(2-methoxypyrimidin-5-yl)-3,4-dihydro-2H-chromen-3-yl]pyridine-2,5-dicarboxamide;

N⁵-[(3S)-5-(2-methylpyrimidin-5-yl)-3,4-dihydro-2H-chromen-3-yl]-N²-(4,4,4-trifluorobutyl)pyridine-2,5-dicarboxamide;

N-[(3S)-5-(2-methylpyrimidin-5-yl)-3,4-dihydro-2H-chromen-3-yl]-6-[2-(2,2,2-trifluoroethoxy)ethoxy]nicotinamide;

N-[(2R)-8-(2-methoxypyrimidin-5-yl)-1,2,3,4-tetrahydronaphthalen-2-yl]-2-[2-(2,2,2-trifluoroethoxy)ethoxy]isonicotinamide;

N⁵-[(3S)-5-(2-methoxypyrimidin-5-yl)-3,4-dihydro-2H-chromen-3-yl]-N²-methyl-N²-(2,2,2-trifluoroethyl)pyridine-2,5-dicarboxamide;

N⁵-[(3S)-5-(5-fluoro-6-methoxypyridin-3-yl)-3,4-dihydro-2H-chromen-3-yl]-N²-methyl -N²-(2,2,2-trifluoroethyl)pyridine-2,5-dicarboxamide;

N-[(3S)-5-(5-fluoro-6-methoxypyridin-3-yl)-3,4-dihydro-2H-chromen-3-yl]-6-[(2,2,2-trifluoroethoxy)methyl]nicotinamide;

N-[(3S)-5-(2-methoxypyrimidin-5-yl)-3,4-dihydro-2H-chromen-3-yl]-6-[(2,2,2-trifluoroethoxy)methyl]nicotinamide;

N-[(3S)-5-(2-methoxypyrimidin-5-yl)-3,4-dihydro-2H-chromen-3-yl]-2-[(3,3,3-trifluoropropyl)amino]pyrimidine-5-carboxamide;

N⁵-[(3S)-5-(2-cyclopropylpyrimidin-5-yl)-3,4-dihydro-2H-chromen-3-yl]-N²-methyl-N²-(2,2,2-trifluoroethyl)pyridine-2,5-dicarboxamide;

N⁵-[(3S)-5-(2-cyclopropylpyrimidin-5-yl)-3,4-dihydro-2H-chromen-3-yl]-N²-(3,3,3-trifluoropropyl)pyridine-2,5-dicarboxamide;

N⁵-[(3S)-5-(2-cyclopropylpyrimidin-5-yl)-3,4-dihydro-2H-chromen-3-yl]-N²-methyl-N²-(3,3,3-trifluoropropyl)pyridine-2,5-dicarboxamide;

N-[(3S)-5-(2-cyclopropylpyrimidin-5-yl)-3,4-dihydro-2H-chromen-3-yl]-2-oxo-1-(3,3,3-trifluoropropyl)-1,2-dihydropyridine-4-carboxamide;

N-[(3S)-5-(5-fluoro-6-methoxypyridin-3-yl)-3,4-dihydro-2H-chromen-3-yl]-2-[(3,3,3-trifluoropropyl)amino]pyrimidine-5-carboxamide;

N-[(3S)-5-(2-methylpyrimidin-5-yl)-3,4-dihydro-2H-chromen-3-yl]-2-[(3,3,3-trifluoropropyl)amino]pyrimidine-5-carboxamide;

N-[(3S)-5-(3,5-dimethylpyrazin-2-yl)-3,4-dihydro-2H-chromen-3-yl]-6-[2-(2,2,2-trifluoroethoxy)ethoxy]nicotinamide;

N-[(3S)-5-(2-methylpyrimidin-5-yl)-3,4-dihydro-2H-chromen-3-yl]-6-[(2,2,2-trifluoroethoxy)methyl]nicotinamide;

2-methoxy-N,N-dimethyl-5-[(3S)-3-({[6-(tetrahydro-2H-pyran-4-yloxy)pyridin-3-yl]carbonyl}amino)-3,4-dihydro-2H-chromen-5-yl]nicotinamide;

5-[(3S)-3-{[(6-isopropoxypyridin-3-yl)carbonyl]amino}-3,4-dihydro-2H-chromen-5-yl]-2-methoxy-N-methylnicotinamide;

2-methoxy-N-methyl-5-[(3S)-3-({[6-(tetrahydro-2H-pyran-4-yloxy)pyridin-3-yl]carbonyl}amino)-3,4-dihydro-2H-chromen-5-yl]nicotinamide;

5-[(3S)-3-{[(6-isopropoxypyridin-3-yl)carbonyl]amino}-3,4-dihydro-2H-chromen-5-yl]-2-methoxy-N,N-dimethylnicotinamide;

2-methoxy-N,N-dimethyl-5-[(3S)-3-({[6-(2,2,2-trifluoroethoxy)pyridin-3-yl]carbonyl}amino)-3,4-dihydro-2H-chromen-5-yl]nicotinamide;

N,N-dimethyl-5-{(3S)-3-[({6-[2-(2,2,2-trifluoroethoxy)ethoxy]pyridin-3-yl}carbonyl)amino]-3,4-dihydro-2H-chromen-5-yl}pyrimidine-2-carboxamide;

N-{(3S)-5-[6-(hydroxymethyl)pyridin-3-yl]-3,4-dihydro-2H-chromen-3-yl}-6-[2-(2,2,2-trifluoroethoxy)ethoxy]nicotinamide;

6-(3-fluoropropoxy)-N-{(3S)-5-[6-(hydroxymethyl)pyridin-3-yl]-3,4-dihydro-2H-chromen-3-yl}nicotinamide;

N-{(3S)-5-[6-(hydroxymethyl)pyridin-3-yl]-3,4-dihydro-2H-chromen-3-yl}-6-(2,2,2-trifluoroethoxy)nicotinamide; and N-{(3S)-5-[5-(hydroxymethyl)pyrazin-2-yl]-3,4-dihydro-2H-chromen-3-yl}-6-[2-(2,2,2-trifluoroethoxy)ethoxy]nicotinamide;

11. A pharmaceutical composition, wherein the composition comprises:
a therapeutically effective amount of a compound or pharmaceutically acceptable salt thereof according to claim 1; and
a pharmaceutically acceptable diluent, excipient, and/or inert carrier.

* * * * *